US011965188B2

(12) United States Patent
Peng et al.

(10) Patent No.: US 11,965,188 B2
(45) Date of Patent: Apr. 23, 2024

(54) RECOMBINANT HUMAN SIALIDASES, SIALIDASE FUSION PROTEINS, AND METHODS OF USING THE SAME

(71) Applicant: Palleon Pharmaceuticals Inc., Waltham, MA (US)

(72) Inventors: Li Peng, Lexington, MA (US); Lizhi Cao, Stoneham, MA (US); Lihui Xu, Chestnut Hill, MA (US)

(73) Assignee: Palleon Pharmaceuticals Inc., Waltham, MA (US)

( * ) Notice: Subject to any disclaimer, the term of this patent is extended or adjusted under 35 U.S.C. 154(b) by 86 days.

(21) Appl. No.: 16/958,914

(22) PCT Filed: Jan. 3, 2019

(86) PCT No.: PCT/US2019/012207
§ 371 (c)(1),
(2) Date: Jun. 29, 2020

(87) PCT Pub. No.: WO2019/136167
PCT Pub. Date: Jul. 11, 2019

(65) Prior Publication Data

US 2020/0339968 A1 Oct. 29, 2020

Related U.S. Application Data

(60) Provisional application No. 62/755,279, filed on Nov. 2, 2018, provisional application No. 62/613,363, filed on Jan. 3, 2018.

(51) Int. Cl.

| | |
|---|---|
| ***A61K 47/68*** | (2017.01) |
| ***A61P 35/00*** | (2006.01) |
| ***C07K 16/28*** | (2006.01) |
| ***C07K 16/32*** | (2006.01) |
| ***C12N 9/24*** | (2006.01) |
| *A61K 39/00* | (2006.01) |

(52) U.S. Cl.
CPC ........ *C12N 9/2402* (2013.01); *A61K 47/6815* (2017.08); *A61K 47/6855* (2017.08); *A61P 35/00* (2018.01); *C07K 16/2863* (2013.01); *C07K 16/32* (2013.01); *A61K 2039/505* (2013.01)

(58) Field of Classification Search
CPC .................................................. A61K 47/6815
See application file for complete search history.

(56) References Cited

U.S. PATENT DOCUMENTS

| | | | |
|---|---|---|---|
| 4,510,129 | A | 4/1985 | Knop et al. |
| 4,975,278 | A | 12/1990 | Senter et al. |
| 6,877,169 | B2 | 4/2005 | Acquaviva |
| 6,977,169 | B2 | 12/2005 | Kline |
| 7,645,448 | B2 | 1/2010 | Fang et al. |
| 7,807,174 | B2 | 10/2010 | Fang et al. |
| 8,012,733 | B2 | 9/2011 | Van Dijk et al. |
| 8,084,036 | B2 | 12/2011 | Yu et al. |
| 8,114,412 | B2 | 2/2012 | Chuenkova et al. |
| 8,187,591 | B2 | 5/2012 | Marth et al. |
| 8,217,149 | B2 | 7/2012 | Irving et al. |
| 8,329,195 | B2 | 12/2012 | Briles et al. |
| 8,398,971 | B2 | 3/2013 | Fang et al. |
| 8,512,710 | B2 | 8/2013 | Fang et al. |
| 8,623,419 | B2 | 1/2014 | Malakhov et al. |
| 8,722,869 | B2 | 5/2014 | Fang et al. |
| 8,999,705 | B2 | 4/2015 | Mills et al. |
| 9,132,179 | B2 | 9/2015 | Van Ginkel et al. |
| 9,212,353 | B2 | 12/2015 | Fang et al. |
| 9,764,007 | B2 | 9/2017 | Fang et al. |
| 10,081,801 | B2 | 9/2018 | Mikkelsen et al. |
| 10,280,191 | B2 | 5/2019 | Deamer et al. |
| 10,300,116 | B2 | 5/2019 | Moss |
| 10,328,128 | B2 | 6/2019 | Moss |
| 10,351,828 | B2 | 7/2019 | Hawley |
| 10,428,318 | B2 | 10/2019 | Vogel et al. |
| 10,525,109 | B2 | 1/2020 | Fang et al. |
| 10,918,736 | B2 | 2/2021 | Kim et al. |
| 10,940,185 | B2 | 3/2021 | Yasukawa et al. |
| 2003/0219433 | A1 | 11/2003 | Hansen et al. |
| 2007/0231333 | A1 | 10/2007 | Boghaert et al. |

(Continued)

FOREIGN PATENT DOCUMENTS

| | | | |
|---|---|---|---|
| CN | 111763259 | B | 12/2020 |
| WO | WO-2007/109376 | A2 | 9/2007 |

(Continued)

OTHER PUBLICATIONS

Ngo et al. in The Protein Folding Problem and Tertiary Structure Prediction, 1994, Merz et al. (ed.), Birkhauser, Boston, MA, pp. 433 and 492-495.*
Chavas et al. (J. Bio. Chem., vol. 280, No. 1, pp. 469-475, 2005).*
UniProt entry QY3R4,.*
PDBe entry 1SNT (Nov. 2004).*
He et al. (Protein Science, 13, 2716-2724, 2004).*
U.S. Appl. No. 17/624,123, Recombinant Sialidases and Methods of Using the Same, filed Dec. 30, 2021.

(Continued)

*Primary Examiner* — Richard G Hutson
(74) *Attorney, Agent, or Firm* — Goodwin Procter LLP

(57) ABSTRACT

The invention relates generally to recombinant human sialidases and recombinant sialidase fusion proteins, wherein the sialidase optionally contains one or more mutations compared to wild-type human sialidase, e.g., a substitution, deletion, or addition of at least one amino acid. The invention also provides antibody conjugates including a sialidase and an antibody or a portion thereof. The invention further relates to methods of using the sialidase fusion proteins or antibody conjugates for treating cancer.

43 Claims, 34 Drawing Sheets

Specification includes a Sequence Listing.

(56) References Cited

U.S. PATENT DOCUMENTS

| | | | |
|---|---|---|---|
| 2011/0135570 A1 | 6/2011 | Janatpour et al. | |
| 2011/0142912 A1 | 6/2011 | Moser et al. | |
| 2011/0171132 A1 | 7/2011 | Fang et al. | |
| 2013/0287802 A1 | 10/2013 | Govindappa et al. | |
| 2014/0271462 A1 | 9/2014 | Ho et al. | |
| 2015/0152187 A1 | 6/2015 | Sun et al. | |
| 2015/0355184 A1 | 12/2015 | Pierce et al. | |
| 2016/0076013 A1 | 3/2016 | Mikkelsen et al. | |
| 2016/0184407 A1 | 6/2016 | Fang et al. | |
| 2017/0119859 A1 | 5/2017 | Moss | |
| 2017/0165334 A1 | 6/2017 | Wang | |
| 2017/0354720 A1 | 12/2017 | Fang et al. | |
| 2018/0200345 A1 | 7/2018 | Schmitt | |
| 2018/0271997 A1 | 9/2018 | Wang | |
| 2019/0037899 A1 | 2/2019 | Juge et al. | |
| 2019/0125859 A1 | 5/2019 | Palese et al. | |
| 2019/0177416 A1 | 6/2019 | Ting et al. | |
| 2019/0192691 A1 | 6/2019 | Barrett et al. | |
| 2019/0211099 A1 | 7/2019 | Burchell et al. | |
| 2019/0247460 A1 | 8/2019 | Connaris et al. | |
| 2019/0248919 A1 | 8/2019 | Woods et al. | |
| 2019/0352420 A1 | 11/2019 | Hofmann et al. | |
| 2020/0164049 A1* | 5/2020 | Moss | A61K 9/0073 |
| 2020/0222511 A1 | 7/2020 | Moss | |
| 2020/0231677 A1 | 7/2020 | West et al. | |
| 2022/0169724 A1 | 6/2022 | Woods et al. | |
| 2022/0356457 A1 | 11/2022 | Peng et al. | |
| 2022/0362351 A1 | 11/2022 | Peng et al. | |
| 2022/0372458 A1 | 11/2022 | Peng et al. | |
| 2022/0380742 A1 | 12/2022 | Peng et al. | |
| 2022/0387616 A1 | 12/2022 | Peng et al. | |
| 2023/0265406 A1 | 8/2023 | Peng et al. | |

FOREIGN PATENT DOCUMENTS

| | | |
|---|---|---|
| WO | WO-2007/115467 A1 | 10/2007 |
| WO | WO-2013/137920 A1 | 9/2013 |
| WO | WO-2014/037785 A2 | 3/2014 |
| WO | WO-2016/038064 A1 | 3/2016 |
| WO | WO-2016/056913 A1 | 4/2016 |
| WO | WO-2016/102436 A1 | 6/2016 |
| WO | WO-2017/100725 A1 | 6/2017 |
| WO | WO-2017/123745 A1 | 7/2017 |
| WO | WO-2018/006034 A1 | 1/2018 |
| WO | WO-2018/188672 A1 | 10/2018 |
| WO | WO-2018/231661 A1 | 12/2018 |
| WO | WO-2019/086554 A1 | 5/2019 |
| WO | WO-2020/018996 A2 | 1/2020 |
| WO | WO-2020/142727 A1 | 7/2020 |
| WO | WO-2020/172072 A1 | 8/2020 |
| WO | WO-2020/223550 A1 | 11/2020 |
| WO | WO-2021/003463 A1 | 1/2021 |
| WO | WO-2021/003464 A1 | 1/2021 |
| WO | WO-2021/003465 A1 | 1/2021 |
| WO | WO-2021/003468 A2 | 1/2021 |
| WO | WO-2021/003469 A2 | 1/2021 |
| WO | WO-2022/006492 A2 | 1/2022 |

OTHER PUBLICATIONS

Albohy et al. (2010) Glycobiology 20(9): 1127-1138.
Basler et al. (1999) Journal of Virology 73(10): 8095-8103.
Chu et al. (2006) Am. J. Clin. Pathol. 126:534-544.
DATABASE UniProt [Online] Dec. 14, 2011 (Dec. 14, 2011), "RecName: Full=Exo-alpha-sialidase [ECO:0000256\ARBA:ARBA00012733}; EC=3.2.1.18 [ECO:0000256|ARBA:ARBA00012733};", XP002804582, retrieved from EBI accession No. UNIPROT:G5BXG6 (1 page).
DATABASE UniProt [Online] Jan. 9, 2013 (Jan. 9, 2013), "RecName: Full=Exo-alpha-sialidase {ECO:0000256 !ARBA:ARBA00012733}; EC=3.2.1.18 {ECO:0000256 !ARBA:ARBA00012733};", XP002805932, retrieved from EBI accession No. UNIPROT:K7GDB1 (2 pages).
Foster et al. (2005) Nat. Rev. Cancer 5(7): 526-42.
Hausmann et al. (1997) Journal of General Virology 78: 3233-3245.
Hudak et al. (2014) Nat. Chem. Biol. 10:69-75.
International Search Report for International Application No. PCT/US2017/040411, dated Sep. 21, 2017 (4 pages).
International Search Report for International Application No. PCT/US2019/012207, dated Apr. 10, 2019 (9 pages).
International Search Report for International Application No. PCT/US2020/040814, dated Dec. 14, 2020 (5 pages).
International Search Report for International Application No. PCT/US2020/040815, dated Dec. 15, 2020 (5 pages).
International Search Report for International Application No. PCT/US2020/040816, dated Dec. 14, 2020 (5 pages).
International Search Report for International Application No. PCT/US2020/040827, dated Dec. 18, 2020 (5 pages).
International Search Report for International Application No. PCT/US2020/040828, dated Dec. 14, 2020 (5 pages).
International Search Report for International Application No. PCT/US2021/040240, dated Jan. 6, 2022 (6 pages).
International Search Report for International Application No. PCT/US2022/011499, dated Apr. 28, 2022 (4 pages).
Ito et al. (2011) Biotechnology Letters 33(1): 103-107.
Itoh et al. (2002) J. Hum. Genet. 47(1): 29-37.
Jandus et al. (2014) J. Clin. Invest. 124: 1810-1820.
Jonson et al. (2015) PLoS One 10(7): e0133272.
Julien S. et al. (2015) Sialic Acid and Cancer Glycoscience: Biology and Medicine 1419-1424.
Kim et al. (2011) Nature 479, 223-227.
Kruse et al. (1998) Glycoconjugate Journal 15: 769-775.
Lukong et al. (2000) Human Molecular Genetics 9(7): 1075-1085.
Läubli et al. (2014) Proc. Natl. Acad. Sci USA 111 (39): 14211-14216.
Malakhov et al. (2006) Antimicrobial Agents and Chemotherapy 50(4): 1470-1479.
Monti et al. (1999) Glycobiology 9(12):1313-1321.
Paris et al. (2001) Glycobiology 11(4): 305-311.
Rahman et al. (2013) Glycobiology 23(4): 495-504.
Seid et al. (2017) Human Vaccines & Immunotherapeutics 13(3): 621-633.
Vahidi et al. (2018) Proc. Natl. Acad. Sci. USA 115(8): E6447-E6456).
Written Opinion for International Application No. PCT/US2017/040411, dated Sep. 21, 2017 (6 pages).
Written Opinion for International Application No. PCT/US2019/012207, dated Apr. 10, 2019 (7 pages).
Written Opinion for International Application No. PCT/US2020/040814, dated Dec. 14, 2020 (6 pages).
Written Opinion for International Application No. PCT/US2020/040815, dated Dec. 15, 2020 (6 pages).
Written Opinion for International Application No. PCT/US2020/040816, dated Dec. 14, 2020 (6 pages).
Written Opinion for International Application No. PCT/US2020/040827, dated Dec. 18, 2020 (6 pages).
Written Opinion for International Application No. PCT/US2020/040828, dated Dec. 14, 2020 (6 pages).
Written Opinion for International Application No. PCT/US2021/040240, dated Jan. 6, 2022 (9 pages).
Written Opinion for International Application No. PCT/US2022/011499, dated Apr. 28, 2022 (4 pages).
Xiao et al. (2016) Proc. Natl. Acad. Sci. USA 113(37): 10304-9.
Yang et al. (2022) "Enhancing the anti-tumor efficacy of Bispecific T cell engagers via cell surface glycocalyx editing," bioRxiv, posted May 23, 2022; https://doi.org/10.1101/2022.05.22.492978 (23 pages).
Monti et al. (2010) Advances in Carbohydrate Chemistry and Biochemistry, 64: 403-479.
U.S. Appl. No. 16/308,732, Conjugates for Targeted Cell Surface Editing, filed Dec. 10, 2018.
U.S. Appl. No. 17/822,638, Conjugates for Targeted Cell Surface Editing, filed Aug. 26, 2022.
U.S. Appl. No. 17/624,116, Sialidase-PD-L1-Antibody Fusion Proteins and Methods of use Thereof, filed Dec. 30, 2021.
U.S. Appl. No. 17/624,118, Sialidase-CD20-Antibody Fusion Proteins and Methods of use Thereof, filed Dec. 30, 2021.

(56) References Cited

OTHER PUBLICATIONS

U.S. Appl. No. 17/624,121, Recombinant Human Sialidases, Sialidase Fusion Proteins, and Methods of using the Same, filed Dec. 30, 2021.
U.S. Appl. No. 17/624,123, Recombinant Sialidases and Method of using the Same, filed Dec. 30, 2021.
U.S. Appl. No. 17/624,124, Sialidase-HER2-Antibody Fusion Proteins and Methods of Use Thereof, filed Dec. 30, 2021.
U.S. Appl. No. 18/003,234, Recombinant Sialidases with Reduced Protease Sensitivity, Sialidase Fusion Proteins, and Methods of Using the Same, filed Dec. 23, 2022.
U.S. Appl. No. 18/260,364, Anti-PD-L1 Antibodies and Fusion Proteins Thereof, filed Jul. 5, 2023.
U.S. Appl. No. 18/260,383, Sialidase-Her2-Antibody Fusion Proteins and Methods of Use Therof, filed Jul. 5, 2023.
"Trastuzumab Product Approval Information—Licensing Action Sep. 25, 1998". U.S. Food and Drug Administration (FDA). Dec. 18, 2015. Archived from the original on Jan. 28, 2017. Retrieved Jun. 7, 2021 (Year: 1998).
Alley et al. (1977) "Effectiveness of Neuraminidase in Experimental Immunotherapy of Two Murine Pulmonary Carcinomas," Cancer Research, 37: 95-101.
Bhat et al., T 2014, Bio Process International, downloaded from https://bioprocessintl.com/manufacturing/monoclonal-antibodies/ next-step-homogenous-bioconjugate-development-optimizing-payload-placement-conjugate-composition/ on Jun. 7, 2021 (Year: 2014).
Bosch et al. (2013) Drugs Targeting B-Cells in Autoimmune Diseases. Springer Science & Business Media. pp. 1-4.
Database accession No. BG076176, Sep. 5, 2019 (Sep. 5, 2019) "Human neu2 protein mutant M1D/V6Y/1187K/C332A," XP093052179, retrieved from EBI accession No. GSP:BG076176 (1 page).
Database accession No. BHZ60027, Sep. 3, 2020 (Sep. 3, 2020) "Human Neu2 mutant/iggl Fc domain fusion protein, SEQ 149," XP093051773, retrieved from EBI accession No. gsp:bhz60027 (1 page).
DATABASE Geneseq [Online] Feb. 8, 2018 (Feb. 8, 2018), "Human NEU2 protein, SEQ ID 8.", XP093052599, retrieved from EBI accession No. GSP:BES28168, Database accession No. BES28168 (1 page).
DATABASE Geneseq [Online], Sep. 1, 2011, "Human NEU4 sialidase protein, SEQ ID No. 9 #2.", XP093053029, retrieved from EBI accession No. GSP:AZK51676, Database accession No. AZK51676 (1 pages).
DATABASE GenPept [Online] Jan. 19, 2018 (Jan. 19, 2018), "Sialidase-2 [Pteropus vampyrus]—Protein—NCBI", XP093053007, retrieved from EBI accession No. XP_011379176 (2 pages).
DATABASE UniProtKB/TrEMBL [Online] May 8, 2018 (May 8, 2018), "Exo-alpha-sialidase Neu2 from *Pan paniscus* (Pygmy chimpanzee) (Bonobo)", retrieved from EBI accession No. A0A2R9BJ98, Database accession No. A0A2R9BJ98_PANPA (2 pages).
Gray et al. (2020) "Targeted glycan degradation potentiates the anticancer immune response in vivo," Nat. Chem. Biol., 16(12): 1376-1384.
Jung et al. (2006) "The complete mitochondrial genome of the Korean soft-shelled turtle *Pelodiscus sinensis* (Testudines, Trionychidae)," DNA Sequence, 17(6): 471-483.
Kim et al. (2011) "Features and applications of bacterial sialidases," Appl. Microbiol. Biotechnol., 91: 1-15.
McCombs et al. (2016) "Enhanced Cross-Linking of Diazirine-Modified Sialylated Glycoproteins Enabled through Profiling of Sialidase Specificities," ACS Chem. Biol., 11: 185-192.
Mitri et al. (2012) "The HER2 Receptor in Breast Cancer: Pathophysiology, Clinical Use, and New Advances in Therapy, "Chemotherapy Research and Practice vol. 2012, Article ID 743193, 7 pages.
Rabuka et al. (2012) "Site-specific chemical protein conjugation using genetically encoded aldehyde tags," Nat. Protoc., 7(6): 1052-1067.
Tseng et al. (2007) "Desialylation of human cancer cells leading apoptosis by treatment with purified and overexpressed nanl cloned from Clostridium perfringens ATCC 10543," Enzyme and Microbial Technology, 41(1-2): 5-12.
Van Rooijen et al. (1992) "Monoclonal antibody mediated targeting of enzymes—A comparative study using the mouse spleen as a model system," J. Immunol. Methods, 151(1-2): 149-155.

* cited by examiner

WT Neu2 (yield 1 μg/ml, 7% monomer, 93% aggregate)

Mutant C332A + C352L (yield 2 μg/ml, 12% monomer, 88% aggregate)

WT Neu2 (yield 1 μg/ml, 7% monomer, 93% aggregate)

Mutant A2K (yield 4.4 μg/ml, 8% monomer, 92% aggregate)

Mutant A2K+V325 (yield 12 μg/ml, 17.4% monomer, 82.6% aggregate)

WT Neu2 (yield 1 μg/ml, 7% monomer, 93% aggregate)

Mutant with N' addition of peptide "MEDLRP"
(yield 1.5 μg/ml, 12.5% monomer, 81% aggregate)

Km: 178 ± 17 uM at pH 5
524 ± 23 uM at pH 7

- Near complete cleavage of α2,3 at pH5
- Substantial cleavage of α2,8 (colominic acid) at pH5

WT Neu2 (yield 1 μg/ml, 7% monomer, 93% aggregate)

Neu2 variant V6Y (yield ~10 μg/ml, 78% monomer, 21% aggregate)

RAPTOR

JANUS

LOBSTER

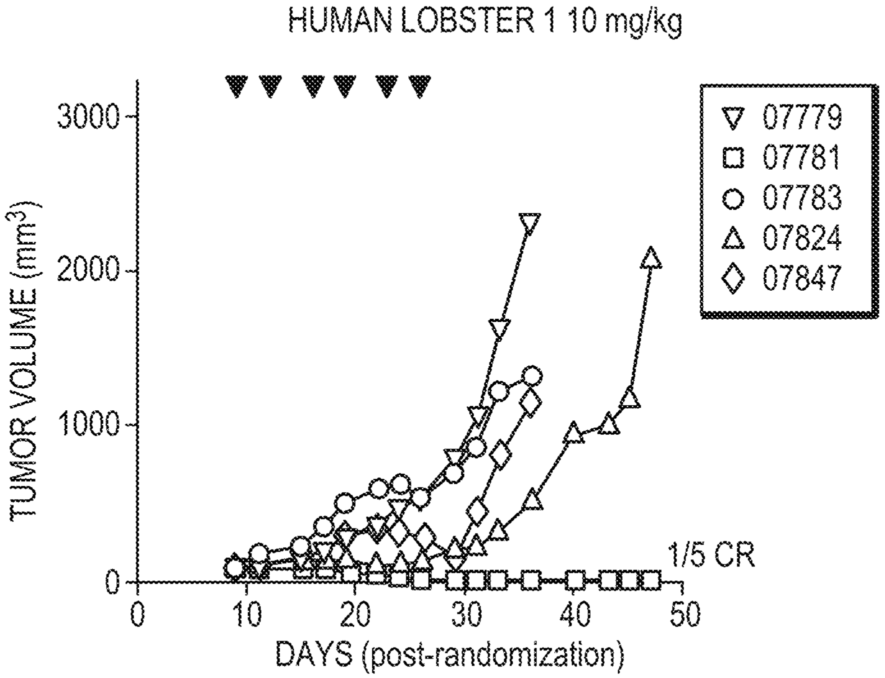
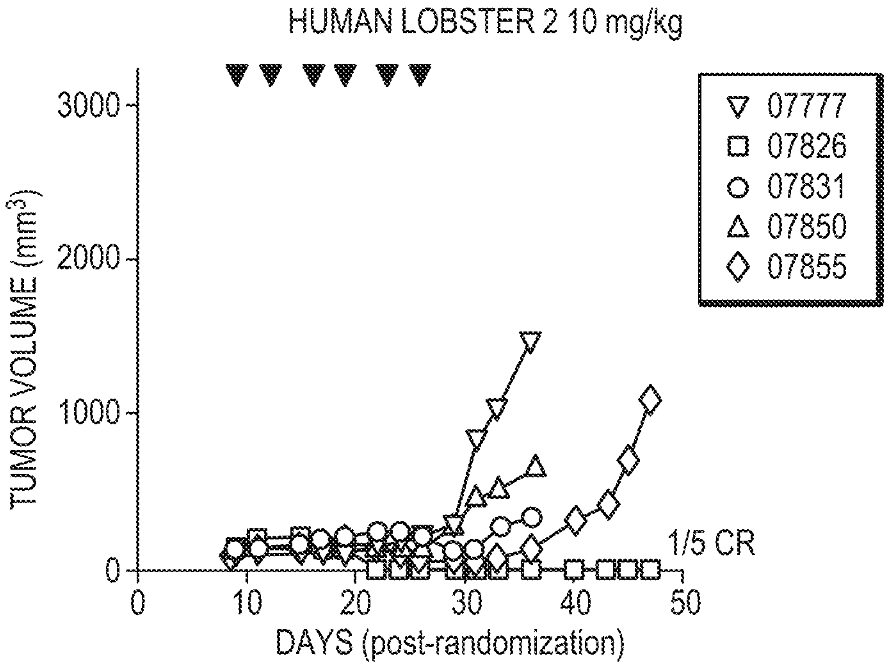
FIG. 27 (CONTD.)

RECOMBINANT HUMAN SIALIDASES, SIALIDASE FUSION PROTEINS, AND METHODS OF USING THE SAME

CROSS REFERENCE TO RELATED APPLICATIONS

This application is a § 371 National Stage of International (PCT) Patent Application No. PCT/US2019/012207, filed Jan. 3, 2019, which claims the benefit of, and priority to, U.S. Provisional Patent Application No. 62/613,363, filed Jan. 3, 2018 and U.S. Provisional Patent Application No. 62/755,279, filed Nov. 2, 2018, the entire disclosure of each of which is hereby incorporated by reference for all purposes.

SEQUENCE LISTING

The instant application contains a Sequence Listing which has been submitted electronically in ASCII format and is hereby incorporated by reference in its entirety. Said ASCII copy, created on Feb. 20, 2019, is named PAL-009WO_SL.txt and is 364,481 bytes in size.

FIELD OF THE INVENTION

The invention relates generally to recombinant human sialidases and recombinant sialidase fusion proteins, and their use in the treatment of cancer.

BACKGROUND

A growing body of evidence supports roles for glycans, and sialoglycans in particular, at various pathophysiological steps of tumor progression. Glycans regulate tumor proliferation, invasion, hematogenous metastasis and angiogenesis (Fuster et al. (2005) Nat. Rev. Cancer 5(7): 526-42). The sialylation of cell surface glycoconjugates is frequently altered in cancers, resulting in the expression of sialylated tumor-associated carbohydrate antigens. The expression of sialylated glycans by tumor cells is often associated with increased aggressiveness and metastatic potential of a tumor.

It has recently become apparent that Siglecs (sialic acid-binding immunoglobulin-like lectins), a family of sialic acid binding lectins, play a role in cancer immune suppression by binding to hypersialylated cancer cells and mediating the suppression of signals from activating NK cell receptors, thereby inhibiting NK cell-mediated killing of tumor cells (Jandus et al. (2014) J. Clin. Invest. 124: 1810-1820; Laubli et al. (2014) Proc. Natl. Acad. Sci. USA 111: 14211-14216; Hudak et al. (2014) Nat. Chem. Biol. 10: 69-75). Likewise, enzymatic removal of sialic acids by treatment with sialidase can enhance NK cell-mediated killing of tumor cells (Jandus, supra; Hudak, supra; Xiao et al. (2016) Proc. Natl. Acad. Sci. USA 113(37): 10304-9.)

Cancer immunotherapy with immune checkpoint inhibitors, including antibodies blocking the PD-1/PD-L1 pathway, has improved the outcome of many cancer patients. However, despite advances that have been made to date, many patients do not respond to currently available immune checkpoint inhibitors. Accordingly, there is still a need for effective interventions that overcome the immune suppressive tumor microenvironment and for treating cancers associated with hypersialylated cancer cells.

SUMMARY OF THE INVENTION

The invention is based, in part, upon the discovery that it is possible to produce recombinant mutant forms of human sialidase enzymes and fusion proteins and/or antibody conjugates containing such enzymes that have suitable substrate specificities and activities to be useful in removing sialic acid and/or sialic acid containing molecules from the surface of cancer cells and/or removing sialic acid and/or sialic acid containing molecules from the tumor microenvironment, and/or reducing the concentration of sialic acid and/or sialic acid containing molecules in the tumor microenvironment.

In one aspect, the invention provides a recombinant mutant human sialidase comprising a substitution of at least one wild-type amino acid residue, wherein the substitution increases at least one of the (a) expression, (b) stability, and (c) activity of the sialidase, or a combination of (a) and (b), combination of (a) and (c), a combination of (b) and (c), or a combination of (a), (b) and (c).

In another aspect, the invention provides a recombinant mutant human sialidase enzyme comprising an N-terminus and a C-terminus and comprising: (a) a substitution of at least one wild-type cysteine residue; (b) a substitution of at least one wild-type amino acid residue, wherein the substitution increases the isoelectric point (pI) of the sialidase and/or decreases the hydrophobicity of the sialidase relative to a sialidase without the substitution; (c) a peptide at least two amino acid residues in length covalently associated with an N-terminal amino acid at the N-terminus of the sialidase; (d) a substitution of at least one wild-type amino acid residue, wherein the substitution increases hydrophobic interactions and/or hydrogen bonding between the N- and C-termini of the sialidase relative to a sialidase without the substitution; or (e) a substitution or deletion of an N-terminal methionine at the N-terminus of the sialidase; or a combination of any of the foregoing. For example, the recombinant mutant sialidase enzyme may comprise a combination of the above-identified features, namely (a), (b), (c), (d), and (e), and may include, for example, a combination selected from: (a) and (b); (a) and (c); (a) and (d); (a) and (e); (b) and (c); (b) and (d); (b) and (e); (c) and (d); (c) and (e); (d) and (e); (a) and (b) and (c); (b) and (c) and (d); (a) and (c) and (d); (a) and (b) and (d); (a) and (b) and (e); (a) and (c) and (e); (a) and (d) and (e); (b) and (c) and (e); (b) and (d) and (e); (c) and (d) and (e); (a) and (b) and (c) and (d); (a) and (b) and (c) and (e); (a) and (c) and (d) and (e); (b) and (c) and (d) and (e); and (a) and (b) and (c) and (d) and (e). In certain embodiments, the sialidase is selected from Neu1, Neu2, Neu3, and Neu4, e.g., the sialidase is Neu2.

In certain embodiments, the sialidase comprises a substitution of at least one wild-type cysteine residue, e.g., a free cysteine residue. The cysteine residue may, for example, be substituted by serine, isoleucine, valine, phenylalanine, leucine, or alanine. In certain embodiments, the sialidase comprises a substitution of a cysteine residue at a position corresponding to position 332 of wild-type human Neu2 (SEQ ID NO: 1), e.g., the cysteine residue at a position corresponding to position 332 of wild-type human Neu2 is substituted by alanine (C332A). In certain embodiments, the sialidase comprises a substitution of a cysteine residue at a position corresponding to position 352 of wild-type human Neu2 (SEQ ID NO: 1), e.g., the cysteine residue at a position corresponding to position 352 of wild-type human Neu2 is substituted by leucine (C352L). In certain embodiments, the sialidase comprises both the C332A and C352L substitutions. In certain embodiments, the sialidase contains an amino acid substitution at 2, 3, 4, 5, or 6 cysteines typically present in a human sialidase, e.g., Neu2 or Neu3.

In certain embodiments, the sialidase comprises a substitution of at least one wild-type amino acid residue, e.g., a solvent exposed wild-type amino acid residue, wherein the substitution increases the isoelectric point (pI) of the sialidase and/or decreases the hydrophobicity of the sialidase relative to a sialidase without the substitution. In certain embodiments, the wild-type amino acid is substituted by lysine, arginine, or histidine, e.g., the wild-type amino acid is substituted by lysine. In certain embodiments, the sialidase comprises a substitution of an alanine residue at a position corresponding to position 2 of wild-type human Neu2 (SEQ ID NO: 1), e.g., the alanine residue at a position corresponding to position 2 of wild-type human Neu2 is substituted by lysine (A2K).

In certain embodiments, the sialidase comprises a peptide at least two amino acid residues in length fused to the N-terminus of the sialidase, e.g., fused to an N-terminal amino acid residue of the sialidase, e.g., by a peptide bond. In certain embodiments, the peptide is between 2 amino acid residues and 20 amino acid residues in length. In certain embodiments, the peptide is at least two, three, four or five amino acid residues in length. In certain embodiments, the peptide comprises an amino acid sequence derived from wild-type mouse thymus Neu2 (SEQ ID NO: 2), e.g., in certain embodiments the peptide comprises EDLRP (SEQ ID NO: 3) or MEDLRP (SEQ ID NO: 4).

In certain embodiments, the sialidase comprises a substitution of at least one wild-type amino acid residue, wherein the substitution increases hydrophobic interactions and/or hydrogen bonding between the N- and C-termini of the sialidase relative to a sialidase without the substitution. For example, in certain embodiments, the sialidase comprises a substitution of a valine residue at a position corresponding to position 6 of wild-type human Neu2 (SEQ ID NO: 1), e.g., the valine residue at a position corresponding to position 6 of wild-type human Neu2 is substituted by tyrosine (V6Y).

In certain embodiments, the sialidase comprises a substitution or deletion of an N-terminal methionine at the N-terminus of the sialidase. For example, in certain embodiments, the sialidase comprises a substitution of a methionine residue at a position corresponding to position 1 of wild-type human Neu2 (SEQ ID NO: 1), e.g., the methionine at a position corresponding to position 1 of wild-type human Neu2 is substituted by alanine (M1A) or aspartic acid (MID).

In certain embodiments, the sialidase has a different substrate specificity than the corresponding wild-type sialidase. For example, in certain embodiments the sialidase can cleave α2,3, α2,6, and/or α2,8 linkages. In certain embodiments the sialidase can cleave α2,3 and α2,8 linkages.

In certain embodiments, the sialidase comprises SEQ ID NO: 5, SEQ ID NO: 6, SEQ ID NO: 36, SEQ ID NO: 37, SEQ ID NO: 38, SEQ ID NO: 39, SEQ ID NO: 70, SEQ ID NO: 71, SEQ ID NO: 72, or SEQ ID NO: 73.

In another aspect, the invention provides a fusion protein comprising: (a) a sialidase enzyme; and (b) an immunoglobulin Fc domain and/or an immunoglobulin antigen-binding domain; wherein the sialidase and the Fc domain and/or the antigen-binding domain are linked by a peptide bond or an amino acid linker. In certain embodiments, the sialidase is a human sialidase, e.g., a recombinant mutant human sialidase disclosed herein. In certain embodiments, the fusion protein further comprises a linker, for example, an amino acid linker, connecting the sialidase enzyme and the Fc domain and/or an antigen-binding domain. In certain embodiments, the immunoglobulin antigen-binding domain is associated (for example, covalently or non-covalently associated) with a second immunoglobulin antigen-binding domain to produce an antigen-binding site.

In certain embodiments, the immunoglobulin Fc domain is derived from a human IgG1, IgG2, IgG3, IgG4, IgA1, IgA2, IgD, IgE, or IgM Fc domain, e.g., the immunoglobulin Fc domain is derived from a human IgG1, IgG2, IgG3, or IgG4 Fc domain, e.g., the immunoglobulin Fc domain is derived from a human IgG1 Fc domain.

In certain embodiments, the immunoglobulin antigen-binding domain is derived from an antibody selected from trastuzumab, cetuximab, daratumumab, girentuximab, panitumumab, ofatumumab, and rituximab. In certain embodiments, the immunoglobulin antigen-binding domain is derived from trastuzumab.

In certain embodiments, the fusion protein comprises SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 63, SEQ ID NO: 74, SEQ ID NO: 75, SEQ ID NO: 76, SEQ ID NO: 77, SEQ ID NO: 78, or SEQ ID NO: 79, or an amino acid sequence that has at least 85%, 90%, 95%, 96%, 97%, 98%, or 99% sequence identity to SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 63, SEQ ID NO: 74, SEQ ID NO: 75, SEQ ID NO: 76, SEQ ID NO: 77, SEQ ID NO: 78, or SEQ ID NO: 79.

In another aspect, the invention provides an antibody conjugate comprising any of the foregoing fusion proteins. In certain embodiments, the antibody conjugate comprises a single sialidase. In other embodiments, the antibody conjugate comprises two sialidases, which can be the same or different. In certain embodiments the antibody conjugate comprises two identical sialidases. In certain embodiments, the antibody conjugate comprises a single antigen-binding site. In other embodiments, the antibody conjugate comprises two antigen-binding sites, which can be the same or different. In certain embodiments, the antibody conjugate comprises two identical antigen-binding sites.

In certain embodiments, the antibody conjugate has a molecular weight from about 135 kDa to about 165 kDa, or the antibody conjugate has a molecular weight from about 215 kDa to about 245 kDa.

In certain embodiments, the antibody conjugate comprises: (a) a first polypeptide comprising an immunoglobulin light chain; (b) a second polypeptide comprising an immunoglobulin heavy chain; and (c) a third polypeptide comprising an immunoglobulin Fc domain and a sialidase; wherein the first and second polypeptides are covalently linked together and the second and third polypeptides are covalently linked together, and wherein the first polypeptide and the second polypeptide together define an antigen-binding site. The third polypeptide may, for example, comprise the sialidase and the immunoglobulin Fc domain in an N- to C-terminal orientation. The first polypeptide may, for example, comprise SEQ ID NO: 49, the second polypeptide may, for example, comprise SEQ ID NO: 50, and/or the third polypeptide may, for example, comprise SEQ ID NO: 51, SEQ ID NO: 52, SEQ ID NO: 53, SEQ ID NO: 54, SEQ ID NO: 76, SEQ ID NO: 77, SEQ ID NO: 78, or SEQ ID NO: 79.

In certain embodiments, the antibody conjugate comprises: (a) a first polypeptide comprising a first immunoglobulin light chain; (b) a second polypeptide comprising a first immunoglobulin heavy chain and a first sialidase; (c) a third polypeptide comprising a second immunoglobulin heavy chain and a second sialidase; and (d) a fourth polypeptide comprising a second immunoglobulin light chain;

wherein the first and second polypeptides are covalently linked together, the third and fourth polypeptides are covalently linked together, and the second and third polypeptides are covalently linked together, and wherein the first polypeptide and the second polypeptide together define a first antigen-binding site, and the third polypeptide and the fourth polypeptide together define a second antigen-binding site. The second and third polypeptides may, for example, comprise the first and second immunoglobulin heavy chain and the first and second sialidase, respectively, in an N- to C-terminal orientation.

In certain embodiments, the antibody conjugate comprises: (a) a first polypeptide comprising a first sialidase, a first immunoglobulin Fc domain, and a first single chain variable fragment (scFv); and (b) a second polypeptide comprising a second sialidase, a second immunoglobulin Fc domain, and an optional second single chain variable fragment (scFv); wherein the first and second polypeptides are covalently linked together, and wherein the first scFv defines a first antigen-binding site, and the second scFv, when present, defines a second antigen-binding site. The first polypeptide may, for example comprise the first sialidase, the first immunoglobulin Fc domain, and the first scFv in an N- to C-terminal orientation. The second polypeptide may, for example, comprise the second sialidase, the second immunoglobulin Fc domain, and the optional second scFv in an N- to C-terminal orientation. The first polypeptide may, for example, comprise SEQ ID NO: 43, SEQ ID NO: 44, SEQ ID NO: 45, SEQ ID NO: 46, SEQ ID NO: 47, SEQ ID NO: 48, SEQ ID NO: 74, or SEQ ID NO: 75, and/or the second polypeptide may, for example, comprise SEQ ID NO: 43, SEQ ID NO: 44, SEQ ID NO: 45, SEQ ID NO: 46, SEQ ID NO: 47, SEQ ID NO: 48, SEQ ID NO: 74, or SEQ ID NO: 75.

In another aspect, the invention provides an isolated nucleic acid comprising a nucleotide sequence encoding any of the foregoing recombinant mutant human sialidases, any of the foregoing fusion proteins, or at least a portion of any of the foregoing antibody conjugates. In another aspect, the invention provides an expression vector comprising any of the foregoing nucleic acids. In another aspect, the invention provides a host cell comprising any of the foregoing expression vectors.

In another aspect, the invention provides a pharmaceutical composition comprising any of the foregoing recombinant mutant human sialidases, any of the foregoing fusion proteins, or any of the foregoing antibody conjugates.

In another aspect, the invention provides a method of treating cancer in a subject in need thereof. The method comprises administering to the subject an effective amount of any of the foregoing sialidases, any of the foregoing fusion proteins, any of the foregoing antibody conjugates, or any of the foregoing pharmaceutical compositions. In certain embodiments, the cancer is an epithelial cancer, e.g., endometrial cancer, ovarian cancer, cervical cancer, vulvar cancer, uterine cancer, fallopian tube cancer, breast cancer, prostate cancer, lung cancer, pancreatic cancer, urinary cancer, bladder cancer, head and neck cancer, oral cancer and liver cancer.

In another aspect, the invention provides a method of increasing expression of HLA-DR, CD86, CD83, IFNγ, IL-1b, IL-6, TNFα, IL-17A, IL-2, or IL-6 in a cell or tissue. The method comprises contacting the cell or tissue with an effective amount of any of the foregoing sialidases, any of the foregoing fusion proteins, any of the foregoing antibody conjugates, or any of the foregoing pharmaceutical compositions. In certain embodiments, the cell is selected from a dendritic cell and a peripheral blood mononuclear cell (PBMC).

These and other aspects and features of the invention are described in the following detailed description and claims.

DESCRIPTION OF THE DRAWINGS

The invention can be more completely understood with reference to the following drawings.

FIG. 16D depicts the mean tumor volume with error bars of the indicated treatment groups from Example 8.

FIG. 17B depicts the rechallenge experiment of either the three mice treated with Janus from FIG. 17A with complete regressions of the original EMT6-Her2 tumors (cured mice) or naïve mice. Cured mice were inoculated with either EMT6-Her2 cells or parental EMT6 cells on the left and right lower flank region. Naïve mice were inoculated with EMT6-Her2 cells.

FIG. 26A shows mean tumor volumes for each treatment group. FIG. 26B shows tumor volumes for individual mice in each treatment group. Complete Responses (CR, defined as regression below the limit of palpation at any point during the study) are shown as well.

DETAILED DESCRIPTION

Figure 1:
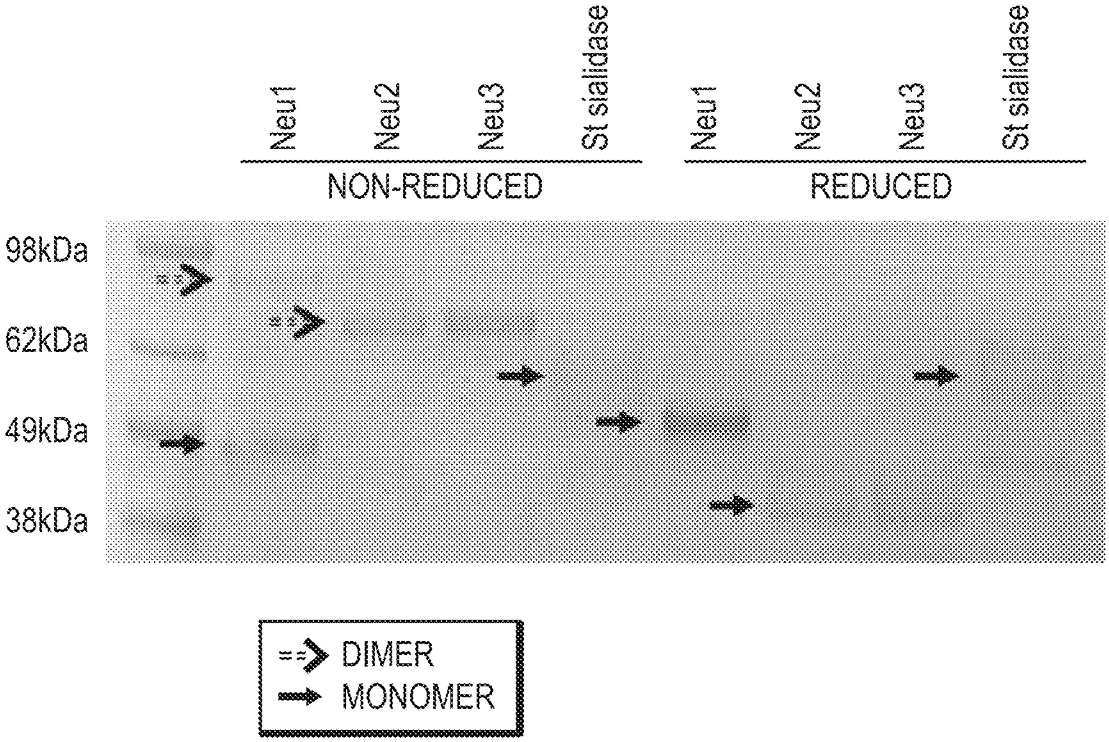
FIG. 1 depicts an SDS-PAGE gel showing recombinant human Neu1, Neu2, Neu3, and *Salmonella typhimurium* (St-sialidase) under non-reducing and reducing conditions. Monomer and dimer species are indicated.

Various features and aspects of the invention are discussed in more detail below. The invention provides a recombinant human sialidase that comprises at least one mutation relative to a wild-type human sialidase, e.g., a substitution, deletion, or addition (insertion) of at least one amino acid. The mutations, or combination of mutations, can improve the expression, activity or both the expression and activity of the sialidase to improve its use in cancer diagnosis and/or treatment.

The invention further relates to fusion proteins and/or antibody conjugates comprising a sialidase enzyme and an antibody or portion thereof, e.g., an immunoglobulin Fc domain and/or an antigen-binding domain. The sialidase enzyme portion of the fusion protein and/or antibody conjugate may comprise at least one mutation relative to a wild-type human sialidase.

The invention further relates to pharmaceutical compositions and methods of using fusion proteins and/or antibody conjugates to treat cancer, e.g., an epithelial cell cancer.

I. Recombinant Human Sialidases

As used herein, the term "sialidase" refers to any enzyme, or a functional fragment thereof, that cleaves a terminal sialic acid residue from a substrate, for example, a glycoprotein or a glycolipid. The term sialidase includes variants having one or more amino acid substitutions, deletions, or insertions relative to a wild-type sialidase sequence, and/or fusion proteins or conjugates including a sialidase. Sialidases are also called neuraminidases, and, unless indicated otherwise, the two terms are used interchangeably herein. As used herein, the term "functional fragment" of a sialidase refers to fragment of a full-length sialidase that retains, for example, at least 10%, at least 20%, at least 30%, at least 40%, at least 50%, at least 60%, at least 70%, at least 80%, at least 90%, or 100% of the enzymatic activity of the corresponding full-length, naturally occurring sialidase. Sialidase enzymatic activity may be assayed by any method known in the art, including, for example, by measuring the release of sialic acid from the fluorogenic substrate 4-methylumbelliferyl-N-acetylneuraminic acid (4MU-NeuAc). In certain embodiments, the functional fragment comprises at least 100, 150, 200, 250, 300, 310, 320, 330, 340, 350, 360, or 370 consecutive amino acids present in a full-length, naturally occurring sialidase.

Four sialidases have been found in the human genome and are referred to as Neu1, Neu2, Neu3 and Neu4.

Human Neu1 is a lysosomal neuraminidase enzyme which functions in a complex with beta-galactosidase and cathepsin A. The amino acid sequence of human Neu1 is depicted in SEQ ID NO: 7, and a nucleotide sequence encoding human Neu1 is depicted in SEQ ID NO: 23.

Human Neu2 is a cytosolic sialidase enzyme. The amino acid sequence of human Neu2 is depicted in SEQ ID NO: 1, and a nucleotide sequence encoding human Neu2 is depicted in SEQ ID NO: 24.

Human Neu3 is a plasma membrane sialidase with an activity specific for gangliosides. Human Neu3 has two isoforms: isoform 1 and isoform 2. The amino acid sequence of human Neu3, isoform 1 is depicted in SEQ ID NO: 8, and a nucleotide sequence encoding human Neu3, isoform 1 is depicted in SEQ ID NO: 25. The amino acid sequence of human Neu3, isoform 2 is depicted in SEQ ID NO: 9, and a nucleotide sequence encoding human Neu3, isoform 2 is depicted in SEQ ID NO: 34.

Human Neu4 has two isoforms: isoform 1 is a peripheral membrane protein and isoform 2 localizes to the lysosome lumen. The amino acid sequence of human Neu4, isoform 1 is depicted in SEQ ID NO: 10, and a nucleotide sequence encoding human Neu4, isoform 1 is depicted in SEQ ID NO: 26. The amino acid sequence of human Neu4, isoform 2 is depicted in SEQ ID NO: 11, and a nucleotide sequence encoding human Neu4, isoform 2 is depicted in SEQ ID NO: 35.

Four sialidases have also been found in the mouse genome and are referred to as Neu1, Neu2, Neu3 and Neu4. The amino acid sequence of mouse Neu1 is depicted in SEQ ID NO: 83, and a nucleotide sequence encoding mouse Neu1 is depicted in SEQ ID NO: 87. The amino acid sequence of mouse Neu2 is depicted in SEQ ID NO: 84 and a nucleotide sequence encoding mouse Neu2 is depicted in SEQ ID NO: 88. The amino acid sequence of mouse Neu3 is depicted in SEQ ID NO: 85, and a nucleotide sequence encoding mouse Neu3 is depicted in SEQ ID NO: 89. The amino acid sequence of mouse Neu4 is depicted in SEQ ID NO: 86, and a nucleotide sequence encoding mouse Neu4 is depicted in SEQ ID NO: 90.

Exemplary prokaryotic sialidases include sialidases from *Salmonella typhimurium* and *Vibrio cholera*. The amino acid sequence of *Salmonella typhimurium* sialidase (St-sialidase) is depicted in SEQ ID NO: 30, and a nucleotide sequence encoding *Salmonella typhimurium* sialidase is depicted in SEQ ID NO: 80. The amino acid sequence of *Vibrio cholera* sialidase is depicted in SEQ ID NO: 81, and a nucleotide sequence encoding *Vibrio cholera* sialidase is depicted in SEQ ID NO: 82.

In certain embodiments, a recombinant mutant human sialidase has about 5%, about 10%, about 15%, about 20%, about 25%, about 30%, about 35%, about 40%, about 45%, about 50%, about 60%, about 65%, about 70%, about 75%, about 80%, about 85%, about 90%, about 95%, about 100%, or more than 100% of the enzymatic activity of a corresponding (or template) wild-type human sialidase.

In certain embodiments, the recombinant mutant human sialidase has the same substrate specificity as the corresponding wild-type human sialidase. In other embodiments, the recombinant mutant human sialidase has a different substrate specificity than the corresponding wild-type human sialidase. For example, in certain embodiments the recombinant mutant human sialidase can cleave α2,3, α2,6, and/or α2,8 linkages. In certain embodiments the sialidase can cleave α2,3 and α2,8 linkages.

In certain embodiments, the expression yield of the recombinant mutant human sialidase in mammalian cells, e.g., HEK293 cells, CHO cells, murine myeloma cells (NS0, Sp2/0), or human fibrosarcoma cells (HT-1080), e.g., HEK293 cells, is greater than about 10%, about 20%, about 50%, about 75%, about 100%, about 150%, about 200%, about 250%, about 300%, about 400%, about 500%, about 600%, about 700%, about 800%, about 900%, or about 1,000% of the expression yield of the corresponding wild-type human sialidase.

In certain embodiments, the recombinant mutant human sialidase has about 5%, about 10%, about 15%, about 20%, about 25%, about 30%, about 35%, about 40%, about 45%, about 50%, about 60%, about 65%, about 70%, about 75%, about 80%, about 85%, about 90%, about 95%, about 100%, or more than 100% of the enzymatic activity of a corresponding wild-type human sialidase, and the expression yield of the recombinant mutant human sialidase in mammalian cells, e.g., HEK293 cells, is greater than about 10%, about 20%, about 50%, about 75%, about 100%, about 150%, about 200%, about 250%, about 300%, about 400%, about 500%, about 600%, about 700%, about 800%, about 900%, or about 1,000% of the expression yield of a corresponding wild-type human sialidase.

a. Substitution of Cysteine Residues

In certain embodiments, the recombinant mutant human sialidase comprises a substitution of at least one cysteine (cys, C) residue. It has been discovered that certain cysteine residues in sialidases may inhibit expression of functional protein as a result of protein aggregation. Accordingly, in certain embodiments, the recombinant mutant human sialidase contains at least one mutation of a free cysteine (e.g., for Neu1 (SEQ ID NO: 7), C111, C117, C171, C183, C218, C240, C242, and C252; for Neu2 (SEQ ID NO: 1), C125, C196, C219, C272, C332, and C352; for Neu3 (SEQ ID NO: 8), C7, C90, C99, C106, C127, C136, C189, C194, C226, C242, C250, C273, C279, C295, C356, C365, C368, C384, C383, C394, and C415; and for Neu4 (SEQ ID NO: 10), C88, C125, C126, C186, C191, C211, C223, C239, C276, C437, C453, C480, and C481). Free cysteines can be substituted with any amino acid. In certain embodiments, the free cysteine is substituted with serine (ser, S), isoleucine (iso, I), valine (val, V), phenylalanine (phe, F), leucine (leu, L), or alanine (ala, A). Exemplary cysteine substitutions in Neu2 include C125A, C1251, C125S, C125V, C196A, C196L, C196V, C272S, C272V, C332A, C332S, C332V, C352L, and C352V.

In certain embodiments, the recombinant mutant human sialidase comprises two or more cysteine substitutions. Exemplary double or triple substitutions in Neu2 include: C125S and C332S; C272V and C332A; C272V and C332S; C332A and C352L; C125S and C196L; C196L and C352L; C196L and C332A; C332A and C352L; and C196L, C332A and C352L.

In certain embodiments, the recombinant mutant human sialidase is a Neu2 sialidase and comprises the substitutions C322A and C352L (SEQ ID NO: 5).

In certain embodiments, the sialidase contains an amino acid substitution at 2, 3, 4, 5, or 6 cysteines typically present in a human sialidase, e.g., Neu2 or Neu3.

In certain embodiments, the recombinant mutant human sialidase comprises a substitution or combination of substitutions corresponding to a substitution or combination of substitutions listed in TABLE 2 herein below.

b. Substitutions of Residues to Increase pI and/or Decrease Hydrophobicity

The isoelectric point (pI) of a protein is the pH at which the net charge is zero. The pI also indicates the pH at which the protein is least soluble, which affects the ability to express and purify the protein. Generally, a protein has good solubility if its pI is greater than 2 units above the pH of the solution. Human Neu2 has a predicted pI of 7.5. Thus, human Neu2 is least soluble around neutral pH, which is undesirable because expression and physiological systems are at neutral pH. In contrast, the sialidase from *Salmonella typhimurium* (St-sialidase), which exhibits good solubility and recombinant expression, has a pI of 9.6. Accordingly, to increase expression of human Neu2 or the other human sialidases, a recombinant mutant human sialidase may be designed to contain one or more amino acid substitution(s) wherein the substitution(s) increase(s) the pI of the sialidase relative to a sialidase without the substitution. Additionally, decreasing the number of hydrophobic amino acids on the surface of a sialidase may improve expression of sialidase by, for example, reducing aggregation. Accordingly, to increase expression of human Neu2 or the other human sialidases, a recombinant mutant human sialidase may be designed to contain one or more amino acid substitution(s) wherein the substitution(s) decrease(s) the hydrophobicity of a surface of the sialidase relative to a sialidase without the substitution(s).

Accordingly, in certain embodiments, the recombinant mutant human sialidase comprises at least one amino acid substitution, wherein the substitution increases the isoelectric point (pI) of the sialidase and/or decreases the hydrophobicity of the sialidase relative to a sialidase without the substitution. This may be achieved by introducing one or more charged amino acids, for example, positively or negatively charged amino acids, into the recombinant sialidase. In certain embodiments, the amino acid substitution is to a charged amino acid, for example, a positively charged amino acid such as lysine (lys, K), histidine (his, H), or arginine (arg, R), or a negatively charged amino acid such as aspartic acid (asp, D) or glutamic acid (glu, E). In certain embodiments, the amino acid substitution is to a lysine residue. In certain embodiments, the substitution increases the pI of the sialidase to about 7.75, about 8, about 8.25, about 8.5, about 8.75, about 9, about 9.25, about 9.5, or about 9.75.

In certain embodiments, the amino acid substitution occurs at a surface exposed D or E amino acid, in a helix or loop, or in a position that has a K or R in the corresponding position of St-sialidase. In certain embodiments, the amino acid substitution occurs at an amino acid that is remote from the catalytic site or otherwise not involved in catalysis, an amino acid that is not conserved with the other human Neu proteins or with an St-Sialidase or *Clostridium* NanH, or an amino acid that is not located in a domain important for function (e.g., an Asp-box or beta strand).

Exemplary amino acid substitutions in Neu2 that increase the isoelectric point (pI) of the sialidase and/or decrease the hydrophobicity of the sialidase relative to a sialidase without the substitution include A2E, A2K, D215K, V325E, V325K, E257K, and E319K. In certain embodiments, the recombinant mutant human sialidase comprises two or more amino acid substitutions, including, for example, A2K and V325E, A2K and V325K, E257K and V325K, A2K and E257K, and E257K and A2K and V325K.

In certain embodiments, the recombinant mutant human sialidase comprises a substitution or combination of substitutions corresponding to a substitution or combination of substitutions listed in TABLE 3 herein below.

c. Addition of N-Terminal Peptides and N- or C-Terminal Substitutions

It has been discovered that the addition of a peptide sequence of two or more amino acids to the N-terminus of a human sialidase can improve expression and/or activity of the sialidase. In certain embodiments, the peptide is at least 2 amino acids in length, for example, from 2 to 20, from 2 to 10, from 2 to 5, or 2, 3, 4, 5, 6, 7, 8, 9, 10, 11, 12, 13, 14, 15, 16, 17, 18, 19, or 20 amino acids in length. In certain embodiments, the peptide may form, or have a propensity to form, an α-helix.

In mice, a Neu2 isoform (type B) found in thymus contains six amino acids not present in the canonical isoform of Neu2 found in skeletal muscle. In certain embodiments herein, the N-terminal six amino acids of the mouse thymus Neu2 isoform, MEDLRP (SEQ ID NO: 4), or variations thereof, can be added onto a human Neu, e.g., human Neu2. In certain embodiments, the recombinant mutant human sialidase comprises a peptide at least two amino acid residues in length covalently associated with an N-terminal amino acid of the sialidase. In certain embodiments the recombinant mutant human sialidase comprises the peptide MEDLRP (SEQ ID NO: 4) or EDLRP (SEQ ID NO: 3) covalently associated with an N-terminal amino acid of the sialidase. In certain embodiments, the sialidase may further comprise a cleavage site, e.g., a proteolytic cleavage site, located between the peptide, e.g., MEDLRP (SEQ ID NO: 4) or EDLRP (SEQ ID NO: 3), and the remainder of the sialidase. In certain embodiments, the peptide, e.g., MEDLRP (SEQ ID NO: 4) or EDLRP (SEQ ID NO: 3), may be post-translationally cleaved from the remainder of the sialidase.

Alternatively to, or in combination with, the N-terminal addition, 1-5 amino acids of the 12 amino acid N-terminal region of the recombinant mutant human sialidase may be removed, e.g., the N-terminal methionine can be removed. In certain embodiments, if the recombinant mutant human sialidase is Neu2, the N-terminal methionine can be removed, the first five amino acids (MASLP; SEQ ID NO: 12) can be removed, or the second through fourth amino acids (ASLP; SEQ ID NO: 13) can be removed.

In certain embodiments, 1-5 amino acids of the 12 amino acid N-terminal region of the recombinant mutant human sialidase are substituted with MEDLRP (SEQ ID NO: 4), EDLRP (SEQ ID NO: 3), or TVEKSVVF (SEQ ID NO: 14). For example, in certain embodiments, if the recombinant mutant human sialidase is Neu2, the amino acids MASLP (SEQ ID NO: 12), ASLP (SEQ ID NO: 13) or M are substituted with MEDLRP (SEQ ID NO: 4), EDLRP (SEQ ID NO: 3) or TVEKSVVF (SEQ ID NO: 14).

Human sialidases have a β-propeller structure, characterized by 6 blade-shaped β-sheets arranged toroidally around a central axis. Generally, hydrophobic interactions between the blades of a β-propeller, including between the N- and C-terminal blades, enhance stability. Accordingly, in order to increase expression of human Neu2 or the other human sialidases, a recombinant mutant human sialidase can be designed comprising an amino acid substitution that increases hydrophobic interactions and/or hydrogen bonding between the N- and C-terminal β-propeller blades of the sialidase.

Accordingly, in certain embodiments, the recombinant mutant human sialidase comprises a substitution of at least one wild-type amino acid residue, wherein the substitution increases hydrophobic interactions and/or hydrogen bonding between the N- and C-termini of the sialidase relative to a sialidase without the substitution. In certain embodiments, the wild-type amino acid is substituted with asparagine (asn, N), lysine (lys, K), tyrosine (tyr, Y), phenylalanine (phe, F), or tryptophan (trp, W). Exemplary substitutions in Neu2 that increase hydrophobic interactions and/or hydrogen bonding between the N- and C-termini include L4N, L4K, V6Y, L7N, L4N and L7N, L4N and V6Y and L7N, V12N, V12Y, V12L, V6Y, V6F, or V6W. In certain embodiments, the sialidase comprises the V6Y substitution.

In certain embodiments, the recombinant mutant human sialidase comprises a combination of the above substitutions. For example, a recombinant mutant human Neu2 sialidase can comprise the additional amino acids MEDLRP (SEQ ID NO: 4), EDLRP (SEQ ID NO: 3), or TVEKSVVF (SEQ ID NO: 14) at the N-terminus and, in combination, can comprise at least one L4N, L4K, V6Y, L7N, L4N and L7N, L4N and V6Y and L7N, V12N, V12Y, V12L, V6Y, V6F, or V6W substitution. In certain embodiments, the amino acids MASLP (SEQ ID NO: 12), ASLP (SEQ ID NO: 13) or M of a recombinant mutant human Neu2 sialidase are replaced with MEDLRP (SEQ ID NO: 4), EDLRP (SEQ ID NO: 3) or TVEKSVVF (SEQ ID NO: 14) and the recombinant mutant human Neu2 sialidase also comprises at least one L4N, L4K, V6Y, L7N, L4N and L7N, L4N and V6Y and L7N, V12N, V12Y, V12L, V6Y, V6F, or V6W substitution.

In certain embodiments, the recombinant mutant human sialidase comprises a substitution or combination of substitutions corresponding to a substitution or combination of substitutions listed in TABLES 4 or 5 herein below.

Additionally, in certain embodiments, the sialidase comprises a substitution or deletion of an N-terminal methionine at the N-terminus of the sialidase. For example, in certain embodiments, the sialidase comprises a substitution of a methionine residue at a position corresponding to position 1 of wild-type human Neu2 (SEQ ID NO: 1), e.g., the methionine at a position corresponding to position 1 of wild-type human Neu2 is substituted by alanine (M1A) or aspartic acid (MID). In other embodiments, the sialidase comprises a deletion of a methionine residue at a position corresponding to position 1 (ΔM1) of wild-type human Neu2 (SEQ ID NO: 1).

In certain embodiments, the recombinant mutant human sialidase comprises a substitution or combination of substitutions corresponding to a substitution or combination of substitutions listed in TABLE 6 herein below.

d. Other Substitutions and Combinations of Substitutions

The invention further provides a recombinant mutant human Neu2 sialidase comprising at least one of the following substitutions: I187K, A328E, K370N, or H210N. In certain embodiments, a recombinant mutant human Neu2 comprises the substitution of the amino acids GDYDAPTHQVQW (SEQ ID NO: 15) with the amino acids SMDQGSTW (SEQ ID NO: 16) or STDGGKTW (SEQ ID NO: 17). In certain embodiments, a recombinant mutant human Neu2 comprises the substitution of the amino acids PRPPAPEA (SEQ ID NO: 18) with the amino acids QTPLEAAC (SEQ ID NO: 19). In certain embodiments, a recombinant mutant human Neu2 comprises the substitution of the amino acids NPRPPAPEA (SEQ ID NO: 20) with the amino acids SQNDGES (SEQ ID NO: 21).

The invention further provides a recombinant mutant human Neu2 sialidase comprising at least one substitution at a position corresponding to V212, A213, Q214, D215, T216, L217, E218, C219, Q220, V221, A222, E223, V224, E225, or T225.

The invention further provides a recombinant mutant human Neu2 sialidase comprising a combination of any of the mutations contemplated herein. For example, the recombinant mutant sialidase enzyme may comprise a combination of 2, 3, 4, 5, 6, 7, 8, 9, 10, or more of the mutations contemplated herein. For example, the recombinant mutant sialidase enzyme may comprise a M1 deletion (ΔM1), M1A substitution, M1D substitution, V6Y substitution, I187K substitution, C332A substitution, or a combination of any of the foregoing. For example, the recombinant mutant sialidase enzyme may comprise a combination of mutations selected from: M1A and V6Y; M1A and I187K; M1A and C332A; M1D and V6Y; M1D and I187K; M1D and C332A; ΔM1 and V6Y; ΔM1 and I187K; ΔM1 and C332A; V6Y and I187K; V6Y and C332A; I187K and C332A; M1A, V6Y, and I187K; M1A, V6Y, and C332A; M1A, I187K, and C332A; MID, V6Y, and I187K; M1D, V6Y, and C332A; M1D, I187K, and C332A; ΔM1, V6Y, and I187K; ΔM1, V6Y, and C332A; ΔM1, I187K, and C332A; V6Y, I187K, and C332A; M1A, V6Y, I187K, and C332A; M1D, V6Y, I187K, and C332A; and ΔM1, V6Y, I187K, and C332A.

In certain embodiments, the recombinant mutant human sialidase comprises a substitution or combination of substitutions corresponding to a substitution or combination of substitutions listed in TABLE 7 herein below.

In certain embodiments, the recombinant mutant human sialidase comprises the amino acid sequence of SEQ ID NO: 5, SEQ ID NO: 6, SEQ ID NO: 36, SEQ ID NO: 37, SEQ ID NO: 38, SEQ ID NO: 39, SEQ ID NO: 70, SEQ ID NO: 71, SEQ ID NO: 72, or SEQ ID NO: 73, or an amino acid sequence that has at least 85%, 90%, 95%, 96%, 97%, 98%, or 99% sequence identity to SEQ ID NO: 5, SEQ ID NO: 6, SEQ ID NO: 36, SEQ ID NO: 37, SEQ ID NO: 38, SEQ ID NO: 39, SEQ ID NO: 70, SEQ ID NO: 71, SEQ ID NO: 72, or SEQ ID NO: 73.

In certain embodiments, the recombinant mutant human sialidase comprises the amino acid sequence of (SEQ ID NO: 100)

$X_1X_2SX_3PX_4$LQKESVFQSGAHAYRIPALLYLPGQQSLLAFAEQRASKKD

EHAELIVLRRGDYDAPTHQVQWQAQEVVAQARLDGHRSMNPCPLYDAQTG

TLFLFFIAIPGQVTEQQQLQTRANVTRL$X_5$QVTSTDHGRTWSSPRDLTDA

AIGPAYREWSTFAVGPGHCLQLHDRARSLVVPAYAYRKLHP$X_6$QRPIPSA

F$X_7$FLSHDHGRTWARGHFVAQDTLECQVAEVETGEQRVVTLNARSHLRAR

VQAQSTNDGLDFQ$X_8$SQLVKKLVEPPPQG$X_9$QGSVISFPSPRSGPGSPAQ

WLLYTHPTHSWQRADLGAYLNPRPPAPEAWSEP$X_{10}$LLAKGS$X_{11}$AYSDL

QSMGTGPDGSPLFG$X_{12}$LYEANDYEEIVFLMFTLKQAFPAEYLPQ, wherein $X_1$ is Ala, Arg, Asn, Asp, Gln, Glu, Gly, His, Leu, Lys, Met, Phe, Thr, Val, or not present, $X_2$ is Ala or Lys, $X_3$ is Asn or Leu, $X_4$ is Phe, Trp, Tyr or Val, $X_5$ is Ala, Cys, Ile, Ser, or Val, $X_6$ is Arg, Ile, or Lys, $X_7$ is Ala, Cys, Leu, or Val, $X_8$ is Glu or Lys, $X_9$ is Cys or Val, $X_{10}$ is Lys or Val, $X_{11}$ is Ala, Cys, Ser, or Val, and $X_{12}$ is Cys, Leu, or Val, and the sialidase comprises at least one mutation relative to wild-type human Neu2 (SEQ ID NO: 1).

In certain embodiments, the recombinant mutant human sialidase comprises the amino acid sequence of (SEQ ID NO: 91)

$X_1$ASLP$X_2$LQKESVFQSGAHAYRIPALLYLPGQQSLLAFAEQRASKKDEH

AELIVLRRGDYDAPTHQVQWQAQEVVAQARLDGHRSMNPCPLYDAQTGTL

FLFFIAIPGQVTEQQQLQTRANVTRLCQVTSTDHGRTWSSPRDLTDAAIG

PAYREWSTFAVGPGHCLQLHDRARSLVVPAYAYRKLHP$X_3$QRPIPSAFCF

LSHDHGRTWARGHFVAQDTLECQVAEVETGEQRVVTLNARSHLRARVQAQ

-continued

STNDGLDFQESQLVKKLVEPPPQGCQGSVISFPSPRSGPGSPAQWLLYTH

PTHSWQRADLGAYLNPRPPAPEAWSEPVLLAKGS$X_4$AYSDLQSMGTGPDG

SPLFGCLYEANDYEEIVFLMFTLKQAFPAEYLPQ, wherein $X_1$ is Ala, Arg, Asn, Asp, Gln, Glu, Gly, His, Leu, Lys, Met, Phe, Thr, Val, or not present, $X_2$ is Phe, Trp, Tyr or Val, $X_3$ is Arg, Ile, or Lys, and $X_4$ is Ala, Cys, Ser, or Val, and the sialidase comprises at least one mutation relative to wild-type human Neu2 (SEQ ID NO: 1). In certain embodiments, $X_1$ is Ala, Asp, Met, or not present, $X_2$ is Tyr or Val, $X_3$ is Ile or Lys, and $X_4$ is Ala or Cys.

In certain embodiments, the recombinant mutant human sialidase comprises a conservative substitution relative to a recombinant mutant human sialidase sequence disclosed herein. As used herein, the term "conservative substitution" refers to a substitution with a structurally similar amino acid. For example, conservative substitutions may include those within the following groups: Ser and Cys; Leu, Ile, and Val; Glu and Asp; Lys and Arg; Phe, Tyr, and Trp; and Gln, Asn, Glu, Asp, and His. Conservative substitutions may also be defined by the BLAST (Basic Local Alignment Search Tool) algorithm, the BLOSUM substitution matrix (e.g., BLOSUM 62 matrix), or the PAM substitution:p matrix (e.g., the PAM 250 matrix).

Sequence identity may be determined in various ways that are within the skill of a person skilled in the art, e.g., using publicly available computer software such as BLAST, BLAST-2, ALIGN or Megalign (DNASTAR) software. BLAST (Basic Local Alignment Search Tool) analysis using the algorithm employed by the programs blastp, blastn, blastx, tblastn and tblastx (Karlin et al., (1990) Proc. Natl. Acad. Sci. USA 87:2264-2268; Altschul, (1993) J. Mol. Evol. 36:290-300; Altschul et al., (1997) Nucleic Acids Res. 25:3389-3402, incorporated by reference herein) are tailored for sequence similarity searching. For a discussion of basic issues in searching sequence databases see Altschul et al., (1994) Nature Genetics 6:119-129, which is fully incorporated by reference herein. Those skilled in the art can determine appropriate parameters for measuring alignment, including any algorithms needed to achieve maximal alignment over the full length of the sequences being compared. The search parameters for histogram, descriptions, alignments, expect (i.e., the statistical significance threshold for reporting matches against database sequences), cutoff, matrix and filter are at the default settings. The default scoring matrix used by blastp, blastx, tblastn, and tblastx is the BLOSUM62 matrix (Henikoff et al., (1992) Proc. Natl. Acad. Sci. USA 89:10915-10919, fully incorporated by reference herein). Four blastn parameters may be adjusted as follows: Q=10 (gap creation penalty); R=10 (gap extension penalty); wink=1 (generates word hits at every wink.sup.th position along the query); and gapw=16 (sets the window width within which gapped alignments are generated). The equivalent blastp parameter settings may be Q=9; R=2; wink=1; and gapw=32. Searches may also be conducted using the NCBI (National Center for Biotechnology Information) BLAST Advanced Option parameter (e.g.: −G, Cost to open gap [Integer]: default=5 for nucleotides/11 for proteins; −E, Cost to extend gap [Integer]: default=2 for nucleotides/1 for proteins; −q, Penalty for nucleotide mismatch [Integer]: default=−3; −r, reward for nucleotide match [Integer]: default=1; −e, expect value [Real]: default=10; −W, wordsize [Integer]: default=11 for nucleotides/28 for megablast/3 for proteins; −y, Dropoff (X) for blast extensions in bits: default=20 for blastn/7 for others; −X, X dropoff value for gapped alignment (in bits): default=15 for all programs, not applicable to blastn; and −Z, final X dropoff value for gapped alignment (in bits): 50 for blastn, 25 for others). ClustalW for pairwise protein alignments may also be used (default parameters may include, e.g., Blosum62 matrix and Gap Opening Penalty=10 and Gap Extension Penalty=0.1). A Bestfit comparison between sequences, available in the GCG package version 10.0, uses DNA parameters GAP=50 (gap creation penalty) and LEN=3 (gap extension penalty). The equivalent settings in Bestfit protein comparisons are GAP=8 and LEN=2.

II. Fusion Proteins/Antibody Conjugates

To promote the selective removal of sialic acids on hypersialylated cancer cells and/or in the tumor microenvironment, it may be helpful to target a sialidase as described herein to such a cell or to such a tumor microenvironment. Additionally, in order to promote the removal of sialic acid by a sialidase in a subject, it may be helpful to extend the plasma half-life of the sialidase in the subject. These can be achieved by including the sialidase in a fusion protein and/or antibody conjugate (e.g., a chemically conjugated conjugate).

Accordingly, the invention further provides fusion proteins comprising a sialidase enzyme, or a functional fragment thereof, and a portion or fragment of an antibody, such as an immunoglobulin Fc domain (also referred to herein as an Fc domain), or an immunoglobulin antigen-binding domain (also referred to herein as an antigen-binding domain). In certain embodiments, the sialidase and antibody or portion thereof (e.g., immunoglobulin Fc domain or antigen-binding domain) are linked by a peptide bond or an amino acid linker.

As used herein, unless otherwise indicated, the term "fusion protein" is understood to refer to a single polypeptide chain comprising amino acid sequences based upon two or more separate proteins or polypeptide chains, where the two amino acid sequences may be fused together directly or via an intervening linker sequence, e.g., via an intervening amino acid linker. A nucleotide sequence encoding a fusion protein can, for example, be created using conventional recombinant DNA technologies.

In certain embodiments, the fusion protein comprises a tag, such as a Strep tag (e.g., a Strep II tag), a His tag (e.g., a 10× His tag (SEQ ID NO: 105)), a myc tag, or a FLAG tag. The tag can be located on the C-terminus or the N-terminus of the fusion protein. In certain embodiments, a fusion protein comprises a sialidase portion joined to a polypeptide comprising an immunoglobulin heavy chain in an N- to C-terminal orientation, wherein the sialidase portion comprises an N-terminal addition of MEDLRP (SEQ ID NO: 4), and a Strep II Tag is located on the C-terminus of the immunoglobulin heavy chain or the N-terminus of the sialidase portion.

a. Sialidase Portion

The sialidase portion of the fusion protein described herein can be any sialidase, e.g., a fungal, bacterial, non-human mammalian or human sialidase. In certain embodiments, the sialidase portion is a recombinant human sialidase comprising at least one mutation relative to a wild-type human sialidase, e.g., a substitution, deletion, or addition of at least one amino acid, as described above.

In certain embodiments, the sialidase is any recombinant mutant human sialidase disclosed herein, or a functional fragment thereof.

In certain embodiments, the sialidase portion comprises a C332A and C352L mutation. In certain embodiments, the sialidase comprises an N-terminal addition of MEDLRP (SEQ ID NO: 4) or EDLRP (SEQ ID NO: 3). In certain embodiments, the sialidase portion comprises a LSHSLST (SEQ ID NO: 22) peptide on the N-terminus. In certain embodiments, the sialidase portion comprises an N-terminal addition of MEDLRP (SEQ ID NO: 4) and an A2K substitution. In certain embodiments, the sialidase portion comprises an N-terminal addition of MEDLRP (SEQ ID NO: 4) and a C332A substitution. In certain embodiments, the sialidase portion comprises an N-terminal addition of MEDLRP (SEQ ID NO: 4), a C332A substitution, and a C352L substitution.

In certain embodiments, the sialidase portion comprises a M1 deletion (ΔM1), M1A substitution, M1D substitution, V6Y substitution, I187K substitution, C332A substitution, or a combination of any of the foregoing. For example, the sialidase portion may comprise a combination of mutations selected from: M1A and V6Y; M1A and I187K; M1A and C332A; M1D and V6Y; M1D and I187K; M1D and C332A; ΔM1 and V6Y; ΔM1 and I187K; ΔM1 and C332A; V6Y and I187K; V6Y and C332A; I187K and C332A; M1A, V6Y, and I187K; M1A, V6Y, and C332A; M1A, I187K, and C332A; M1D, V6Y, and I187K; M1D, V6Y, and C332A; M1D, I187K, and C332A; ΔM1, V6Y, and I187K; ΔM1, V6Y, and C332A; ΔM1, I187K, and C332A; V6Y, I187K, and C332A; M1A, V6Y, I187K, and C332A; M1D, V6Y, I187K, and C332A; and ΔM1, V6Y, I187K, and C332A.

In certain embodiments, the sialidase portion comprises the amino acid sequence of SEQ ID NO: 5, SEQ ID NO: 6, SEQ ID NO: 36, SEQ ID NO: 37, SEQ ID NO: 38, SEQ ID NO: 39, SEQ ID NO: 70, SEQ ID NO: 71, SEQ ID NO: 72, or SEQ ID NO: 73, or an amino acid sequence that has at least 85%, 90%, 95%, 96%, 97%, 98%, or 99% sequence identity to SEQ ID NO: 5, SEQ ID NO: 6, SEQ ID NO: 36, SEQ ID NO: 37, SEQ ID NO: 38, SEQ ID NO: 39, SEQ ID NO: 70, SEQ ID NO: 71, SEQ ID NO: 72, or SEQ ID NO: 73.

b. Antibody Portion

As used herein, unless otherwise indicated, the term "antibody" is understood to mean an intact antibody (e.g., an intact monoclonal antibody), or a fragment thereof, such as a Fc fragment of an antibody (e.g., an Fc fragment of a monoclonal antibody), or an antigen-binding fragment of an antibody (e.g., an antigen-binding fragment of a monoclonal antibody), including an intact antibody, antigen-binding fragment, or Fc fragment that has been modified, engineered, or chemically conjugated. Examples of antigen-binding fragments include Fab, Fab', $(Fab')_2$, Fv, single chain antibodies (e.g., scFv), minibodies, and diabodies. Examples of antibodies that have been modified or engineered include chimeric antibodies, humanized antibodies, and multispecific antibodies (e.g., bispecific antibodies). An example of a chemically conjugated antibody is an antibody conjugated to a toxin moiety.

In certain embodiments, the fusion protein comprises an immunoglobulin Fc domain. As used herein, unless otherwise indicated, the term "immunoglobulin Fc domain" refers to a fragment of an immunoglobulin heavy chain constant region which, either alone or in combination with a second immunoglobulin Fc domain, is capable of binding to an Fc receptor. An immunoglobulin Fc domain may include, e.g., immunoglobulin CH2 and CH3 domains. An immunoglobulin Fc domain may include, e.g., immunoglobulin CH2 and CH3 domains and an immunoglobulin hinge region. Boundaries between immunoglobulin hinge regions, CH2, and CH3 domains are well known in the art, and can be found, e.g., in the PROSITE database (available on the world wide web at prosite.expasy.org).

In certain embodiments, the immunoglobulin Fc domain is derived from a human IgG1, IgG2, IgG3, IgG4, IgA1, IgA2, IgD, IgE, and IgM Fc domain. A single amino acid substitution (S228P according to Kabat numbering; designated IgG4Pro) may be introduced to abolish the heterogeneity observed in recombinant IgG4 antibody. See Angal, S. et al. (1993) MOL. IMMUNOL. 30:105-108.

In certain embodiments, the immunoglobulin Fc domain is derived from a human IgG1 isotype or another isotype that elicits antibody-dependent cell-mediated cytotoxicity (ADCC) and/or complement mediated cytotoxicity (CDC). In certain embodiments, the immunoglobulin Fc domain is derived from a human IgG1 isotype (e.g., SEQ ID NO: 31 or SEQ ID NO: 69).

In certain embodiments, the immunoglobulin Fc domain is derived from a human IgG4 isotype or another isotype that elicits little or no antibody-dependent cell-mediated cytotoxicity (ADCC) and/or complement mediated cytotoxicity (CDC). In certain embodiments, the immunoglobulin Fc domain is derived from a human IgG4 isotype.

In certain embodiments, the immunoglobulin Fc domain comprises either a "knob" mutation, e.g., T366Y or a "hole" mutation, e.g., Y407T for heterodimerization with a second polypeptide (residue numbers according to EU numbering, Kabat, E. A., et al. (1991) SEQUENCES OF PROTEINS OF IMMUNOLOGICAL INTEREST, FIFTH EDITION, U.S. Department of Health and Human Services, NIH Publication No. 91-3242).

In certain embodiments, the fusion protein comprises an immunoglobulin antigen-binding domain. The inclusion of such a domain may improve targeting of a fusion protein to a sialylated cancer cell and/or to the tumor microenvironment. As used herein, unless otherwise indicated, the term "immunoglobulin antigen-binding domain" refers to a polypeptide that, alone or in combination with another immunoglobulin antigen-binding domain, defines an antigen-binding site. Exemplary immunoglobulin antigen-binding domains include, for example, immunoglobulin heavy chain variable region and an immunoglobulin light chain variable region, where the variable regions together define an antigen binding site.

The immunoglobulin antigen-binding domain and/or antigen binding site can be derived from an antibody selected from, for example, adecatumumab, ascrinvacumab, cixutumumab, conatumumab, daratumumab, drozitumab, duligotumab, durvalumab, dusigitumab, enfortumab, enoticumab, epratuxumab, figitumumab, ganitumab, glembatumumab, intetumumab, ipilimumab, iratumumab, icrucumab, lexatumumab, lucatumumab, mapatumumab, narnatumab, necitumumab, nesvacumab, ofatumumab, olaratumab, panitumumab, patritumab, pritumumab, radretumab, ramucirumab, rilotumumab, robatumumab, seribantumab, tarextumab, teprotumumab, tovetumab, vantictumab, vesencumab, votumumab, zalutumumab, flanvotumab, altumomab, anatumomab, arcitumomab, bectumomab, blinatumomab, detumomab, ibritumomab, minretumomab, mitumomab, moxetumomab, naptumomab, nofetumomab, pemtumomab, pintumomab, racotumomab, satumomab, solitomab, taplitumomab, tenatumomab, tositumomab, tremelimumab, abagovomab, atezolizumab, durvalumab, avelumab, igovomab, oregovomab, capromab, edrecolomab, nacolomab, amatuximab, bavituximab, brentuximab, cetuximab, derlotuximab, dinutuximab, ensituximab, futuximab, girentuximab, indatuximab, isatuximab, margetuximab, rituximab, siltuximab, ublituximab, ecromeximab, abituzumab, alemtuzumab, bevacizumab, bivatuzumab, brontictuzumab, cantuzumab, cantuzumab, citatuzumab, clivatuzumab, dacetuzumab, demcizumab, dalotuzumab, denintuzumab, elotuzumab, emactuzumab, emibetuzumab, enoblituzumab, etaracizumab, farletuzumab, ficlatuzumab, gemtuzumab, imgatuzumab, inotuzumab, labetuzumab, lifastuzumab, lintuzumab, lirilumab, lorvotuzumab, lumretuzumab, matuzumab, milatuzumab, moxetumomab, nimotuzumab, obinutuzumab, ocaratuzumab, otlertuzumab, onartuzumab, oportuzumab, parsatuzumab, pertuzumab, pidilizumab, pinatuzumab, polatuzumab, sibrotuzumab, simtuzumab, tacatuzumab, tigatuzumab, trastuzumab, tucotuzumab, urelumab, vandortuzumab, vanucizumab, veltuzumab, vorsetuzumab, sofituzumab, catumaxomab, ertumaxomab, depatuxizumab, ontuxizumab, blontuvetmab, tamtuvetmab, nivolumab, pembrolizumab, epratuzumab, MEDI9447, urelumab, utomilumab, hu3F8, hu14.18-IL-2, 3F8/OKT3BsAb, lirilumab, BMS-986016 pidilizumab, AMP-224, AMP-514, BMS-936559, atezolizumab, and avelumab. In certain embodiments, the immunoglobulin antigen-binding domain can be derived from an antibody selected from trastuzumab, cetuximab, daratumumab, girentuximab, panitumumab, ofatumumab, and rituximab.

In certain embodiments, the immunoglobulin antigen-binding domain is derived from trastuzumab. The trastuzumab heavy chain amino acid sequence is depicted in SEQ ID NO: 40, and the trastuzumab light chain amino acid sequence is depicted in SEQ ID NO: 41. The amino acid sequence of an exemplary scFv derived from trastuzumab is depicted in SEQ ID NO: 42.

The immunoglobulin antigen-binding domain and/or antigen binding site can be derived from an antibody that binds a cancer antigen selected from, for example, adenosine A2a receptor (A2aR), A kinase anchor protein 4 (AKAP4), B melanoma antigen (BAGE), brother of the regulator of imprinted sites (BORIS), breakpoint cluster region Abelson tyrosine kinase (BCR/ABL), CA125, CAIX, CD19, CD20, CD22, CD30, CD33, CD52, CD73, CD137, carcinoembryonic antigen (CEA), CS1, cytotoxic T-lymphocyte-associated antigen 4 (CTLA-4), estrogen receptor binding site associated antigen 9 (EBAG9), epidermal growth factor (EGF), epidermal growth factor receptor (EGFR), EGF-like module receptor 2 (EMR2), epithelial cell adhesion molecule (EpCAM) (17-1A), FR-alpha, G antigen (GAGE), disialoganglioside GD2 (GD2), glycoprotein 100 (gp100), human epidermal growth factor receptor 2 (Her2), hepatocyte growth factor (HGF), human papillomavirus 16 (HPV-16), heat-shock protein 105 (HSP105), isocitrate dehydrogenase type 1 (IDH1), idiotype (NeuGcGM3), indoleamine-2,3-dioxygenase 1 (IDO1), IGF-1, IGF1R, IGG1K, killer cell immunoglobulin-like receptor (KIR), lymphocyte activation gene 3 (LAG-3), lymphocyte antigen 6 complex K (LY6K), Matrix-metalloproteinase-16 (MMP16), melanotransferrin (MFI2), melanoma antigen 3 (MAGE-A3), melanoma antigen C2 (MAGE-C2), melanoma antigen D4 (MAGE-D4), melanoma antigen recognized by T-cells 1 (Melan-A/MART-1), N-methyl-N'-nitroso-guanidine human osteosarcoma transforming gene (MET), mucin 1 (MUC1), mucin 4 (MUC4), mucin 16 (MUC16), New York esophageal squamous cell carcinoma 1 (NY-ESO-1), prostatic acid phosphatase (PAP), programmed cell death receptor 1 (PD-1), programmed cell death receptor ligand 1 (PD-L1), phosphatidylserine, preferentially expressed antigen of melanoma (PRAME), prostate specific antigen (PSA), protein tyrosine kinase 7 (PTK7, also known as colon carcinoma kinase 4 (CCK4)), receptor tyrosine kinase orphan receptor 1 (ROR1), scatter factor receptor kinase, sialyl-Tn, sperm-associated antigen 9 (SPAG-9), synovial sarcoma X-chromosome breakpoint 1 (SSX1), survivin, telomerase, T-cell immunoglobulin domain and mucin domain-3 (TIM-3), vascular endothelial growth factor (VEGF) (e.g., VEGF-A), vascular endothelial growth factor Receptor 2 (VEGFR2), V-domain immunoglobulin-containing suppressor of T-cell activation (VISTA), Wilms' Tumor-1 (WT1), X chromosome antigen 1b (XAGE-1b), 5T4, Mesothelin, Glypican 3 (GPC3), Folate Receptor α (FRα), Prostate Specific Membrane Antigen (PSMA), cMET, CD38, B Cell Maturation Antigen (BCMA), CD123, CLDN6, CLDN9, LRRC15, PRLR (Prolactin Receptor), RING finger protein 43 (RNF43), Uroplakin-1 B (UPK1 B), tumor necrosis factor superfamily member 9 (TNFSF9), tumor necrosis factor receptor superfamily member 21 (TNFSRF21), bone morphogenetic protein receptor type-1B (BMPR1B), Kringle domain-containing transmembrane protein 2 (KREMEN2), Delta-like protein 3 (DLL3), Siglec7 and Siglec9. Additional exemplary cancer antigens include those found on cancer stem cells, e.g., SSEA3, SSEA4, TRA-1-60, TRA-1-81, SSEA1, CD133 (AC133), CD90 (Thy-1), CD326 (EpCAM), Cripto-1 (TDGF1), PODXL-1 (Podocalyxin-like protein 1), ABCG2, CD24, CD49f (Integrin α6), Notch2, CD146 (MCAM), CD10 (Neprilysin), CD117 (c-KIT), CD26 (DPP-4), CXCR4, CD34, CD271, CD13 (Alanine aminopeptidase), CD56 (NCAM), CD105 (Endoglin), LGR5, CD114 (CSF3R), CD54 (ICAM-1), CXCR1, 2, TIM-3 (HAVCR2), CD55 (DAF), DLL4 (Delta-like ligand 4), CD20 (MS4A1), and CD96.

The invention further provides antibody conjugates containing one or more of the fusion proteins disclosed herein. As used herein, unless otherwise indicated, the term "antibody conjugate" is understood to refer to an antibody, or a functional fragment thereof, that comprises antigen-binding activity and/or Fc receptor-binding activity, conjugated (e.g., covalently coupled) to an additional functional moiety. In certain embodiments, the antibody or functional antibody fragment is conjugated to a sialidase enzyme, e.g., a recombinant mutant human sialidase enzyme disclosed herein. In certain embodiments, an antibody conjugate comprises a single polypeptide chain. In certain embodiments, an antibody conjugate comprises two, three, four, or more polypeptide chains that are covalently or non-covalently associated together to produce a multimeric complex, e.g., a dimeric, trimeric or tetrameric complex.

TABLE 1 shows antibodies and antibody-drug conjugates suitable for use in accordance with the present invention, the antigen bound by the antibody or antibody-drug conjugate, and for certain antibodies, the type of cancer targeted by the antibody or antibody-drug conjugate.

TABLE 1

| Antibody or antibody-drug conjugate | Cancer Antigen | Cancer Type |
|---|---|---|
| oregovomab | CA125 | |
| girentuximab | CAIX | |
| obinutuzumab | CD20 | |
| ofatumumab | CD20 | |
| rituximab | CD20 | |
| alemtuzumab | CD52 | |
| Ipilimumab | cytotoxic T-lymphocyte-associated antigen 4 (CTLA-4) | |
| tremelimumab | CTLA-4 | |
| Cetuximab | epidermal growth factor receptor (EGFR) | |
| necitumumab | EGFR | |
| panitumumab | EGFR | |
| zalutumumab | EGFR | |
| edrecolomab | epithelial cell adhesion molecule (EpCAM) (17-1A) | |
| farletuzumab | FR-alpha | |
| Pertuzumab | human epidermal growth factor receptor 2 (Her2) | |
| trastuzumab | Her2 | |
| rilotumumab | HGF | |
| figitumumab | IGF-1 | |
| Ganitumab | IGF1R | |
| durvalumab | IGG1K | |
| bavituximab | Phosphatidylserine | |
| onartuzumab | scatter factor receptor kinase | |
| bevacizumab | vascular endothelial growth factor-A (VEGF-A) | |
| ramucirumab | vascular endothelial growth factor Receptor 2 (VEGFR2) | |
| blinatumomab | CD19 | acute lymphoblastic leukemia (ALL) |
| Rituximab; ofatumumab, ibritumomab (e.g., $^{90}$Y-ibritumomab; tositumomab (e.g., $^{131}$I-tositumomab | CD20 | non-Hodgkin's lymphoma (NHL), chronic lymphocytic leukemia (CLL) B-cell NHL pre-B ALL |
| brentuximab (e.g., brentuximab vedotin | CD30 | Hodgkin's lymphoma |
| gemtuzumab (e.g., gemtuzumab ozogamicin | CD33 | acute myelogenous leukemia (AML) |
| Alemtuzumab | CD52 | CLL |
| Ipilimumab | cytotoxic T-lymphocyte-associated antigen 4 (CTLA-4) | Unresectable or metastatic melanoma |

TABLE 1-continued

| Antibody or antibody-drug conjugate | Cancer Antigen | Cancer Type |
|---|---|---|
| cetuximab; panitumumab | epidermal growth factor receptor (EGFR) | colorectal cancer (CRC) Head and Neck |
| Catumaxomab | epithelial cell adhesion molecule (EpCAM) | Malignant ascites |
| trastuzumab; pertuzumab | human epidermal growth factor receptor 2 (HER2) | Breast |
| nivolumab, pembrolizumab | programmed cell death receptor 1 (PD-1) | Metastatic melanoma, non-small cell lung cancer (NSCLC) |
| Bevacizumab | vascular endothelial growth factor (VEGF) | Breast, Cervical CRC, NSCLC renal cell carcinoma (RCC), Ovarian Glioblastoma |
| Ramucirumab | vascular endothelial growth factor receptor 2 (VEGF-R2) | Gastric NSCLC |
| Epratuzumab; moxetumomab; inotuzumab (e.g., inotuzumab ozogamicin) | CD22 | acute lymphoblastic leukemia (ALL) |
| MEDI9447 | CD73 | Advanced solid tumors |
| Urelumab; utomilumab (PF-05082566) | CD137 | Advanced solid tumors |
| Elotuzumab | CD2 subset 1 (CS1) | Multiple myeloma |
| Tremelimumab | cytotoxic T-lymphocyte-associated antigen 4 (CTLA-4) | Malignant mesothelioma |
| Necitumumab | epidermal growth factor receptor (EGFR) | non-small cell lung cancer (NSCLC) |
| dinutuximab, hu3F8; hu14.18-IL-2; 3F8/OKT3BsAb | disialoganglioside GD2 (GD2) | Neuroblastoma Retinoblastoma Melanoma other solid tumors |
| Racotumomab | Idiotype (NeuGcGM3) | NSCLC, Breast Melanoma |
| Lirilumab | killer cell immunoglobulin-like receptor (KIR) | Lymphoma |
| BMS-986016 | lymphocyte activation gene 3 (LAG-3) | Breast, Hematological, Advanced solid tumors |
| Onartuzumab | N-methyl-N'-nitroso-guanidine human osteosarcoma transforming gene (MET) | NSCLC |
| abagovomab; oregovomab | mucin 16 (MUC16) | Ovarian |
| pidilizumab; AMP-224; AMP-514 | programmed cell death receptor 1 (PD-1) | B-cell lymphoma Melanoma, CRC |
| BMS-936559; atezolizumab; durvalumab; avelumab | programmed cell death receptor ligand 1 (PD-L1) | NSCLC, renal cell carcinoma (RCC) Bladder, Breast Melanoma, squamous cell carcinoma of the head and neck (SCCHN) |
| naptumomab (e.g., naptumomab estafenatox) | 5T4 | RCC, CRC Prostate |

c. Linker

In certain embodiments, the sialidase portion of the fusion protein can be linked or fused directly to the antibody portion (e.g., immunoglobulin Fc domain and/or immunoglobulin antigen-binding domain) of the fusion protein. In other embodiments, the sialidase portion can be covalently bound to the antibody portion by a linker.

The linker may couple, with one or more natural amino acids, the sialidase, or functional fragment thereof, and the antibody portions or fragments, where the amino acid (for example, a cysteine amino acid) may be introduced by site-directed mutagenesis. The linker may include one or more unnatural amino acids. It is contemplated that, in certain circumstances, a linker containing for example, one or more sulfhydryl reactive groups (e.g., a maleimide) may covalently link a cysteine in the sialidase portion or the antibody portion that is a naturally occurring cysteine residue or is the product of site-specific mutagenesis.

The linker may be a cleavable linker or a non-cleavable linker. Optionally or in addition, the linker may be a flexible linker or an inflexible linker.

The linker should be a length sufficiently long to allow the sialidase and the antibody portions to be linked without steric hindrance from one another and sufficiently short to retain the intended activity of the fusion protein. The linker preferably is sufficiently hydrophilic to avoid or minimize instability of the fusion protein. The linker preferably is sufficiently hydrophilic to avoid or minimize insolubility of the fusion protein. The linker should be sufficiently stable in vivo (e.g., it is not cleaved by serum, enzymes, etc.) to permit the fusion protein to be operative in vivo.

The linker may be from about 1 angstroms (Å) to about 150 Å in length, or from about 1 Å to about 120 Å in length, or from about 5 Å to about 110 Å in length, or from about 10 Å to about 100 Å in length. The linker may be greater than about 2, 3, 4, 5, 6, 7, 8, 9, 10, 11, 12, 13, 14, 15, 16, 17, 18, 19, 20, 25, 27, 30 or greater angstroms in length and/or less than about 110, 100, 90, 85, 80, 75, 70, 65, 60, 55, 50, 45, 43, 42, 41, 40, 39, 38, 37, 36, 35, 34, 33, 32, 31, or fewer Å in length. Furthermore, the linker may be about 5, 10, 15, 20, 25, 30, 35, 40, 45, 50, 55, 60, 65, 70, 75, 80, 85, 90, 95, 100, 110, and 120 Å in length.

In certain embodiments, the linker comprises a polypeptide linker that connects or fuses the sialidase portion of the fusion protein to the antibody portion (e.g., immunoglobulin Fc domain and/or immunoglobulin antigen-binding domain) of the fusion protein. For example, it is contemplated that a gene encoding a sialidase portion linked directly or indirectly (for example, via an amino acid containing linker) to an antibody portion can be created and expressed using conventional recombinant DNA technologies. For example, the amino terminus of a sialidase portion can be linked to the carboxy terminus of either the light or the heavy chain of an antibody portion. For example, for a Fab fragment, the amino terminus or carboxy terminus of the sialidase can be linked to the first constant domain of the heavy antibody chain (CH1). When a linker is employed, the linker may comprise hydrophilic amino acid residues, such as Gln, Ser, Gly, Glu, Pro, His and Arg. In certain embodiments, the linker is a peptide containing 1-25 amino acid residues, 1-20 amino acid residues, 2-15 amino acid residues, 3-10 amino acid residues, 3-7 amino acid residues, 4-25 amino acid residues, 4-20 amino acid residues, 4-15 amino acid residues, 4-10 amino acid residues, 5-25 amino acid residues, 5-20 amino acid residues, 5-15 amino acid residues, or 5-10 amino acid residues. Exemplary linkers include glycine and serine-rich linkers, e.g., $(GlyGlyPro)_n$ (SEQ ID NO: 106), or $(GlyGlyGlyGlySer)_n$ (SEQ ID NO: 107), where n is 1-5. In certain embodiments, the linker is $(Gly_4Ser)_2$ (SEQ ID NO: 108). Additional exemplary linker sequences are disclosed, e.g., in George et al. (2003) Protein Engineering 15:871-879, and U.S. Pat. Nos. 5,482,858 and 5,525,491.

d. Antibody Conjugates

The invention further provides antibody conjugates comprising a fusion protein disclosed herein. The antibody conjugate may comprise a single polypeptide chain (i.e., a fusion protein disclosed herein) or, the antibody conjugate may comprise additional polypeptide chains (e.g., one, two, or three additional polypeptide chains). For example, an antibody conjugate may comprise a first polypeptide (fusion protein) comprising a recombinant mutant human sialidase enzyme and an immunoglobulin heavy chain, and a second polypeptide comprising an immunoglobulin light chain, where, for example, the immunoglobulin heavy and light chains together define a single antigen-binding site.

In certain embodiments, the antibody conjugate can include a single sialidase. In other embodiments, the antibody conjugate can include more than one (e.g., two) sialidases. If more than one sialidase is included, the sialidases can be the same or different. In certain embodiments, the antibody conjugate can include a single antigen-binding site. In other embodiments, the antibody conjugate can include more than one (e.g., two) antigen-binding sites. If two antigen-binding sites are used, they can be the same or different. In certain embodiments, the antibody conjugate comprises an immunoglobulin Fc fragment.

In certain embodiments, the antibody conjugate comprises one or two immunoglobulin heavy chains, or a functional fragment thereof. In certain embodiments, the antibody conjugate comprises one or two immunoglobulin light chains, or a functional fragment thereof. In certain embodiments, the antibody conjugate comprises a sialidase fused to the N- or C-terminus of an immunoglobulin heavy chain or an immunoglobulin light chain.

FIG. 9 depicts exemplary antibody conjugate constructs containing one or more sialidase enzymes. For example, in FIG. 9A, a first antigen-binding site is depicted as 10, a second antigen-binding site is depicted as 20, a sialidase is depicted as 30, and a Fab is depicted as 40. In each of the constructs depicted in FIGS. 9A-9I it is understood that the Fc may optionally be modified in some manner, e.g. using Knobs-into-Holes type technology, e.g., as depicted by 50 in FIG. 9B. Throughout FIG. 9 similar structures are depicted by similar schematic representations.

Figure 9A:
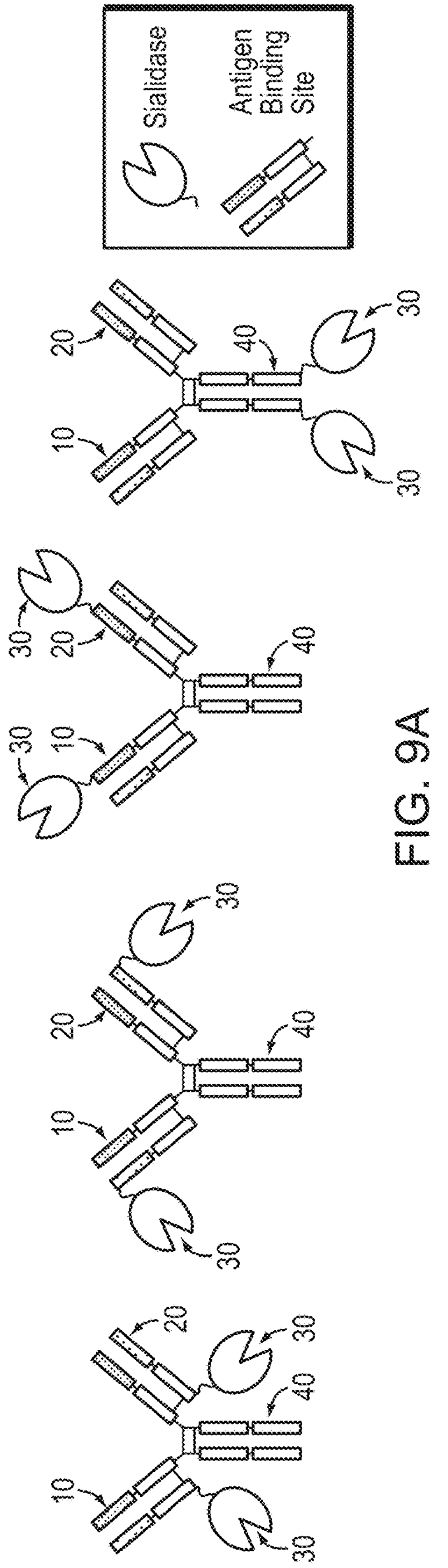
FIGS. 9A-9I depict schematic representations of certain antibody conjugate constructs containing a sialidase enzyme, e.g., a human sialidase enzyme, and an antigen binding site. For each antibody conjugate construct that contains more than one (e.g., two) sialidase, each sialidase may be the same or different. For each antibody conjugate construct that contains more than one (e.g., two) antigen binding site, each antigen binding site may be the same or different.

FIG. 9A depicts antibody conjugate constructs comprising a first polypeptide comprising a first immunoglobulin light chain; a second polypeptide comprising a first immunoglobulin heavy chain; a third polypeptide comprising a second immunoglobulin heavy chain; and a fourth polypeptide comprising a second immunoglobulin light chain. The first and second polypeptides can be covalently linked together, the third and fourth polypeptides can be covalently linked together, and the second and third polypeptides can be covalently linked together. The covalent linkages can be disulfide bonds. In certain embodiments, the first polypeptide and the second polypeptide together define a first antigen-binding site as depicted as 10, and the third polypeptide and the fourth polypeptide together define a second antigen-binding site as depicted as 20. A sialidase enzyme as depicted as 30 can be conjugated to the N- or C-terminus of the first and second immunoglobulin light chain or the first and second immunoglobulin heavy chain.

Figure 9B:
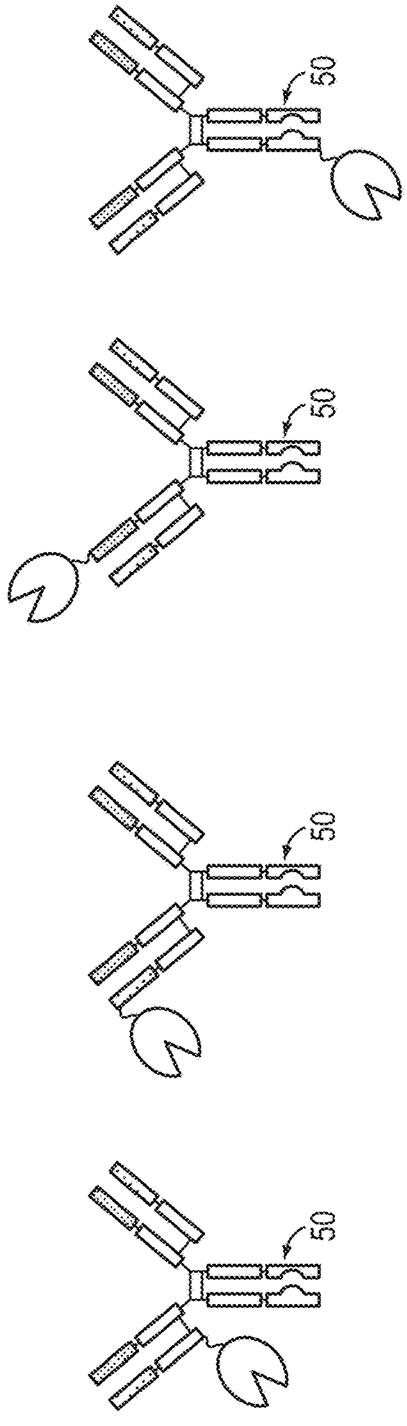

FIG. 9B depicts antibody conjugate constructs comprising a first polypeptide comprising a first immunoglobulin light chain; a second polypeptide comprising a first immunoglobulin heavy chain; a third polypeptide comprising a second immunoglobulin heavy chain; and a fourth polypeptide comprising a second immunoglobulin light chain. The first and second polypeptides can be covalently linked together, the third and fourth polypeptides can be covalently linked together, and the second and third polypeptides can be covalently linked together. The covalent linkages can be disulfide bonds. In certain embodiments, the first polypeptide and the second polypeptide together define a first antigen-binding site, and the third polypeptide and the fourth polypeptide together define a second antigen-binding site. A sialidase enzyme can be conjugated to the N- or C-terminus of the first immunoglobulin light chain or the first immunoglobulin heavy chain.

Figure 9C:
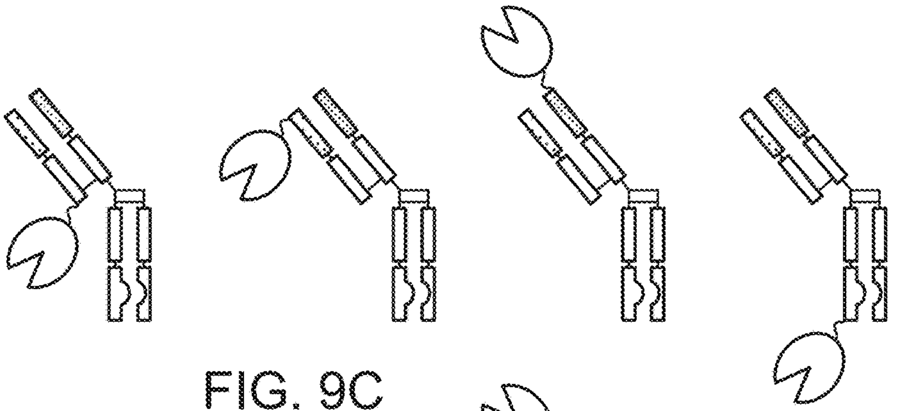

FIG. 9C depicts antibody conjugate constructs comprising a first polypeptide comprising an immunoglobulin light chain; a second polypeptide comprising an immunoglobulin heavy chain; and a third polypeptide comprising an immunoglobulin Fc domain. The first and second polypeptides can be covalently linked together and the second and third polypeptides can be covalently linked together. The covalent linkages can be disulfide bonds. In certain embodiments, the first polypeptide and the second polypeptide together define an antigen-binding site. A sialidase enzyme can be conjugated to the N- or C-terminus of the first immunoglobulin light chain or the first immunoglobulin heavy chain.

Figure 9D:
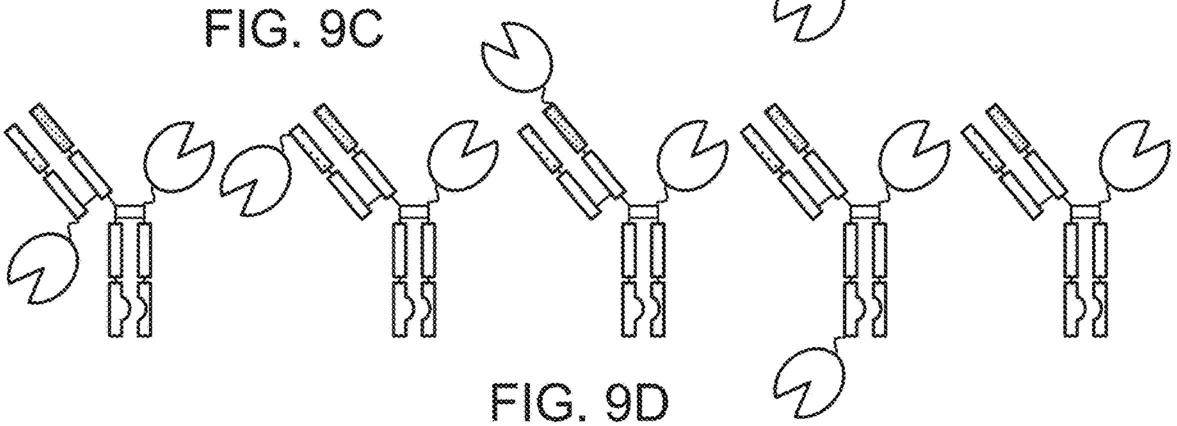

FIG. 9D depicts antibody conjugate constructs comprising a first polypeptide comprising an immunoglobulin light chain; a second polypeptide comprising an immunoglobulin heavy chain; and a third polypeptide comprising an immunoglobulin Fc domain and a first sialidase enzyme. The first and second polypeptides can be covalently linked together and the second and third polypeptides can be covalently linked together. The covalent linkages can be disulfide bonds. The third polypeptide comprises the sialidase and the immunoglobulin Fc domain in an N- to C-terminal orientation. In certain embodiments, the first polypeptide and the second polypeptide together define an antigen-binding site. An optional second sialidase enzyme can be conjugated to the N- or C-terminus of the first immunoglobulin light chain or the first immunoglobulin heavy chain.

Figure 9E:
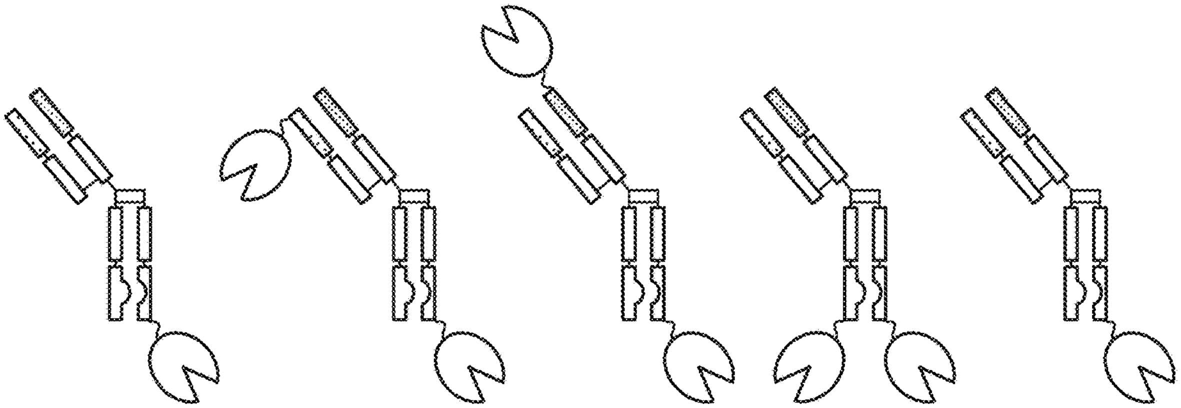

FIG. 9E depicts antibody conjugate constructs comprising a first polypeptide comprising an immunoglobulin light chain; a second polypeptide comprising an immunoglobulin heavy chain; and a third polypeptide comprising an immunoglobulin Fc domain and a first sialidase enzyme. The first and second polypeptides can be covalently linked together and the second and third polypeptides can be covalently linked together. The covalent linkages can be disulfide bonds. The third polypeptide comprises the immunoglobulin Fc domain and the sialidase in an N- to C-terminal orientation. In certain embodiments, the first polypeptide and the second polypeptide together define an antigen-binding site. An optional second sialidase enzyme can be conjugated to the N- or C-terminus of the first immunoglobulin light chain or the first immunoglobulin heavy chain.

Figure 9F:
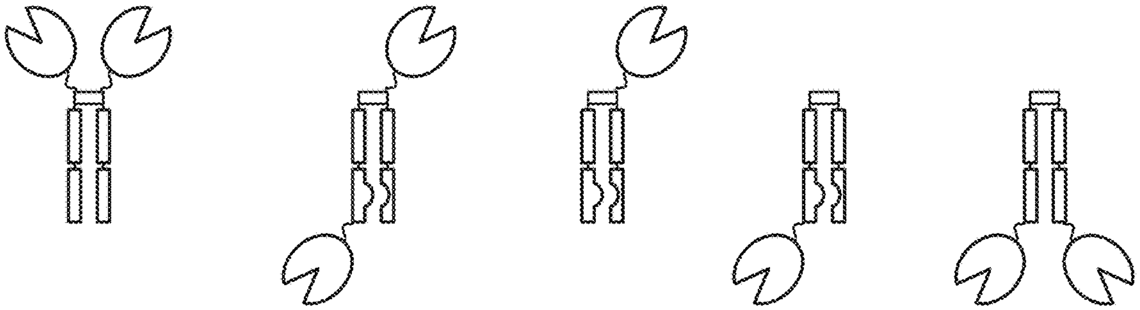

FIG. 9F depicts antibody conjugate constructs comprising a first polypeptide comprising a first immunoglobulin Fc domain, and a second polypeptide comprising a second immunoglobulin Fc domain. The first and second polypeptides can be covalently linked together. The covalent linkages can be disulfide bonds. A sialidase enzyme can be conjugated to the N- or C-terminus of the first immunoglobulin Fc domain or to the N- or C-terminus of the second immunoglobulin Fc domain. An optional second sialidase enzyme can be conjugated to the N- or C-terminus of the first immunoglobulin Fc domain or to the N- or C-terminus of the second immunoglobulin Fc domain.

Figure 9G:
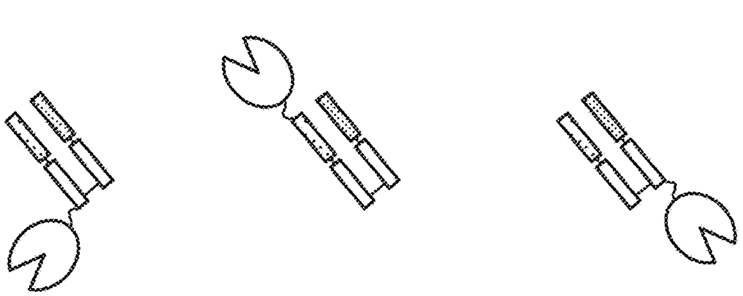

FIG. 9G depicts antibody conjugate constructs comprising a first polypeptide comprising an immunoglobulin light chain; and a second polypeptide comprising an immunoglobulin heavy chain variable region. The first and second polypeptides can be covalently linked together. The covalent linkages can be disulfide bonds. In certain embodiments, the first polypeptide and the second polypeptide together define an antigen-binding site. The sialidase enzyme can be conjugated to the N- or C-terminus of the immunoglobulin light chain or the immunoglobulin heavy chain variable region.

Figure 9H:
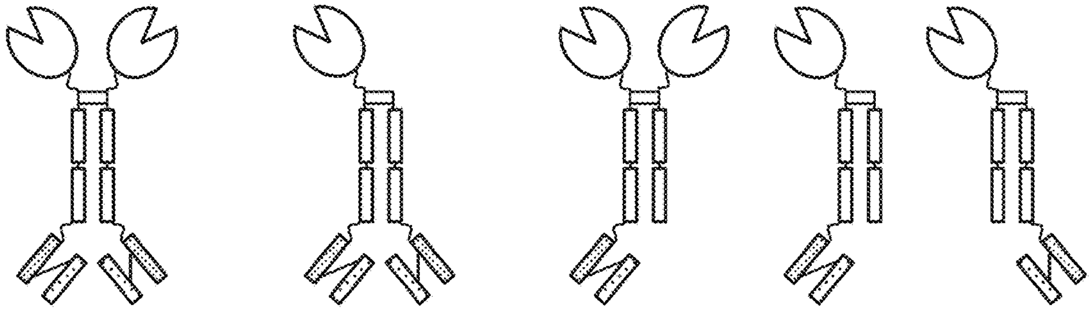

FIG. 9H depicts antibody conjugate constructs comprising a first polypeptide comprising a first immunoglobulin Fc domain, and a second polypeptide comprising a second immunoglobulin Fc domain. The first and second polypeptides can be covalently linked together. The covalent linkages can be disulfide bonds. A sialidase enzyme can be conjugated to the N-terminus of the first immunoglobulin Fc domain or the second immunoglobulin Fc domain. An optional second sialidase enzyme can be conjugated to the N-terminus of the second immunoglobulin Fc domain or the first immunoglobulin Fc domain, respectively. A single chain variable fragment (scFv) can be conjugated to the C-terminus of the first immunoglobulin Fc domain or the second immunoglobulin Fc domain. An optional second single chain variable fragment (scFv) can be conjugated to the C-terminus of the first immunoglobulin Fc domain or the second immunoglobulin Fc domain, respectively.

Figure 9I:
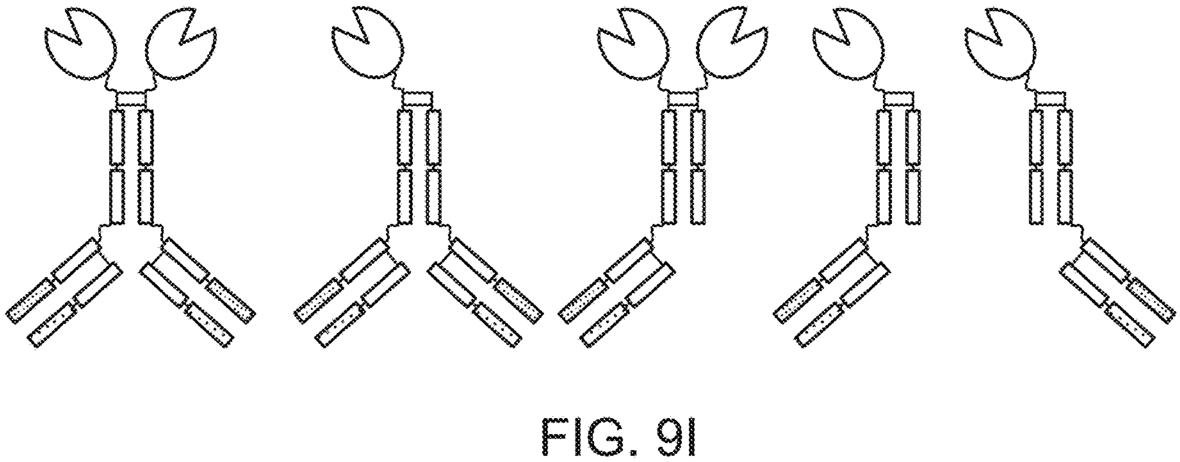

FIG. 9I depicts antibody conjugate constructs similar to those depicted in FIG. 9H except that each scFv is replaced with an immunoglobulin antigen binding fragment, e.g., an Fab. For example, FIG. 9I depicts antibody conjugate constructs comprising a first polypeptide comprising a first immunoglobulin Fc domain, and a second polypeptide comprising a second immunoglobulin Fc domain. The first and second polypeptides can be covalently linked together. The covalent linkages can be disulfide bonds. A sialidase enzyme can be conjugated to the N-terminus of the first immunoglobulin Fc domain or the second immunoglobulin Fc domain. An optional second sialidase enzyme can be conjugated to the N-terminus of the second immunoglobulin Fc domain or the first immunoglobulin Fc domain, respectively. An antibody fragment (Fab) can be conjugated or fused to the C-terminus of the first immunoglobulin Fc domain or the second immunoglobulin Fc domain. An optional second antibody fragment (Fab) can be conjugated or fused to the C-terminus of the second immunoglobulin Fc domain or the first immunoglobulin Fc domain, respectively. In the case of a fusion, the C terminus of the Fc domain is linked (either by a bond or an amino acid linker) to a first polypeptide chain defining an immunoglobulin antigen binding fragment. In the case of antibodies that have an antigen binding site defined by a single variable region, then this may be sufficient to impart binding affinity to a target antigen. In other instances, e.g., in the case of a human antibody, the first polypeptide chain defining an immunoglobulin antigen binding fragment can be conjugated (e.g., covalently conjugated, e.g., via a disulfide bond) to a second polypeptide chain defining an immunoglobulin antigen binding fragment, there the two antigen binding fragments together define an antigen binding site for binding the target antigen.

Figure 10A:
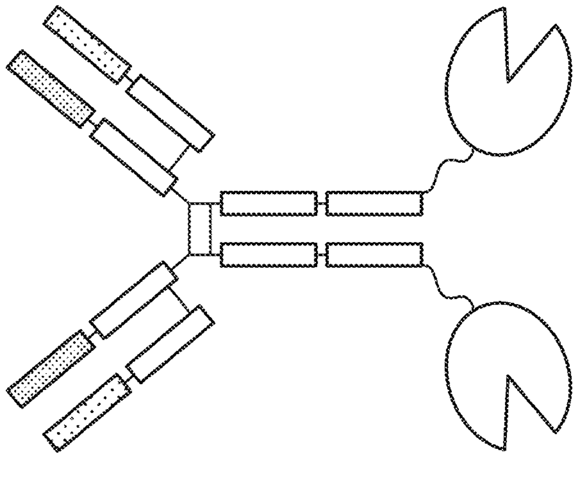
FIGS. 10A-C are schematic representations of fusion protein conjugates referred to as a Raptor antibody sialidase conjugate (FIG. 10A), a Janus antibody sialidase conjugate (FIG. 10B), and a Lobster antibody sialidase conjugate (FIG. 10C).

In certain embodiments, the antibody conjugate comprises a first polypeptide comprising a first immunoglobulin light chain; a second polypeptide comprising a first immunoglobulin heavy chain and a first sialidase; a third polypeptide comprising a second immunoglobulin heavy chain and a second sialidase; and a fourth polypeptide comprising a second immunoglobulin light chain. An example of this embodiment is shown in FIG. 10A. The first and second polypeptides can be covalently linked together, the third and fourth polypeptides can be covalently linked together, and the second and third polypeptides can be covalently linked together. The covalent linkages can be disulfide bonds. In certain embodiments, the first polypeptide and the second polypeptide together define a first antigen-binding site, and the third polypeptide and the fourth polypeptide together define a second antigen-binding site. In certain embodiments, the second and third polypeptides comprise the first and second immunoglobulin heavy chain and the first and second sialidase, respectively, in an N- to C-terminal orientation. In certain embodiments, the second and third polypeptides comprise the first and second sialidase and the first and second immunoglobulin heavy chain, respectively, in an N- to C-terminal orientation.

Figure 10B:
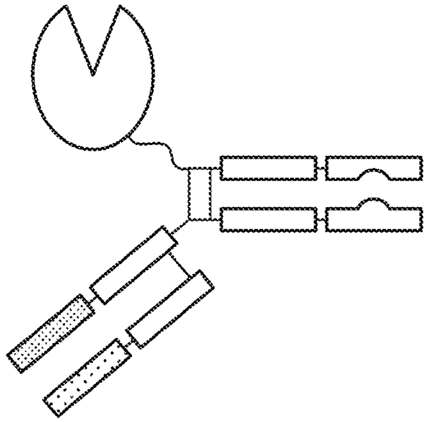

In certain embodiments, the antibody conjugate comprises a first polypeptide comprising an immunoglobulin light chain; a second polypeptide comprising an immunoglobulin heavy chain; and a third polypeptide comprising an immunoglobulin Fc domain and a sialidase. An example of this embodiment is shown in FIG. 10B. The first and second polypeptides can be covalently linked together and the second and third polypeptides can be covalently linked together. The covalent linkages can be disulfide bonds. In certain embodiments, the first polypeptide and the second polypeptide together define an antigen-binding site. In certain embodiments, the third polypeptide comprises the sialidase and the immunoglobulin Fc domain in an N- to C-terminal orientation or the immunoglobulin Fc domain and the sialidase in an N- to C-terminal orientation.

In certain embodiments, the first polypeptide comprises the amino acid sequence of SEQ ID NO: 49, or an amino acid sequence that has at least 85%, 90%, 95%, 96%, 97%, 98%, or 99% sequence identity to SEQ ID NO: 49. In certain embodiments, the second polypeptide comprises the amino acid sequence of SEQ ID NO: 50 or an amino acid sequence that has at least 85%, 90%, 95%, 96%, 97%, 98%, or 99% sequence identity to SEQ ID NO: 50. In certain embodiments, the third polypeptide comprises the amino acid sequence of SEQ ID NO: 51, SEQ ID NO: 52, SEQ ID NO: 53, SEQ ID NO: 54, SEQ ID NO: 63, SEQ ID NO: 76, SEQ ID NO: 77, SEQ ID NO: 78, or SEQ ID NO: 79, or an amino acid sequence that has at least 85%, 90%, 95%, 96%, 97%, 98%, or 99% sequence identity to SEQ ID NO: 51, SEQ ID NO: 52, SEQ ID NO: 53, SEQ ID NO: 54, SEQ ID NO: 63, SEQ ID NO: 76, SEQ ID NO: 77, SEQ ID NO: 78, or SEQ ID NO: 79.

In certain embodiments, the third polypeptide comprises the amino acid sequence of (SEQ ID NO: 101)

$X_1X_2SX_3PX_4$LQKESVFQSGAHAYRIPALLYLPGQQSLLAFAEQRASKKD

EHAELIVLRRGDYDAPTHQVQWQAQEVVAQARLDGHRSMNPCPLYDAQTG

TLFLFFIAIPGQVTEQQQLQTRANVTRL$X_5$QVTSTDHGRTWSSPRDLTDA

AIGPAYREWSTFAVGPGHCLQLHDRARSLVVPAYAYRKLHP$X_6$QRPIPSA

F$X_7$FLSHDHGRTWARGHFVAQDTLECQVAEVETGEQRVVTLNARSHLRAR

VQAQSTNDGLDFQ$X_8$SQLVKKLVEPPPQG$X_9$QGSVISFPSPRSGPGSPAQ

WLLYTHPTHSWQRADLGAYLNPRPPAPEAWSEP$X_{10}$LLAKGS$X_{11}$AYSDL

QSMGTGPDGSPLFG$X_{12}$LYEANDYEEIVFLMFTLKQAFPAEYLPQGGGGS

GGGGSDKTHTCPPCPAPELLGGPSVFLFPPKPKDTLMISRTPEVTCVVVD

VSHEDPEVKFNWYVDGVEVHNAKTKPREEQYNSTYRVVSVLTVLHQDWLN

GKEYKCKVSNKALPAPIEKTISKAKGQPREPQVYTLPPSREEMTKNQVSL

TCLVKGFYPSDIAVEWESNGQPENNYKTTPPVLDSDGSFFLTSKLTVDKS

RWQQGNVFSCSVMHEALHNHYTQKSLSLSPGK, wherein $X_1$ is Ala, Arg, Asn, Asp, Gln, Glu, Gly, His, Leu, Lys, Met, Phe, Thr, Val, or not present, $X_2$ is Ala or Lys, $X_3$ is Asn or Leu, $X_4$ is Phe, Trp, Tyr or Val, $X_5$ is Ala, Cys, Ile, Ser, or Val, $X_6$ is Arg, Ile, or Lys, $X_7$ is Ala, Cys, Leu, or Val, $X_8$ is Glu or Lys, $X_9$ is Cys or Val, $X_{10}$ is Lys or Val, $X_{11}$ is Ala, Cys, Ser, or Val, and $X_{12}$ is Cys, Leu, or Val.

In certain embodiments, the third polypeptide comprises the amino acid sequence of (SEQ ID NO: 92)

$X_1$ASLP$X_2$LQKESVFQSGAHAYRIPALLYLPGQQSLLAFAEQRASKKDEH

AELIVLRRGDYDAPTHQVQWQAQEVVAQARLDGHRSMNPCPLYDAQTGTL

FLFFIAIPGQVTEQQQLQTRANVTRLCQVTSTDHGRTWSSPRDLTDAAIG

PAYREWSTFAVGPGHCLQLHDRARSLVVPAYAYRKLHP$X_3$QRPIPSAFCF

LSHDHGRTWARGHFVAQDTLECQVAEVETGEQRVVTLNARSHLRARVQAQ

STNDGLDFQESQLVKKLVEPPPQGCQGSVISFPSPRSGPGSPAQWLLYTH

PTHSWQRADLGAYLNPRPPAPEAWSEPVLLAKGS$X_4$AYSDLQSMGTGPDG

SPLFGCLYEANDYEEIVFLMFTLKQAFPAEYLPQGGGGSGGGGSDKTHTC

PPCPAPELLGGPSVFLFPPKPKDTLMISRTPEVTCVVVDVSHEDPEVKFN

-continued

WYVDGVEVHNAKTKPREEQYNSTYRVVSVLTVLHQDWLNGKEYKCKVSNK

ALPAPIEKTISKAKGQPREPQVYTLPPSREEMTKNQVSLTCLVKGFYPSD

IAVEWESNGQPENNYKTTPPVLDSDGSFFLTSKLTVDKSRWQQGNVFSCS

VMHEALHNHYTQKSLSLSPGK, wherein $X_1$ is Ala, Arg, Asn, Asp, Gln, Glu, Gly, His, Leu, Lys, Met, Phe, Thr, Val, or not present, $X_2$ is Phe, Trp, Tyr or Val, $X_3$ is Arg, Ile, or Lys, and $X_4$ is Ala, Cys, Ser, or Val. In certain embodiments, $X_1$ is Ala, Asp, Met, or not present, $X_2$ is Tyr or Val, $X_3$ is Ile or Lys, and $X_4$ is Ala or Cys.

In certain embodiments, the first polypeptide comprises SEQ ID NO: 49, the second polypeptide comprises SEQ ID NO: 50, and the third polypeptide comprises SEQ ID NO: 51. In certain embodiments, the first polypeptide comprises SEQ ID NO: 49, the second polypeptide comprises SEQ ID NO: 50, and the third polypeptide comprises SEQ ID NO: 52. In certain embodiments, the first polypeptide comprises SEQ ID NO: 49, the second polypeptide comprises SEQ ID NO: 50, and the third polypeptide comprises SEQ ID NO: 53. In certain embodiments, the first polypeptide comprises SEQ ID NO: 49, the second polypeptide comprises SEQ ID NO: 50, and the third polypeptide comprises SEQ ID NO: 54. In certain embodiments, the first polypeptide comprises SEQ ID NO: 49, the second polypeptide comprises SEQ ID NO: 50, and the third polypeptide comprises SEQ ID NO: 63. In certain embodiments, the first polypeptide comprises SEQ ID NO: 49, the second polypeptide comprises SEQ ID NO: 50, and the third polypeptide comprises SEQ ID NO: 76. In certain embodiments, the first polypeptide comprises SEQ ID NO: 49, the second polypeptide comprises SEQ ID NO: 50, and the third polypeptide comprises SEQ ID NO: 77. In certain embodiments, the first polypeptide comprises SEQ ID NO: 49, the second polypeptide comprises SEQ ID NO: 50, and the third polypeptide comprises SEQ ID NO: 78. In certain embodiments, the first polypeptide comprises SEQ ID NO: 49, the second polypeptide comprises SEQ ID NO: 50, and the third polypeptide comprises SEQ ID NO: 79.

Figure 10C:
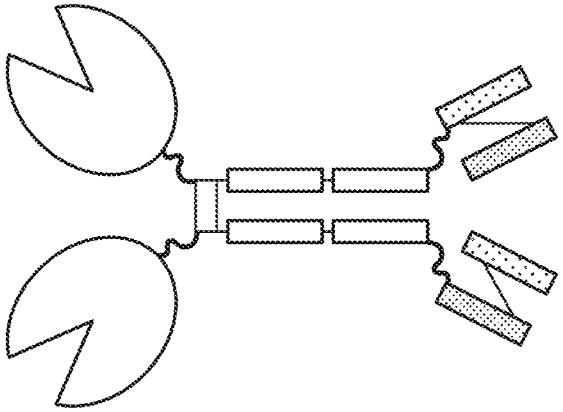

In certain embodiments, the antibody conjugate comprises a first polypeptide comprising a first sialidase, a first immunoglobulin Fc domain, and a first single chain variable fragment (scFv) (it is also understood that the scFv may be replaced by a first polypeptide chain of an immunoglobulin antigen binding fragment, e.g., Fab fragment); and a second polypeptide comprising a second sialidase, a second immunoglobulin Fc domain, and a second single chain variable fragment (scFv) (it is also understood that the scFv may be replaced by a second polypeptide chain of an immunoglobulin antigen binding fragment, e.g., Fab fragment). An example of this embodiment is shown in FIG. 10C. The first and second polypeptides can be covalently linked together. The covalent linkages can be disulfide bonds. In certain embodiments, the first scFv defines a first antigen-binding site, and the second scFv defines a second antigen-binding site. In certain embodiments, the first polypeptide comprises the first sialidase, the first immunoglobulin Fc domain, and the first scFv in an N- to C-terminal orientation. In certain embodiments, the first polypeptide comprises the first scFv, the first immunoglobulin Fc domain, and the first sialidase in an N- to C-terminal orientation. In certain embodiments, the second polypeptide comprises the second sialidase, the second immunoglobulin Fc domain, and the second scFv in an N- to C-terminal orientation. In certain embodiments, the second polypeptide comprises the second scFv, the second immunoglobulin Fc domain, and the second sialidase in an N- to C-terminal orientation.

In certain embodiments, the first polypeptide comprises the amino acid sequence of SEQ ID NO: 43, SEQ ID NO: 44, SEQ ID NO: 45, SEQ ID NO: 46, SEQ ID NO: 47, SEQ ID NO: 48, SEQ ID NO: 74, or SEQ ID NO: 75, or an amino acid sequence that has at least 85%, 90%, 95%, 96%, 97%, 98%, or 99% sequence identity to SEQ ID NO: 43, SEQ ID NO: 44, SEQ ID NO: 45, SEQ ID NO: 46, SEQ ID NO: 47, SEQ ID NO: 48, SEQ ID NO: 74, or SEQ ID NO: 75. In certain embodiments, the second polypeptide comprises the amino acid sequence of SEQ ID NO: 43, SEQ ID NO: 44, SEQ ID NO: 45, SEQ ID NO: 46, SEQ ID NO: 47, SEQ ID NO: 48, SEQ ID NO: 74, or SEQ ID NO: 75, or an amino acid sequence that has at least 85%, 90%, 95%, 96%, 97%, 98%, or 99% sequence identity to SEQ ID NO: 43, SEQ ID NO: 44, SEQ ID NO: 45, SEQ ID NO: 46, SEQ ID NO: 47, SEQ ID NO: 48, SEQ ID NO: 74, or SEQ ID NO: 75.

In certain embodiments, the first and/or second polypeptide comprises the amino acid sequence of (SEQ ID NO: 102)

$X_1X_2SX_3PX_4$LQKESVFQSGAHAYRIPALLYLPGQQSLLAFAEQRASKKD

EHAELIVLRRGDYDAPTHQVQWQAQEVVAQARLDGHRSMNPCPLYDAQTG

TLFLFFIAIPGQVTEQQQLQTRANVTRL$X_5$QVTSTDHGRTWSSPRDLTDA

AIGPAYREWSTFAVGPGHCLQLHDRARSLVVPAYAYRKLHP$X_6$QRPIPSA

F$X_7$FLSHDHGRTWARGHFVAQDTLECQVAEVETGEQRVVTLNARSHLRAR

VQAQSTNDGLDFQ$X_8$SQLVKKLVEPPPQG$X_9$QGSVISFPSPRSGPGSPAQ

WLLYTHPTHSWQRADLGAYLNPRPPAPEAWSEP$X_{10}$LLAKGS$X_{11}$AYSDL

QSMGTGPDGSPLFG$X_{12}$LYEANDYEEIVFLMFTLKQAFPAEYLPQGGGGS

GGGGSDKTHTCPPCPAPELLGGPSVFLFPPKPKDTLMISRTPEVTCVVVD

VSHEDPEVKFNWYVDGVEVHNAKTKPREEQYNSTYRVVSVLTVLHQDWLN

GKEYKCKVSNKALPAPIEKTISKAKGQPREPQVYTLPPSREEMTKNQVSL

TCLVKGFYPSDIAVEWESNGQPENNYKTTPPVLDSDGSFFLYSKLTVDKS

RWQQGNVFSCSVMHEALHNHYTQKSLSLSPGKGGGGSGGGGSGGGGSEVQ

LVESGGGLVQPGGSLRLSCAASGFNIKDTYIHWVRQAPGKGLEWVARIYP

TNGYTRYADSVKGRFTISADTSKNTAYLQMNSLRAEDTAVYYCSRWGGDG

FYAMDYWGQGTLVTVSSGGGGSGGGGSGGGGSDIQMTQSPSSLSASVGDR

VTITCRASQDVNTAVAWYQQKPGKAPKLLIYSASFLYSGVPSRFSGSRSG

TDFTLTISSLQPEDFATYYCQQHYTTPPTFGQGTKVEIK, wherein $X_1$ is Ala, Arg, Asn, Asp, Gln, Glu, Gly, His, Leu, Lys, Met, Phe, Thr, Val, or not present, $X_2$ is Ala or Lys, $X_3$ is Asn or Leu, $X_4$ is Phe, Trp, Tyr or Val, $X_5$ is Ala, Cys, Ile, Ser, or Val, $X_6$ is Arg, Ile, or Lys, $X_7$ is Ala, Cys, Leu, or Val, $X_8$ is Glu or Lys, $X_9$ is Cys or Val, $X_{10}$ is Lys or Val, $X_{11}$ is Ala, Cys, Ser, or Val, and $X_{12}$ is Cys, Leu, or Val.

In certain embodiments, the first and/or second polypeptide comprises the amino acid sequence of (SEQ ID NO: 93)

$X_1$ASLP$X_2$LQKESVFQSGAHAYRIPALLYLPGQQSLLAFAEQRASKKDEH

AELIVLRRGDYDAPTHQVQWQAQEVVAQARLDGHRSMNPCPLYDAQTGTL

-continued

FLFFIAIPGQVTEQQQLQTRANVTRLCQVTSTDHGRTWSSPRDLTDAAIG

PAYREWSTFAVGPGHCLQLHDRARSLVVPAYAYRKLHP$X_3$QRPIPSAFCF

LSHDHGRTWARGHFVAQDTLECQVAEVETGEQRVVTLNARSHLRARVQAQ

STNDGLDFQESQLVKKLVEPPPQGCQGSVISFPSPRSGPGSPAQWLLYTH

PTHSWQRADLGAYLNPRPPAPEAWSEPVLLAKGS$X_4$AYSDLQSMGTGPDG

SPLFGCLYEANDYEEIVFLMFTLKQAFPAEYLPQGGGGSGGGGSDKTHTC

PPCPAPELLGGPSVFLFPPKPKDTLMISRTPEVTCVVVDVSHEDPEVKFN

WYVDGVEVHNAKTKPREEQYNSTYRVVSVLTVLHQDWLNGKEYKCKVSNK

ALPAPIEKTISKAKGQPREPQVYTLPPSREEMTKNQVSLTCLVKGFYPSD

IAVEWESNGQPENNYKTTPPVLDSDGSFFLYSKLTVDKSRWQQGNVFSCS

VMHEALHNHYTQKSLSLSPGKGGGGSGGGGSGGGGSEVQLVESGGGLVQP

GGSLRLSCAASGFNIKDTYIHWVRQAPGKGLEWVARIYPTNGYTRYADSV

KGRFTISADTSKNTAYLQMNSLRAEDTAVYYCSRWGGDGFYAMDYWGQGT

LVTVSSGGGGSGGGGSGGGGSDIQMTQSPSSLSASVGDRVTITCRASQDV

NTAVAWYQQKPGKAPKLLIYSASFLYSGVPSRFSGSRSGTDFTLTISSLQ

PEDFATYYCQQHYTTPPTFGQGTKVEIK, wherein $X_1$ is Ala, Arg, Asn, Asp, Gln, Glu, Gly, His, Leu, Lys, Met, Phe, Thr, Val, or not present, $X_2$ is Phe, Trp, Tyr or Val, $X_3$ is Arg, Ile, or Lys, and $X_4$ is Ala, Cys, Ser, or Val. In certain embodiments, $X_1$ is Ala, Asp, Met, or not present, $X_2$ is Tyr or Val, $X_3$ is Ile or Lys, and $X_4$ is Ala or Cys.

In certain embodiments, the first and second polypeptide comprise SEQ ID NO: 43. In certain embodiments, the first and second polypeptide comprise SEQ ID NO: 44. In certain embodiments, the first and second polypeptide comprise SEQ ID NO: 45. In certain embodiments, the first and second polypeptide comprise SEQ ID NO: 46. In certain embodiments, the first and second polypeptide comprise SEQ ID NO: 47. In certain embodiments, the first and second polypeptide comprise SEQ ID NO: 48. In certain embodiments, the first and second polypeptide comprise SEQ ID NO: 74. In certain embodiments, the first and second polypeptide comprise SEQ ID NO: 75.

In certain embodiments, the antibody conjugate has a molecular weight from about 135 kDa to about 165 kDa, e.g., about 140 kDa. In other embodiments, the antibody conjugate has a molecular weight from about 215 kDa to about 245 kDa, e.g., about 230 kDa.

In certain embodiments, the antibody conjugate comprises two polypeptides that each comprise an immunoglobulin Fc domain, and the first polypeptide has either a "knob" mutation, e.g., T366Y, or a "hole" mutation, e.g., Y407T, for heterodimerization with the second polypeptide, and the second polypeptide has either a respective "knob" mutation, e.g., T366Y, or a "hole" mutation, e.g., Y407T, for heterodimerization with the first polypeptide (residue numbers according to EU numbering, Kabat, E. A., et al. (1991) supra). For example, in certain embodiments, the antibody comprises two polypeptides that each comprise an immunoglobulin Fc domain derived from human IgG1 Fc domain, and the first polypeptide comprises a Y407T mutation (e.g., the first polypeptide comprises SEQ ID NO: 32), and the second polypeptide comprises a T366Y mutation (e.g., the second polypeptide comprises SEQ ID NO: 33).

As used herein, the term "multispecific antibody" is understood to mean an antibody that specifically binds to at least two different antigens, i.e., an antibody that comprises at least two antigen-binding sites that bind to at least two different antigens. As used herein, the term "bispecific antibody" is understood to mean an antibody that specifically binds to two different antigens, i.e., an antibody that comprises two antigen-binding sites each of which bind to separate and distinct antigens. In other words, a first binding site binds a first antigen and a second binding site binds a second, different antigen. A multispecific or bispecific antibody may, for example, be a human or humanized antibody, and/or be a full length antibody or an antibody fragment (e.g., a $F(ab')_2$ bispecific antibody).

The present invention encompasses antibody conjugates comprising antibody fragments, which may be generated by traditional means, such as enzymatic digestion, or by recombinant techniques. For a review of certain antibody fragments, see Hudson et al. (2003) supra.

In certain embodiments, the antibody conjugate or fusion protein can be covalently or non-covalently associated with a biological modifier, wherein the biological modifier can be used to enhance the solubility of the antibody, increase binding specificity, decrease immunogenicity or toxicity or modify the pharmacokinetic profile of the antibody. For example, the biological modifier can be used to increase the molecular weight of the antibody to increase its circulating half-life.

It is contemplated that the antibody conjugate or fusion protein may be covalently bound to one or more (for example, 2, 3, 4, 5, 6, 8, 9, 10 or more) biological modifiers that may comprise linear or branched polymers. Exemplary biological modifiers may include, for example, a variety of polymers, such as those described in U.S. Pat. No. 7,842,789. Particularly useful are polyalkylene ethers such as polyethylene glycol (PEG) and derivatives thereof (for example, alkoxy polyethylene glycol, for example, methoxypolyethylene glycol, ethoxypolyethylene glycol and the like); block copolymers of polyoxyethylene and polyoxypropylene (Pluronics); polymethacrylates; carbomers; and branched or unbranched polysaccharides which comprise the saccharide monomers such as D-mannose, D- and L-galactose, fucose, fructose, D-xylose, L-arabinose, and D-glucuronic acid.

In other embodiments, the biological modifier can be a hydrophilic polyvinyl polymer such as polyvinyl alcohol and polyvinylpyrrolidone (PVP)-type polymers. The biological modifier can be a functionalized polyvinylpyrrolidone, for example, carboxy or amine functionalized on one (or both) ends of the polymer (as available from PolymerSource). Alternatively, the biological modifier can include Poly N-(2-hydroxypropyl)methacrylamide (HPMA), or functionalized HPMA (amine, carboxy, etc.), Poly(N-isopropylacrylamide) or functionalized poly(N-isopropylacrylamide). Alternatively, the biological modifier can include Poly N-(2-hydroxypropyl)methacrylamide (HPMA), or functionalized HPMA (amine, carboxy, etc.), Poly(N-isopropylacrylamide) or functionalized poly(N-isopropylacrylamide). The modifier prior to conjugation need not be, but preferably is, water soluble, but the final conjugate should be water soluble.

In general, the biological modifier may have a molecular weight from about 2 kDa to about 5 kDa, from about 2 kDa to about 10 kDa, from about 2 kDa to about 20 kDa, from about 2 kDa to about 30 kDa, from about 2 kDa to about 40 kDa, from about 2 kDa to about 50 kDa, from about 2 kDa to about 60 kDa, from about 2 kDa to about 70 kDa, from about 2 kDa to about 80 kDa, from about 2 kDa to about 90 kDa, from about 2 kDa to about 100 kDa, from about 2 kDa to about 150 kDa, from about 5 kDa to about 10 kDa, from about 5 kDa to about 20 kDa, from about 5 kDa to about 30 kDa, from about 5 kDa to about 40 kDa, from about 5 kDa to about 50 kDa, from about 5 kDa to about 60 kDa, from about 5 kDa to about 70 kDa, from about 5 kDa to about 80 kDa, from about 5 kDa to about 90 kDa, from about 5 kDa to about 100 kDa, from about 5 kDa to about 150 kDa, from about 10 kDa to about 20 kDa, from about 10 kDa to about 30 kDa, from about 10 kDa to about 40 kDa, from about 10 kDa to about 50 kDa, from about 10 kDa to about 60 kDa, from about 10 kDa to about 70 kDa, from about 10 kDa to about 80 kDa, from about 10 kDa to about 90 kDa, from about 10 kDa to about 100 kDa, from about 10 kDa to about 150 kDa, from about 20 kDa to about 30 kDa, from about 20 kDa to about 40 kDa, from about 20 kDa to about 50 kDa, from about 20 kDa to about 60 kDa, from about 20 kDa to about 70 kDa, from about 20 kDa to about 80 kDa, from about 20 kDa to about 90 kDa, from about 20 kDa to about 100 kDa, from about 20 kDa to about 150 kDa, from about 30 kDa to about 40 kDa, from about 30 kDa to about 50 kDa, from about 30 kDa to about 60 kDa, from about 30 kDa to about 70 kDa, from about 30 kDa to about 80 kDa, from about 30 kDa to about 90 kDa, from about 30 kDa to about 100 kDa, from about 30 kDa to about 150 kDa, from about 40 kDa to about 50 kDa, from about 40 kDa to about 60 kDa, from about 40 kDa to about 70 kDa, from about 40 kDa to about 80 kDa, from about 40 kDa to about 90 kDa, from about 40 kDa to about 100 kDa, from about 40 kDa to about 150 kDa, from about 50 kDa to about 60 kDa, from about 50 kDa to about 70 kDa, from about 50 kDa to about 80 kDa, from about 50 kDa to about 90 kDa, from about 50 kDa to about 100 kDa, from about 50 kDa to about 150 kDa, from about 60 kDa to about 70 kDa, from about 60 kDa to about 80 kDa, from about 60 kDa to about 90 kDa, from about 60 kDa to about 100 kDa, from about 60 kDa to about 150 kDa, from about 70 kDa to about 80 kDa, from about 70 kDa to about 90 kDa, from about 70 kDa to about 100 kDa, from about 70 kDa to about 150 kDa, from about 80 kDa to about 90 kDa, from about 80 kDa to about 100 kDa, from about 80 kDa to about 150 kDa, from about 90 kDa to about 100 kDa, from about 90 kDa to about 150 kDa, or from about 100 kDa to about 150 kDa.

It is contemplated that the antibody conjugate or fusion protein is attached to about 10 or fewer polymer molecules (e.g., 9, 8, 7, 6, 5, 4, 3, 2, or 1), each polymer molecule having a molecular weight of at least about 20,000 D, or at least about 30,000 D, or at least about 40,000 D.

Although a variety of polymers can be used as biological modifiers, it is contemplated that the antibody conjugates or fusion proteins described herein may be attached to polyethylene glycol (PEG) polymers. In one embodiment, the antibody conjugate or fusion protein described herein is covalently attached to at least one PEG having an actual MW of at least about 20,000 D. In another embodiment, the antibody conjugate or fusion protein described herein is covalently attached to at least one PEG having an actual MW of at least about 30,000 D. In another embodiment, the antibody conjugate or fusion protein described herein is covalently attached to at least one PEG having an actual MW of at least about 40,000 D. In certain embodiments, the PEG is methoxyPEG (5000)-succinimidylpropionate (mPEG-SPA), methoxyPEG (5000)-succinimidylsuccinate (mPEG-SS). Such PEGS are commercially available from Nektar Therapeutics or SunBiowest.

Attachment sites on an antibody conjugate or fusion protein for a biological modifier include the N-terminal amino group and epsilon amino groups found on lysine residues, as well as other amino, imino, carboxyl, sulfhydryl, hydroxyl or other hydrophilic groups. The polymer may be covalently bonded directly to the antibody conjugate or fusion protein with or without the known use of a multifunctional (ordinarily bifunctional) crosslinking agent using chemistries and used in the art. For example, sulfhydryl groups can be derivatized by coupling to maleimido-substituted PEG (e.g. alkoxy-PEG amine plus sulfosuccinimidyl 4-(N-maleimidomethyl)cyclohexane-1-carboxylate), or PEG-maleimide commercially available from Shearwater Polymers, Inc., Huntsville, Ala.).

III. Methods of Making a Recombinant Human Sialidase, Fusion Protein, or Antibody Conjugate Methods for producing recombinant human sialidases, fusion proteins, e.g., those disclosed herein, antibodies, or antibody conjugates, e.g., those disclosed herein, are known in the art. For example, DNA molecules encoding light chain variable regions and/or heavy chain variable regions can be synthesized chemically or by recombinant DNA methodologies. For example, the sequences of the antibodies can be cloned from hybridomas by conventional hybridization techniques or polymerase chain reaction (PCR) techniques, using the appropriate synthetic nucleic acid primers. The resulting DNA molecules encoding the variable regions of interest can be ligated to other appropriate nucleotide sequences, including, for example, constant region coding sequences, and expression control sequences, to produce conventional gene expression constructs (i.e., expression vectors) encoding the desired antibodies. Production of defined gene constructs is within routine skill in the art.

Nucleic acids encoding desired recombinant human sialidases, fusion proteins, and/or antibody conjugates can be incorporated (ligated) into expression vectors, which can be introduced into host cells through conventional transfection or transformation techniques. Exemplary host cells are *E. coli* cells, Chinese hamster ovary (CHO) cells, human embryonic kidney 293 (HEK 293) cells, HeLa cells, baby hamster kidney (BHK) cells, monkey kidney cells (COS), human hepatocellular carcinoma cells (e.g., Hep G2), and myeloma cells that do not otherwise produce IgG protein. Transformed host cells can be grown under conditions that permit the host cells to express the genes that encode the immunoglobulin light and/or heavy chain variable regions.

Specific expression and purification conditions will vary depending upon the expression system employed. For example, if a gene is to be expressed in *E. coli*, it is first cloned into an expression vector by positioning the engineered gene downstream from a suitable bacterial promoter, e.g., Trp or Tac, and a prokaryotic signal sequence. The expressed protein may be secreted. The expressed protein may accumulate in refractile or inclusion bodies, which can be harvested after disruption of the cells by French press or sonication. The refractile bodies then are solubilized, and the protein may be refolded and/or cleaved by methods known in the art.

If the engineered gene is to be expressed in eukaryotic host cells, e.g., CHO cells, it is first inserted into an expression vector containing a suitable eukaryotic promoter, a secretion signal, a poly A sequence, and a stop codon. Optionally, the vector or gene construct may contain enhancers and introns. In embodiments involving fusion proteins comprising an antibody or portion thereof, the expression vector optionally contains sequences encoding all or part of a constant region, enabling an entire, or a part of, a heavy or light chain to be expressed. The gene construct can be introduced into eukaryotic host cells using conventional techniques.

The host cells express a recombinant human sialidase or a fusion protein and/or antibody conjugate comprising a sialidase and $V_L$ or $V_H$ fragments, $V_L$-$V_H$ heterodimers, $V_H$-$V_L$ or $V_L$-$V_H$ single chain polypeptides, complete heavy or light immunoglobulin chains, or portions thereof, each of which may be attached to a moiety having another function (e.g., cytotoxicity). In some embodiments involving fusion proteins and/or antibody conjugates, a host cell is transfected with a single vector expressing a polypeptide expressing a sialidase and an entire, or part of, a heavy chain (e.g., a heavy chain variable region) or a sialidase and a light chain (e.g., a light chain variable region), or a polypeptide expressing an entire, or part of, a heavy chain (e.g., a heavy chain variable region) or a light chain (e.g., a light chain variable region). In some embodiments, a host cell is transfected with a single vector encoding (a) a polypeptide comprising a heavy chain variable region and a polypeptide comprising a light chain variable region, or (b) an entire immunoglobulin heavy chain and an entire immunoglobulin light chain, wherein in (a) or in (b), the polypeptide may also comprise a sialidase. In some embodiments, a host cell is co-transfected with more than one expression vector (e.g., one expression vector expressing a polypeptide comprising an entire, or part of, a heavy chain or heavy chain variable region, optionally comprising a sialidase fused thereto, and another expression vector expressing a polypeptide comprising an entire, or part of, a light chain or light chain variable region, optionally comprising a sialidase fused thereto).

A polypeptide comprising a sialidase or a fusion protein, e.g., a fusion protein comprising an immunoglobulin heavy chain variable region or light chain variable region, can be produced by growing (culturing) a host cell transfected with an expression vector encoding such a variable region, under conditions that permit expression of the polypeptide. Following expression, the polypeptide can be harvested and purified or isolated using techniques known in the art, e.g., affinity tags such as glutathione-S-transferase (GST) or histidine tags.

In embodiments in which a fusion protein and/or antibody conjugate is produced, a sialidase fused to a monoclonal antibody, Fc domain, or an antigen-binding domain of the antibody, can be produced by growing (culturing) a host cell transfected with: (a) an expression vector that encodes a complete or partial immunoglobulin heavy chain, and a separate expression vector that encodes a complete or partial immunoglobulin light chain; or (b) a single expression vector that encodes both chains (e.g., complete or partial heavy and light chains), under conditions that permit expression of both chains. The sialidase will be fused to one or more of the chains. The intact fusion protein and/or antibody conjugate can be harvested and purified or isolated using techniques known in the art, e.g., Protein A, Protein G, affinity tags such as glutathione-S-transferase (GST) or histidine tags. It is within ordinary skill in the art to express the heavy chain and the light chain from a single expression vector or from two separate expression vectors.

In certain embodiments, in order to express a protein, e.g., a recombinant human sialidase, as a secreted protein, a native N-terminal signal sequence of the protein is replaced, e.g., with MDMRVPAQLLGLLLLWLPGARC (SEQ ID NO: 28). In certain embodiments, to express a protein, e.g., a recombinant human sialidase, as a secreted protein, an N-terminal signal sequence, e.g., MDMRVPAQLLGLLLL- WLPGARC (SEQ ID NO: 28), is added. Additional exemplary N-terminal signal sequences include signal sequences from interleukin-2, CD-5, IgG kappa light chain, trypsinogen, serum albumin, and prolactin. In certain embodiments, in order to express a protein, e.g., a recombinant human sialidase, as a secreted protein, a C terminal lysosomal signal motif, e.g., YGTL (SEQ ID NO: 29) is removed.

Methods for reducing or eliminating the antigenicity of antibodies and antibody fragments are known in the art. When the antibodies are to be administered to a human, the antibodies preferably are "humanized" to reduce or eliminate antigenicity in humans. Preferably, each humanized antibody has the same or substantially the same affinity for the antigen as the non-humanized mouse antibody from which it was derived.

In one humanization approach, chimeric proteins are created in which mouse immunoglobulin constant regions are replaced with human immunoglobulin constant regions. See, e.g., Morrison et al., 1984, Proc. Nat. Acad. Sci. 81:6851-6855, Neuberger et al., 1984, Nature 312:604-608; U.S. Pat. No. 6,893,625 (Robinson); U.S. Pat. No. 5,500,362 (Robinson); and U.S. Pat. No. 4,816,567 (Cabilly).

In an approach known as CDR grafting, the CDRs of the light and heavy chain variable regions are grafted into frameworks from another species. For example, murine CDRs can be grafted into human FRs. In some embodiments, the CDRs of the light and heavy chain variable regions of an antibody are grafted into human FRs or consensus human FRs. To create consensus human FRs, FRs from several human heavy chain or light chain amino acid sequences are aligned to identify a consensus amino acid sequence. CDR grafting is described in U.S. Pat. No. 7,022,500 (Queen); U.S. Pat. No. 6,982,321 (Winter); U.S. Pat. No. 6,180,370 (Queen); U.S. Pat. No. 6,054,297 (Carter); U.S. Pat. No. 5,693,762 (Queen); U.S. Pat. No. 5,859,205 (Adair); U.S. Pat. No. 5,693,761 (Queen); U.S. Pat. No. 5,565,332 (Hoogenboom); U.S. Pat. No. 5,585,089 (Queen); U.S. Pat. No. 5,530,101 (Queen); Jones et al. (1986) NATURE 321: 522-525; Riechmann et al. (1988) Nature 332: 323-327; Verhoeyen et al. (1988) Science 239: 1534-1536; and Winter (1998) Febs Lett 430: 92-94.

In an approach called "SUPERHUMANIZATION™," human CDR sequences are chosen from human germline genes, based on the structural similarity of the human CDRs to those of the mouse antibody to be humanized. See, e.g., U.S. Pat. No. 6,881,557 (Foote); and Tan et al., 2002, J. Immunol. 169:1119-1125.

Other methods to reduce immunogenicity include "reshaping," "hyperchimerization," and "veneering/resurfacing." See, e.g., Vaswami et al., 1998, Annals Of Allergy, Asthma, & Immunol. 81:105; Roguska et al., 1996, Prot. Engineer 9:895-904; and U.S. Pat. No. 6,072,035 (Hardman). In the veneering/resurfacing approach, the surface accessible amino acid residues in the murine antibody are replaced by amino acid residues more frequently found at the same positions in a human antibody. This type of antibody resurfacing is described, e.g., in U.S. Pat. No. 5,639,641 (Pedersen).

Another approach for converting a mouse antibody into a form suitable for medical use in humans is known as ACTIVMAB™ technology (Vaccinex, Inc., Rochester, N.Y.), which involves a vaccinia virus-based vector to express antibodies in mammalian cells. High levels of combinatorial diversity of IgG heavy and light chains can be produced. See, e.g., U.S. Pat. No. 6,706,477 (Zauderer); U.S. Pat. No. 6,800,442 (Zauderer); and U.S. Pat. No. 6,872,518 (Zauderer). Another approach for converting a mouse antibody into a form suitable for use in humans is technology practiced commercially by KaloBios Pharmaceuticals, Inc. (Palo Alto, Calif.). This technology involves the use of a proprietary human "acceptor" library to produce an "epitope focused" library for antibody selection. Another approach for modifying a mouse antibody into a form suitable for medical use in humans is HUMAN ENGINEERING™ technology, which is practiced commercially by XOMA (US) LLC. See, e.g., International (PCT) Publication No. WO 93/11794 and U.S. Pat. No. 5,766,886 (Studnicka); U.S. Pat. No. 5,770,196 (Studnicka); U.S. Pat. No. 5,821,123 (Studnicka); and U.S. Pat. No. 5,869,619 (Studnicka).

Any suitable approach, including any of the above approaches, can be used to reduce or eliminate human immunogenicity of an antibody.

In addition, it is possible to create fully human antibodies in mice. Fully human mAbs lacking any non-human sequences can be prepared from human immunoglobulin transgenic mice by techniques referenced in, e.g., Lonberg et al., Nature 368:856-859, 1994; Fishwild et al., Nature Biotechnology 14:845-851, 1996; and Mendez et al., Nature Genetics 15:146-156, 1997. Fully human monoclonal antibodies can also be prepared and optimized from phage display libraries by techniques referenced in, e.g., Knappik et al., J. Mol. Biol. 296:57-86, 2000; and Krebs et al., J. Immunol. Meth. 254:67-84 2001).

The present invention encompasses fusion proteins comprising antibody fragments, which may be generated by traditional means, such as enzymatic digestion, or by recombinant techniques. For a review of certain antibody fragments, see Hudson et al. (2003) Nat. Med. 9:129-134.

Various techniques have been developed for the production of antibody fragments. Traditionally, these fragments were derived via proteolytic digestion of intact antibodies (see, e.g., Morimoto et al. (1992) Journal of Biochemical and Biophysical Methods 24:107-117; and Brennan et al. (1985) Science 229:81). However, these fragments can now be produced directly by recombinant host cells. Fab, Fv and ScFv antibody fragments can all be expressed in and secreted from *E. coli*, thus allowing the facile production of large amounts of these fragments. Antibody fragments can be isolated from the antibody phage libraries. Alternatively, Fab'-SH fragments can be directly recovered from *E. coli* and chemically coupled to form $F(ab')_2$ fragments (Carter et al. (1992) Bio/Technology 10:163-167). According to another approach, $F(ab')_2$ fragments can be isolated directly from recombinant host cell culture. Fab and $F(ab')_2$ fragments with increased in vivo half-life comprising salvage receptor binding epitope residues are described in U.S. Pat. No. 5,869,046. Other techniques for the production of antibody fragments will be apparent to the skilled practitioner. In certain embodiments, an antibody is a single chain Fv fragment (scFv). See U.S. Pat. Nos. 5,571,894 and 5,587,458.

Methods for making bispecific antibodies are known in the art. See Milstein and Cuello (1983) Nature 305:537, International (PCT) Publication No. WO93/08829, and Traunecker et al. (1991) EMBO J., 10:3655. For further details of generating bispecific antibodies see, for example, Suresh et al. (1986) Methods Enzymol. 121:210. Bispecific antibodies include cross-linked or "heteroconjugate" or "heterodimer" antibodies. For example, one of the antibodies in the heterodimer can be coupled to avidin, the other to biotin. Heterodimer antibodies may be made using any convenient cross-linking method. Suitable cross-linking agents are well known in the art, and are disclosed in U.S. Pat. No. 4,676,980, along with a number of cross-linking techniques.

Examples of heterodimeric or asymmetric IgG-like molecules include but are not limited to those obtained with the following technologies or using the following formats: Triomab/Quadroma, Knobs-into-Holes, CrossMabs, electrostatically-matched antibodies, LUZ-Y, Strand Exchange Engineered Domain body, Biclonic and DuoBody.

Advantages of using antibody fragments (e.g., F(ab) and $F(ab')_2$ fragments) include the elimination of non-specific binding between Fc portions of antibodies and Fc receptors on cells (such as macrophages, dendritic cells, neutrophils, NK cells and B cells). In addition, they may be able to penetrate tissues more efficiently due to their smaller size.

Heterodimeric antibodies, or asymmetric antibodies, allow for greater flexibility and new formats for attaching a variety of drugs to the antibody arms. One of the general formats for creating a heterodimeric antibody is the "knobs-into-holes" format. This format is specific to the heavy chain part of the constant region in antibodies. The "knobs" part is engineered by replacing a small amino acid with a larger one, which fits into a "hole", which is engineered by replacing a large amino acid with a smaller one. What connects the "knobs" to the "holes" are the disulfide bonds between each chain. The "knobs-into-holes" shape facilitates antibody dependent cell mediated cytotoxicity. Single chain variable fragments (scFv) are connected to the variable domain of the heavy and light chain via a short linker peptide. The linker is rich in glycine, which gives it more flexibility, and serine/threonine, which gives it specificity. Two different scFv fragments can be connected together, via a hinge region, to the constant domain of the heavy chain or the constant domain of the light chain. This gives the antibody bispecificity, allowing for the binding specificities of two different antigens. The "knobs-into-holes" format enhances heterodimer formation but doesn't suppress homodimer formation.

Several approaches to support heterodimerization have been described, for example in International (PCT) Publication Nos. WO96/27011, WO98/050431, WO2007/110205, WO2007/147901, WO2009/089004, WO2010/129304, WO2011/90754, WO2011/143545, WO2012/058768, WO2013/157954, and WO2013/096291, and European Patent Publication No. EP1870459. Typically, in the approaches known in the art, the $CH_3$ domain of the first heavy chain and the $CH_3$ domain of the second heavy chain are both engineered in a complementary manner so that the heavy chain comprising one engineered $CH_3$ domain can no longer homodimerize with another heavy chain of the same structure (e.g. a $CH_3$-engineered first heavy chain can no longer homodimerize with another $CH_3$-engineered first heavy chain; and a $CH_3$-engineered second heavy chain can no longer homodimerize with another $CH_3$-engineered second heavy chain). Thereby the heavy chain comprising one engineered $CH_3$ domain is forced to heterodimerize with another heavy chain comprising the $CH_3$ domain, which is engineered in a complementary manner. As a result, the $CH_3$ domain of the first heavy chain and the $CH_3$ domain of the second heavy chain are engineered in a complementary manner by amino acid substitutions, such that the first heavy chain and the second heavy chain are forced to heterodimerize, whereas the first heavy chain and the second heavy chain can no longer homodimerize (e.g., for steric reasons).

IV. Pharmaceutical Compositions

For therapeutic use, a recombinant human sialidase or a fusion protein and/or antibody conjugate thereof preferably is combined with a pharmaceutically acceptable carrier. The term "pharmaceutically acceptable" as used herein refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The term "pharmaceutically acceptable carrier" as used herein refers to buffers, carriers, and excipients suitable for use in contact with the tissues of human beings and animals without excessive toxicity, irritation, allergic response, or other problem or complication, commensurate with a reasonable benefit/risk ratio. Pharmaceutically acceptable carriers include any of the standard pharmaceutical carriers, such as a phosphate buffered saline solution, water, emulsions (e.g., such as an oil/water or water/oil emulsions), and various types of wetting agents. The compositions also can include stabilizers and preservatives. For examples of carriers, stabilizers and adjuvants, see, e.g., Martin, Remington's Pharmaceutical Sciences, 15th Ed., Mack Publ. Co., Easton, Pa. [1975]. Pharmaceutically acceptable carriers include buffers, solvents, dispersion media, coatings, isotonic and absorption delaying agents, and the like, that are compatible with pharmaceutical administration. The use of such media and agents for pharmaceutically active substances is known in the art.

In certain embodiments, a pharmaceutical composition may contain formulation materials for modifying, maintaining or preserving, for example, the pH, osmolarity, viscosity, clarity, color, isotonicity, odor, sterility, stability, rate of dissolution or release, adsorption or penetration of the composition. In such embodiments, suitable formulation materials include, but are not limited to, amino acids (such as glycine, glutamine, asparagine, arginine or lysine); antimicrobials; antioxidants (such as ascorbic acid, sodium sulfite or sodium hydrogen-sulfite); buffers (such as borate, bicarbonate, Tris-HCl, citrates, phosphates or other organic acids); bulking agents (such as mannitol or glycine); chelating agents (such as ethylenediamine tetraacetic acid (EDTA)); complexing agents (such as caffeine, polyvinylpyrrolidone, beta-cyclodextrin or hydroxypropyl-beta-cyclodextrin); fillers; monosaccharides; disaccharides; and other carbohydrates (such as glucose, mannose or dextrins); proteins (such as serum albumin, gelatin or immunoglobulins); coloring, flavoring and diluting agents; emulsifying agents; hydrophilic polymers (such as polyvinylpyrrolidone); low molecular weight polypeptides; salt-forming counterions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as pluronics, PEG, sorbitan esters, polysorbates such as polysorbate 20, polysorbate, triton, tromethamine, lecithin, cholesterol, tyloxapal); stability enhancing agents (such as sucrose or sorbitol); tonicity enhancing agents (such as alkali metal halides, preferably sodium or potassium chloride, mannitol sorbitol); delivery vehicles; diluents; excipients and/or pharmaceutical adjuvants (see, *Remington's Pharmaceutical Sciences,* 18th ed. (Mack Publishing Company, 1990).

In certain embodiments, a pharmaceutical composition may contain nanoparticles, e.g., polymeric nanoparticles, liposomes, or micelles (See Anselmo et al. (2016) Bioeng. Transl. Med. 1: 10-29).

In certain embodiments, a pharmaceutical composition may contain a sustained- or controlled-delivery formulation. Techniques for formulating sustained- or controlled-delivery means, such as liposome carriers, bio-erodible microparticles or porous beads and depot injections, are also known to those skilled in the art. Sustained-release preparations may include, e.g., porous polymeric microparticles or semi-permeable polymer matrices in the form of shaped articles, e.g., films, or microcapsules. Sustained release matrices may include polyesters, hydrogels, polylactides, copolymers of L-glutamic acid and gamma ethyl-L-glutamate, poly (2-hydroxyethyl-inethacrylate), ethylene vinyl acetate, or poly-D (−)-3-hydroxybutyric acid. Sustained release compositions may also include liposomes that can be prepared by any of several methods known in the art.

Pharmaceutical compositions containing a recombinant human sialidase, a recombinant human sialidase fusion protein, or an antibody conjugate disclosed herein can be presented in a dosage unit form and can be prepared by any suitable method. A pharmaceutical composition should be formulated to be compatible with its intended route of administration. Examples of routes of administration are intravenous (IV), intradermal, inhalation, transdermal, topical, transmucosal, intrathecal and rectal administration. In certain embodiments, a recombinant human sialidase, a recombinant human sialidase fusion protein, or an antibody conjugate disclosed herein is administered by IV infusion. In certain embodiments, a recombinant human sialidase, a recombinant human sialidase fusion protein, or an antibody conjugate disclosed herein is administered by intratumoral injection. Useful formulations can be prepared by methods known in the pharmaceutical art. For example, see Remington's Pharmaceutical Sciences, 18th ed. (Mack Publishing Company, 1990). Formulation components suitable for parenteral administration include a sterile diluent such as water for injection, saline solution, fixed oils, polyethylene glycols, glycerin, propylene glycol or other synthetic solvents; antibacterial agents such as benzyl alcohol or methyl parabens; antioxidants such as ascorbic acid or sodium bisulfite; chelating agents such as EDTA; buffers such as acetates, citrates or phosphates; and agents for the adjustment of tonicity such as sodium chloride or dextrose.

For intravenous administration, suitable carriers include physiological saline, bacteriostatic water, Cremophor EL™ (BASF, Parsippany, N.J.) or phosphate buffered saline (PBS). The carrier should be stable under the conditions of manufacture and storage, and should be preserved against microorganisms. The carrier can be a solvent or dispersion medium containing, for example, water, ethanol, polyol (for example, glycerol, propylene glycol, and liquid polyethylene glycol), and suitable mixtures thereof.

Pharmaceutical formulations preferably are sterile. Sterilization can be accomplished by any suitable method, e.g., filtration through sterile filtration membranes. Where the composition is lyophilized, filter sterilization can be conducted prior to or following lyophilization and reconstitution.

The compositions described herein may be administered locally or systemically. Administration will generally be parenteral administration. In a preferred embodiment, the pharmaceutical composition is administered subcutaneously and in an even more preferred embodiment intravenously. Preparations for parenteral administration include sterile aqueous or non-aqueous solutions, suspensions, and emulsions.

Generally, a therapeutically effective amount of active component, for example, a recombinant human sialidase or fusion protein and/or antibody conjugate thereof, is in the range of 0.1 mg/kg to 100 mg/kg, e.g., 1 mg/kg to 100 mg/kg, 1 mg/kg to 10 mg/kg. The amount administered will depend on variables such as the type and extent of disease or indication to be treated, the overall health of the patient, the in vivo potency of the antibody, the pharmaceutical formulation, and the route of administration. The initial dosage can be increased beyond the upper level in order to rapidly achieve the desired blood-level or tissue-level. Alternatively, the initial dosage can be smaller than the optimum, and the daily dosage may be progressively increased during the course of treatment. Human dosage can be optimized, e.g., in a conventional Phase I dose escalation study designed to run from 0.5 mg/kg to 20 mg/kg. Dosing frequency can vary, depending on factors such as route of administration, dosage amount, serum half-life of the recombinant human sialidase or fusion protein and/or antibody conjugate thereof, and the disease being treated. Exemplary dosing frequencies are once per day, once per week and once every two weeks. A preferred route of administration is parenteral, e.g., intravenous infusion. In certain embodiments, a recombinant human sialidase or a fusion protein and/or antibody conjugate thereof is lyophilized, and then reconstituted in buffered saline, at the time of administration.

V. Therapeutic Uses

The compositions and methods disclosed herein can be used to treat various forms of cancer in a subject or inhibit cancer growth in a subject. The invention provides a method of treating a cancer in a subject. The method comprises administering to the subject an effective amount of a recombinant human sialidase or a fusion protein and/or antibody conjugate thereof, e.g., a recombinant human sialidase, fusion protein, or antibody conjugate disclosed herein, either alone or in a combination with another therapeutic agent to treat the cancer in the subject. The term "effective amount" as used herein refers to the amount of an active agent (e.g., recombinant human sialidase or fusion protein thereof according to the present invention) sufficient to effect beneficial or desired results. An effective amount can be administered in one or more administrations, applications or dosages and is not intended to be limited to a particular formulation or administration route.

As used herein, "treat", "treating" and "treatment" mean the treatment of a disease in a subject, e.g., in a human. This includes: (a) inhibiting the disease, i.e., arresting its development; and (b) relieving the disease, i.e., causing regression of the disease state. As used herein, the terms "subject" and "patient" refer to an organism to be treated by the methods and compositions described herein. Such organisms preferably include, but are not limited to, mammals (e.g., murines, simians, equines, bovines, porcines, canines, felines, and the like), and more preferably includes humans.

Examples of cancers include solid tumors, soft tissue tumors, hematopoietic tumors and metastatic lesions. Examples of hematopoietic tumors include, leukemia, acute leukemia, acute lymphoblastic leukemia (ALL), B-cell, T-cell or FAB ALL, acute myeloid leukemia (AML), chronic myelocytic leukemia (CML), chronic lymphocytic leukemia (CLL), e.g., transformed CLL, diffuse large B-cell lymphomas (DLBCL), follicular lymphoma, hairy cell leukemia, myelodysplastic syndrome (MDS), a lymphoma, Hodgkin's disease, a malignant lymphoma, non-Hodgkin's lymphoma, Burkitt's lymphoma, multiple myeloma, or Richter's Syndrome (Richter's Transformation). Examples of solid tumors include malignancies, e.g., sarcomas, adenocarcinomas, and carcinomas, of the various organ systems, such as those affecting head and neck (including pharynx), thyroid, lung (small cell or non-small cell lung carcinoma (NSCLC)), breast, lymphoid, gastrointestinal (e.g., oral, esophageal, stomach, liver, pancreas, small intestine, colon and rectum, anal canal), genitals and genitourinary tract (e.g., renal, urothelial, bladder, ovarian, uterine, cervical, endometrial, prostate, testicular), CNS (e.g., neural or glial cells, e.g., neuroblastoma or glioma), or skin (e.g., melanoma).

In certain embodiments the cancer is an epithelial cancer, e.g., an epithelial cancer that upregulates the expression of sialylated glycans. Exemplary epithelial cancers include, but are not limited to, endometrial cancer, colon cancer, ovarian cancer, cervical cancer, vulvar cancer, uterine cancer or fallopian tube cancer, breast cancer, prostate cancer, lung cancer, pancreatic cancer, urinary cancer, bladder cancer, head and neck cancer, oral cancer and liver cancer. Epithelial cancers also include carcinomas, for example, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, baso squamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatiniforni carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypemephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, nasopharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tuberous carcinoma, verrucous carcinoma, and carcinoma villosum.

In certain embodiments, the cancer is breast cancer. In certain embodiments, the cancer is an adenocarcinoma. In certain embodiments, the cancer is a metastatic cancer. In certain embodiments, the cancer is a refractory cancer.

In certain embodiments, the cancer is resistant to or non-responsive to treatment with an antibody, e.g., an antibody with ADCC activity, e.g., trastuzumab.

The methods and compositions described herein can be used alone or in combination with other therapeutic agents and/or modalities. The term administered "in combination," as used herein, is understood to mean that two (or more) different treatments are delivered to the subject during the course of the subject's affliction with the disorder, such that the effects of the treatments on the patient overlap at a point in time. In certain embodiments, the delivery of one treatment is still occurring when the delivery of the second begins, so that there is overlap in terms of administration. This is sometimes referred to herein as "simultaneous" or "concurrent delivery." In other embodiments, the delivery of one treatment ends before the delivery of the other treatment begins. In certain embodiments of either case, the treatment is more effective because of combined administration. For example, the second treatment is more effective, e.g., an equivalent effect is seen with less of the second treatment, or the second treatment reduces symptoms to a greater extent, than would be seen if the second treatment were administered in the absence of the first treatment, or the analogous situation is seen with the first treatment. In certain embodiments, delivery is such that the reduction in a symptom, or other parameter related to the disorder is greater than what would be observed with one treatment delivered in the absence of the other. The effect of the two treatments can be partially additive, wholly additive, or greater than additive. The delivery can be such that an effect of the first treatment delivered is still detectable when the second is delivered.

In certain embodiments, a method or composition described herein, is administered in combination with one or more additional therapies, e.g., surgery, radiation therapy, or administration of another therapeutic preparation. In certain embodiments, the additional therapy may include chemotherapy, e.g., a cytotoxic agent. In certain embodiments the additional therapy may include a targeted therapy, e.g. a tyrosine kinase inhibitor, a proteasome inhibitor, or a protease inhibitor. In certain embodiments, the additional therapy may include an anti-inflammatory, anti-angiogenic, anti-fibrotic, or anti-proliferative compound, e.g., a steroid, a biologic immunomodulator, a monoclonal antibody, an antibody fragment, an aptamer, an siRNA, an antisense molecule, a fusion protein, a cytokine, a cytokine receptor, a bronchodialator, a statin, an anti-inflammatory agent (e.g. methotrexate), or an NSAID. In certain embodiments, the additional therapy may include a combination of therapeutics of different classes.

In certain embodiments, a method or composition described herein is administered in combination with a checkpoint inhibitor. The checkpoint inhibitor may, for example, be selected from a PD-1 antagonist, PD-L1 antagonist, CTLA-4 antagonist, adenosine A2A receptor antagonist, B7-H3 antagonist, B7-H4 antagonist, BTLA antagonist, KIR antagonist, LAG3 antagonist, TIM-3 antagonist, VISTA antagonist or TIGIT antagonist.

In certain embodiments, the checkpoint inhibitor is a PD-1 or PD-L1 inhibitor. PD-1 is a receptor present on the surface of T-cells that serves as an immune system checkpoint that inhibits or otherwise modulates T-cell activity at the appropriate time to prevent an overactive immune response. Cancer cells, however, can take advantage of this checkpoint by expressing ligands, for example, PD-L1, that interact with PD-1 on the surface of T-cells to shut down or modulate T-cell activity. Exemplary PD-1/PD-L1 based immune checkpoint inhibitors include antibody based therapeutics. Exemplary treatment methods that employ PD-1/PD-L1 based immune checkpoint inhibition are described in U.S. Pat. Nos. 8,728,474 and 9,073,994, and EP Patent No. 1537878B1, and, for example, include the use of anti-PD-1 antibodies. Exemplary anti-PD-1 antibodies are described, for example, in U.S. Pat. Nos. 8,952,136, 8,779,105, 8,008, 449, 8,741,295, 9,205,148, 9,181,342, 9,102,728, 9,102,727, 8,952,136, 8,927,697, 8,900,587, 8,735,553, and 7,488,802. Exemplary anti-PD-1 antibodies include, for example, nivolumab (Opdivo®, Bristol-Myers Squibb Co.), pembrolizumab (Keytruda®, Merck Sharp & Dohme Corp.), PDR001 (Novartis Pharmaceuticals), and pidilizumab (CT-011, Cure Tech). Exemplary anti-PD-L1 antibodies are described, for example, in U.S. Pat. Nos. 9,273,135, 7,943, 743, 9,175,082, 8,741,295, 8,552,154, and 8,217,149. Exemplary anti-PD-L1 antibodies include, for example, atezolizumab (Tecentriq®, Genentech), duvalumab (AstraZeneca), MEDI4736, avelumab, and BMS 936559 (Bristol Myers Squibb Co.).

In certain embodiments, a method or composition described herein is administered in combination with a CTLA-4 inhibitor. In the CTLA-4 pathway, the interaction of CTLA-4 on a T-cell with its ligands (e.g., CD80, also known as B7-1, and CD86) on the surface of an antigen presenting cells (rather than cancer cells) leads to T-cell inhibition. Exemplary CTLA-4 based immune checkpoint inhibition methods are described in U.S. Pat. Nos. 5,811, 097, 5,855,887, 6,051,227. Exemplary anti-CTLA-4 antibodies are described in U.S. Pat. Nos. 6,984,720, 6,682,736, 7,311,910; 7,307,064, 7,109,003, 7,132,281, 6,207,156, 7,807,797, 7,824,679, 8,143,379, 8,263,073, 8,318,916, 8,017,114, 8,784,815, and 8,883,984, International (PCT) Publication Nos. WO98/42752, WO00/37504, and WO01/14424, and European Patent No. EP 1212422 B1. Exemplary CTLA-4 antibodies include ipilimumab or tremelimumab.

In certain embodiments, a method or composition described herein is administered in combination with (i) a PD-1 or PD-L1 inhibitor, e.g., a PD-1 or PD-L1 inhibitor disclosed herein, and (ii) CTLA-4 inhibitor, e.g., a CTLA-4 inhibitor disclosed herein.

In certain embodiments, a method or composition described herein is administered in combination with an IDO inhibitor. Exemplary IDO inhibitors include 1-methyl-D-tryptophan (known as indoximod), epacadostat (INCB24360), navoximod (GDC-0919), and BMS-986205.

Exemplary cytotoxic agents that can be administered in combination with a method or composition described herein include, for example, antimicrotubule agents, topoisomerase inhibitors, antimetabolites, protein synthesis and degradation inhibitors, mitotic inhibitors, alkylating agents, platinating agents, inhibitors of nucleic acid synthesis, histone deacetylase inhibitors (HDAC inhibitors, e.g., vorinostat (SAHA, MK0683), entinostat (MS-275), panobinostat (LBH589), trichostatin A (TSA), mocetinostat (MGCD0103), belinostat (PXD101), romidepsin (FK228, depsipeptide)), DNA methyltransferase inhibitors, nitrogen mustards, nitrosoureas, ethylenimines, alkyl sulfonates, triazenes, folate analogs, nucleoside analogs, ribonucleotide reductase inhibitors, vinca alkaloids, taxanes, epothilones, intercalating agents, agents capable of interfering with a signal transduction pathway, agents that promote apoptosis and radiation, or antibody molecule conjugates that bind surface proteins to deliver a toxic agent. In one embodiment, the cytotoxic agent that can be administered with a method or composition described herein is a platinum-based agent (such as cisplatin), cyclophosphamide, dacarbazine, methotrexate, fluorouracil, gemcitabine, capecitabine, hydroxyurea, topotecan, irinotecan, azacytidine, vorinostat, ixabepilone, bortezomib, taxanes (e.g., paclitaxel or docetaxel), cytochalasin B, gramicidin D, ethidium bromide, emetine, mitomycin, etoposide, tenoposide, vincristine, vinblastine, vinorelbine, colchicin, anthracyclines (e.g., doxorubicin or epirubicin) daunorubicin, dihydroxy anthracin dione, mitoxantrone, mithramycin, actinomycin D, adriamycin, 1-dehydrotestosterone, glucocorticoids, procaine, tetracaine, lidocaine, propranolol, puromycin, ricin, or maytansinoids.

The invention also provides a method of increasing the expression of HLA-DR, CD86, CD83, IFNγ, IL-1b, IL-6, TNFα, IL-17A, IL-2, or IL-6 in a cell or tissue. The method comprises contacting the cell or tissue with an effective amount of a recombinant human sialidase or a fusion protein and/or antibody conjugate thereof, e.g., a recombinant human sialidase, fusion protein, or antibody conjugate disclosed herein. In certain embodiments, the cell is selected from a dendritic cell and a peripheral blood mononuclear cell (PBMC).

In certain embodiments, expression of HLA-DR, CD86, CD83, IFNγ, IL-1b, IL-6, TNFα, IL-17A, IL-2, or IL-6 in the cell or tissue is increased by at least about 10%, at least about 20%, at least about 50%, at least about 75%, at least about 100%, at least about 150%, at least about 200%, at least about 250%, at least about 300%, at least about 400%, at least about 500%, at least about 600%, at least about 700%, at least about 800%, at least about 900%, or at least about 1,000%, relative to a similar or otherwise identical cell or tissue that has not been contacted with the recombinant human sialidase, fusion protein, or antibody conjugate. Gene expression may be measured by any suitable method known in the art, for example, by ELISA, or by Luminex multiplex assays, as described in Example 13 herein.

Throughout the description, where compositions are described as having, including, or comprising specific components, or where processes and methods are described as having, including, or comprising specific steps, it is contemplated that, additionally, there are compositions of the present invention that consist essentially of, or consist of, the recited components, and that there are processes and methods according to the present invention that consist essentially of, or consist of, the recited processing steps.

In the application, where an element or component is said to be included in and/or selected from a list of recited elements or components, it should be understood that the element or component can be any one of the recited elements or components, or the element or component can be selected from a group consisting of two or more of the recited elements or components.

Further, it should be understood that elements and/or features of a composition or a method described herein can be combined in a variety of ways without departing from the spirit and scope of the present invention, whether explicit or implicit herein. For example, where reference is made to a particular compound, that compound can be used in various embodiments of compositions of the present invention and/or in methods of the present invention, unless otherwise understood from the context. In other words, within this application, embodiments have been described and depicted in a way that enables a clear and concise application to be written and drawn, but it is intended and will be appreciated that embodiments may be variously combined or separated without parting from the present teachings and invention(s). For example, it will be appreciated that all features described and depicted herein can be applicable to all aspects of the invention(s) described and depicted herein.

It should be understood that the expression "at least one of" includes individually each of the recited objects after the expression and the various combinations of two or more of the recited objects unless otherwise understood from the context and use. The expression "and/or" in connection with three or more recited objects should be understood to have the same meaning unless otherwise understood from the context.

The use of the term "include," "includes," "including," "have," "has," "having," "contain," "contains," or "containing," including grammatical equivalents thereof, should be understood generally as open-ended and non-limiting, for example, not excluding additional unrecited elements or steps, unless otherwise specifically stated or understood from the context.

Where the use of the term "about" is before a quantitative value, the present invention also includes the specific quantitative value itself, unless specifically stated otherwise. As used herein, the term "about" refers to a ±10% variation from the nominal value unless otherwise indicated or inferred.

It should be understood that the order of steps or order for performing certain actions is immaterial so long as the present invention remain operable. Moreover, two or more steps or actions may be conducted simultaneously.

The use of any and all examples, or exemplary language herein, for example, "such as" or "including," is intended merely to illustrate better the present invention and does not pose a limitation on the scope of the invention unless claimed. No language in the specification should be construed as indicating any non-claimed element as essential to the practice of the present invention.

EXAMPLES

The following Examples are merely illustrative and are not intended to limit the scope or content of the invention in any way.

Example 1

This example describes the construction of recombinant human sialidases (Neu1, Neu2, and Neu3) with substitutions of cysteine residues to enhance expression and/or reduce aggregation.

The human sialidases Neu1, Neu2, Neu3 (isoform 1), and Neu4 (isoform 1) were expressed as secreted proteins with a 10×His tag (SEQ ID NO: 105). To express Neu1 as a secreted protein, the native N terminal signal peptide (MTGERPSTALPDRRWGPRILGFWGGCRVWVFAAIFLLLSLAASWSKA; SEQ ID NO: 27) was replaced by MDMRVPAQLLGLLLLWLPGARC (SEQ ID NO: 28), and the C terminal lysosomal signal motif (YGTL; SEQ ID NO: 29) was removed. To express Neu2, Neu3, and Neu4 as secreted proteins, the N terminal signal peptide MDMRVPAQLLGLLLLWLPGARC (SEQ ID NO: 28) was added to each.

Sialidases were expressed in a 200 mL transfection of HEK293F human cells in 24-well plates using the pCEP4 mammalian expression vector with an N-terminal 6×His tag (SEQ ID NO: 109). Sialidases were purified using Ni-NTA columns, quantified with a UV-Vis spectrophotometer (NanoDrop), and examined by SDS-PAGE as shown in FIG. 1. Neu1 expressed well, with a yield of ~3 μg/ml, and was present primarily in a monomeric form. Neu2 and Neu3 expression each gave yields of ~0.15 μg/mL and each were present primarily in a dimeric form. Neu4 had no detectable expression yield as measured by NanoDrop. Bacterial sialidase from *Salmonella typhimurium* (St-sialidase; SEQ ID NO: 30), which was used as a positive control for expression, gave a comparable yield to Neu1, and was present primarily in a monomeric form.

Figure 2:
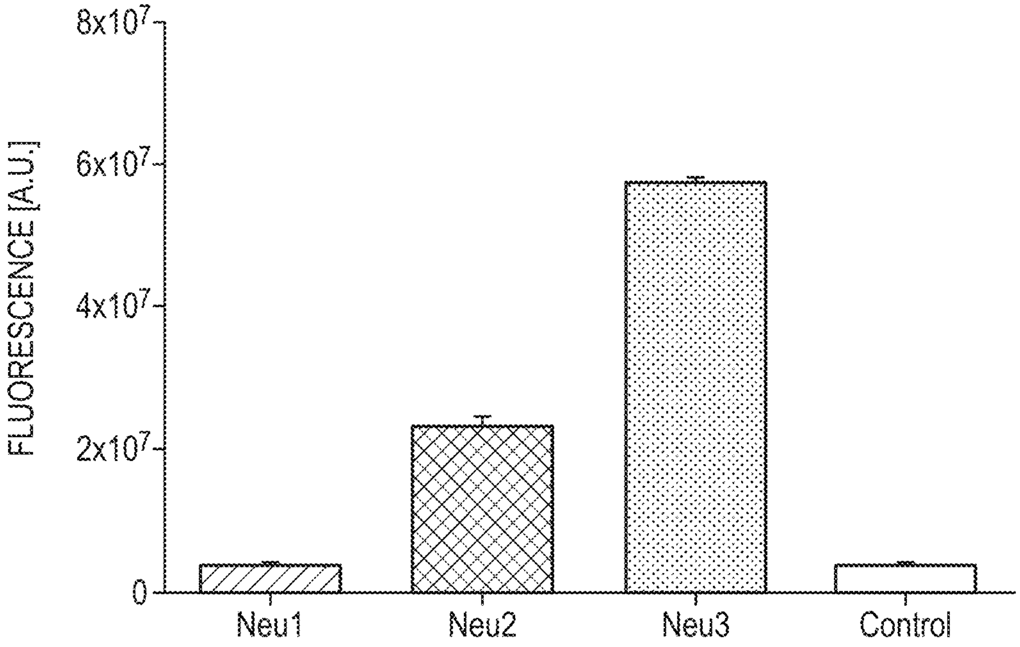
FIG. 2 is a bar graph showing the enzymatic activity of recombinant human Neu1, Neu2, and Neu3.
Figure 3:
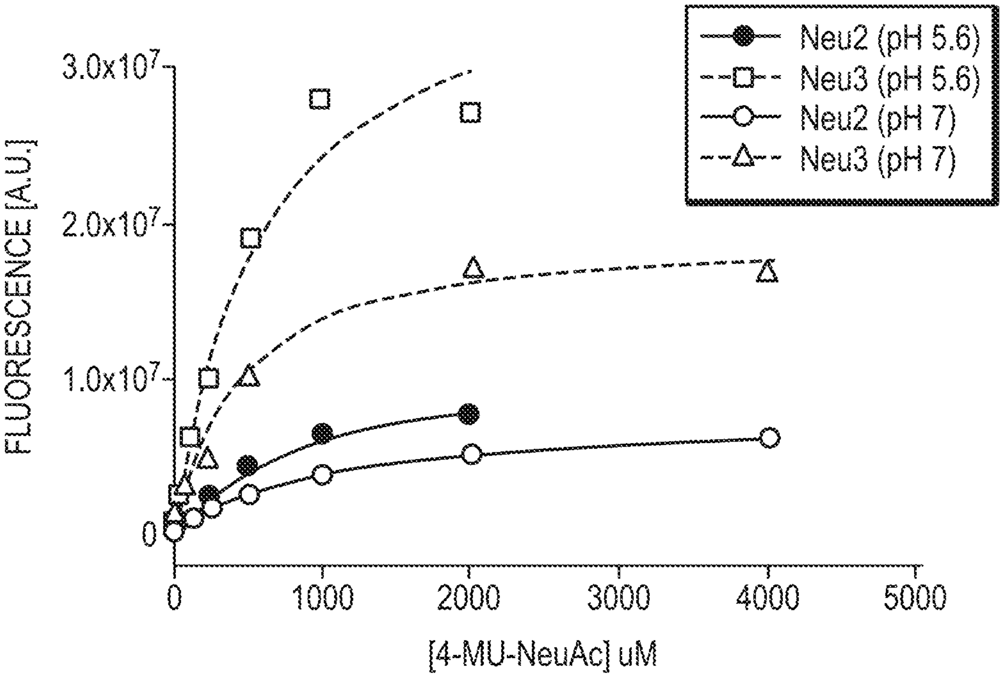
FIG. 3 is a line graph showing enzymatic activity as a function of substrate concentration for recombinant human Neu2 and Neu3 at the indicated pH.

The activity of the recombinantly expressed sialidases was assayed by measuring the release of sialic acid from the fluorogenic substrate 4-methylumbelliferyl-N-acetyl-neuraminic acid (4MU-NeuAc). As shown in FIG. 2, Neu1 has no detectable activity above a no-enzyme control, which is consistent with previous reports indicating that Neu1 is inactive unless it is in complex with beta-galactosidase and protective protein/cathepsin A (PPCA). Neu2 and Neu3 were active. An enzyme kinetics assay was performed with Neu2 and Neu3. A fixed concentration of enzyme at 1 nM was incubated with fluorogenic substrate 4MU-NeuAc at concentrations ranging from 4000 μM to 7.8 μM. Assays were conducted at both acidic (pH 5.6) and neutral (pH 7) conditions. As shown in FIG. 3, both Neu2 and Neu3 were active at acidic and neutral conditions and showed enzyme kinetics that were comparable to those previously reported.

Most of the recombinantly expressed sialidases ran as aggregates or dimers on a non-reducing SDS-PAGE gel. Subsequent treatment with the reducing agent dithiothreitol (DTT) resulted in a monomeric form of the enzyme that ran at 42 kDa on a reducing SDS-PAGE gel (FIG. 1). Thus, free cysteine residues in the sialidases may cause aggregation, dimerization, and/or low expression. Accordingly, each of the six free cysteine residues of Neu2 (125, 196, 219, 272, 332, 352) were substituted with the amino acids S, I, V, F, L, or A, using site-directed mutagenesis. The resulting mutant sialidases were expressed in 24-well plates as secreted proteins with an N-terminal human Fc tag in Expi293F cells using the pCEP4 mammalian expression vector. Expression was assayed using a ForteBio Octet with anti-human Fc sensors and Western blot and enzymatic activity was assayed using the fluorogenic substrate 4MU-NeuAc as described above. Expression and activity levels for the mutant sialidases are shown in TABLE 2.

In TABLE 2, enzymatic activity is indicated as "++," which denotes activity comparable to wild-type Neu2, "+," which denotes activity lower than wild-type Neu2, or "–," which denotes no detectable activity, and expression is indicated as "+++," which denotes expression >6 fold higher than wild-type Neu2, "++," which denotes expression 2-5 fold higher than wild-type Neu2, "+," which denotes expression comparable to wild-type Neu2, or "–," which denotes no detectable expression.

TABLE 2

| Identifier | Mutation(s) | Activity | Expression |
|---|---|---|---|
| Neu2 | Wild-type Neu2 | ++ | + |
| Neu2-M1 | C125A | ++ | + |
| Neu2-M2 | C125I | ++ | + |
| Neu2-M3 | C125S | ++ | + |
| Neu2-M4 | C125V | ++ | + |
| Neu2-M5 | C196A | ++ | + |
| Neu2-M6 | C196L | ++ | + |
| Neu2-M7 | C196F | – | – |
| Neu2-M8 | C196S | – | – |
| Neu2-M9 | C196V | ++ | + |
| Neu2-M10 | C219A | – | +++ |
| Neu2-M11 | C219N | – | +++ |
| Neu2-M12 | C219S | – | – |
| Neu2-M13 | C219V | – | – |
| Neu2-M14 | C219D | – | +++ |

TABLE 2-continued

| Identifier | Mutation(s) | Activity | Expression |
|---|---|---|---|
| Neu2-M15 | C219I | − | + |
| Neu2-M16 | C219L | − | + |
| Neu2-M17 | C219Q | − | +++ |
| Neu2-M18 | C219M | − | +++ |
| Neu2-M19 | C219T | − | +++ |
| Neu2-M20 | C272S | + | + |
| Neu2-M21 | C272V | ++ | + |
| Neu2-M22 | C332A | ++ | + |
| Neu2-M23 | C332S | ++ | + |
| Neu2-M24 | C332V | ++ | + |
| Neu2-M25 | C352L | ++ | + |
| Neu2-M26 | C352S | − | − |
| Neu2-M27 | C352V | ++ | + |
| Neu2-M28 | C196S + 219S + 332S | − | +++ |
| Neu2-M29 | C125S + C196S + C272S + C352S + C332S | − | − |
| Neu2-M30 | C125S + C196S + C219S + C272S + C352S + C332S | − | − |
| Neu2-M31 | C125S + C332S | ++ | + |
| Neu2-M32 | C196A + C219A | − | + |
| Neu2-M33 | C196V + C219V | − | − |
| Neu2-M34 | C196L + C219N | − | − |
| Neu2-M35 | C196L + C219A | − | + |
| Neu2-M36 | C272V + C332A | ++ | + |
| Neu2-M37 | C272V + C332S | ++ | + |
| Neu2-M38 | C332A + C352L | + | ++ |
| Neu2-M39 | C125S + C196L | ++ | + |
| Neu2-M40 | C196L + C219N + C332S | − | + |
| Neu2-M41 | C196L + C352L | ++ | + |
| Neu2-M42 | C196L + C219N + C332A | − | +++ |
| Neu2-M43 | C196L + C272V + C352L | − | + |
| Neu2-M44 | C272V + C332A + C352L | − | +++ |
| Neu2-M45 | C196L + C272V + C352L + C332A | − | + |
| Neu2-M46 | C196L + C272V + C352L + C332S | − | + |
| Neu2-M47 | C196L + C332S | + | − |
| Neu2-M48 | C196L + C332A | ++ | + |
| Neu2-M49 | C125S + C196L + C272V + C352L + C332A | − | + |
| Neu2-M50 | C125S + C196L + C272V + C352L + C332S | − | + |
| Neu2-M51 | C196L + C332A + C352L | + | + |
| Neu2-M52 | C125S + C272V + C332A + C352L | − | + |
| Neu2-M53 | C272V + C332A + C352L + K45A | − | + |

TABLE 2-continued

| Identifier | Mutation(s) | Activity | Expression |
|---|---|---|---|
| Neu2-M54 | C196L + C219T + C332S | − | ++ |
| Neu2-M55 | C196L + C219T + C332A | − | +++ |
| Neu2-M56 | C125S + C196L + C219T + C272V + C352L + C332A | − | +++ |
| Neu2-M57 | C125S + C196L + C219T + C272V + C352L + C332S | − | +++ |
| Neu2-M58 | C196L + C219N + C332A | − | + |
| Neu2-M59 | C219N + C332A | − | +++ |
| Neu2-M60 | C219A + C332A | − | +++ |
| Neu2-M61 | C196L + C219A + C332A | − | +++ |

Figure 4A:
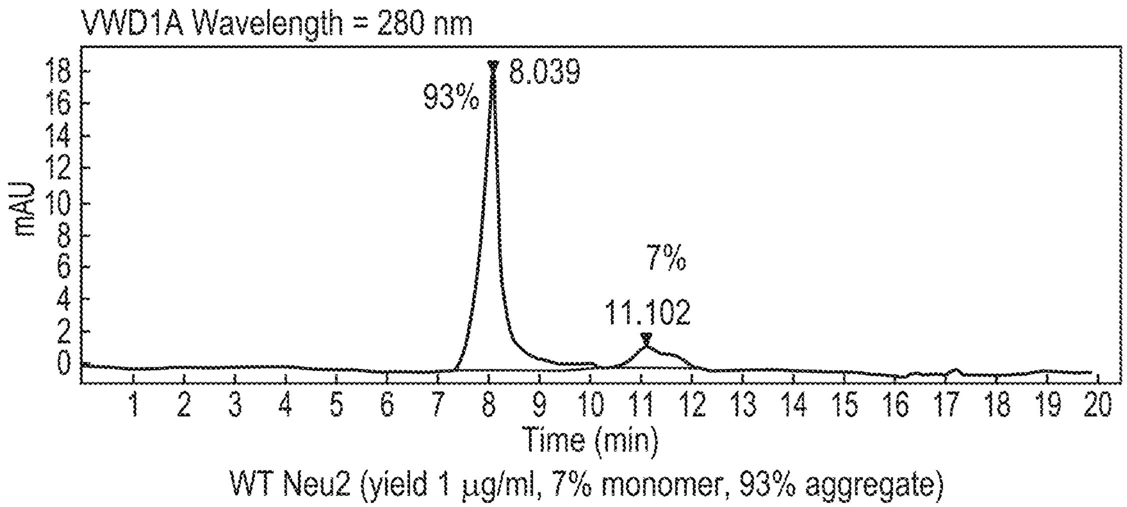
FIG. 4A is an SEC-HPLC trace of wild-type Neu2.
Figure 4B:
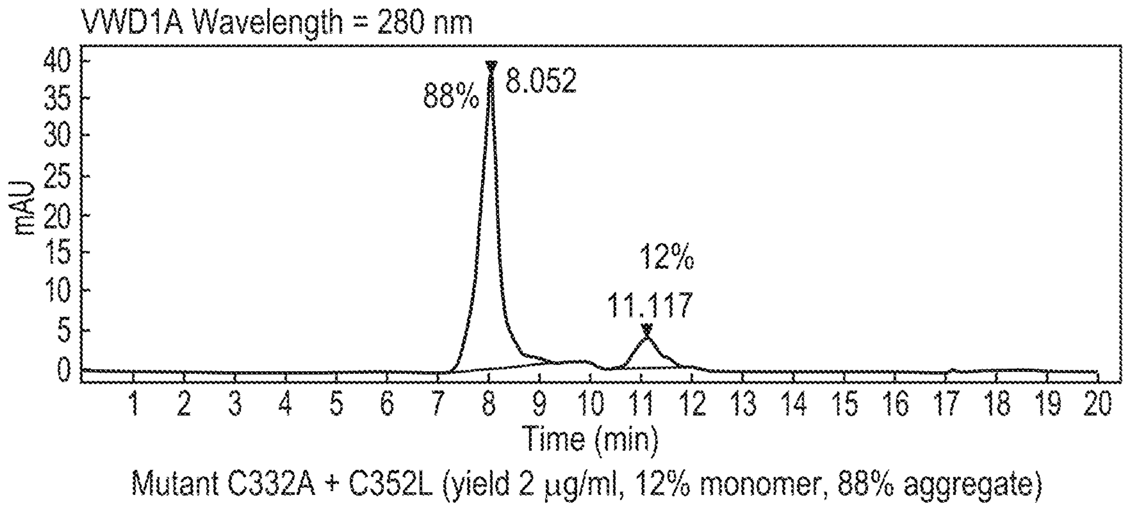
FIG. 4B is an SEC-HPLC trace of Neu2-M38 (containing C332A and C352L substitutions). Quantities of monomer and aggregate species are indicated.

As seen in TABLE 2, mutation of cysteine 219 greatly enhances expression, but negatively effects enzymatic activity. This may be due to the effects of the cysteine 219 mutation on the neighboring amino acid glutamate 218, which is believed to be a critical catalytic residue that acts a nucleophile for catalysis. Individual mutations of the other five cysteines (125, 196, 272, 332, and 352) had minimal impact on expression. However, through extensive combinatorial mutagenesis, a mutant sialidase with both the C332A and C352L substitutions (Neu2-M38) was identified that had improved expression and maintained enzymatic activity (although with reduced enzymatic activity relative to wild-type). To confirm these results, Neu2-M38 was expressed in a 100 mL transfection in shaking flasks and purified with a protein A column. Neu2-M38 had 2 fold higher expression than wild-type Neu2 under the same conditions and improved monomer content (12% vs 7%) as characterized by SEC-HPLC (FIGS. 4A and 4B). Together, these results show that mutating free cysteine residues in a human sialidase can be advantageous for producing secreted recombinant human sialidases and improving expression of recombinant human sialidases.

Example 2

This example demonstrates that engineering surface exposed residues of a human sialidase can increase the isoelectric point (pI) of the sialidase and/or reduce the hydrophobicity of a surface on the sialidase to improve solubility and/or decrease protein aggregation.

Human Neu2 has a predicted pI of 7.5, as compared to pI of 9.6 of the *Salmonella typhimurium* sialidase (St-sialidase). Additionally, an analysis of the surface hydrophobicity of Neu2 using the available crystal structure revealed a large exposed hydrophobic patch on the surface of Neu2, primarily including the N-terminal amino acids of Neu2, e.g., A2, as well as V325. These features may be suboptimal for protein stability and solubility in neutral aqueous conditions, possibly as a result of aggregation due to intermolecular hydrophobic interactions.

Surface residues of Neu2 were chosen as candidates for substitutions to increase solubility and/or expression, according to the following criteria: surface exposed D or E residues; hydrophobic residues contributing to surface hydrophobic patches; residues not involved in catalysis; residues not well conserved between human Neu 1, 3, 4, St-sialidase; and residues at positions that have a homologous K or R in other sialidases. Using these criteria, the acidic amino acids E72, D215, and E257 in Neu2 were mutated to lysine to increase pI, and the hydrophobic amino acids A2 and V325 in Neu2 were mutated to lysine or glutamate to reduce the hydrophobicity of the predicted Neu2 surface hydrophobic patch. The resulting mutant sialidases were expressed in 24-well plates as secreted proteins with a human Fc tag in Expi293F cells using the pCEP4 mammalian expression vector and assayed for expression and activity as described above in Example 1.

Expression and activity levels for the mutant sialidases are shown in TABLE 3. In TABLE 3, enzymatic activity is indicated as "++," which denotes activity comparable to wild-type Neu2, "+," which denotes activity lower than wild-type Neu2, or "−," which denotes no detectable activity, and expression is indicated as "+++," which denotes expression >6 fold higher than wild-type Neu2, "++," which denotes expression 2-5 fold higher than wild-type Neu2, "+," which denotes expression comparable to wild-type Neu2, or "−," which denotes no detectable expression.

TABLE 3

| Identifier | Mutation(s) | Activity | Expression |
|---|---|---|---|
| Neu2 | Wild-type Neu2 | ++ | + |
| Neu2-M62 | A2K | ++ | ++ |
| Neu2-M63 | E72K | + | − |
| Neu2-M64 | D215K | + | + |
| Neu2-M65 | E257K | + | ++ |
| Neu2-M66 | E319K | − | ++ |
| Neu2-M67 | V325K | + | ++ |
| Neu2-M68 | A2K + E257K | + | +++ |
| Neu2-M69 | A2K + V325E | + | + |
| Neu2-M70 | A2E + V325K | + | − |
| Neu2-M71 | A2K + V325K | + | +++ |
| Neu2-M72 | E257K + V325K | + | ++ |
| Neu2-M73 | E257K + A2K + V325K | − | +++ |

Figure 5A:
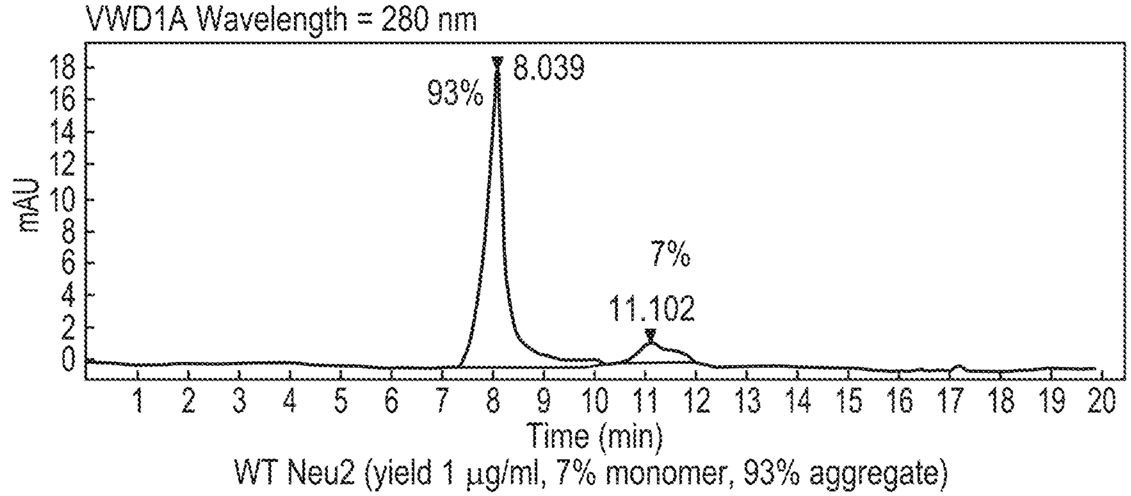
FIG. 5A is an SEC-HPLC trace of wild-type Neu2.
Figure 5B:
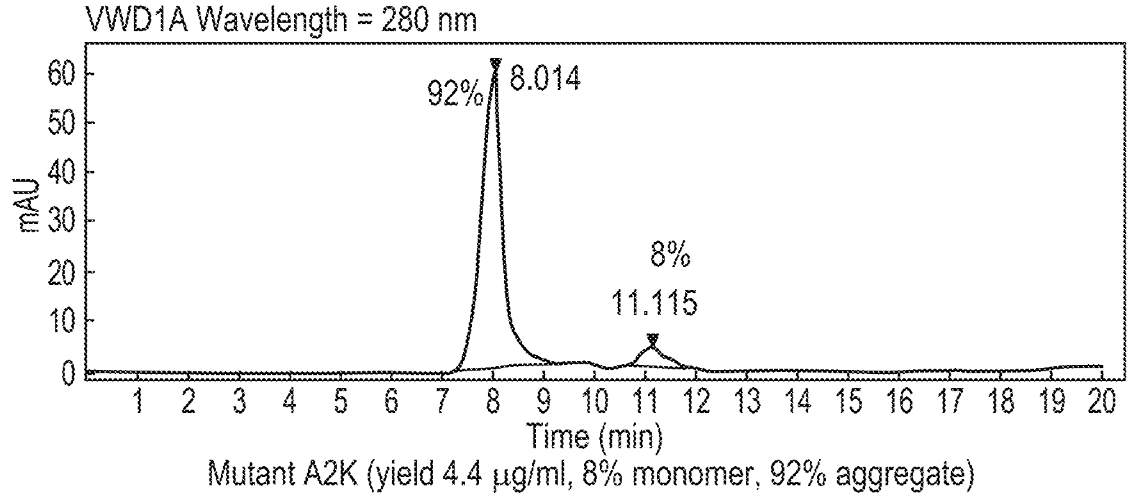
FIG. 5B is an SEC-HPLC trace of Neu2-M62 (containing the A2K substitution)
Figure 5C:
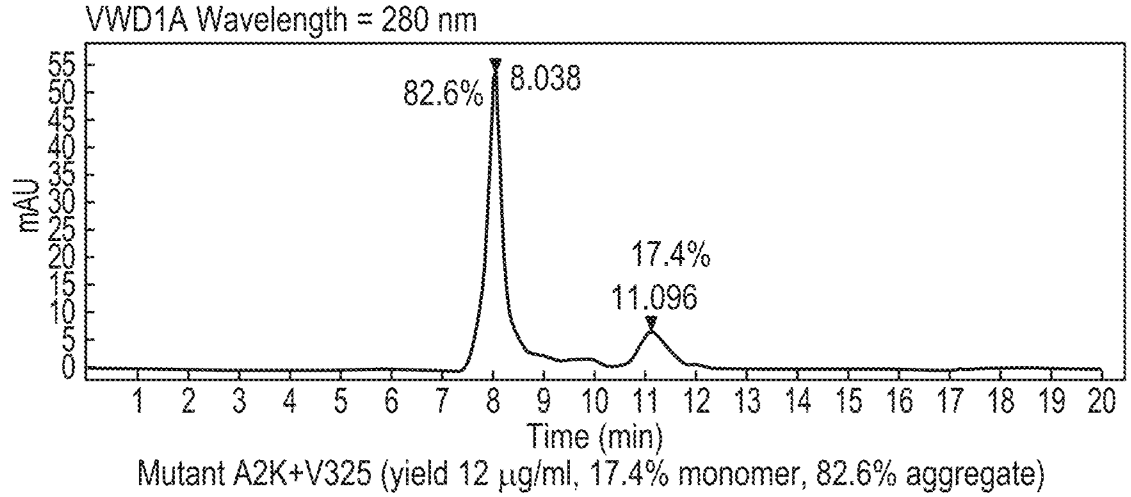
FIG. 5C is an SEC-HPLC trace of Neu2-M71 (containing A2K and V325 substitutions). Quantities of monomer and aggregate species are indicated.

As seen in TABLE 3, the Neu2-M62 (A2K), Neu2-M68 (A2K+E257K), and Neu2-M71 (A2K+V325K) mutant sialidases showed improved expression and comparable or reduced enzymatic activity compared to wild-type Neu2. To confirm these results, the Neu2-M62 and Neu2-M71 mutant sialidases were expressed in a 100 mL transfection in shaking flasks and purified with a protein A column. Neu2-M62 had ~4.4 fold higher expression than wild-type Neu2 (4.4 μg/mL vs 1 μg/mL) and similar monomer content (8% vs 7%) as characterized by SEC-HPLC (FIGS. 5A and 5B). Neu2-M71 had ~12 fold higher expression than wild-type Neu2 (12 μg/mL vs 1 μg/mL) and improved monomer content (17% vs 7%) as characterized by SEC-HPLC (FIGS. 5A and 5C), but had no enzymatic activity.

Together, these results show that mutating surface exposed residues in a human sialidase can increase the isoelectric point (pI) of the sialidase and/or reduce the hydrophobicity of a surface on the sialidase to improve solubility, decrease protein aggregation, and/or improve expression of recombinant human sialidase.

Example 3

This Example demonstrates that the addition of a short peptide to the N-terminus of a human sialidase can increase expression and/or activity of the sialidase.

Using homology-based engineering, we grafted variants of an N-terminal sequence (MEDLRP; SEQ ID NO: 4) from mouse thymus Neu2 onto human Neu2 by overlapping PCR. The resulting mutant sialidases were expressed in 24-well plates as secreted proteins with a human Fc tag in Expi293F cells using the pCEP4 mammalian expression vector and assayed for expression and activity as described in Example 1.

Expression and activity levels for the mutant sialidases are shown in TABLE 4. In TABLE 4, enzymatic activity is indicated as "+++," which denotes activity greater than wild-type Neu2, "++," which denotes activity comparable to wild-type Neu2, "+," which denotes activity lower than wild-type Neu2, or "−," which denotes no activity, and expression is indicated as "+++," which denotes expression >6 fold higher than wild-type Neu2, "++," which denotes expression 2-5 fold higher than wild-type Neu2, or "+," which denotes expression comparable to wild-type Neu2.

TABLE 4

| Identifier | Mutation(s) | Activity | Expression |
|---|---|---|---|
| Neu2 | Wild-type Neu2 | ++ | + |
| Neu2-M74 | Substitute M at the N-terminus of Neu2 with EDLRP (SEQ ID NO: 3) | ++ | + |
| Neu2-M75 | Substitute M at the N-terminus of Neu2 with MEDLRP (SEQ ID NO: 4) | +++ | +++ |
| Neu2-M76 | Insert MEDLRP (SEQ ID NO: 4) at the N-terminus of Neu2 | +++ | +++ |
| Neu2-M77 | Substitute MASLP (SEQ ID NO: 12) at the N-terminus of Neu2 with MEDLRP (SEQ ID NO: 4) | +++ | +++ |

As shown in TABLE 4, all variants tested that included the MEDLRP (SEQ ID NO: 4) N-terminal sequence had both increased expression and activity relative to wild-type Neu2.

Figure 6A:
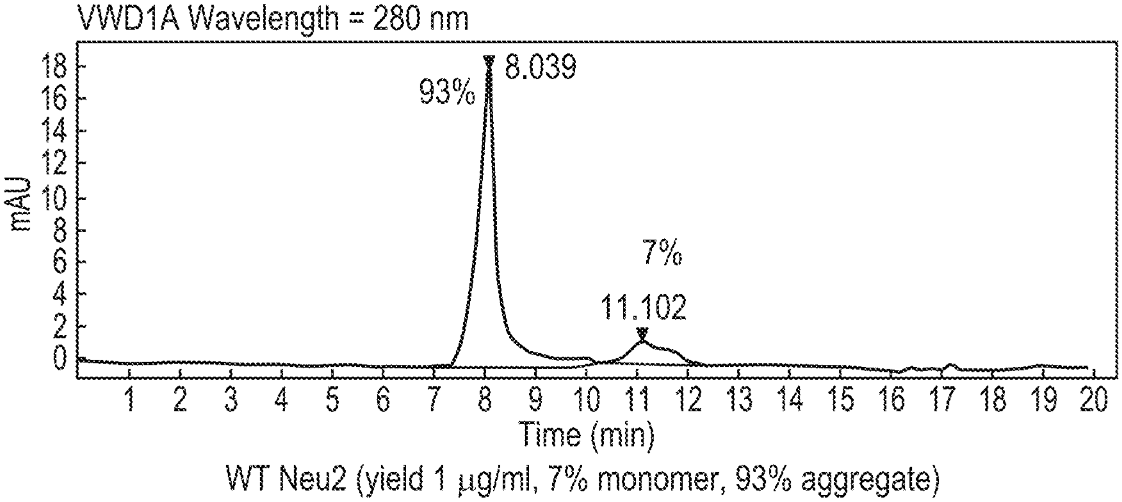
FIG. 6A is an SEC-HPLC trace of wild-type Neu2 and FIG. 6B is an SEC-HPLC trace of Neu2-M76 (which included MEDLRP (SEQ ID NO: 4) inserted at the N-terminus). Quantities of monomer and aggregate species are indicated.
Figure 6B:
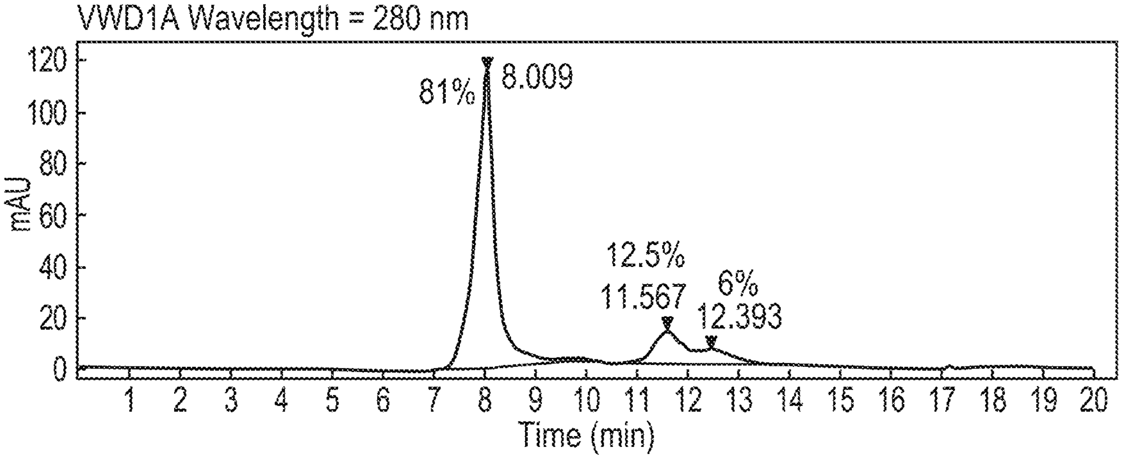

To confirm these results, the mutant Neu2-M76 (which included MEDLRP (SEQ ID NO: 4) inserted at the N-terminus) was expressed in a 100 mL transfection in shaking flasks and purified with a protein A column. Compared to the 24-well format, Neu2-M76 only showed a modest improvement in expression, ~1.5 fold higher than that of wild-type Neu2 (1.5 μg/mL vs 1 μg/mL) with improved monomer content (12.5% vs 7%) as characterized by SEC-HPLC (FIGS. 6A and 6B).

Figure 7A:
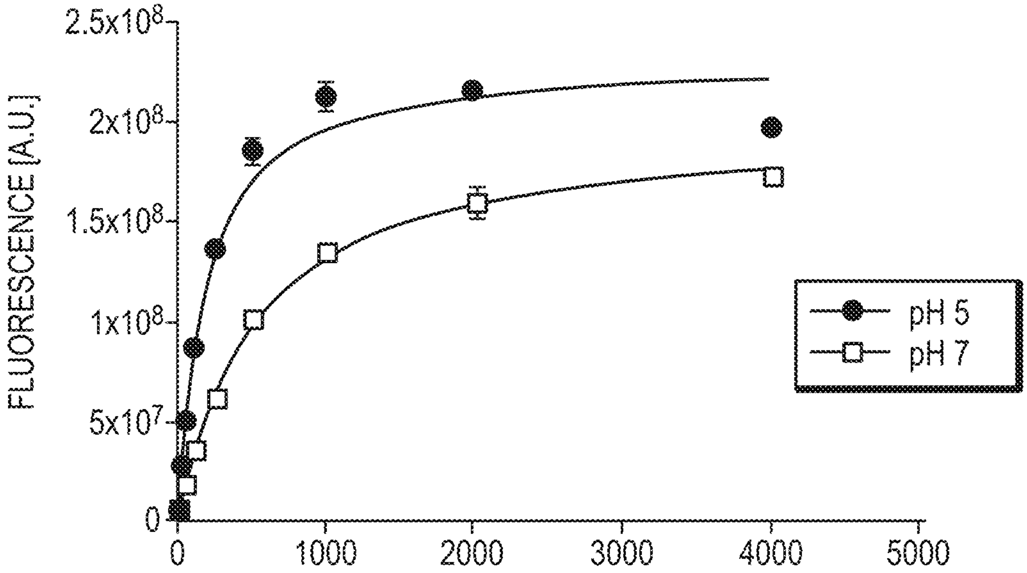
FIG. 7A is a line graph showing the enzymatic activity as a function of substrate concentration for Neu2-M76 at the indicated pH.
Figure 7B:
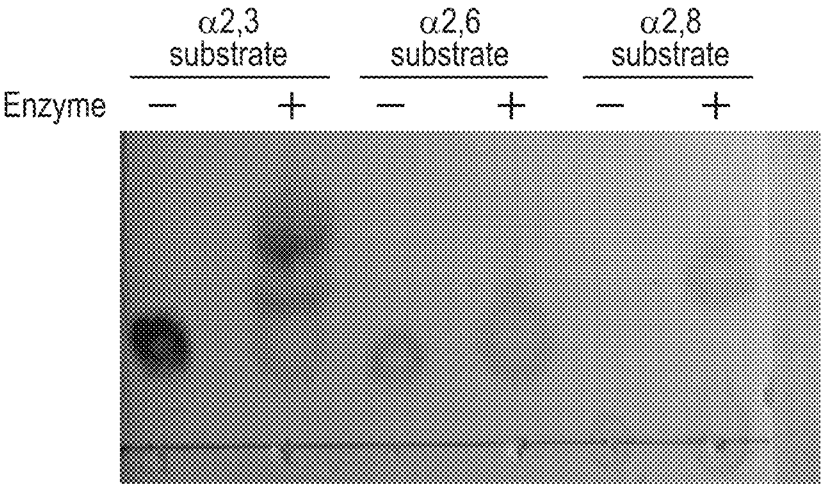
FIG. 7B depicts cleavage of α2-3, α2-6, or α2-8 substrate by Neu2-M76.

Enzyme kinetics measurements were carried out with purified Neu2-M76. A fixed concentration of Neu2-M76 at 100 nM was incubated with fluorogenic substrate 4MU-NeuAc at concentrations ranging from 4000 μM to 7.8 As shown in FIG. 7A, this variant had a $K_M$ of ~175 5 fold more potent than that of wild-type Neu2 ($K_M$ of ~867 μM). Additionally, as shown in FIG. 7B, Neu2-M76 also had an altered substrate specificity relative to wild-type Neu2, as it cleaved sialic acid with α2,8 linkages (colominic acid) at pH 5, while wild-type Neu2 had no such activity.

Together, these results show that the addition of a short peptide to the N-terminus of a human sialidase can increase expression, increase activity, and/or modify the substrate specificity of the sialidase.

Example 4

This Example demonstrates that mutating residues in the N- or C-terminus of a human sialidase to increase hydrophobic interactions and/or hydrogen bonding between the N- and C-termini can increase stability and/or expression of the sialidase.

Based on the crystal structure of Neu2, residues L4, V6, L7, and L12 were mutated to promote hydrophobic interactions or hydrogen bonding between the N- and C-termini of Neu2. The resulting mutant sialidases were expressed in 24-well plates as secreted proteins with a human Fc tag in Expi293F cells using the pCEP4 mammalian expression vector and assayed for expression and activity as described in Example 1.

Expression and activity levels for the mutant sialidases are shown in TABLE 5. In TABLE 5, enzymatic activity is indicated as "++," which denotes activity comparable to wild-type Neu2, "+," which denotes activity lower than wild-type Neu2, or "–," which denotes no detectable activity, and expression is indicated as "+++," which denotes expression >6 fold higher than wild-type Neu2, "++," which denotes expression 2-5 fold higher than wild-type Neu2, "+," which denotes expression comparable to wild-type Neu2, or "–," which denotes no detectable expression.

TABLE 5

| Identifier | Mutation(s) | Activity | Expression |
|---|---|---|---|
| Neu2 | Wild-type Neu2 | ++ | + |
| Neu2-M78 | L4N | ++ | + |
| Neu2-M79 | V6Y | ++ | +++ |
| Neu2-M80 | L7N | + | + |
| Neu2-M81 | L4N + L7N | – | – |
| Neu2-M82 | V12N | – | + |
| Neu2-M83 | V6F | + | +++ |
| Neu2-M84 | V6W | + | ++ |

As shown in TABLE 5, the V6Y substitution (Neu2-M79) resulted in improved expression and enzymatic activity compared to wild-type Neu2.

Figure 8A:
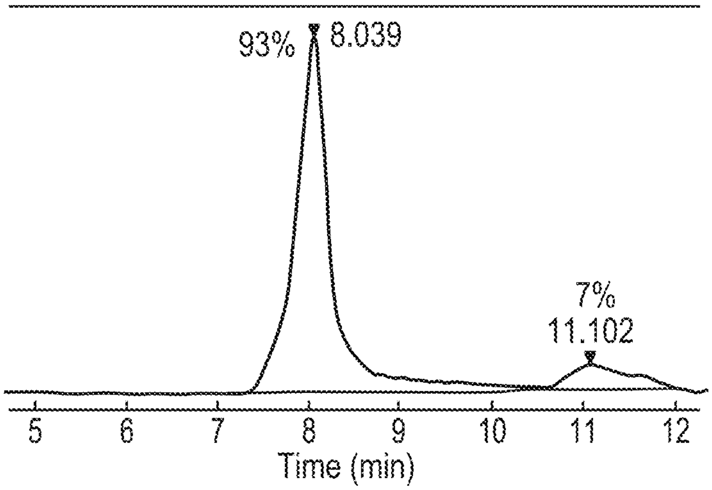
FIG. 8A is an SEC-HPLC trace of wild-type Neu2 and FIG. 8B is an SEC-HPLC trace of Neu2-M79 (containing the V6Y substitution). Quantities of monomer and aggregate species are indicated.
Figure 8B:
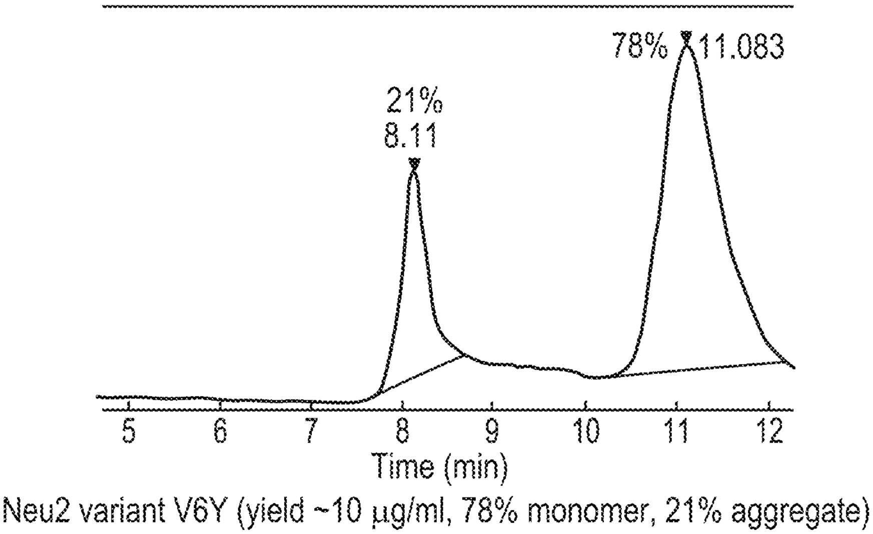

To confirm these results, Neu2-M79 was expressed in a 100 mL transfection in shaking flasks and purified with a protein A column. Neu2-M79 had ~10 fold higher expression than wild-type Neu2 (10 μg/mL vs 1 μg/mL), substantially improved monomer content (78% vs 7%) as characterized by SEC-HPLC (FIGS. 8A and 8B), and was as active as wild-type Neu2.

Together, these results show that mutating residues in the N- or C-termini of a human sialidase to increase hydrophobic interactions and/or hydrogen bonding between the N- and C-termini can increase stability and/or expression of the sialidase.

Example 5

This Example demonstrates that mutating the N-terminal methionine of a human sialidase can increase stability and/or expression of the sialidase.

The first residue (M1) of human Neu2 was deleted or mutated to R, H, K, D, E, S, T, N, Q, G, P, A, V, L, F, and Y. All mutations were tested in combination with V6Y and I187K substitutions. The resulting mutant sialidases were expressed in shaking flasks as secreted proteins with a human Fc tag in Expi293F cells using the pCEP4 mammalian expression vector. The proteins were purified with a protein A column, quantified by Nanodrop, and characterized for enzymatic activity as described in Example 1.

Expression and activity levels for the mutant sialidases are shown in TABLE 6. In TABLE 6, enzymatic activity is indicated as "++," which denotes activity comparable to wild-type Neu2, "+," which denotes activity lower than wild-type Neu2, or "–," which denotes no detectable activity, and expression is indicated as "+++," which denotes expression >6 fold higher than wild-type Neu2, "++," which denotes expression 2-5 fold higher than wild-type Neu2, "+," which denotes expression comparable to wild-type Neu2, or "–," which denotes no detectable expression.

TABLE 6

| Identifier | Mutation(s) | Activity | Expression |
|---|---|---|---|
| Neu2 | None - Wild-type Neu2 | ++ | + |
| Neu2-M85 | Deletion of M1, V6Y, I187K | + | +++ |
| Neu2-M86 | M1R, V6Y, I187K | + | +++ |
| Neu2-M87 | M1H, V6Y, I187K | +++ | ++ |
| Neu2-M88 | M1K, V6Y, I187K | + | +++ |
| Neu2-M89 | M1D, V6Y, I187K | +++ | +++ |
| Neu2-M90 | M1E, V6Y, I187K | – | +++ |
| Neu2-M91 | M1S, V6Y, I187K | – | – |
| Neu2-M92 | M1T, V6Y, I187K | ++ | ++ |
| Neu2-M93 | M1N, V6Y, I187K | ++ | +++ |
| Neu2-M94 | M1Q, V6Y, I187K | + | ++ |
| Neu2-M95 | M1G, V6Y, I187K | + | +++ |
| Neu2-M96 | M1P, V6Y, I187K | – | – |
| Neu2-M97 | M1A, V6Y, I187K | ++ | +++ |
| Neu2-M98 | M1V, V6Y, I187K | + | +++ |
| Neu2-M99 | M1L, V6Y, I187K | +++ | +++ |
| Neu2-M100 | M1F, V6Y, I187K | +++ | ++ |
| Neu2-M101 | M1Y, V6Y, I187K | + | + |

As shown in TABLE 6, deletion of M1 or mutation of M1 to R, H, K, D, E, T, N, Q, G, A, V, L, or F in combination with V6Y and I187K substitutions increased expression of the sialidase, with the M1H, M1D, M1L, and M1F mutations resulting in increased expression and enzymatic activity. Together, these results show that mutating the N-terminal methionine of a human sialidase can increase stability and/or expression of the sialidase.

Example 6

This Example describes mutations and combinations of mutations that can increase stability and/or expression of the sialidase.

Human Neu2 was mutated as shown in TABLE 7. The resulting mutant sialidases were expressed in shaking flasks as secreted proteins with a human Fc tag in Expi293F cells using the pCEP4 mammalian expression vector. The proteins were purified with a protein A column, quantified by Nanodrop, and characterized for enzymatic activity as described in Example 1.

Expression and activity levels for the mutant sialidases are shown in TABLE 7. In TABLE 7, enzymatic activity is indicated as "++," which denotes activity comparable to wild-type Neu2, "+," which denotes activity lower than wild-type Neu2, or "–," which denotes no detectable activity, and expression is indicated as "+++," which denotes expression >6 fold higher than wild-type Neu2, "++," which denotes expression 2-5 fold higher than wild-type Neu2, "+," which denotes expression comparable to wild-type Neu2, or "–," which denotes no detectable expression.

TABLE 7

| Identifier | Mutation(s) | Activity | Expression |
|---|---|---|---|
| Neu2-M102 | M1D, V6Y, I187K, C332A | +++ | +++ |
| Neu2-M103 | V6Y, I187K, C332A | +++ | ++ |

Example 7

This Example describes the construction and expression of antibody-sialidase genetic fusion proteins, and antibody sialidase conjugates (ASCs) containing the fusion proteins, with bacterial and mutated human sialidases.

The architecture for three types of ASCs used in this Example is depicted in FIG. 10. The first type of ASC, referred to as "Raptor," includes an antibody (with two heavy chains and two light chains) with a sialidase fused at the C-terminus of each heavy chain of the antibody. The second type of ASC, referred to as "Janus," contains one antibody arm (with one heavy chain and one light chain), and one sialidase-Fc fusion with a sialidase fused at the N-terminus of the Fc. Each Fc domain polypeptide in the Janus ASC contains either the "knob" (T366Y) or "hole" (Y407T) mutation for heterodimerization (residue numbers according to EU numbering, Kabat, E. A., et al. (1991) supra). The third type of ASC, referred to as "Lobster," contains two Fc domain polypeptides each with a sialidase fused at the N-terminus of the Fc and a scFv fused at the C-terminus of the Fc.

The following ASCs were expressed and characterized for purity using SDS-PAGE and SEC-HPLC, and assayed for enzymatic using 4MU-NeuAc as described in Example 1: (i) a Janus ASC including *Salmonella typhimurium* sialidase (St-sialidase) and trastuzumab (including a first polypeptide chain with amino acid sequence SEQ ID NO: 67, encoded by nucleotide sequence SEQ ID NO: 68, a second polypeptide chain with amino acid sequence SEQ ID NO: 57, encoded by nucleotide sequence SEQ ID NO: 58, and a third polypeptide chain with amino acid sequence SEQ ID NO: 55, encoded by nucleotide sequence SEQ ID NO: 56); (ii) a Raptor ASC including St-sialidase and trastuzumab (including first and fourth polypeptide chains with amino acid sequence SEQ ID NO: 67, encoded by nucleotide sequence SEQ ID NO: 68, and second and third polypeptide chains with amino acid sequence SEQ ID NO: 59, encoded by nucleotide sequence SEQ ID NO: 60); and (iii) a Janus ASC including St-sialidase with two loss of function mutations, D100V and G231V, and trastuzumab ("Janus-LOF," including a first polypeptide chain with amino acid sequence SEQ ID NO: 67, encoded by nucleotide sequence SEQ ID NO: 68, a second polypeptide chain with amino acid sequence SEQ ID NO: 57, encoded by nucleotide sequence SEQ ID NO: 58, and a third polypeptide chain with amino acid sequence SEQ ID NO: 61, encoded by nucleotide sequence SEQ ID NO: 62).

Figure 11A:
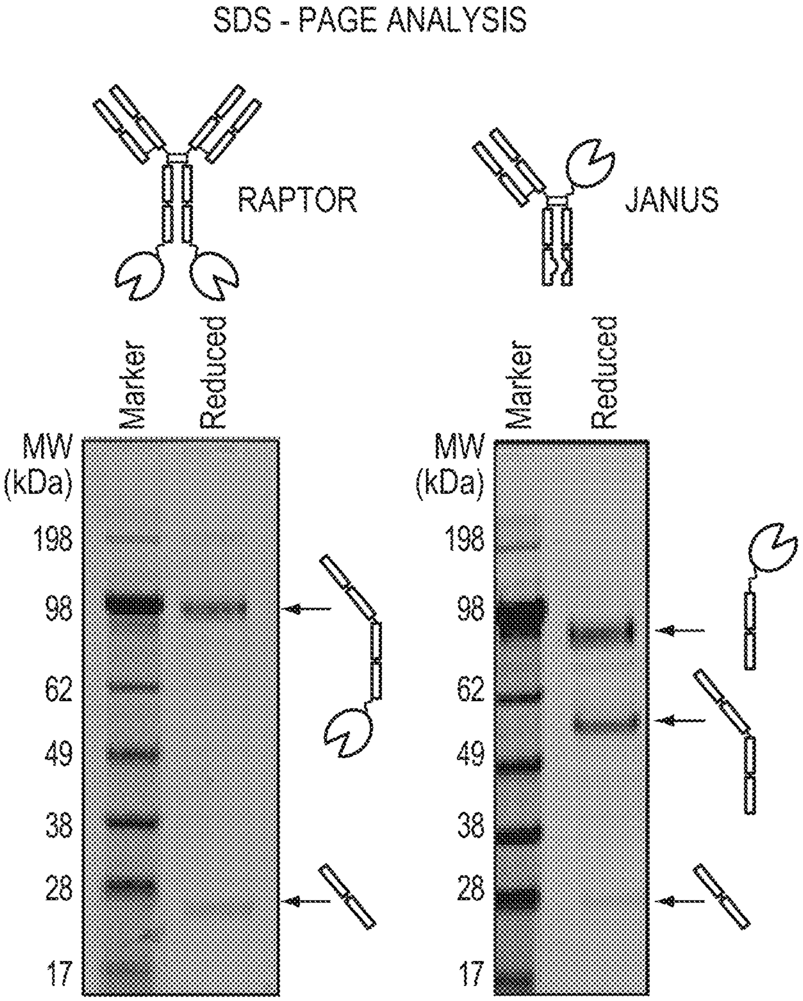
FIG. 11A is an SDS-PAGE gel showing antibody-sialidase conjugates (ASCs) made using *Salmonella typhimurium* sialidase (St-sialidase) and trastuzumab in the Raptor (left) and Janus (right) formats.
Figure 11B:
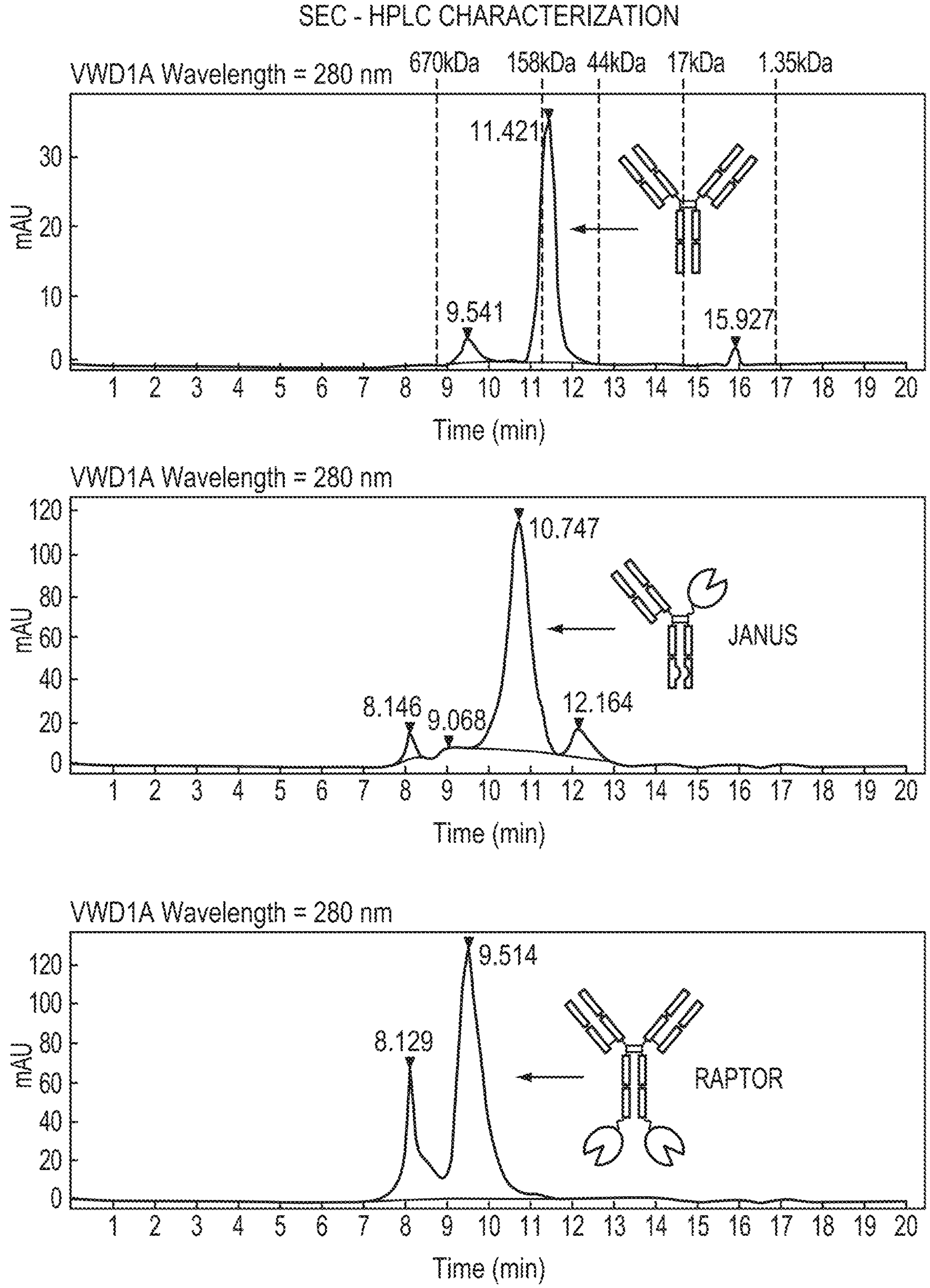
FIG. 11B is an SEC-HPLC trace of trastuzumab (top), and ASCs made using St-sialidase and trastuzumab in the Janus (middle) and Raptor (bottom) formats.
Figure 12A:
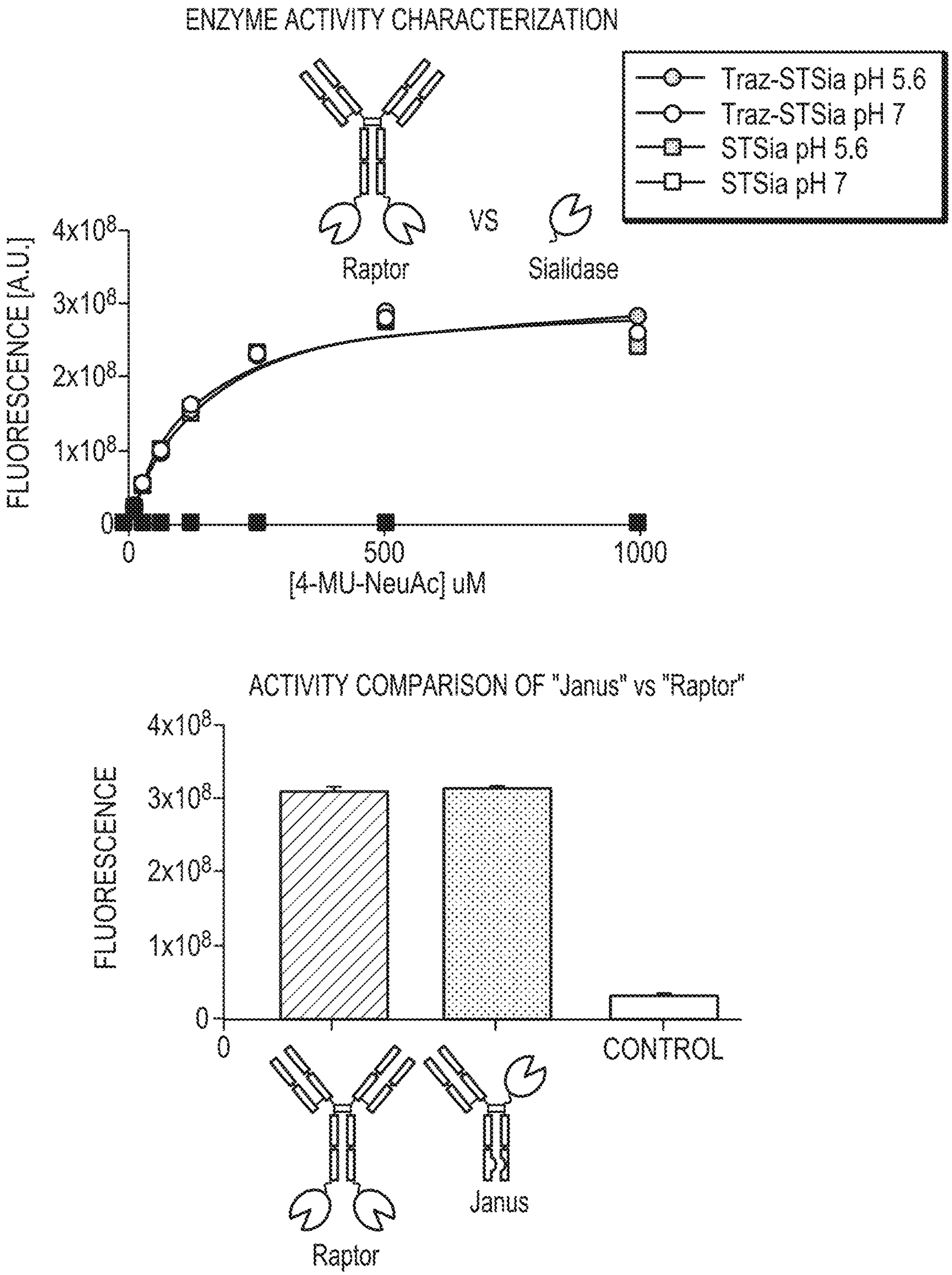
FIG. 12A is a line graph (top) and a bar graph (bottom) showing the enzymatic activity for St-sialidase and ASCs made using St-sialidase and trastuzumab in the Raptor and Janus formats.
Figure 12B:
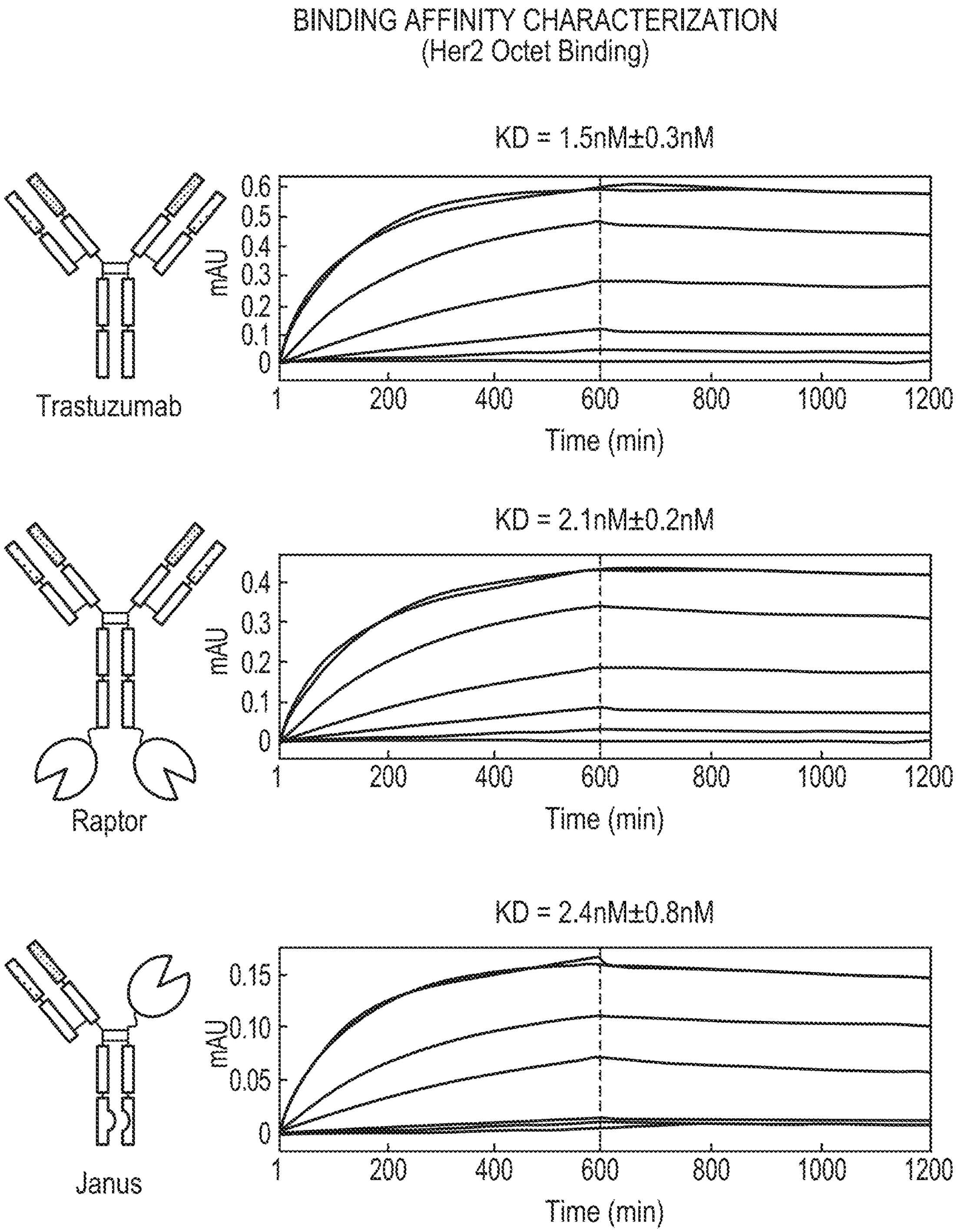
FIG. 12B depicts binding to Her2 as determined by ForteBio Octet for trastuzumab (top), and ASCs made using St-sialidase and trastuzumab in the Raptor (middle) and Janus (bottom) formats.

The ASCs were tested for antigen (Her2) binding by using ForteBio Octet with the ASC captured on anti-Fc sensors with dipping into serial dilutions of His-tagged Her2 (50 to 0.78 nM at 1:2 dilutions). The ASCs had good expression with a yield of 30 μg/mL and high purity, were as active as unconjugated St-sialidase, and bound to Her2 with comparable binding affinities to trastuzumab (FIGS. 11 and 12). Janus-LOF mutant abolished the sialidase activity as expected, and expressed well with similar biochemical characteristics as the parent Janus ASC.

Figure 13A:
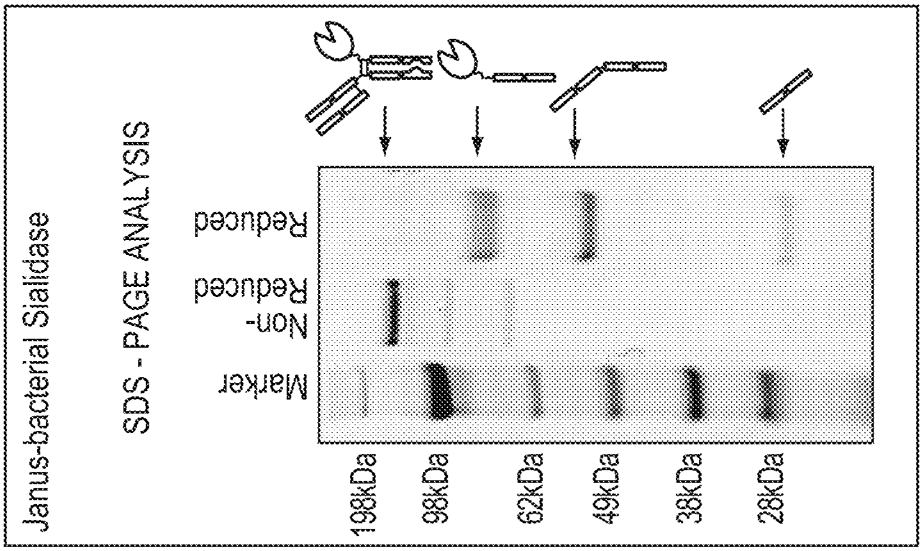
FIGS. 13A-C show an SDS-PAGE gel depicting an ASC made using St-sialidase and trastuzumab in the Janus format (FIG. 13A), an SDS-PAGE gel depicting an ASC made using Neu2-M76 (which included MEDLRP (SEQ ID NO: 4) inserted at the N-terminus) and trastuzumab in the Janus format (FIG. 13B), and an SDS-PAGE gel depicting an ASC made using a Neu2-M85 (which included a deletion of M1 and V6Y and I187K mutations) and a scFv derived from trastuzumab in the Lobster format (FIG. 13C).
Figure 13B:
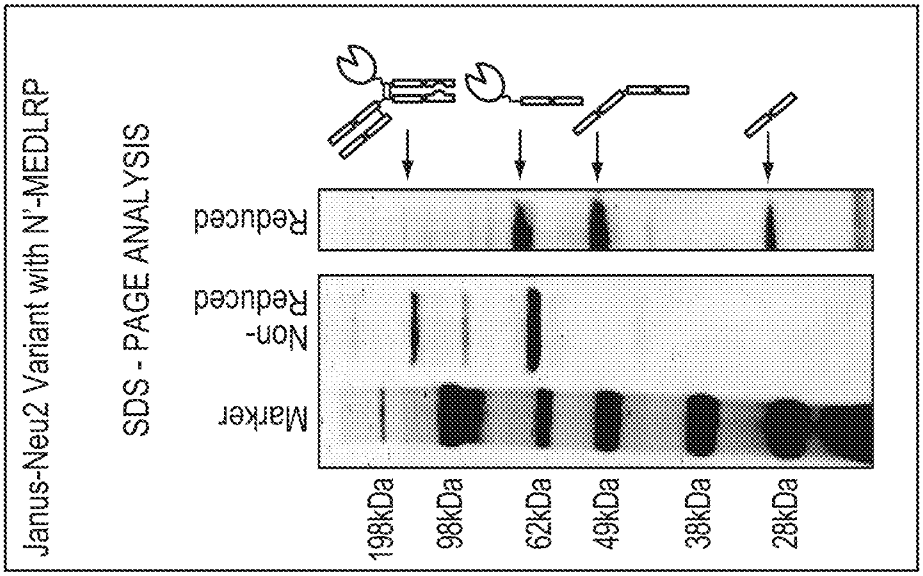
Figure 13C:
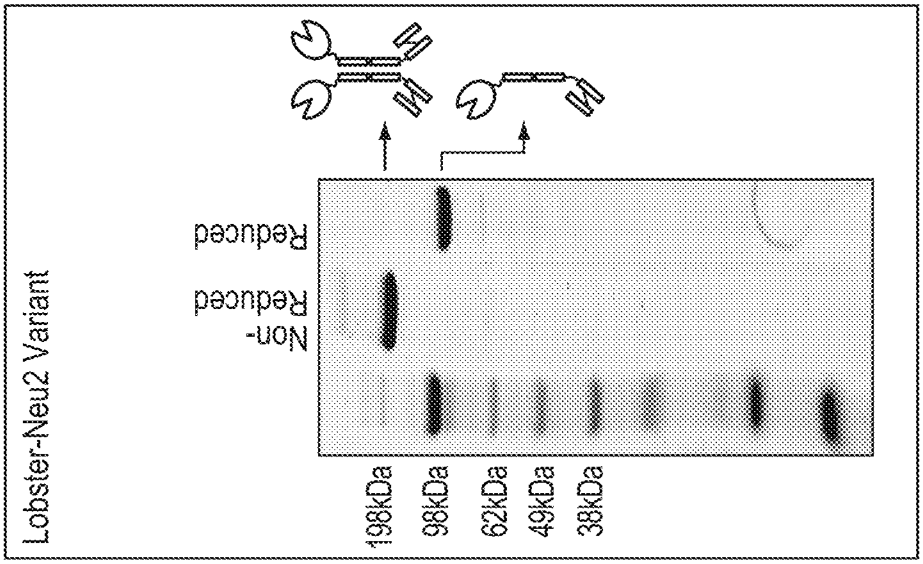
Figure 14A:
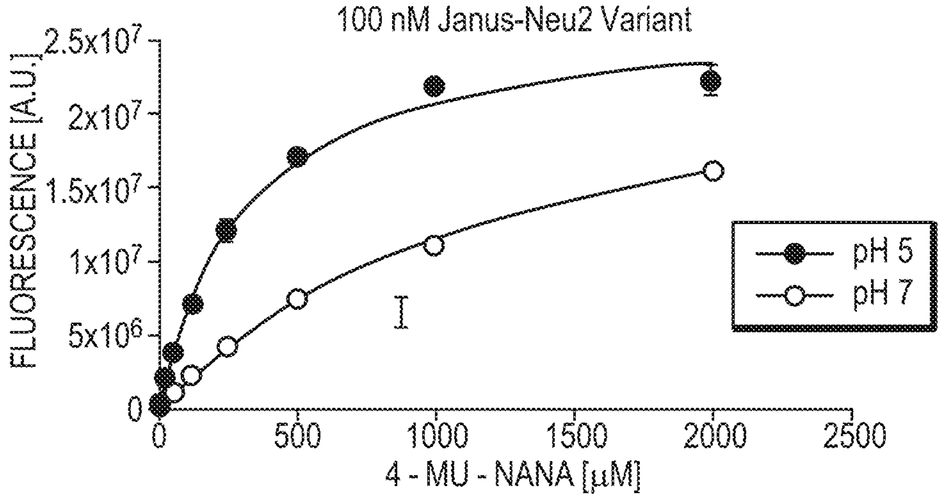
FIGS. 14A-C show line graphs depicting enzymatic activity as a function of substrate concentration for an ASC made using Neu2-M76 (which included MEDLRP (SEQ ID NO: 4) inserted at the N-terminus) and trastuzumab in the Janus format (FIG. 14A), wild-type Neu2 (FIG. 14B), and an ASC made using a Neu2-M85 (which included a deletion of M1 and V6Y and I187K mutations) and a scFv derived from trastuzumab in the Lobster format (FIG. 14C).
Figure 14B:
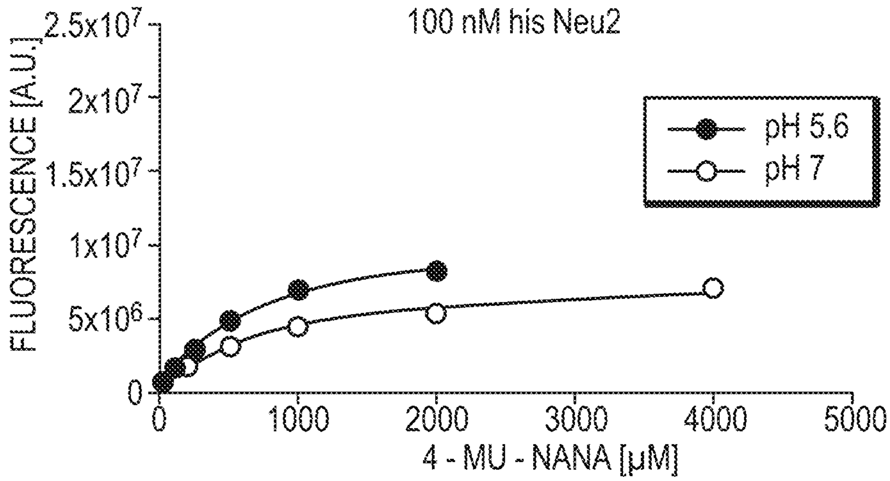
Figure 14C:
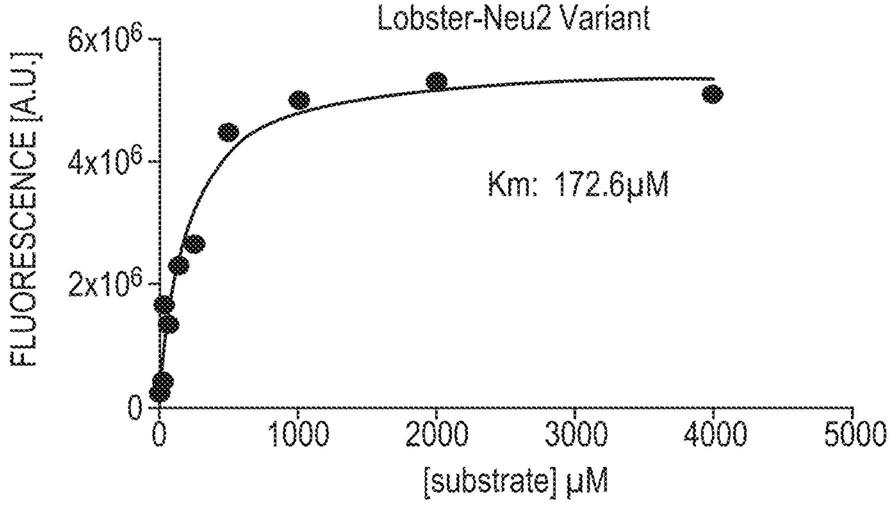

A Janus ASC was made using Neu2-M76 (which included MEDLRP (SEQ ID NO: 4) inserted at the N-terminus) and trastuzumab. This Janus ASC (including a first polypeptide chain with amino acid sequence SEQ ID NO: 67, encoded by nucleotide sequence SEQ ID NO: 68, a second polypeptide chain with amino acid sequence SEQ ID NO: 57, encoded by nucleotide sequence SEQ ID NO: 58, and a third polypeptide chain with amino acid sequence SEQ ID NO: 63, encoded by nucleotide sequence SEQ ID NO: 64) was expressed and characterized for purity using SDS-PAGE and enzymatic activity using 4MU-NeuAc as described in Example 1. The Janus ASC had an expression yield of ~5 μg/mL with good purity after purification (FIG. 13), and showed improved activity compared to a Janus ASC wild-type conjugated Neu2 (FIG. 14).

Additionally a Lobster ASC was made using Neu2-M85 (which included a deletion of M1 and mutations V6Y and I187K) and a scFv derived from trastuzumab. This Lobster ASC (including first and second polypeptide chains with amino acid sequence SEQ ID NO: 65, encoded by nucleotide sequence SEQ ID NO: 66) was expressed and characterized for purity using SDS-PAGE and enzymatic activity using 4MU-NeuAc as described in Example 1. The Lobster ASC had an expression yield of ~5 μg/mL with good purity after purification (FIG. 13), and a Km of 172.6 μM (FIG. 14).

Example 8

This Example describes the in vivo administration of antibody sialidase conjugates (ASCs) containing bacterial sialidases.

The following ASCs were made and tested in this Example: (i) a Janus ASC including *Salmonella typhimurium* sialidase (St-sialidase) and trastuzumab (including a first polypeptide chain with amino acid sequence SEQ ID NO: 67, encoded by nucleotide sequence SEQ ID NO: 68, a second polypeptide chain with amino acid sequence SEQ ID NO: 57, encoded by nucleotide sequence SEQ ID NO: 58, and a third polypeptide chain with amino acid sequence SEQ ID NO: 55, encoded by nucleotide sequence SEQ ID NO: 56); (ii) a Raptor ASC including St-sialidase and trastuzumab (including first and fourth polypeptide chains with amino acid sequence SEQ ID NO: 67, encoded by nucleotide sequence SEQ ID NO: 68, and second and third polypeptide chains with amino acid sequence SEQ ID NO: 59, encoded by nucleotide sequence SEQ ID NO: 60); and (iii) a Lobster ASC including St-sialidase and an scFv derived from trastuzumab (including first and second polypeptide chains with amino acid sequence SEQ ID NO: 103, encoded by nucleotide sequence SEQ ID NO: 104). ASCs were made as described in Example 7.

These ASCs were compared to trastuzumab in a mouse syngeneic tumor model injected with a murine breast cancer cell line expressing human Her2 (EMT6-hHer2 cells). Female BALB/c mice, 6-8 weeks of age, were inoculated subcutaneously in the right lower flank region with EMT6-Her2 tumor cells ($5\times10^5$) in 0.1 ml of PBS for tumor development. Mice were randomly allocated to 8 groups when tumors reached 50-100 $mm^3$, mean~75-100 $mm^3$. Treatment groups are described in TABLE 8 with dosing schedule indicated post randomization. Anti-mouse NK1.1 (Clone: PK136; BioXcell, 621717N1), anti-mouse CD8α (Clone: 53-6.7; BioXcell, BE0004-1) and liposomal clodronate (FormuMax Scientific, Inc.) were included in treatment groups as indicated.

TABLE 8

| Group | Animal No. | Treatment | Dose (mg/kg) | Dose volume (μL/g) | Route | Schedule (Days) |
|---|---|---|---|---|---|---|
| 1 | 8 | Vehicle (PBS) | NA | 10 | i.p. | 0, 3, 7, 10, 14, 17 |
| 2 | 8 | Trastuzumab | 10 | 10 | i.p. | 0, 3, 7, 10, 14, 17 |
| 3 | 8 | Raptor | 10 | 10 | i.p. | 0, 3, 7, 10, 14, 17 |

TABLE 8-continued

| Group | Animal No. | Treatment | Dose (mg/kg) | Dose volume (μL/g) | Route | Schedule (Days) |
|---|---|---|---|---|---|---|
| 4 | 8 | Janus | 10 | 10 | i.p. | 0, 3, 7, 10, 14, 17 |
| 5 | 8 | Lobster | 10 | 10 | i.p. | 0, 3, 7, 10, 14, 17 |
| 6 | 8 | Janus | 10 | 10 | i.p. | 0, 3, 7, 10, 14, 17 |
| | | anti-mouse NK1.1 (Clone: PK136) | 10 | 10 | i.p. | 0, 3, 7, 10, 14, 17 |
| 7 | 8 | Janus | 10 | 10 | i.p. | 0, 3, 7, 10, 14, 17 |
| | | anti-mouse CD8α (Clone: 53-6.7) | 10 | 10 | i.p. | 0, 3, 7, 10, 14, 17 |
| 8 | 8 | Janus | 10 | 10 | i.p. | 0, 3, 7, 10, 14, 17 |
| | | liposomal clodronate | 0.5 mg/ mouse | 100 μL/ mouse | i.p. | TIW × 2 wks |

Figure 15A:
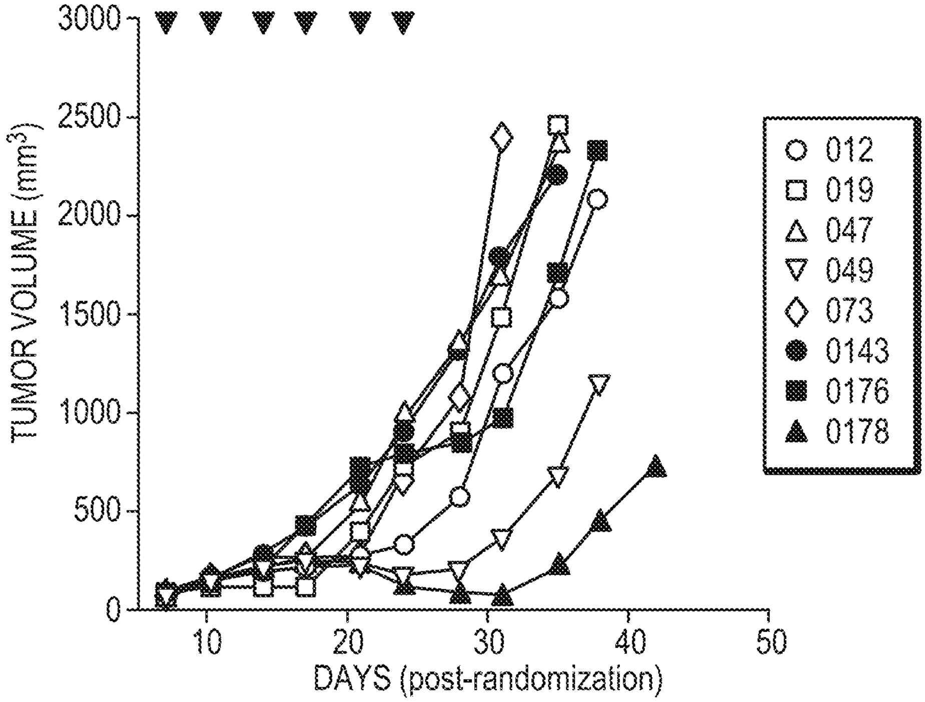
FIGS. 15A-D depict the testing of various configurations of antibody sialidase conjugates in a mouse syngeneic tumor model utilizing EMT6 mouse breast cancer cells engineered to express human Her2. Mice are treated via intraperitoneal injection of 10 mg/kg of each test article on the days marked with black triangles and tumor volume ($mm^3$) recorded. Each line represents an individual mouse. Mice are treated with either trastuzumab (FIG. 15A), Raptor (FIG. 15B), Janus (FIG. 15C) or Lobster (FIG. 15D).
Figure 15B:
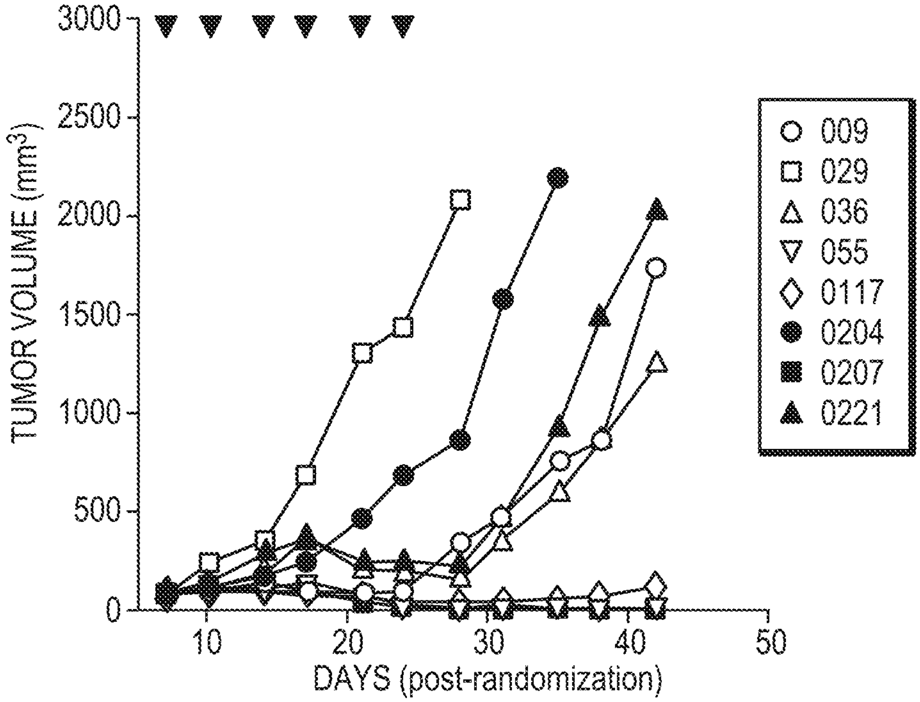
Figure 15C:
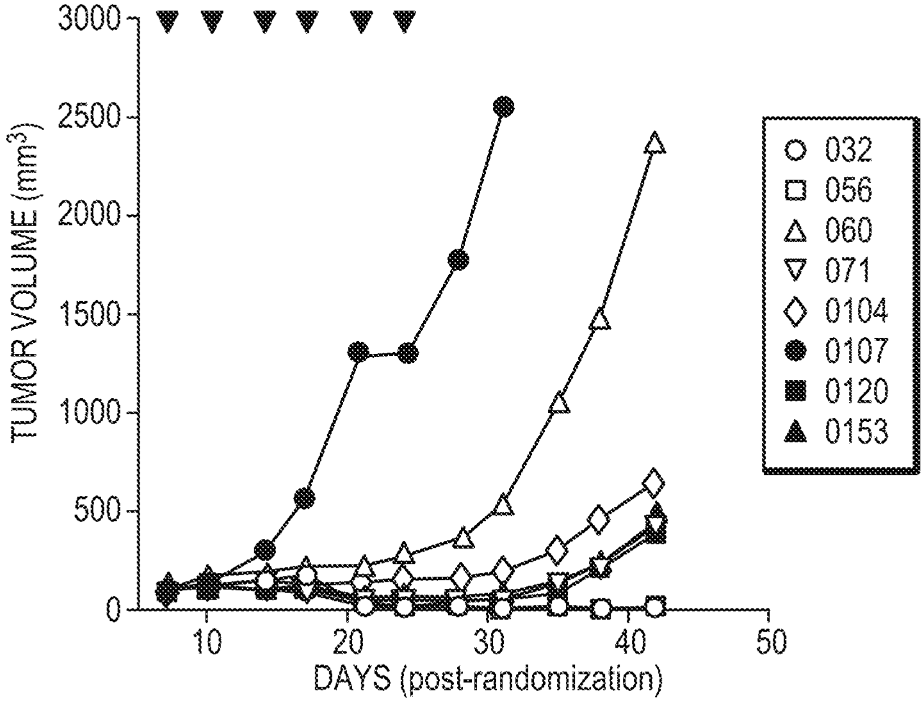
Figure 15D:
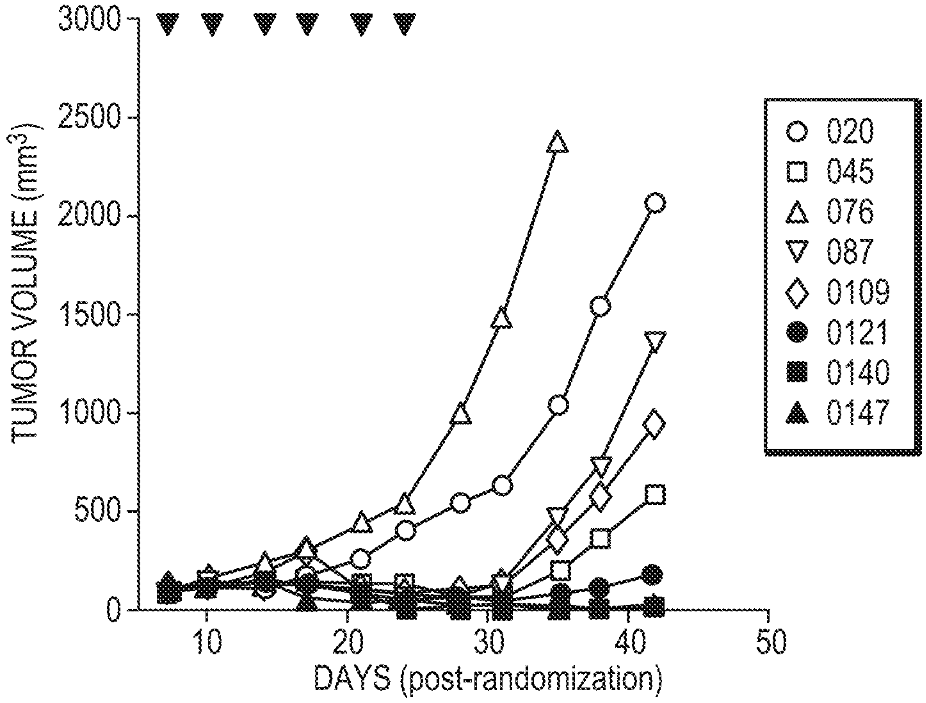
Figure 16A:
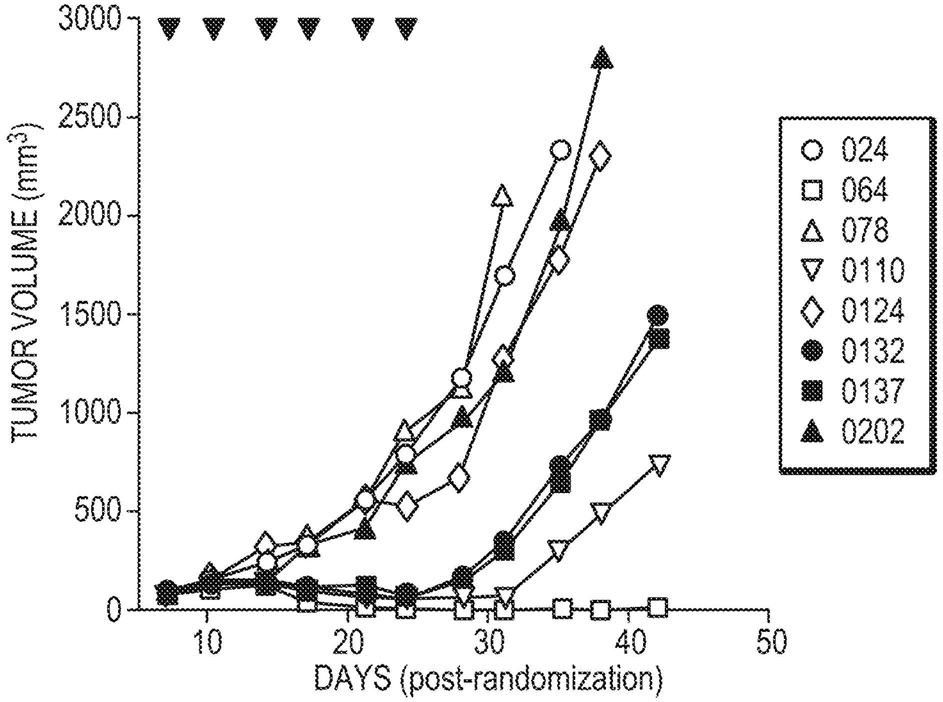
FIGS. 16A-D depict the testing of the Janus antibody sialidase conjugate in a mouse syngeneic tumor model utilizing EMT6 mouse breast cancer cells engineered to express human Her2. Mice were treated via intraperitoneal injection of 10 mg/kg of Janus on the days marked with black triangles and tumor volume ($mm^3$) recorded. Mice were also treated on the same days as Janus with either anti-mouse NK1.1 (10 mg/kg) to deplete natural killer cells (FIG. 16A), liposomal clodronate (0.5 mg/mouse, three times a week for two weeks) to deplete macrophages (FIG. 16B), or anti-mouse CD8α (10 mg/kg) to deplete CD8+ T cells (FIG. 16C). Each line represents an individual mouse.
Figure 16B:
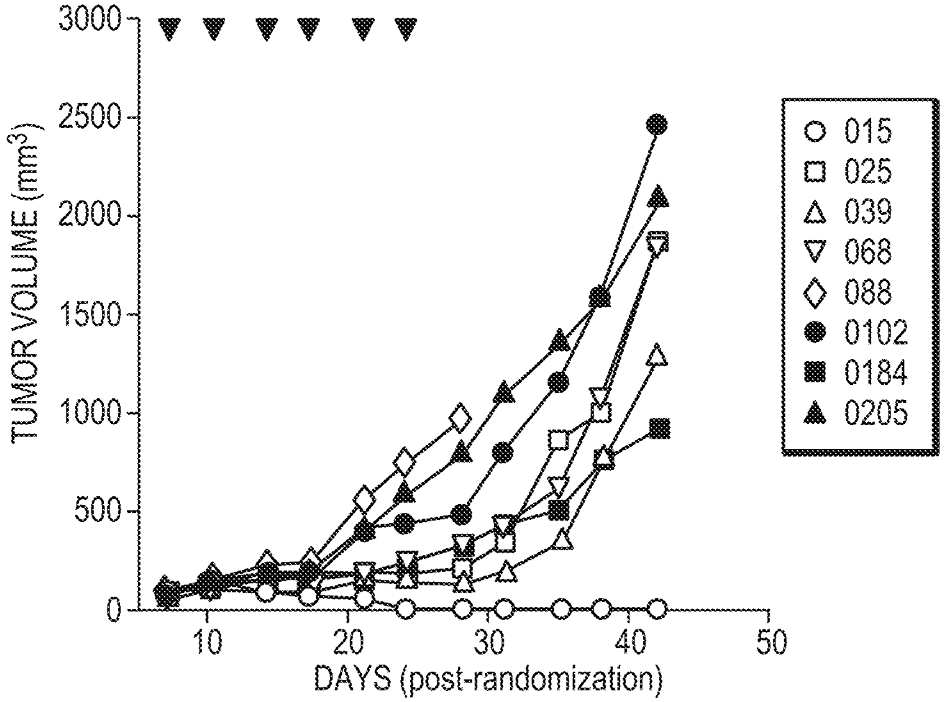
Figure 16C:
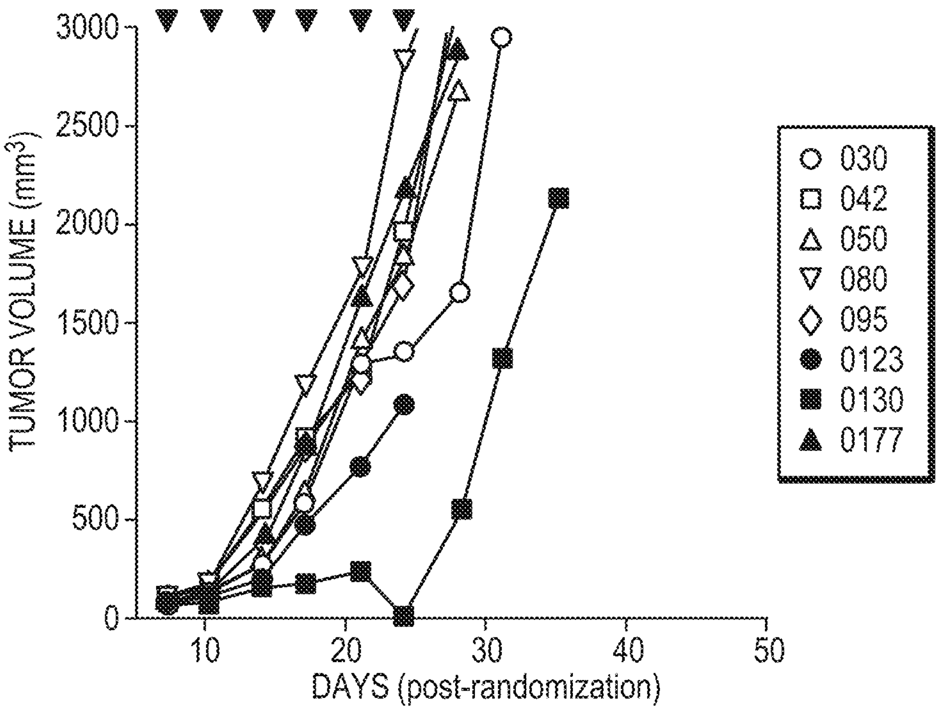
Figure 16D:
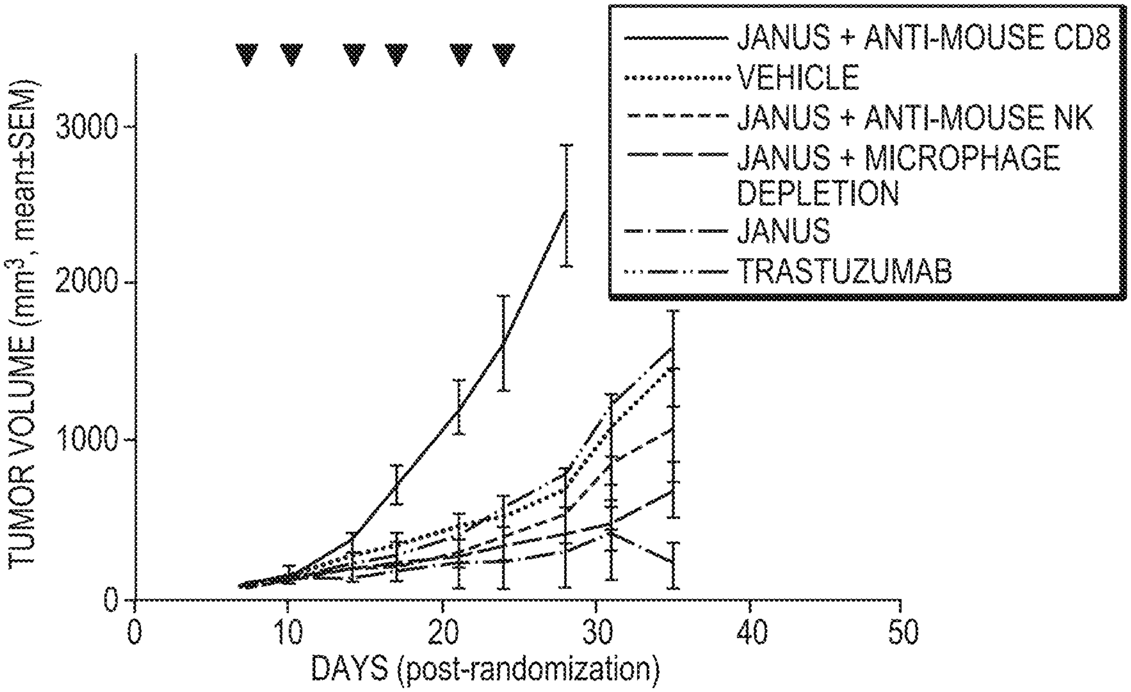

The results from for treatment with trastuzumab, and Raptor, Janus and Lobster ASCs are shown in FIGS. 15A, 15B, 15C and 15D respectively. As can be seen, trastuzumab resulted in no complete responses in eight individual mice as treated (defined as regression below the limit of palpation at any point for the duration of the study, FIG. 15A). This is in contrast to Raptor which demonstrated 2 out of 8 animals with a complete response (FIG. 15B), Janus which demonstrated 3 out of 8 animals with a complete response (FIG. 15C) and Lobster which demonstrated 2 out of 8 animals with a complete response (FIG. 15D).

The results of administration of Janus with NK depletion (anti-mouse NK1.1), macrophage depletion (liposomal clodronate) and CD8 T cell depletion (anti-mouse CD8α) are shown in FIG. 16. As can be seen, compared to Janus treatment alone (FIG. 15C), where there was a complete response in 3 out of 8 animals, NK depletion reduced the number of complete responses to 1 out of 8 animals (FIG. 16A). Macrophage depletion also reduced the number of complete responses to 1 out of 8 animals (FIG. 16B). CD8 T cell depletion completely reversed the effects of Janus, with no animals showing a complete response (FIG. 16C). FIG. 16D shows the mean tumor volume for vehicle, Janus alone, trastuzumab alone and Janus with NK, macrophage and CD8 T cell depletions. These results demonstrate that innate immunity (NK and macrophage dependent) as well as adaptive immunity (CD8 T cells) contribute to in vivo ASC activity.

Example 9

This Example describes the in vivo administration of antibody sialidase conjugates (ASCs) with bacterial sialidases.

The following ASCs were made and tested in this Example: (i) a Janus ASC including *Salmonella typhimurium* sialidase (St-sialidase) and trastuzumab (including a first polypeptide chain with amino acid sequence SEQ ID NO: 67, encoded by nucleotide sequence SEQ ID NO: 68, a second polypeptide chain with amino acid sequence SEQ ID NO: 57, encoded by nucleotide sequence SEQ ID NO: 58, and a third polypeptide chain with amino acid sequence SEQ ID NO: 55, encoded by nucleotide sequence SEQ ID NO: 56); and (ii) a Janus ASC including St-sialidase with two loss of function mutations, D100V and G231V, and trastuzumab ("Janus-LOF," including a first polypeptide chain with amino acid sequence SEQ ID NO: 67, encoded by nucleotide sequence SEQ ID NO: 68, a second polypeptide chain with amino acid sequence SEQ ID NO: 57, encoded by nucleotide sequence SEQ ID NO: 58, and a third polypeptide chain with amino acid sequence SEQ ID NO: 61, encoded by nucleotide sequence SEQ ID NO: 62). ASCs were made as described in Example 7.

These ASCs were tested in a mouse syngeneic orthotopic tumor model injected with an independent EMT6 cell line expressing human Her2 (EMT6-hHer2 cells as described in D'Amico et al. (2016) Annals of Oncology, Volume 27, Issue suppl_8, 41P. Female BALB/c mice, 6-8 weeks of age, were inoculated via intra mammary implantation with EMT6-Her2 tumor cells ($5\times10^6$). Mice were randomly allocated to 6 groups when tumors reached approximately 250 $mm^3$. The treatment groups are described in TABLE 9 with dosing schedule indicated post randomization. Anti-mouse PD1 was obtained from BioXcell (RMP1-14, Cat. #665418F1). Janus and Janus Loss of Function (Janus LOF) are described above in Example 7.

TABLE 9

| Group | Animal No. | Treatment | Dose (mg/kg) | Dose volume (μL/g) | Route | Schedule (Days) |
|---|---|---|---|---|---|---|
| 1 | 6 | Vehicle (PBS) | NA | 10 | i.p. | 0, 3, 7, 10 |
| 2 | 6 | Trastuzumab | 10 | 10 | i.p. | 0, 3, 7, 10 |
| 3 | 6 | Janus | 10 | 10 | i.p. | 0, 3, 7, 10 |
| 4 | 6 | Janus Loss of Function (LOF) | 10 | 10 | i.p. | 0, 3, 7, 10 |
| 5 | 6 | anti-mouse PD1 | 10 | 10 | i.p. | 0, 3, 7, 10 |
| 6 | 6 | Janus | 10 | 10 | i.p. | 0, 3, 7, 10 |
| | | anti-mouse PD1 | 10 | 10 | i.p. | 0, 3, 7, 10 |

Figure 17A:
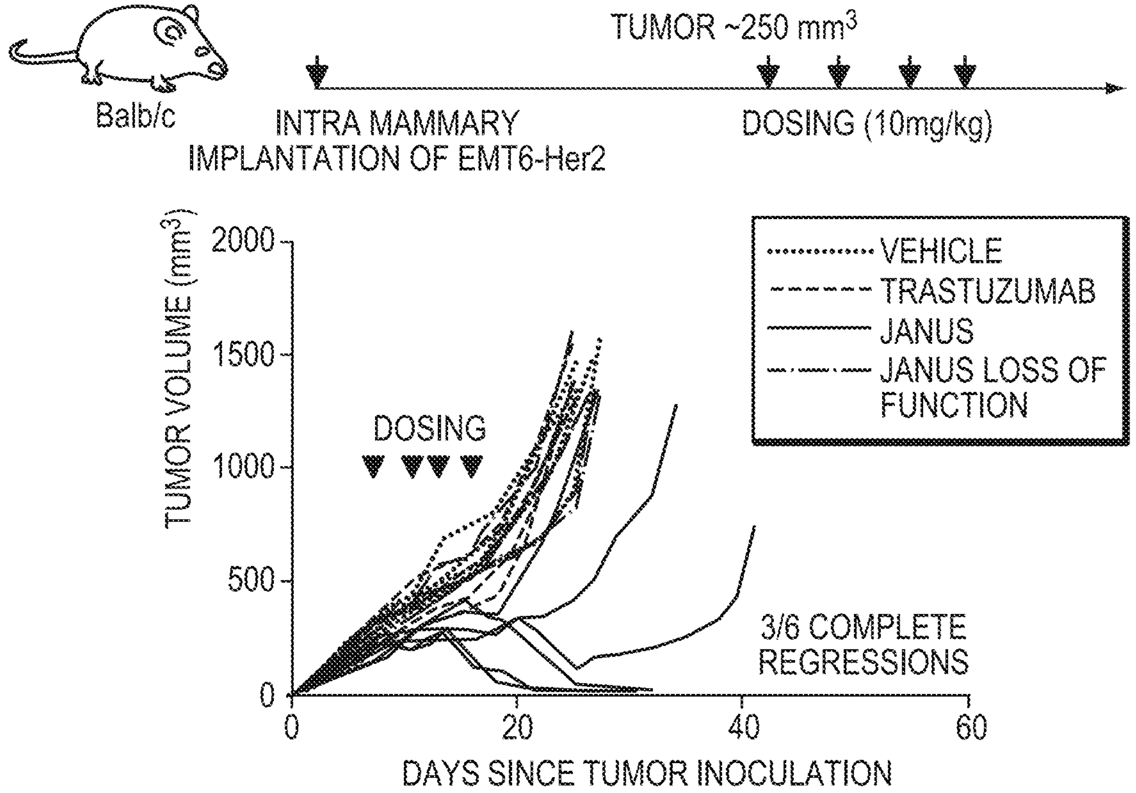
FIGS. 17A-B depict the testing of the Janus antibody sialidase conjugate in a mouse syngeneic orthotopic tumor model utilizing a second source of EMT6 mouse breast cancer cells engineered to express human Her2. Mice are treated via intraperitoneal injection of 10 mg/kg of each test article on the days marked with black triangles and tumor volume ($mm^3$) recorded. Each line represents an individual mouse. Mice are treated (▼) with either vehicle, trastuzumab, Janus or Janus Loss of Function (FIG. 17A).

The results for Groups 1 through 4 (vehicle, trastuzumab, Janus and Janus LOF) are shown in FIG. 17A. As can be seen, 3 out of 6 animals treated with Janus had a complete regression of tumor growth. Notably, Janus LOF and trastuzumab were both comparable to vehicle treated animals.

Figure 17B:
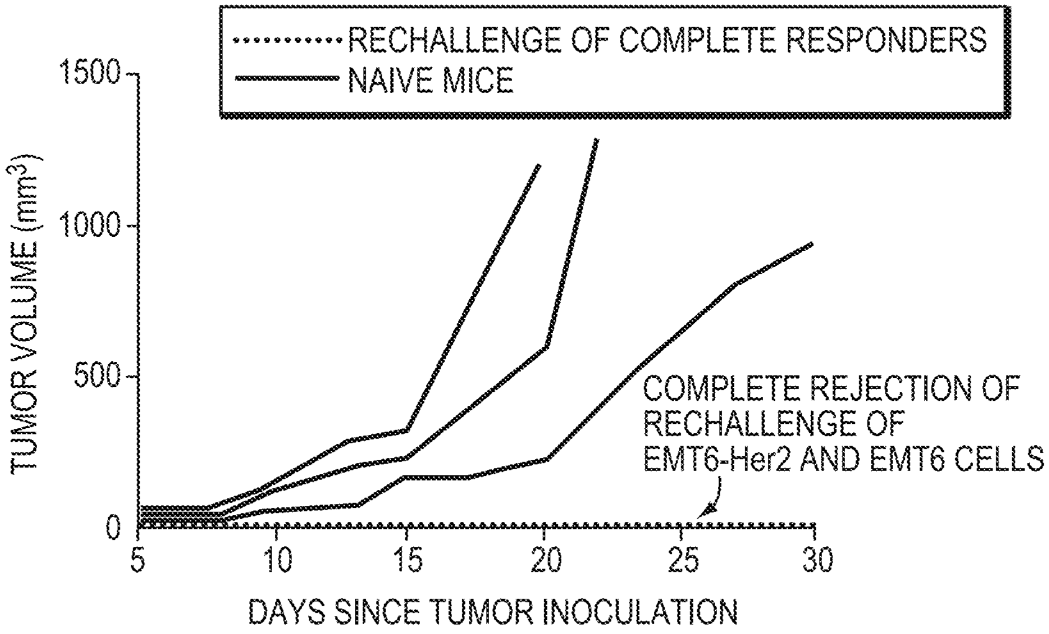

The 3 mice with a complete regression ("cured mice") were rechallenged with either the same EMT6-Her2 cells used originally or parental EMT6 cells (lacking engineered human Her2 expression). EMT6 cells and EMT6-Her2 cells were inoculated subcutaneously in the right or left lower flank region respectively ($5\times10^5$) in 0.1 ml of PBS for tumor development of all three cured mice. EMT6-Her2 cells were also inoculated subcutaneously into naïve mice as a control. As can be seen in FIG. 17B, neither EMT6-Her2 cells nor parental EMT6 cells resulted in tumor growth in the cured mice while EMT6-Her2 cells developed into tumors as expected in the naïve mice. These results suggest that the antibody sialidase conjugates of the present invention are capable of inducing long term memory against tumors. In addition, the long term memory is towards the tumor cell and is independent of the originally targeted cancer antigen (Her2 in this case).

Figure 18A:
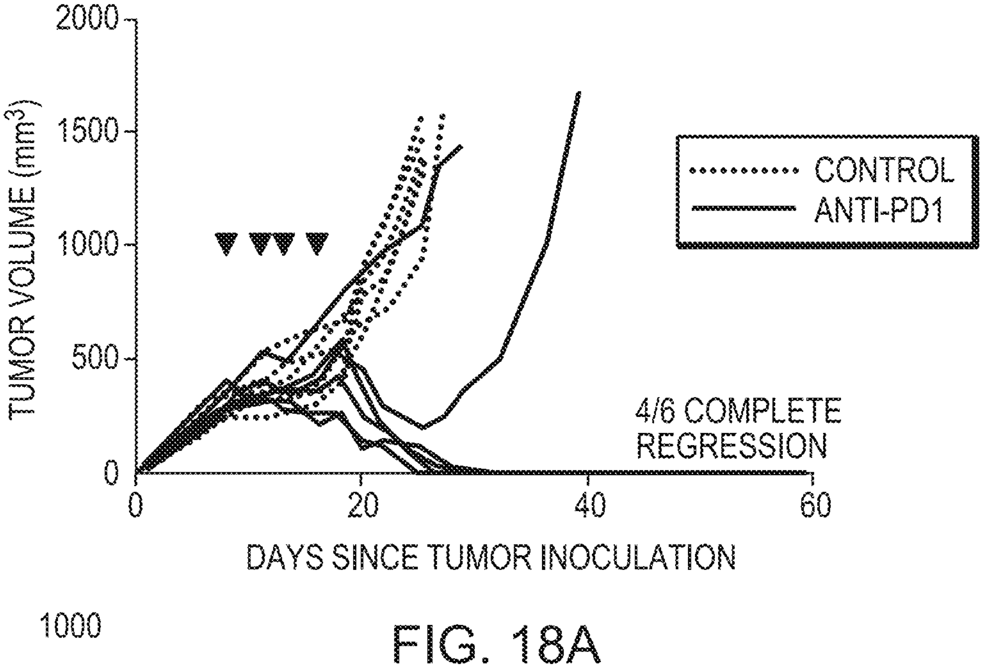
FIGS. 18A-B depict the testing of the Janus antibody sialidase conjugate in a mouse syngeneic orthotopic tumor model in combination with anti-mouse PD1. Mice are treated via intraperitoneal injection of 10 mg/kg of either anti-mouse PD1 alone (FIG. 18A) or Janus and anti-mouse PD1 (10 mg/kg of each, FIG. 18B) on the days marked with black triangles (▼) and tumor volume ($mm^3$) recorded. Each line represents an individual mouse.
Figure 18B:
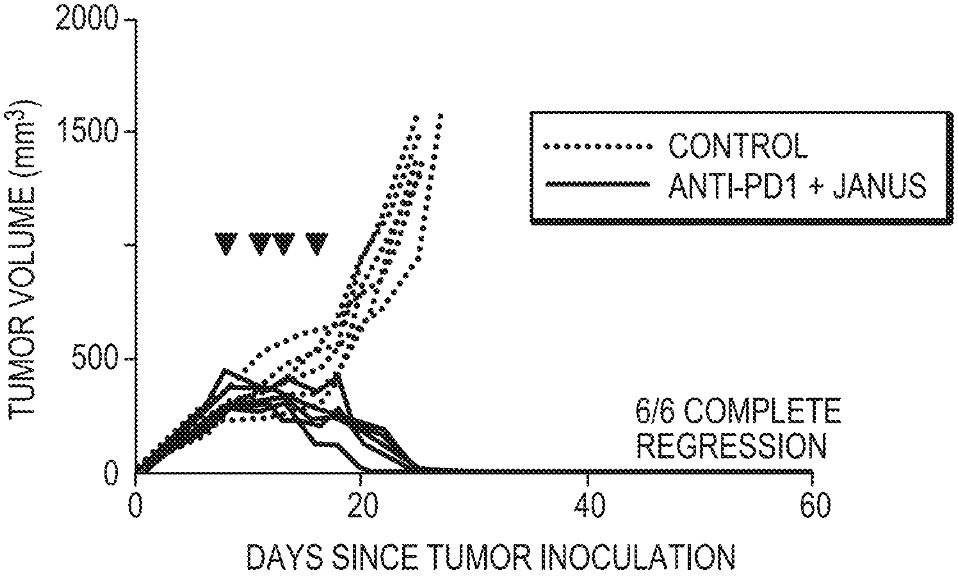

The results for Groups 1, 5 and 6 (vehicle, anti-mouse PD1 and anti-mouse PD1 combined with Janus) are shown in FIG. 18A and FIG. 18B. While anti-mouse PD1 had good activity with 4 out of 6 mice demonstrating complete regressions (similar to Janus alone with 3 out of 6 mice demonstrating complete regression, see FIG. 17A), the combination of anti-mouse PD1 with Janus demonstrated complete regression of tumor growth in all 6 mice (FIG. 18B). There was no body weight loss in any of the animals given this combination.

Example 10

This Example describes the in vivo administration of antibody sialidase conjugates (ASCs) with bacterial sialidases.

A Janus ASC including *Salmonella typhimurium* sialidase (St-sialidase) and trastuzumab (including a first polypeptide chain with amino acid sequence SEQ ID NO: 67, encoded by nucleotide sequence SEQ ID NO: 68, a second polypeptide chain with amino acid sequence SEQ ID NO: 57, encoded by nucleotide sequence SEQ ID NO: 58, and a third polypeptide chain with amino acid sequence SEQ ID NO: 55, encoded by nucleotide sequence SEQ ID NO: 56) was made as described in Example 7.

The ASC was tested in a mouse syngeneic tumor model injected with a B16 melanoma cell line expressing human Her2 (B16D5-Her2, Surana et al. CANCER IMMUNOL RES, 2(11): 1103-1112). Female C57BL/6 mice, 6-8 weeks of age, were inoculated subcutaneously in the right lower flank region with B16D5-Her2 tumor cells ($5\times10^5$). Mice were randomly allocated to 3 groups when tumors reached approximately 50 to 100 $mm^3$. Treatment groups are described in TABLE 10 with dosing schedule indicated post randomization. Anti-mouse PD1, obtained from BioXcell (RMP1-14, Cat. No. 665418F1) and anti-mouse CTLA4, obtained from BioXcell (9D9, Cat. #BE0164), and were used in combination.

TABLE 10

| Group | No. of Animal | Treatment | Dose (mg/kg) | Dose volume (uL/g) | Route | Schedule (Days) |
|---|---|---|---|---|---|---|
| 1 | 6 | Janus | NA | 10 | i.p. | 0, 3, 7, 10 |
| 2 | 6 | Trastuzumab | 10 | 10 | i.p. | 0, 3, 7, 10 |
| 3 | 6 | anti-mouse CTLA4 | 10 | 10 | i.p. | 0, 3, 7, 10 |
| | | anti-mouse PD1 | 10 | 10 | i.p. | 0, 3, 7, 10 |

Figure 19:
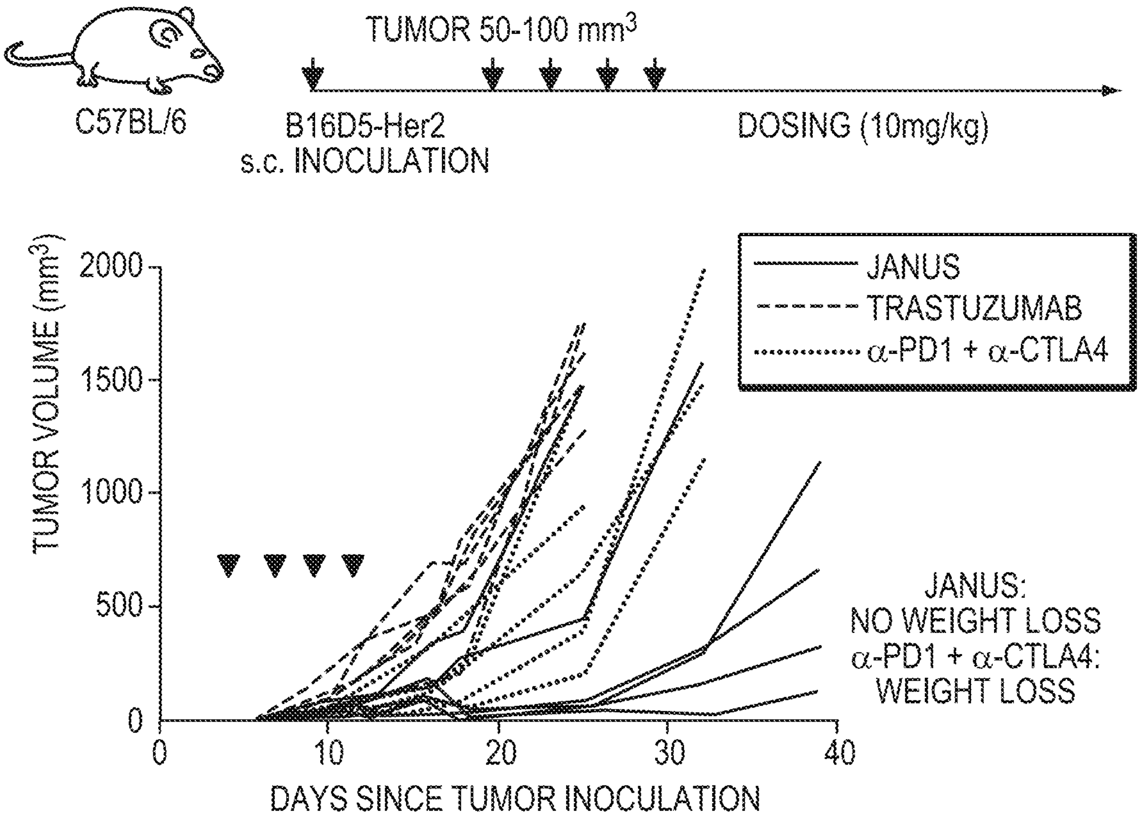
FIG. 19 depicts the testing of various test articles in a mouse syngeneic tumor model injected with a B16 melanoma cell line expressing human Her2. Mice are treated via intraperitoneal injection of 10 mg/kg of either Janus, trastuzumab or a combination of anti-mouse PD1 and anti-mouse CTLA4 (10 mg/kg of each) on the days marked with black triangles (▼) and tumor volume ($mm^3$) recorded. Each line represents an individual mouse.

The B16 melanoma mouse model is considered a difficult tumor model to treat with immuno-oncology approaches. A comparison of Janus to a combination of anti-mouse PD1 and anti-mouse CTLA4 was carried out. The results are shown in FIG. 19. Anti-mouse PD1 combined with anti-mouse CTLA4 had an impact on B16D5-Her2 tumor growth, but this combination also demonstrated significant weight loss in the treated animals. By comparison, Janus demonstrated a more robust anti-tumor activity with no significant weight loss. Trastuzumab alone demonstrated marginal activity in this model.

Example 11

This example describes targeted cleavage of terminal sialic acids from tumor cells by antibody sialidase conjugates (ASCs).

The following ASCs were made and tested in this Example: (i) a Raptor ASC including St-sialidase and trastuzumab (including first and fourth polypeptide chains with amino acid sequence SEQ ID NO: 67, encoded by nucleotide sequence SEQ ID NO: 68, and second and third polypeptide chains with amino acid sequence SEQ ID NO: 59, encoded by nucleotide sequence SEQ ID NO: 60); (ii) a Janus ASC including *Salmonella typhimurium* sialidase (St-sialidase) and trastuzumab (including a first polypeptide chain with amino acid sequence SEQ ID NO: 67, encoded by nucleotide sequence SEQ ID NO: 68, a second polypeptide chain with amino acid sequence SEQ ID NO: 57, encoded by nucleotide sequence SEQ ID NO: 58, and a third polypeptide chain with amino acid sequence SEQ ID NO: 55, encoded by nucleotide sequence SEQ ID NO: 56); (iii) a Lobster ASC including St-sialidase and an scFv derived from trastuzumab (including first and second polypeptide chains with amino acid sequence SEQ ID NO: 103, encoded by nucleotide sequence SEQ ID NO: 104); (iv) a Janus ASC including St-sialidase with two loss of function mutations, D100V and G231V, and trastuzumab ("Janus-LOF," including a first polypeptide chain with amino acid sequence SEQ ID NO: 67, encoded by nucleotide sequence SEQ ID NO: 68, a second polypeptide chain with amino acid sequence SEQ ID NO: 57, encoded by nucleotide sequence SEQ ID NO: 58, and a third polypeptide chain with amino acid sequence SEQ ID NO: 61, encoded by nucleotide sequence SEQ ID NO: 62); and (v) a non-Her2 binding Janus ASC including St-sialidase and an antibody recognizing respiratory syncytial virus F protein ("Janus non-Her2"; including a first polypeptide chain with amino acid sequence SEQ ID NO: 94, encoded by nucleotide sequence SEQ ID NO: 95, a second polypeptide chain with amino acid sequence SEQ ID NO: 96, encoded by nucleotide sequence SEQ ID NO: 97, and a third polypeptide chain with amino acid sequence SEQ ID NO: 55, encoded by nucleotide sequence SEQ ID NO: 56). ASCs were made as described in Example 7.

Figure 20:
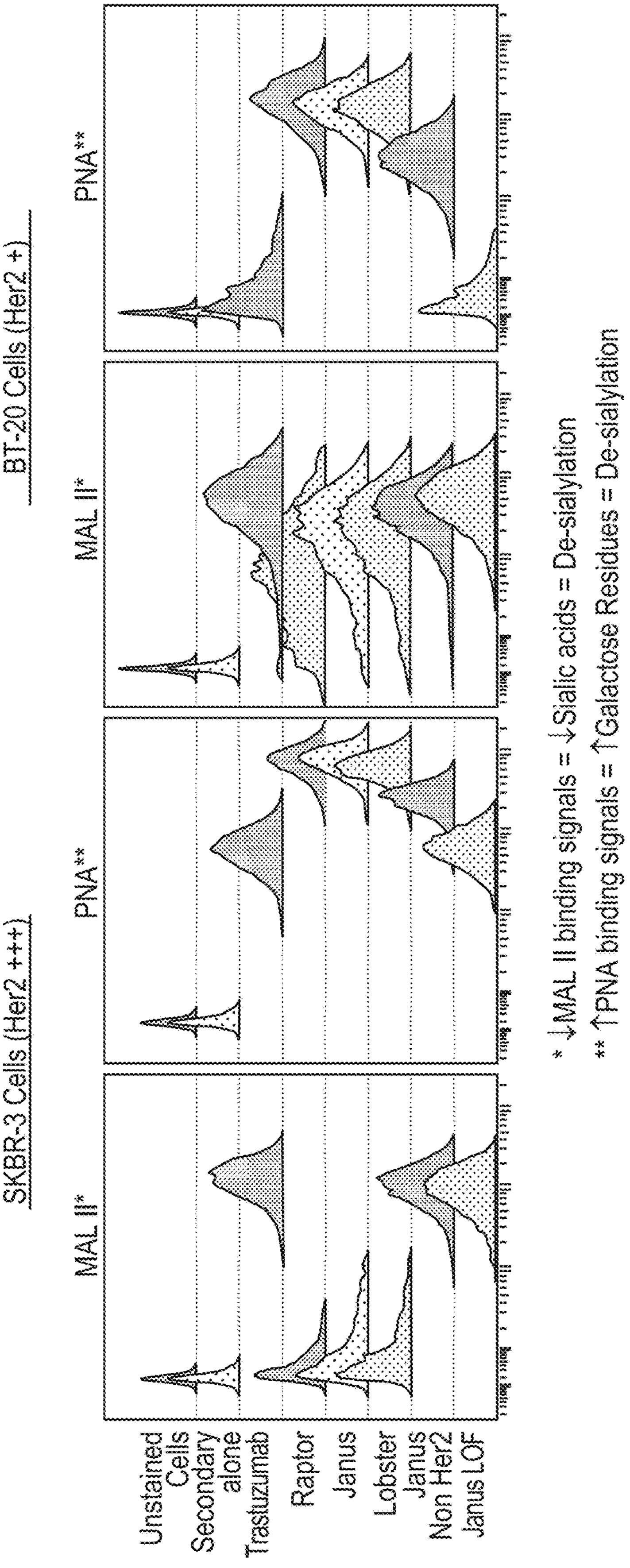
FIG. 20 depicts binding of MAL II and PNA lectins to tumor cells, as assayed by FACS staining, following the indicated treatment. MAL II and PNA staining are indicative of cleavage of terminal sialic acids from the tumor cells, MAL II staining is expected to decrease upon loss of cell surface sialic acid and PNA staining is expected to increase with loss of cell surface sialic acid.

SKBR-3 cells (Her2+++) or BT-20 cells (Her2+) were incubated with trastuzumab or the indicated ASCs, and FACS staining with MAL II and PNA was used to measure the degree of sialic acid removal (see, FIG. 20). MAL II is a lectin with high affinity for sialic acid, and therefore MAL II staining was expected to decrease upon loss of cell surface sialic acid following cleavage by an ASC. PNA is a lectin with high affinity for terminal galactose residues and therefore PNA staining was expected to increase with loss of cell surface galactose coupled sialic acid following cleavage by an ASC. Compared to trastuzumab, treatment with Janus, Raptor and Lobster ASCs decreased sialic acid levels on cancer cells with high or low levels of Her2 (SKBR-3 and BT-20 cells, respectively). No sialic acid cleavage was observed for the Janus LOF construct and substantially reduced sialic acid cleavage was observed for the Janus non-Her2 binding construct.

Example 12

This example describes a reduction in cancer-cell mediated inhibition of dendritic cell (DC) activation by antibody sialidase conjugates (ASCs).

DCs play a major role in initiating and sustaining an immune response. They seek antigens in tissues (including tumor sites). Once DCs encounter antigens, they mature, activate, and move to draining lymph nodes for presentation of the processed antigen to T cells. This process of DC activation can be inhibited by the interaction of hypersialylated proteins on cancer cells with Siglecs on the surface of DCs. Desilylation of hypersialylated proteins on cancer cells by an ASC can potentially reduce this inhibition and result in increased activation of DCs.

To test this, SKBR-3 cells (which express high levels of Her2) were initially incubated with either: (i) a Janus ASC including *Salmonella typhimurium* sialidase (St-sialidase) and trastuzumab (including a first polypeptide chain with amino acid sequence SEQ ID NO: 67, encoded by nucleotide sequence SEQ ID NO: 68, a second polypeptide chain with amino acid sequence SEQ ID NO: 57, encoded by nucleotide sequence SEQ ID NO: 58, and a third polypeptide chain with amino acid sequence SEQ ID NO: 55, encoded by nucleotide sequence SEQ ID NO: 56); (ii) a Janus ASC including St-sialidase with two loss of function mutations, D100V and G231V, and trastuzumab ("Janus-LOF," including a first polypeptide chain with amino acid sequence SEQ ID NO: 67, encoded by nucleotide sequence SEQ ID NO: 68, a second polypeptide chain with amino acid sequence SEQ ID NO: 57, encoded by nucleotide sequence SEQ ID NO: 58, and a third polypeptide chain with amino acid sequence SEQ ID NO: 61, encoded by nucleotide sequence SEQ ID NO: 62); or (iii) a non-Her2 binding Janus ASC including St-sialidase and an antibody recognizing respiratory syncytial virus F protein ("Janus non-Her2"; including a first polypeptide chain with amino acid sequence SEQ ID NO: 94, encoded by nucleotide sequence SEQ ID NO: 95, a second polypeptide chain with amino acid sequence SEQ ID NO: 96, encoded by nucleotide sequence SEQ ID NO: 97, and a third polypeptide chain with amino acid sequence SEQ ID NO: 55, encoded by nucleotide sequence SEQ ID NO: 56). ASCs were made as described in Example 7. Cells were then washed and co-cultured with DCs for 16 hours in presence or absence of lipopolysaccharide (LPS; a DC activation signal). DC surface activation markers were assessed by flow cytometry.

Figure 21:
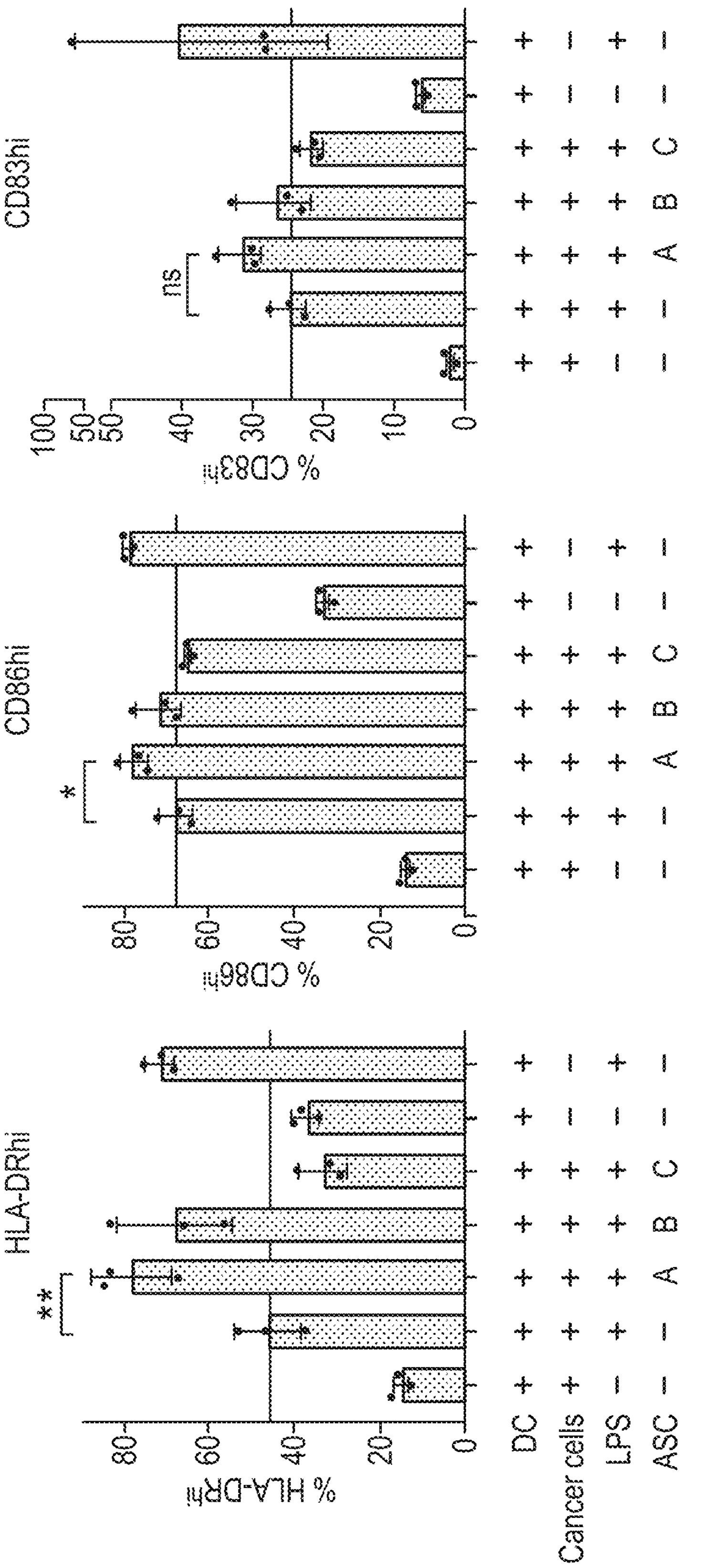
FIG. 21 depicts cell surface expression of dendritic cell (DC) activation markers HLA-DR, CD86 and CD83, as assayed by flow cytometry, following the indicated treatment. A indicates a Janus ASC made with St-sialidase and trastuzumab, B indicates a non-Her2 binding Janus ASC made with St-sialidase, and C indicates a Janus ASC made with a loss of function St-sialidase mutant and trastuzumab. * $P\leq0.05$,  $P\leq0.01$, * $P\leq0.001$, and **** $P\leq0.0001$.
Figure 22A:
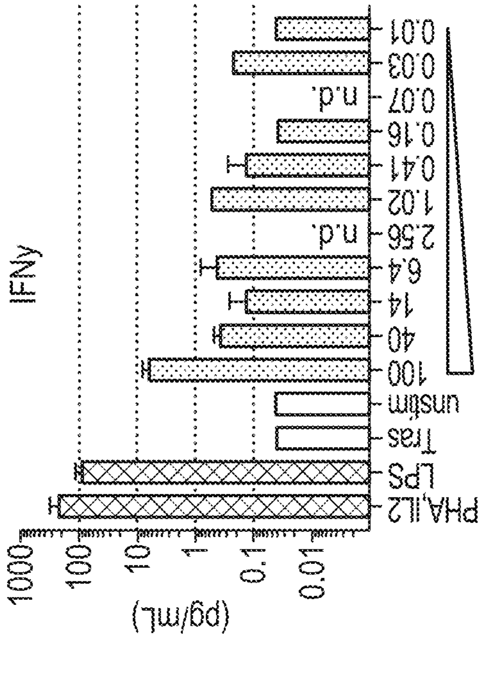
FIGS. 22A-D depict IFNγ (FIG. 22A), IL-1b (FIG. 22B), IL-6 (FIG. 22C), and TNFα (FIG. 22D) release following treatment with a Janus ASC including human Neu2 with ΔM1, V6Y, I187K, and C332A mutations and trastuzumab. Freshly isolated human peripheral blood mononuclear cells (PBMCs) were incubated with Janus at the indicated concentrations (shown in μg/ml) for 24 hours. PHA-L with IL-2 or LPS were used as positive controls to stimulate cytokine release. Trastuzumab (Tras) was used as a negative control.
Figure 22B:
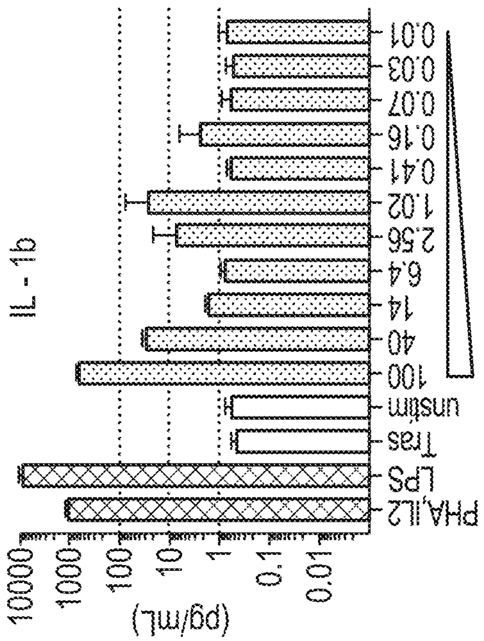
Figure 22C:
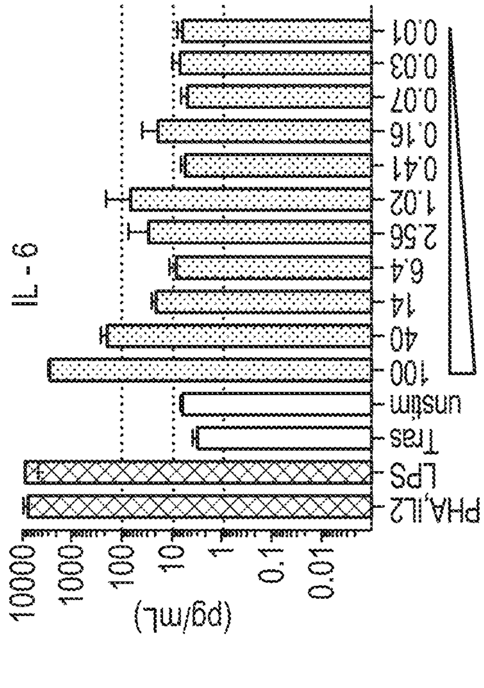
Figure 22D:
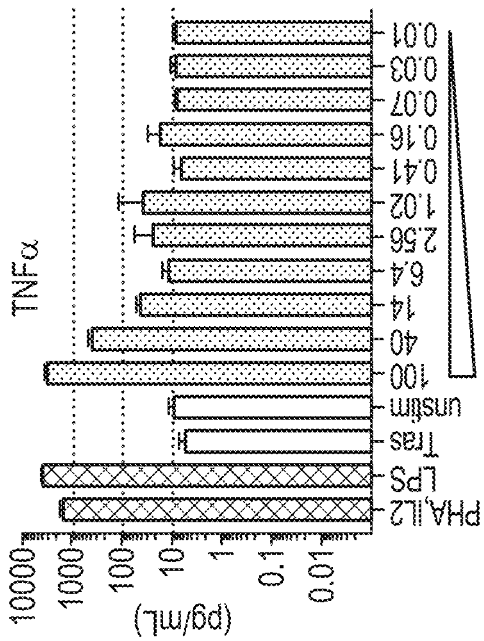
Figure 23A:
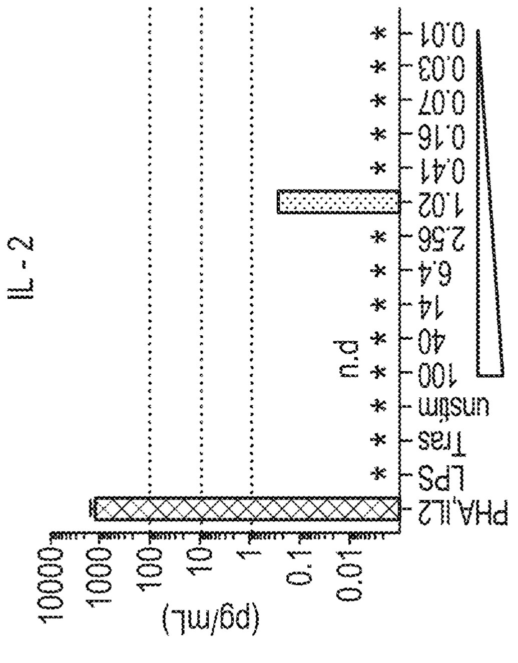
FIGS. 23A-D depict IL-2 (FIG. 23A), IL-4 (FIG. 23B), IL-10 (FIG. 23C), and IL-13 (FIG. 23D) release following treatment with a Janus ASC including human Neu2 with ΔM1, V6Y, I187K, and C332A mutations and trastuzumab. Freshly isolated human peripheral blood mononuclear cells (PBMCs) were incubated with Janus at the indicated concentrations (shown in μg/ml) for 24 hours. PHA-L with IL-2 or LPS were used as positive controls to stimulate cytokine release. Trastuzumab (Tras) was used as a negative control.
Figure 23B:
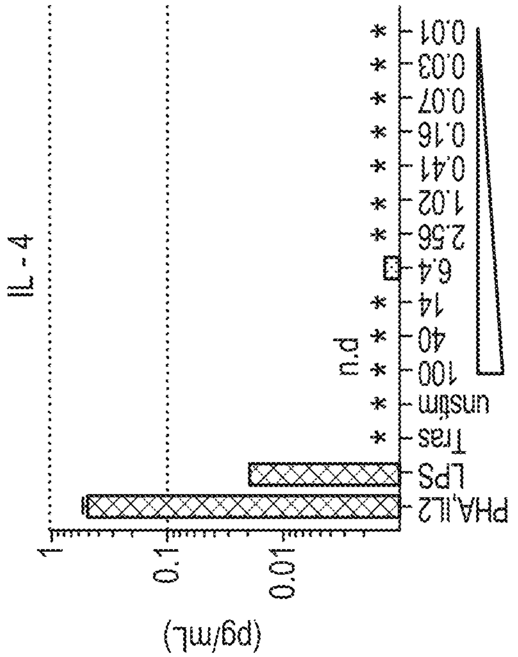
Figure 23C:
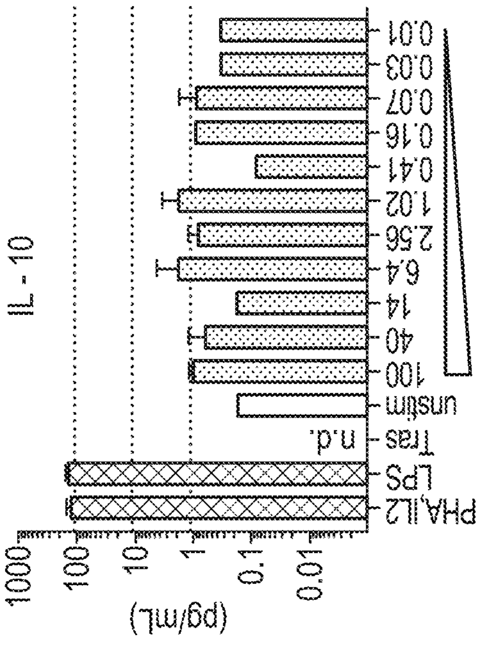
Figure 23D:
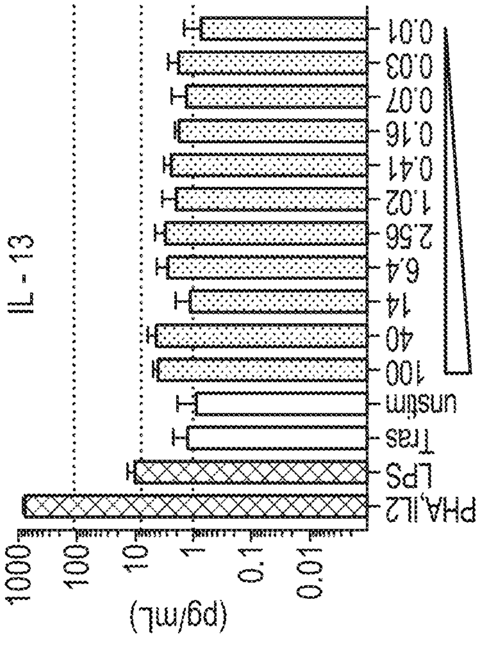

As can be seen in FIG. 21, co-culture of DCs with LPS increased levels of the surface activation markers HLA-DR, CD86 and CD83. However, this increase was reduced in the presence of SKBR-3 cancer cells, reflecting inhibition of DC activation by the cancer cells. Treatment of the SKBR-3 cell line with Janus blocked SKBR-3-mediated inhibition of DCs, as evidenced by increased cell surface expression of HLA-DR, CD86 and CD83 on the DCs. The effect was reduced for Janus non-Her2 and completely absent for Janus LOF versions of the ASC, indicating that both active and targeted sialidase activity in the ASC is required for an optimal effect.

These results demonstrate that targeted desilylation of cancer cells by ASCs can reduce cancer-cell mediated inhibition of dendritic cell (DC) activation. Accordingly, treatment with ASCs may be an effective strategy for enhancing immunogenicity of tumor antigens by enhancing their presentation by DCs.

Example 13

This Example describes induction of proinflammatory cytokines in peripheral blood mononuclear cells (PBMCs) by an antibody sialidase conjugate (ASC) with a human sialidase.

A Janus ASC was constructed that includes Neu2 with M1D, V6Y, I187K, and C332 Å mutations and trastuzumab (including a first polypeptide chain with amino acid sequence SEQ ID NO: 67, encoded by nucleotide sequence SEQ ID NO: 68, a second polypeptide chain with amino acid sequence SEQ ID NO: 57, encoded by nucleotide sequence SEQ ID NO: 58, and a third polypeptide chain with amino acid sequence SEQ ID NO: 54, encoded by nucleotide sequence SEQ ID NO: 98)

Human PBMCs were freshly isolated, washed two times, and plated in culture medium (RPMI 1640+L-glut, 10% FBS, 1% P/S) at 250,000 PBMCs per well. PBMCs were incubated in quadruplicate with the Janus ASC at 2.5× serial dilutions, with a maximum concentration of 100 μg/ml. After 24 hours at 37° C., cells were removed by centrifugation and supernatants collected for cytokine measurement using Luminex multiplex assays according to manufacturer's instruction.

As positive controls, phytohemagglutinin-L (PHA-L; 5 μg/mL) with IL-2 (10 U/mL) or LPS (10 ng/mL) were used to stimulate cytokine release. As a negative control, trastuzumab (10 μg/mL) was used. As seen FIG. 22, the human Janus ASC induced proinflammatory cytokine secretion in PBMCs (e.g., INFγ, IL-1b, IL-6 and TNFα). FIG. 23 depicts the effects of the human Janus ASC on PBMC secretion of proinflammatory cytokine IL-2, antiinflammatory cytokines IL-4 and IL-10, and pro- and antiinflammatory cytokine IL-13.

These results demonstrate that ASCs can induce secretion of proinflammatory cytokines in PBMCs.

Example 14

This example describes increased immune-related activities following addition of antibody sialidase conjugates (ASCs) to a host-tumor microenvironment model system.

BioMAP Oncology Panels (Eurofins, Fremont, Calif.) are a complex co-culture of tumor cell lines and early passage primary human cells (endothelial cells/fibroblasts and PBMCs) that mimic cancer-induced immune suppression. In certain circumstances, BioMAP results have correlated with clinical outcomes. For example, pembrolizumab has been shown to increase immune response in the model, while IDO inhibitors had no effect.

The following constructs were tested in a blinded study using the BioMAP VascHT29 co-culture system: (i) a Janus ASC including *Salmonella typhimurium* sialidase (St-sialidase) and trastuzumab (including a first polypeptide chain with amino acid sequence SEQ ID NO: 67, encoded by nucleotide sequence SEQ ID NO: 68, a second polypeptide chain with amino acid sequence SEQ ID NO: 57, encoded by nucleotide sequence SEQ ID NO: 58, and a third polypeptide chain with amino acid sequence SEQ ID NO: 55, encoded by nucleotide sequence SEQ ID NO: 56); (ii) a Janus ASC including St-sialidase with two loss of function mutations, D100V and G231V, and trastuzumab ("Janus-LOF," including a first polypeptide chain with amino acid sequence SEQ ID NO: 67, encoded by nucleotide sequence SEQ ID NO: 68, a second polypeptide chain with amino acid sequence SEQ ID NO: 57, encoded by nucleotide sequence SEQ ID NO: 58, and a third polypeptide chain with amino acid sequence SEQ ID NO: 61, encoded by nucleotide sequence SEQ ID NO: 62); (iii) isotype control; (iv) trastuzumab; or (v) pembrolizumab. All ASCs were made as described in Example 7.

Figure 24:
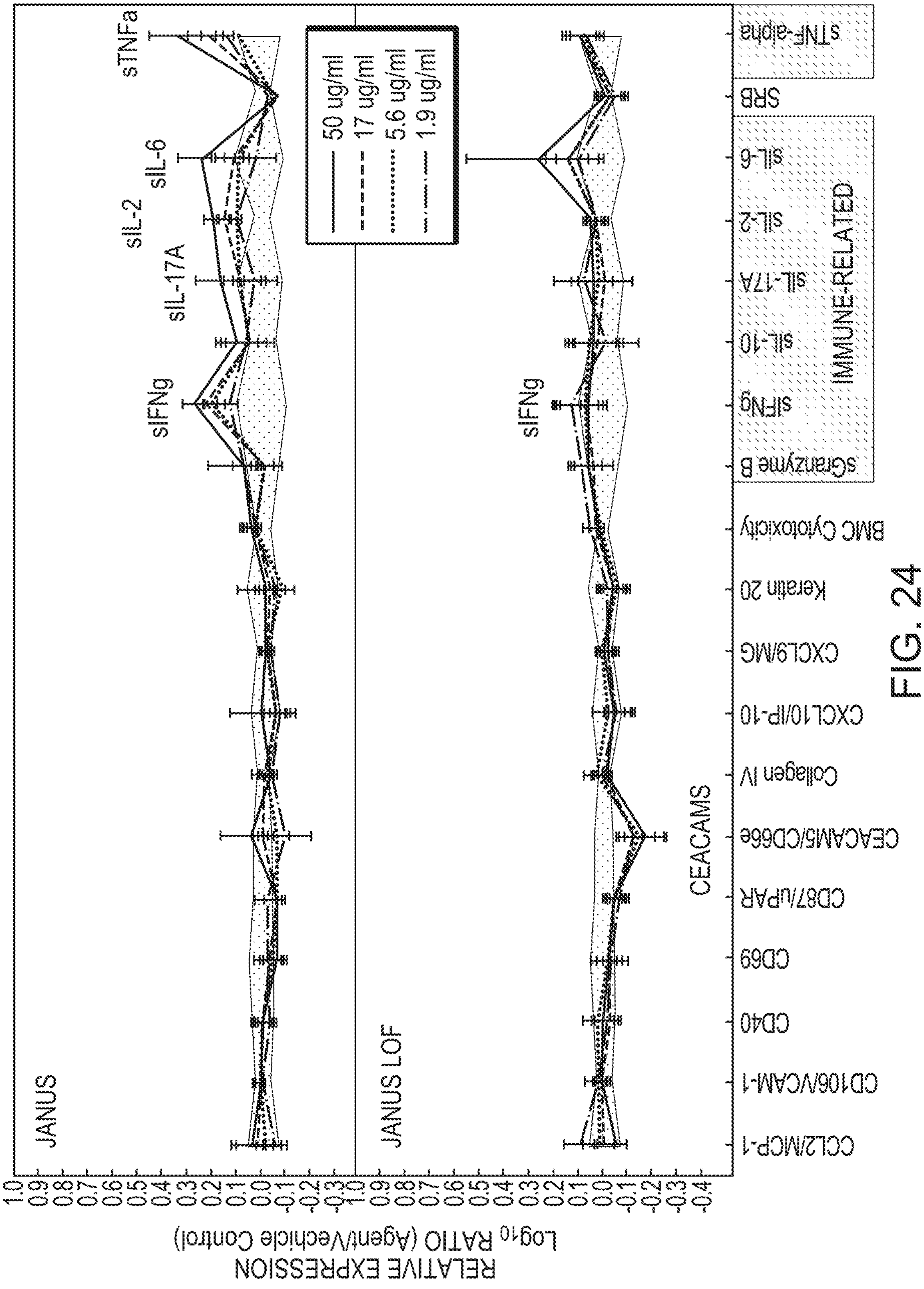
FIG. 24 depicts relative expression of the indicated markers following addition of Janus and Janus LOF to the BioMAP VascHT29 co-culture tumor microenvironment model. The historical range of vehicle response is represented by the shaded area along the zero baseline. Values for each measurement are represented by the log of the ratio of test article to vehicle control. Analytes with a statistically meaningful value above historical ranges are annotated.
Figure 25:
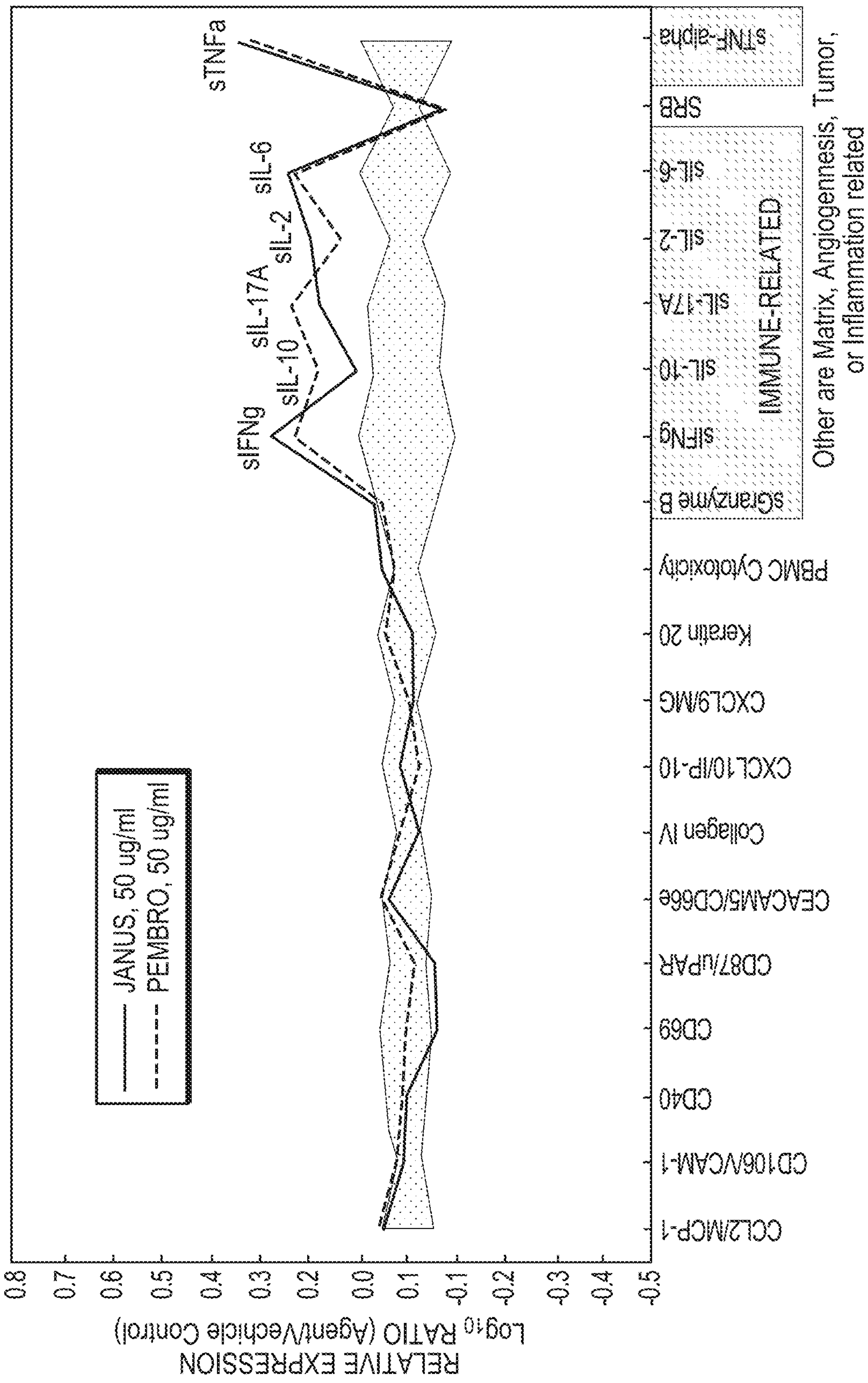
FIG. 25 depicts relative expression of the indicated markers following addition of Janus and pembrolizumab to the BioMAP VascHT29 co-culture tumor microenvironment model. The historical range of vehicle response is represented by the shaded area along the zero baseline. Values for each measurement are represented by the log of the ratio of test article to vehicle control. Analytes with a statistically meaningful value above historical ranges are annotated.

Test reagents were tested at a range of concentrations (50, 17, 5.6 and 1.9 μg/ml) for 48 hours. Following exposure, a number of parameters were analyzed as depicted in FIG. 24 and FIG. 25. In both figures, the historical range of vehicle response is represented by the shaded area along the zero baseline. Values for each measurement are represented by the log of the ratio of test article to vehicle control. Analytes with a statistically meaningful value above historical ranges are annotated.

FIG. 24 demonstrates that Janus is not cytotoxic at the concentrations tested in this study. Janus demonstrated a dose dependent increase in a number of immune-related activities, including increased soluble IL-17A, IL-6, IL-2, and IFNγ as well as inflammation-related activities as seen by increased TNFα. Janus LOF is not cytotoxic at the concentrations tested in this study and demonstrated modest immune-related activities with increased IFNγ and tumor-related activities with decreased CEACAMS. FIG. 25 is a comparison of Janus to pembrolizumab. As can be seen in FIG. 25, Janus has a similar activity to pembrolizumab in this tumor microenvironment model.

Example 15

This Example describes the in vivo administration of antibody sialidase conjugates (ASCs) containing bacterial sialidases.

The following ASCs were made and tested in this Example: (i) a Janus ASC including *Salmonella typhimurium* sialidase (St-sialidase) and trastuzumab (including a first polypeptide chain with amino acid sequence SEQ ID NO: 67, encoded by nucleotide sequence SEQ ID NO: 68, a second polypeptide chain with amino acid sequence SEQ ID NO: 57, encoded by nucleotide sequence SEQ ID NO: 58, and a third polypeptide chain with amino acid sequence SEQ ID NO: 55, encoded by nucleotide sequence SEQ ID NO: 56); and (ii) a non-Her2 binding Janus ASC including St-sialidase and an antibody recognizing respiratory syncytial virus F protein ("Janus non-Her2"; including a first polypeptide chain with amino acid sequence SEQ ID NO: 94, encoded by nucleotide sequence SEQ ID NO: 95, a second polypeptide chain with amino acid sequence SEQ ID NO: 96, encoded by nucleotide sequence SEQ ID NO: 97, and a third polypeptide chain with amino acid sequence SEQ ID NO: 55, encoded by nucleotide sequence SEQ ID NO: 56). ASCs were made as described in Example 7.

The ASCs were compared to trastuzumab in a mouse syngeneic tumor model. Female BALB/c mice, 6-8 weeks of age, were inoculated subcutaneously in the right lower flank region with a murine breast cancer cell line expressing human Her2 (EMT6-hHer2 cells; $5\times10^5$ cells) in 0.1 ml of PBS for tumor development. Mice were randomly allocated to 4 groups of 8 animals each when tumors reached 50-100 $mm^3$, mean~75-100 $mm^3$.

Figure 26:
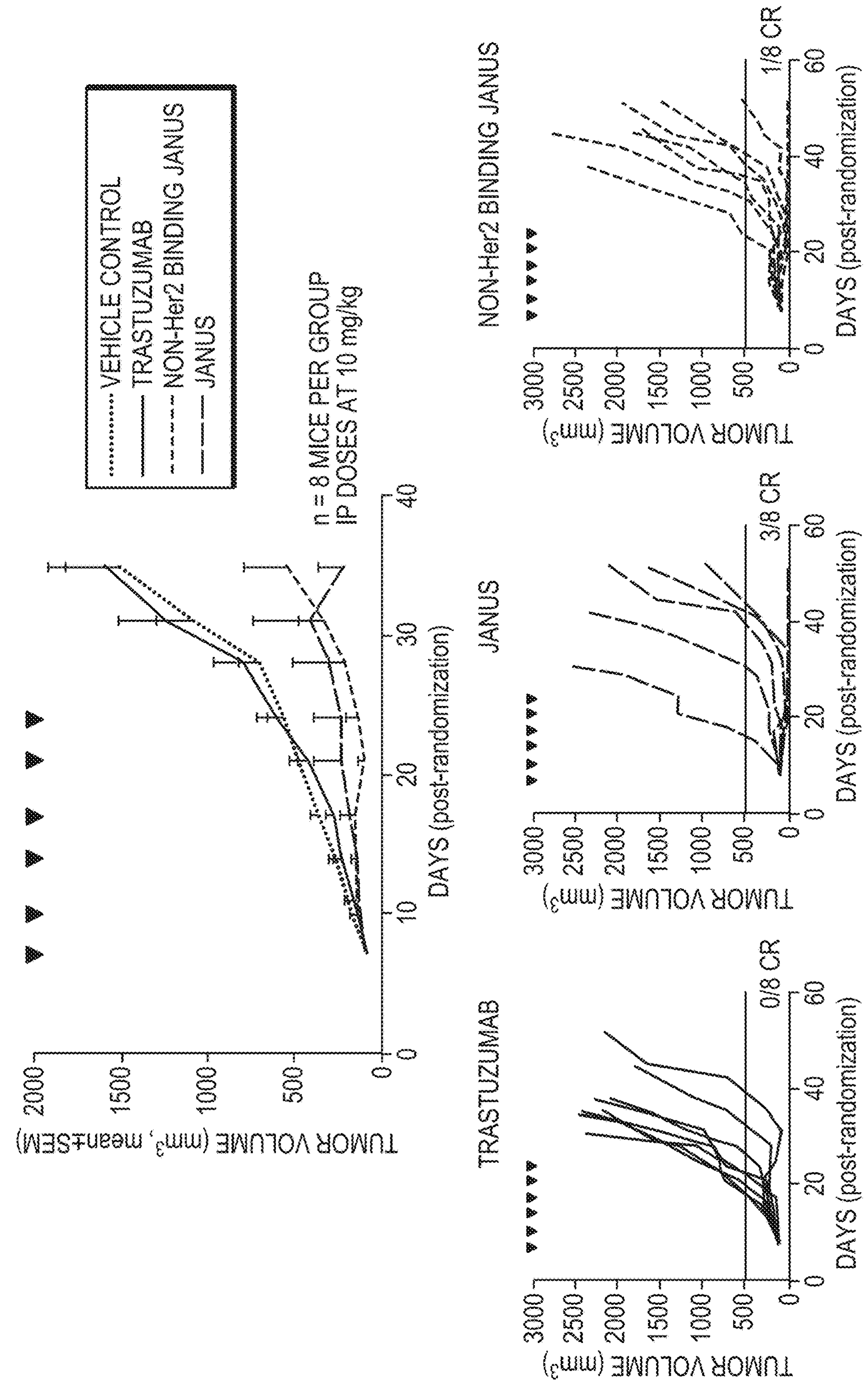
FIGS. 26A-B depict the testing of the Janus antibody sialidase conjugate in a mouse syngeneic tumor model utilizing EMT6 mouse breast cancer cells engineered to express human Her2. Mice were treated via intraperitoneal injection of 10 mg/kg of Janus, trastuzumab or a non-Her2 binding Janus versus vehicle on the days marked with black triangles (▼) and tumor volume ($mm^3$) was recorded.
Figure 27:
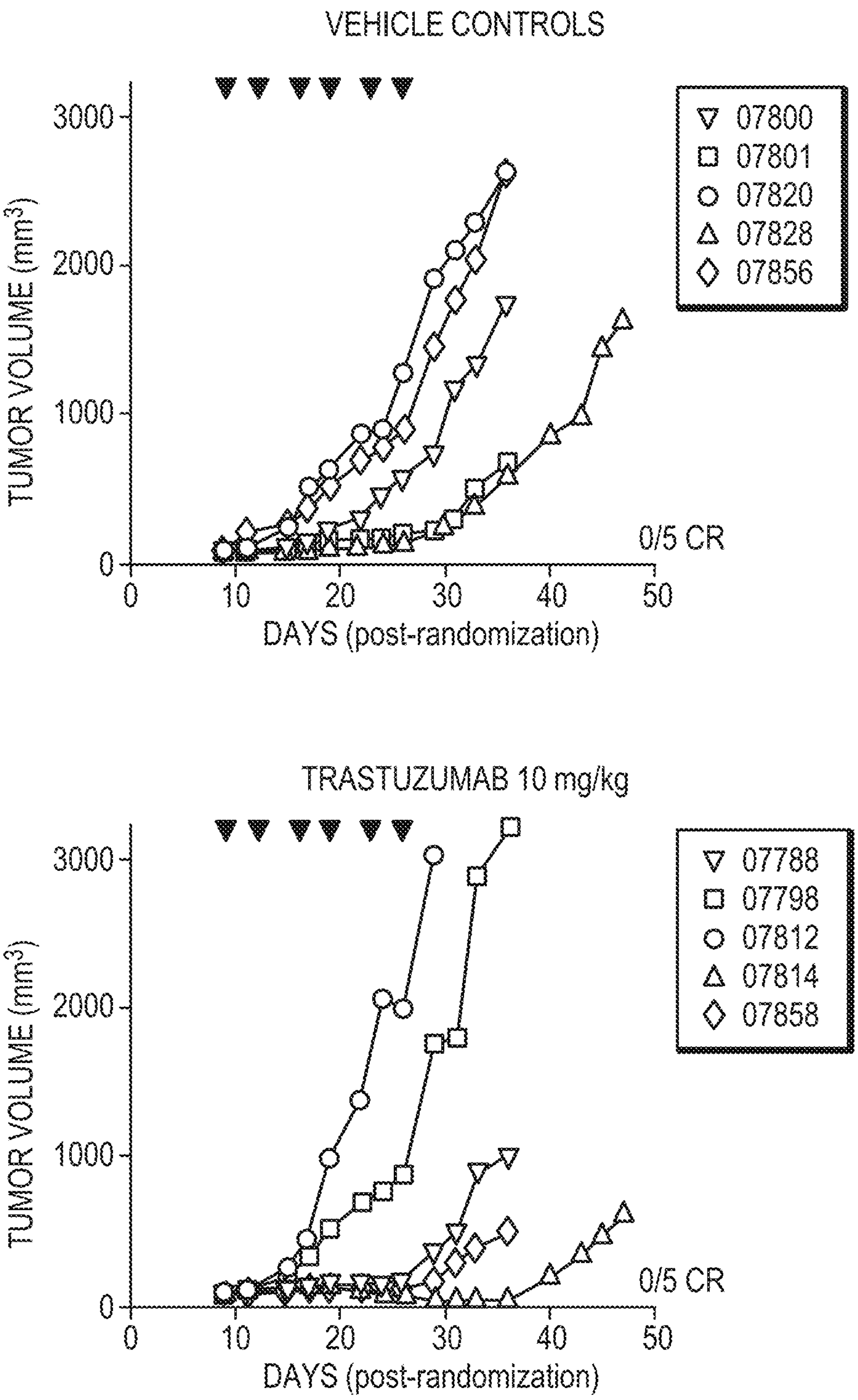
FIGS. 27A-D depict the testing of human Lobster antibody sialidase conjugates in a mouse syngeneic tumor model utilizing EMT6 mouse breast cancer cells engineered to express human Her2. Mice were treated via intraperitoneal injection of 10 mg/kg of trastuzumab (FIG. 27B), human Lobster 1 (FIG. 27C), human Lobster 2 (FIG. 27D), and vehicle (FIG. 27A) on the days marked with black triangles (▼) and tumor volume ($mm^3$) was recorded. Graphs show the individual mice for the indicated treatments. Complete Responses (CR, defined as regression below the limit of palpation at any point during the study) are shown as well.

Mice were treated via intraperitoneal injection of 10 mg/kg of Janus, trastuzumab or non-Her2 binding Janus and tumor volume ($mm^3$) was recorded. FIG. 26A shows mean tumor volumes for each treatment group. FIG. 26B shows tumor volumes for individual mice in each treatment group. Complete Responses (CR, defined as regression below the limit of palpation at any point during the study) are shown as well. Trastuzumab and vehicle control demonstrated similar tumor growth curves and no CRs. In contrast, Janus demonstrated reduced tumor growth compared to vehicle with 3 out of 8 mice demonstrating CR. Non-Her2 binding Janus demonstrated a reduced tumor growth compared to vehicle with 1 out of 8 mice demonstrating CR. These results show that ASCs may be active towards a tumor with low expression levels of the tumor antigen targeted by the ASC. Additionally, these results suggest that a non-targeted ASC, e.g., a sialidase-Fc fusion protein, may be active towards a tumor lacking a specific tumor-associated antigen.

Example 16

This Example describes the in vivo administration of antibody sialidase conjugates (ASCs) containing human sialidases.

The following ASCs were made and tested in this Example: (i) a Lobster ASC including Neu2 with ΔM1, V6Y and I187K mutations and an scFv derived from trastuzumab (including first and second polypeptide chains with amino acid sequence SEQ ID NO: 65, encoded by nucleotide sequence SEQ ID NO: 66, and referred to as "Lobster 1" in this example); and (ii) a Lobster ASC including Neu2 with V6Y and I187K mutations and an scFv derived from trastuzumab (including first and second polypeptide chains with amino acid sequence SEQ ID NO: 74, encoded by nucleotide sequence SEQ ID NO: 99, and referred to as "Lobster 2" in this example). ASCs were made as described in Example 7.

These ASCs were compared to trastuzumab in a mouse syngeneic tumor model injected with a murine breast cancer cell line expressing human Her2 (EMT6-hHer2 cells). Female BALB/c mice, 6-8 weeks of age, were inoculated subcutaneously in the right lower flank region with EMT6-Her2 tumor cells ($5\times10^5$) in 0.1 ml of PBS for tumor development. Mice were randomly allocated to 4 groups of 5 animals each when tumors reached 50-100 $mm^3$, mean~75-100 $mm^3$.

Mice were treated via intraperitoneal injection of 10 mg/kg of either human Lobster 1, human Lobster 2, or trastuzumab and tumor volume ($mm^3$) was recorded. FIGS. 27A-D shows mean tumor volumes for the individual mice for the indicated treatments. Complete Responses (CR, defined as regression below the limit of palpation at any point during the study) are shown. Trastuzumab and vehicle control demonstrated no CRs. In contrast, both human Lobster 1 and human Lobster 2 demonstrated a reduced tumor growth compared to vehicle with 1 out of 5 mice in both groups demonstrating CR. This example demonstrates that human sialidase based ASCs demonstrate efficacy in an in vivo tumor model.

INCORPORATION BY REFERENCE

The entire disclosure of each of the patent and scientific documents referred to herein is incorporated by reference for all purposes.

EQUIVALENTS

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes that come within the meaning and range of equivalency of the claims are intended to be embraced therein.

What is claimed is:

1. A recombinant mutant human sialidase enzyme comprising an amino acid sequence having at least 90% sequence identity to SEQ ID NO: 1, a substitution of the cysteine residue at position 332 of SEQ ID NO: 1; and sialidase enzymatic activity.

2. The sialidase of claim 1, wherein the cysteine residue at position 332 is substituted by alanine (C332A).

3. A recombinant mutant human sialidase enzyme comprising an amino acid sequence having at least 90% sequence identity to SEQ ID NO: 1, a substitution of the valine residue at position 6 of SEQ ID NO: 1, and sialidase enzymatic activity.

4. The sialidase of claim 3, wherein the valine residue at position 6 is substituted by tyrosine (V6Y).

5. A recombinant mutant human sialidase enzyme, wherein the sialidase comprising an amino acid sequence having at least 90% sequence identity to SEQ ID NO: 1, comprises a substitution of the methionine residue at a position corresponding to position 1 of SEQ ID NO: 1, wild type human Neu2 (SEQ ID NO: 1) and wherein the methionine residue at position 1 is substituted by aspartic acid (M1D).

6. A fusion protein comprising:

(a) the sialidase enzyme of claim 1 or claim 2; and (b) an immunoglobulin Fc domain and/or an immunoglobulin antigen-binding domain;

wherein the sialidase and the immunoglobulin Fc domain and/or the immunoglobulin antigen-binding domain are linked by a peptide bond or an amino acid linker.

7. An antibody conjugate comprising the fusion protein of claim 6.

8. The antibody conjugate of claim 7, wherein the antibody conjugate comprises:

(a) a first polypeptide comprising an immunoglobulin light chain;

(b) a second polypeptide comprising an immunoglobulin heavy chain; and (c) a third polypeptide comprising the immunoglobulin Fc domain and the sialidase;

wherein the first and second polypeptides are covalently linked together and the second and third polypeptides are linked together, and wherein the first polypeptide and the second polypeptide together define the immunoglobulin antigen-binding domain.

9. An isolated nucleic acid comprising a nucleotide sequence encoding the recombinant mutant human sialidase of claim 1 or claim 2.

10. An expression vector comprising the nucleic acid of claim 9.

11. A host cell comprising the expression vector of claim 10.

12. A pharmaceutical composition comprising the recombinant mutant human sialidase of claim 1 or claim 2.

13. A method of treating cancer in a subject in need thereof, the method comprising administering to the subject an effective amount of the recombinant mutant human sialidase of claim 1 or claim 2.

14. A method of treating cancer in a subject in need thereof, the method comprising administering to the subject an effective amount of the antibody conjugate of claim 7.

15. A method of increasing expression of HLA-DR, CD86, CD83,IFNγ, IL-1b, IL-6, TNFα, IL-17A, IL-2, or IL-6 in a cell or tissue, the method comprising contacting the cell or tissue with an effective amount of the recombinant mutant human sialidase of claim 1 or claim 2.

16. A fusion protein comprising:
(a) the sialidase enzyme of claim 3 or claim 4; and
(b) an immunoglobulin Fc domain and/or an immunoglobulin antigen-binding domain;
wherein the sialidase and the immunoglobulin Fc domain and/or the immunoglobulin antigen-binding domain are linked by a peptide bond or an amino acid linker.

17. An antibody conjugate comprising the fusion protein of claim 16.

18. The antibody conjugate of claim 17, wherein the antibody conjugate comprises:
(a) a first polypeptide comprising an immunoglobulin light chain;
(b) a second polypeptide comprising an immunoglobulin heavy chain; and
(c) a third polypeptide comprising an immunoglobulin Fc domain and the sialidase;
wherein the first and second polypeptides are covalently linked together and the second and third polypeptides are linked together, and wherein the first polypeptide and the second polypeptide together define an antigen-binding site.

19. An isolated nucleic acid comprising a nucleotide sequence encoding the recombinant mutant human sialidase of claim 3 or claim 4.

20. An expression vector comprising the nucleic acid of claim 19.

21. A host cell comprising the expression vector of claim 20.

22. A pharmaceutical composition comprising the recombinant mutant human sialidase of claim 3 or claim 4.

23. A method of treating cancer in a subject in need thereof, the method comprising administering to the subject an effective amount of the recombinant mutant human sialidase of claim 3 or claim 4.

24. A method of treating cancer in a subject in need thereof, the method comprising administering to the subject an effective amount of the antibody conjugate of claim 18.

25. A method of increasing expression of HLA-DR, CD86, CD83, IFNγ, IL-1b, IL-6, TNFα, IL-17A, IL-2, or IL-6 in a cell or tissue, the method comprising contacting the cell or tissue with an effective amount of the recombinant mutant human sialidase of claim 3 or claim 4.

26. A fusion protein comprising:
(a) the sialidase enzyme of claim 5; and
(b) an immunoglobulin Fc domain and/or an immunoglobulin antigen-binding domain;
wherein the sialidase and the immunoglobulin Fc domain and/or the immunoglobulin antigen-binding domain are linked by a peptide bond or an amino acid linker.

27. An antibody conjugate comprising the fusion protein of claim 26.

28. The antibody conjugate of claim 27, wherein the antibody conjugate comprises:
(a) a first polypeptide comprising an immunoglobulin light chain;
(b) a second polypeptide comprising an immunoglobulin heavy chain; and
(c) a third polypeptide comprising an immunoglobulin Fc domain and the sialidase;
wherein the first and second polypeptides are covalently linked together and the second and third polypeptides are linked together, and wherein the first polypeptide and the second polypeptide together define an antigen-binding site.

29. An isolated nucleic acid comprising a nucleotide sequence encoding the recombinant mutant human sialidase of claim 5.

30. An expression vector comprising the nucleic acid of claim 29.

31. A host cell comprising the expression vector of claim 30.

32. A pharmaceutical composition comprising the recombinant mutant human sialidase of claim 5.

33. A method of treating cancer in a subject in need thereof, the method comprising administering to the subject an effective amount of the recombinant mutant human sialidase of claim 5.

34. A method of treating cancer in a subject in need thereof, the method comprising administering to the subject an effective amount of the antibody conjugate of claim 28.

35. A method of increasing expression of HLA-DR, CD86, CD83, IFNγ, IL-1b, IL-6, TNFα, IL-17A, IL-2, or IL-6 in a cell or tissue, the method comprising contacting the cell or tissue with an effective amount of the recombinant mutant human sialidase of claim 5.

36. The sialidase of claim 1, further comprising one or more of (a) a substitution of the valine residue at position 6 of SEQ ID NO: 1; (b) a substitution of the methionine residue at a position position 1 of SEQ ID NO: 1; and a substitution of an isoleucine residue at position 187 of SEQ ID NO: 1 with a lysine (I187K).

37. The sialidase of claim 36, wherein the valine is substituted by tyrosine (V6Y) and/or the methionine is substituted by aspartic acid (M1D).

38. The sialidase of claim 3, further comprising one or more of (a) a substitution of the cysteine residue at position 332 of SEQ ID NO: 1; (b) a substitution of the methionine residue at position 1 of SEQ ID NO: 1; and a substitution of the isoleucine residue at position 187 of SEQ ID NO: 1 with a lysine (I187K).

39. The sialidase of claim 38, wherein the cysteine residue is substituted by alanine (C332A) and/or the methionine is substituted by aspartic acid (M1D).

40. The sialidase of claim 5, further comprising one or more of (a) a substitution of the valine residue at position 6 of SEQ ID NO: 1; (b) a substitution of the cysteine residue at a position position 332 of SEQ ID NO: 1; and a substitution of the isoleucine residue at a position corresponding to position 187 of SEQ ID NO: 1 with a lysine (I187K).

41. The sialidase of claim 40, wherein the cysteine residue is substituted by alanine (C332A) and/or the valine is substituted by tyrosine (V6Y).

42. The sialidase of claim 41, wherein the sialidase comprises a M1D substitution, a V6Y substitution, an I187K substitution, and a C332A substitution.

43. The sialidase of claim 41, wherein the sialidase comprises a M1D substitution, a V6Y substitution and a C332A substitution.

* * * * *

UNITED STATES PATENT AND TRADEMARK OFFICE

CERTIFICATE OF CORRECTION

PATENT NO. : 11,965,188 B2
APPLICATION NO. : 16/958914
DATED : April 23, 2024
INVENTOR(S) : Li Peng et al.

It is certified that error appears in the above-identified patent and that said Letters Patent is hereby corrected as shown below:

In the Claims

In Claim 5, Column 299, Lines 60-61, please delete ", wherein the sialidase";

In Claim 5, Column 299, Line 63, please delete "comprises";

In Claim 5, Column 299, Lines 63-64, please delete "a position corresponding to";

In Claim 5, Column 299, Lines 64-65, please delete "wild type human Neu2 (SEQ ID NO: 1)";

In Claim 5, Column 299, Line 65, between "and" and "wherein" please insert --sialidase enzymatic activity--;

In Claim 36, Column 302, Line 44, please delete "a position";

In Claim 36, Column 302, Line 45, please replace --an-- with --the--;

In Claim 40, Column 302, Line 62, please delete "a position".

Signed and Sealed this
Seventeenth Day of September, 2024

Katherine Kelly Vidal

Katherine Kelly Vidal
*Director of the United States Patent and Trademark Office*

SEQUENCE LISTING

```
<160> NUMBER OF SEQ ID NOS: 109

<210> SEQ ID NO 1
<211> LENGTH: 380
<212> TYPE: PRT
<213> ORGANISM: Homo sapiens

<400> SEQUENCE: 1

Met Ala Ser Leu Pro Val Leu Gln Lys Glu Ser Val Phe Gln Ser Gly
1               5                   10                  15

Ala His Ala Tyr Arg Ile Pro Ala Leu Leu Tyr Leu Pro Gly Gln Gln
            20                  25                  30

Ser Leu Leu Ala Phe Ala Glu Gln Arg Ala Ser Lys Lys Asp Glu His
        35                  40                  45

Ala Glu Leu Ile Val Leu Arg Arg Gly Asp Tyr Asp Ala Pro Thr His
    50                  55                  60

Gln Val Gln Trp Gln Ala Gln Glu Val Val Ala Gln Ala Arg Leu Asp
65                  70                  75                  80

Gly His Arg Ser Met Asn Pro Cys Pro Leu Tyr Asp Ala Gln Thr Gly
                85                  90                  95

Thr Leu Phe Leu Phe Phe Ile Ala Ile Pro Gly Gln Val Thr Glu Gln
            100                 105                 110

Gln Gln Leu Gln Thr Arg Ala Asn Val Thr Arg Leu Cys Gln Val Thr
        115                 120                 125

Ser Thr Asp His Gly Arg Thr Trp Ser Ser Pro Arg Asp Leu Thr Asp
    130                 135                 140

Ala Ala Ile Gly Pro Ala Tyr Arg Glu Trp Ser Thr Phe Ala Val Gly
145                 150                 155                 160

Pro Gly His Cys Leu Gln Leu His Asp Arg Ala Arg Ser Leu Val Val
                165                 170                 175

Pro Ala Tyr Ala Tyr Arg Lys Leu His Pro Ile Gln Arg Pro Ile Pro
            180                 185                 190

Ser Ala Phe Cys Phe Leu Ser His Asp His Gly Arg Thr Trp Ala Arg
        195                 200                 205

Gly His Phe Val Ala Gln Asp Thr Leu Glu Cys Gln Val Ala Glu Val
    210                 215                 220

Glu Thr Gly Glu Gln Arg Val Val Thr Leu Asn Ala Arg Ser His Leu
225                 230                 235                 240

Arg Ala Arg Val Gln Ala Gln Ser Thr Asn Asp Gly Leu Asp Phe Gln
                245                 250                 255

Glu Ser Gln Leu Val Lys Lys Leu Val Glu Pro Pro Pro Gln Gly Cys
            260                 265                 270

Gln Gly Ser Val Ile Ser Phe Pro Ser Pro Arg Ser Gly Pro Gly Ser
        275                 280                 285
```

-continued

```
Pro Ala Gln Trp Leu Leu Tyr Thr His Pro Thr His Ser Trp Gln Arg
    290                 295                 300

Ala Asp Leu Gly Ala Tyr Leu Asn Pro Arg Pro Pro Ala Pro Glu Ala
305                 310                 315                 320

Trp Ser Glu Pro Val Leu Leu Ala Lys Gly Ser Cys Ala Tyr Ser Asp
                325                 330                 335

Leu Gln Ser Met Gly Thr Gly Pro Asp Gly Ser Pro Leu Phe Gly Cys
            340                 345                 350

Leu Tyr Glu Ala Asn Asp Tyr Glu Glu Ile Val Phe Leu Met Phe Thr
        355                 360                 365

Leu Lys Gln Ala Phe Pro Ala Glu Tyr Leu Pro Gln
    370                 375                 380


<210> SEQ ID NO 2
<211> LENGTH: 385
<212> TYPE: PRT
<213> ORGANISM: Mus sp.

<400> SEQUENCE: 2

Met Glu Asp Leu Arg Pro Met Ala Thr Cys Pro Val Leu Gln Lys Glu
1               5                   10                  15

Thr Leu Phe Arg Thr Gly Val His Ala Tyr Arg Ile Pro Ala Leu Leu
            20                  25                  30

Tyr Leu Lys Lys Gln Lys Thr Leu Leu Ala Phe Ala Glu Lys Arg Ala
        35                  40                  45

Ser Lys Thr Asp Glu His Ala Glu Leu Ile Val Leu Arg Arg Gly Ser
    50                  55                  60

Tyr Asn Glu Ala Thr Asn Arg Val Lys Trp Gln Pro Glu Glu Val Val
65                  70                  75                  80

Thr Gln Ala Gln Leu Glu Gly His Arg Ser Met Asn Pro Cys Pro Leu
                85                  90                  95

Tyr Asp Lys Gln Thr Lys Thr Leu Phe Leu Phe Phe Ile Ala Val Pro
            100                 105                 110

Gly Arg Val Ser Glu His His Gln Leu His Thr Lys Val Asn Val Thr
        115                 120                 125

Arg Leu Cys Cys Val Ser Ser Thr Asp His Gly Arg Thr Trp Ser Pro
    130                 135                 140

Ile Gln Asp Leu Thr Glu Thr Thr Ile Gly Ser Thr His Gln Glu Trp
145                 150                 155                 160

Ala Thr Phe Ala Val Gly Pro Gly His Cys Leu Gln Leu Arg Asn Pro
                165                 170                 175

Ala Gly Ser Leu Leu Val Pro Ala Tyr Ala Tyr Arg Lys Leu His Pro
            180                 185                 190

Ala Gln Lys Pro Thr Pro Phe Ala Phe Cys Phe Ile Ser Leu Asp His
        195                 200                 205

Gly His Thr Trp Lys Leu Gly Asn Phe Val Ala Glu Asn Ser Leu Glu
    210                 215                 220

Cys Gln Val Ala Glu Val Gly Thr Gly Ala Gln Arg Met Val Tyr Leu
225                 230                 235                 240

Asn Ala Arg Ser Phe Leu Gly Ala Arg Val Gln Ala Gln Ser Pro Asn
                245                 250                 255

Asp Gly Leu Asp Phe Gln Asp Asn Arg Val Val Ser Lys Leu Val Glu
            260                 265                 270

Pro Pro His Gly Cys His Gly Ser Val Val Ala Phe His Asn Pro Ile
        275                 280                 285
```

Ser Lys Pro His Ala Leu Asp Thr Trp Leu Leu Tyr Thr His Pro Thr
    290                 295                 300

Asp Ser Arg Asn Arg Thr Asn Leu Gly Val Tyr Leu Asn Gln Met Pro
305                 310                 315                 320

Leu Asp Pro Thr Ala Trp Ser Glu Pro Thr Leu Leu Ala Met Gly Ile
                325                 330                 335

Cys Ala Tyr Ser Asp Leu Gln Asn Met Gly Gln Gly Pro Asp Gly Ser
            340                 345                 350

Pro Gln Phe Gly Cys Leu Tyr Glu Ser Gly Asn Tyr Glu Glu Ile Ile
        355                 360                 365

Phe Leu Ile Phe Thr Leu Lys Gln Ala Phe Pro Thr Val Phe Asp Ala
    370                 375                 380

Gln
385

<210> SEQ ID NO 3
<211> LENGTH: 5
<212> TYPE: PRT
<213> ORGANISM: Mus sp.

<400> SEQUENCE: 3

Glu Asp Leu Arg Pro
1               5

<210> SEQ ID NO 4
<211> LENGTH: 6
<212> TYPE: PRT
<213> ORGANISM: Mus sp.

<400> SEQUENCE: 4

Met Glu Asp Leu Arg Pro
1               5

<210> SEQ ID NO 5
<211> LENGTH: 380
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Met Ala Ser Leu Pro Val Leu Gln Lys Glu Ser Val Phe Gln Ser Gly
1               5                   10                  15

Ala His Ala Tyr Arg Ile Pro Ala Leu Leu Tyr Leu Pro Gly Gln Gln
            20                  25                  30

Ser Leu Leu Ala Phe Ala Glu Gln Arg Ala Ser Lys Lys Asp Glu His
        35                  40                  45

Ala Glu Leu Ile Val Leu Arg Arg Gly Asp Tyr Asp Ala Pro Thr His
    50                  55                  60

Gln Val Gln Trp Gln Ala Gln Glu Val Val Ala Gln Ala Arg Leu Asp
65                  70                  75                  80

Gly His Arg Ser Met Asn Pro Cys Pro Leu Tyr Asp Ala Gln Thr Gly
                85                  90                  95

Thr Leu Phe Leu Phe Phe Ile Ala Ile Pro Gly Gln Val Thr Glu Gln
            100                 105                 110

Gln Gln Leu Gln Thr Arg Ala Asn Val Thr Arg Leu Cys Gln Val Thr
        115                 120                 125

-continued

```
Ser Thr Asp His Gly Arg Thr Trp Ser Ser Pro Arg Asp Leu Thr Asp
    130                 135                 140

Ala Ala Ile Gly Pro Ala Tyr Arg Glu Trp Ser Thr Phe Ala Val Gly
145                 150                 155                 160

Pro Gly His Cys Leu Gln Leu His Asp Arg Ala Arg Ser Leu Val Val
                165                 170                 175

Pro Ala Tyr Ala Tyr Arg Lys Leu His Pro Ile Gln Arg Pro Ile Pro
            180                 185                 190

Ser Ala Phe Cys Phe Leu Ser His Asp His Gly Arg Thr Trp Ala Arg
        195                 200                 205

Gly His Phe Val Ala Gln Asp Thr Leu Glu Cys Gln Val Ala Glu Val
    210                 215                 220

Glu Thr Gly Glu Gln Arg Val Val Thr Leu Asn Ala Arg Ser His Leu
225                 230                 235                 240

Arg Ala Arg Val Gln Ala Gln Ser Thr Asn Asp Gly Leu Asp Phe Gln
                245                 250                 255

Glu Ser Gln Leu Val Lys Lys Leu Val Glu Pro Pro Pro Gln Gly Cys
            260                 265                 270

Gln Gly Ser Val Ile Ser Phe Pro Ser Pro Arg Ser Gly Pro Gly Ser
        275                 280                 285

Pro Ala Gln Trp Leu Leu Tyr Thr His Pro Thr His Ser Trp Gln Arg
    290                 295                 300

Ala Asp Leu Gly Ala Tyr Leu Asn Pro Arg Pro Pro Ala Pro Glu Ala
305                 310                 315                 320

Trp Ser Glu Pro Val Leu Leu Ala Lys Gly Ser Ala Ala Tyr Ser Asp
                325                 330                 335

Leu Gln Ser Met Gly Thr Gly Pro Asp Gly Ser Pro Leu Phe Gly Leu
            340                 345                 350

Leu Tyr Glu Ala Asn Asp Tyr Glu Glu Ile Val Phe Leu Met Phe Thr
        355                 360                 365

Leu Lys Gln Ala Phe Pro Ala Glu Tyr Leu Pro Gln
    370                 375                 380


<210> SEQ ID NO 6
<211> LENGTH: 386
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Met Glu Asp Leu Arg Pro Met Ala Ser Leu Pro Val Leu Gln Lys Glu
1               5                   10                  15

Ser Val Phe Gln Ser Gly Ala His Ala Tyr Arg Ile Pro Ala Leu Leu
            20                  25                  30

Tyr Leu Pro Gly Gln Gln Ser Leu Leu Ala Phe Ala Glu Gln Arg Ala
        35                  40                  45

Ser Lys Lys Asp Glu His Ala Glu Leu Ile Val Leu Arg Arg Gly Asp
    50                  55                  60

Tyr Asp Ala Pro Thr His Gln Val Gln Trp Gln Ala Gln Glu Val Val
65                  70                  75                  80

Ala Gln Ala Arg Leu Asp Gly His Arg Ser Met Asn Pro Cys Pro Leu
                85                  90                  95

Tyr Asp Ala Gln Thr Gly Thr Leu Phe Leu Phe Phe Ile Ala Ile Pro
            100                 105                 110
```

-continued

```
Gly Gln Val Thr Glu Gln Gln Gln Leu Gln Thr Arg Ala Asn Val Thr
        115                 120                 125

Arg Leu Cys Gln Val Thr Ser Thr Asp His Gly Arg Thr Trp Ser Ser
    130                 135                 140

Pro Arg Asp Leu Thr Asp Ala Ala Ile Gly Pro Ala Tyr Arg Glu Trp
145                 150                 155                 160

Ser Thr Phe Ala Val Gly Pro Gly His Cys Leu Gln Leu His Asp Arg
                165                 170                 175

Ala Arg Ser Leu Val Val Pro Ala Tyr Ala Tyr Arg Lys Leu His Pro
            180                 185                 190

Ile Gln Arg Pro Ile Pro Ser Ala Phe Cys Phe Leu Ser His Asp His
        195                 200                 205

Gly Arg Thr Trp Ala Arg Gly His Phe Val Ala Gln Asp Thr Leu Glu
    210                 215                 220

Cys Gln Val Ala Glu Val Glu Thr Gly Glu Gln Arg Val Val Thr Leu
225                 230                 235                 240

Asn Ala Arg Ser His Leu Arg Ala Arg Val Gln Ala Gln Ser Thr Asn
                245                 250                 255

Asp Gly Leu Asp Phe Gln Glu Ser Gln Leu Val Lys Lys Leu Val Glu
            260                 265                 270

Pro Pro Pro Gln Gly Cys Gln Gly Ser Val Ile Ser Phe Pro Ser Pro
        275                 280                 285

Arg Ser Gly Pro Gly Ser Pro Ala Gln Trp Leu Leu Tyr Thr His Pro
    290                 295                 300

Thr His Ser Trp Gln Arg Ala Asp Leu Gly Ala Tyr Leu Asn Pro Arg
305                 310                 315                 320

Pro Pro Ala Pro Glu Ala Trp Ser Glu Pro Val Leu Leu Ala Lys Gly
                325                 330                 335

Ser Cys Ala Tyr Ser Asp Leu Gln Ser Met Gly Thr Gly Pro Asp Gly
            340                 345                 350

Ser Pro Leu Phe Gly Cys Leu Tyr Glu Ala Asn Asp Tyr Glu Glu Ile
        355                 360                 365

Val Phe Leu Met Phe Thr Leu Lys Gln Ala Phe Pro Ala Glu Tyr Leu
    370                 375                 380

Pro Gln
385


<210> SEQ ID NO 7
<211> LENGTH: 364
<212> TYPE: PRT
<213> ORGANISM: Homo sapiens

<400> SEQUENCE: 7

Glu Asn Asp Phe Gly Leu Val Gln Pro Leu Val Thr Met Glu Gln Leu
1               5                   10                  15

Leu Trp Val Ser Gly Arg Gln Ile Gly Ser Val Asp Thr Phe Arg Ile
            20                  25                  30

Pro Leu Ile Thr Ala Thr Pro Arg Gly Thr Leu Leu Ala Phe Ala Glu
        35                  40                  45

Ala Arg Lys Met Ser Ser Ser Asp Glu Gly Ala Lys Phe Ile Ala Leu
    50                  55                  60

Arg Arg Ser Met Asp Gln Gly Ser Thr Trp Ser Pro Thr Ala Phe Ile
65                  70                  75                  80

Val Asn Asp Gly Asp Val Pro Asp Gly Leu Asn Leu Gly Ala Val Val
```

-continued

```
                85                  90                  95

Ser Asp Val Glu Thr Gly Val Val Phe Leu Phe Tyr Ser Leu Cys Ala
            100                 105                 110

His Lys Ala Gly Cys Gln Val Ala Ser Thr Met Leu Val Trp Ser Lys
        115                 120                 125

Asp Asp Gly Val Ser Trp Ser Thr Pro Arg Asn Leu Ser Leu Asp Ile
    130                 135                 140

Gly Thr Glu Val Phe Ala Pro Gly Pro Gly Ser Gly Ile Gln Lys Gln
145                 150                 155                 160

Arg Glu Pro Arg Lys Gly Arg Leu Ile Val Cys Gly His Gly Thr Leu
                165                 170                 175

Glu Arg Asp Gly Val Phe Cys Leu Leu Ser Asp Asp His Gly Ala Ser
            180                 185                 190

Trp Arg Tyr Gly Ser Gly Val Ser Gly Ile Pro Tyr Gly Gln Pro Lys
        195                 200                 205

Gln Glu Asn Asp Phe Asn Pro Asp Glu Cys Gln Pro Tyr Glu Leu Pro
    210                 215                 220

Asp Gly Ser Val Val Ile Asn Ala Arg Asn Gln Asn Asn Tyr His Cys
225                 230                 235                 240

His Cys Arg Ile Val Leu Arg Ser Tyr Asp Ala Cys Asp Thr Leu Arg
                245                 250                 255

Pro Arg Asp Val Thr Phe Asp Pro Glu Leu Val Asp Pro Val Val Ala
            260                 265                 270

Ala Gly Ala Val Val Thr Ser Ser Gly Ile Val Phe Phe Ser Asn Pro
        275                 280                 285

Ala His Pro Glu Phe Arg Val Asn Leu Thr Leu Arg Trp Ser Phe Ser
    290                 295                 300

Asn Gly Thr Ser Trp Arg Lys Glu Thr Val Gln Leu Trp Pro Gly Pro
305                 310                 315                 320

Ser Gly Tyr Ser Ser Leu Ala Thr Leu Glu Gly Ser Met Asp Gly Glu
                325                 330                 335

Glu Gln Ala Pro Gln Leu Tyr Val Leu Tyr Glu Lys Gly Arg Asn His
            340                 345                 350

Tyr Thr Glu Ser Ile Ser Val Ala Lys Ile Ser Val
        355                 360


<210> SEQ ID NO 8
<211> LENGTH: 428
<212> TYPE: PRT
<213> ORGANISM: Homo sapiens

<400> SEQUENCE: 8

Met Glu Glu Val Thr Thr Cys Ser Phe Asn Ser Pro Leu Phe Arg Gln
1               5                   10                  15

Glu Asp Asp Arg Gly Ile Thr Tyr Arg Ile Pro Ala Leu Leu Tyr Ile
            20                  25                  30

Pro Pro Thr His Thr Phe Leu Ala Phe Ala Glu Lys Arg Ser Thr Arg
        35                  40                  45

Arg Asp Glu Asp Ala Leu His Leu Val Leu Arg Arg Gly Leu Arg Ile
    50                  55                  60

Gly Gln Leu Val Gln Trp Gly Pro Leu Lys Pro Leu Met Glu Ala Thr
65                  70                  75                  80

Leu Pro Gly His Arg Thr Met Asn Pro Cys Pro Val Trp Glu Gln Lys
                85                  90                  95
```

-continued

```
Ser Gly Cys Val Phe Leu Phe Phe Ile Cys Val Arg Gly His Val Thr
            100                 105                 110

Glu Arg Gln Gln Ile Val Ser Gly Arg Asn Ala Ala Arg Leu Cys Phe
        115                 120                 125

Ile Tyr Ser Gln Asp Ala Gly Cys Ser Trp Ser Glu Val Arg Asp Leu
    130                 135                 140

Thr Glu Glu Val Ile Gly Ser Glu Leu Lys His Trp Ala Thr Phe Ala
145                 150                 155                 160

Val Gly Pro Gly His Gly Ile Gln Leu Gln Ser Gly Arg Leu Val Ile
                165                 170                 175

Pro Ala Tyr Thr Tyr Tyr Ile Pro Ser Trp Phe Phe Cys Phe Gln Leu
            180                 185                 190

Pro Cys Lys Thr Arg Pro His Ser Leu Met Ile Tyr Ser Asp Asp Leu
        195                 200                 205

Gly Val Thr Trp His His Gly Arg Leu Ile Arg Pro Met Val Thr Val
    210                 215                 220

Glu Cys Glu Val Ala Glu Val Thr Gly Arg Ala Gly His Pro Val Leu
225                 230                 235                 240

Tyr Cys Ser Ala Arg Thr Pro Asn Arg Cys Arg Ala Glu Ala Leu Ser
                245                 250                 255

Thr Asp His Gly Glu Gly Phe Gln Arg Leu Ala Leu Ser Arg Gln Leu
            260                 265                 270

Cys Glu Pro Pro His Gly Cys Gln Gly Ser Val Val Ser Phe Arg Pro
        275                 280                 285

Leu Glu Ile Pro His Arg Cys Gln Asp Ser Ser Ser Lys Asp Ala Pro
    290                 295                 300

Thr Ile Gln Gln Ser Ser Pro Gly Ser Ser Leu Arg Leu Glu Glu Glu
305                 310                 315                 320

Ala Gly Thr Pro Ser Glu Ser Trp Leu Leu Tyr Ser His Pro Thr Ser
                325                 330                 335

Arg Lys Gln Arg Val Asp Leu Gly Ile Tyr Leu Asn Gln Thr Pro Leu
            340                 345                 350

Glu Ala Ala Cys Trp Ser Arg Pro Trp Ile Leu His Cys Gly Pro Cys
        355                 360                 365

Gly Tyr Ser Asp Leu Ala Ala Leu Glu Glu Glu Gly Leu Phe Gly Cys
    370                 375                 380

Leu Phe Glu Cys Gly Thr Lys Gln Glu Cys Glu Gln Ile Ala Phe Arg
385                 390                 395                 400

Leu Phe Thr His Arg Glu Ile Leu Ser His Leu Gln Gly Asp Cys Thr
                405                 410                 415

Ser Pro Gly Arg Asn Pro Ser Gln Phe Lys Ser Asn
            420                 425


<210> SEQ ID NO 9
<211> LENGTH: 461
<212> TYPE: PRT
<213> ORGANISM: Homo sapiens

<400> SEQUENCE: 9

Met Arg Pro Ala Asp Leu Pro Pro Arg Pro Met Glu Glu Ser Pro Ala
1               5                   10                  15

Ser Ser Ser Ala Pro Thr Glu Thr Glu Glu Pro Gly Ser Ser Ala Glu
            20                  25                  30

Val Met Glu Glu Val Thr Thr Cys Ser Phe Asn Ser Pro Leu Phe Arg
        35                  40                  45
```

-continued

```
Gln Glu Asp Asp Arg Gly Ile Thr Tyr Arg Ile Pro Ala Leu Leu Tyr
    50                  55                  60

Ile Pro Pro Thr His Thr Phe Leu Ala Phe Ala Glu Lys Arg Ser Thr
65                  70                  75                  80

Arg Arg Asp Glu Asp Ala Leu His Leu Val Leu Arg Arg Gly Leu Arg
                85                  90                  95

Ile Gly Gln Leu Val Gln Trp Gly Pro Leu Lys Pro Leu Met Glu Ala
            100                 105                 110

Thr Leu Pro Gly His Arg Thr Met Asn Pro Cys Pro Val Trp Glu Gln
        115                 120                 125

Lys Ser Gly Cys Val Phe Leu Phe Phe Ile Cys Val Arg Gly His Val
    130                 135                 140

Thr Glu Arg Gln Gln Ile Val Ser Gly Arg Asn Ala Ala Arg Leu Cys
145                 150                 155                 160

Phe Ile Tyr Ser Gln Asp Ala Gly Cys Ser Trp Ser Glu Val Arg Asp
                165                 170                 175

Leu Thr Glu Glu Val Ile Gly Ser Glu Leu Lys His Trp Ala Thr Phe
            180                 185                 190

Ala Val Gly Pro Gly His Gly Ile Gln Leu Gln Ser Gly Arg Leu Val
        195                 200                 205

Ile Pro Ala Tyr Thr Tyr Tyr Ile Pro Ser Trp Phe Phe Cys Phe Gln
    210                 215                 220

Leu Pro Cys Lys Thr Arg Pro His Ser Leu Met Ile Tyr Ser Asp Asp
225                 230                 235                 240

Leu Gly Val Thr Trp His His Gly Arg Leu Ile Arg Pro Met Val Thr
                245                 250                 255

Val Glu Cys Glu Val Ala Glu Val Thr Gly Arg Ala Gly His Pro Val
            260                 265                 270

Leu Tyr Cys Ser Ala Arg Thr Pro Asn Arg Cys Arg Ala Glu Ala Leu
        275                 280                 285

Ser Thr Asp His Gly Glu Gly Phe Gln Arg Leu Ala Leu Ser Arg Gln
    290                 295                 300

Leu Cys Glu Pro Pro His Gly Cys Gln Gly Ser Val Val Ser Phe Arg
305                 310                 315                 320

Pro Leu Glu Ile Pro His Arg Cys Gln Asp Ser Ser Ser Lys Asp Ala
                325                 330                 335

Pro Thr Ile Gln Gln Ser Ser Pro Gly Ser Ser Leu Arg Leu Glu Glu
            340                 345                 350

Glu Ala Gly Thr Pro Ser Glu Ser Trp Leu Leu Tyr Ser His Pro Thr
        355                 360                 365

Ser Arg Lys Gln Arg Val Asp Leu Gly Ile Tyr Leu Asn Gln Thr Pro
    370                 375                 380

Leu Glu Ala Ala Cys Trp Ser Arg Pro Trp Ile Leu His Cys Gly Pro
385                 390                 395                 400

Cys Gly Tyr Ser Asp Leu Ala Ala Leu Glu Glu Glu Gly Leu Phe Gly
                405                 410                 415

Cys Leu Phe Glu Cys Gly Thr Lys Gln Glu Cys Glu Gln Ile Ala Phe
            420                 425                 430

Arg Leu Phe Thr His Arg Glu Ile Leu Ser His Leu Gln Gly Asp Cys
        435                 440                 445

Thr Ser Pro Gly Arg Asn Pro Ser Gln Phe Lys Ser Asn
    450                 455                 460
```

<210> SEQ ID NO 10
<211> LENGTH: 484
<212> TYPE: PRT
<213> ORGANISM: Homo sapiens

<400> SEQUENCE: 10

```
Met Gly Val Pro Arg Thr Pro Ser Arg Thr Val Leu Phe Glu Arg Glu
1               5                   10                  15

Arg Thr Gly Leu Thr Tyr Arg Val Pro Ser Leu Leu Pro Val Pro Pro
            20                  25                  30

Gly Pro Thr Leu Leu Ala Phe Val Glu Gln Arg Leu Ser Pro Asp Asp
        35                  40                  45

Ser His Ala His Arg Leu Val Leu Arg Arg Gly Thr Leu Ala Gly Gly
    50                  55                  60

Ser Val Arg Trp Gly Ala Leu His Val Leu Gly Thr Ala Ala Leu Ala
65                  70                  75                  80

Glu His Arg Ser Met Asn Pro Cys Pro Val His Asp Ala Gly Thr Gly
                85                  90                  95

Thr Val Phe Leu Phe Phe Ile Ala Val Leu Gly His Thr Pro Glu Ala
            100                 105                 110

Val Gln Ile Ala Thr Gly Arg Asn Ala Ala Arg Leu Cys Cys Val Ala
        115                 120                 125

Ser Arg Asp Ala Gly Leu Ser Trp Gly Ser Ala Arg Asp Leu Thr Glu
    130                 135                 140

Glu Ala Ile Gly Gly Ala Val Gln Asp Trp Ala Thr Phe Ala Val Gly
145                 150                 155                 160

Pro Gly His Gly Val Gln Leu Pro Ser Gly Arg Leu Leu Val Pro Ala
                165                 170                 175

Tyr Thr Tyr Arg Val Asp Arg Arg Glu Cys Phe Gly Lys Ile Cys Arg
            180                 185                 190

Thr Ser Pro His Ser Phe Ala Phe Tyr Ser Asp Asp His Gly Arg Thr
        195                 200                 205

Trp Arg Cys Gly Gly Leu Val Pro Asn Leu Arg Ser Gly Glu Cys Gln
    210                 215                 220

Leu Ala Ala Val Asp Gly Gly Gln Ala Gly Ser Phe Leu Tyr Cys Asn
225                 230                 235                 240

Ala Arg Ser Pro Leu Gly Ser Arg Val Gln Ala Leu Ser Thr Asp Glu
                245                 250                 255

Gly Thr Ser Phe Leu Pro Ala Glu Arg Val Ala Ser Leu Pro Glu Thr
            260                 265                 270

Ala Trp Gly Cys Gln Gly Ser Ile Val Gly Phe Pro Ala Pro Ala Pro
        275                 280                 285

Asn Arg Pro Arg Asp Asp Ser Trp Ser Val Gly Pro Gly Ser Pro Leu
    290                 295                 300

Gln Pro Pro Leu Leu Gly Pro Gly Val His Glu Pro Pro Glu Glu Ala
305                 310                 315                 320

Ala Val Asp Pro Arg Gly Gly Gln Val Pro Gly Gly Pro Phe Ser Arg
                325                 330                 335

Leu Gln Pro Arg Gly Asp Gly Pro Arg Gln Pro Gly Pro Arg Pro Gly
            340                 345                 350

Val Ser Gly Asp Val Gly Ser Trp Thr Leu Ala Leu Pro Met Pro Phe
        355                 360                 365

Ala Ala Pro Pro Gln Ser Pro Thr Trp Leu Leu Tyr Ser His Pro Val
    370                 375                 380
```

Gly Arg Arg Ala Arg Leu His Met Gly Ile Arg Leu Ser Gln Ser Pro
385 390 395 400

Leu Asp Pro Arg Ser Trp Thr Glu Pro Trp Val Ile Tyr Glu Gly Pro
405 410 415

Ser Gly Tyr Ser Asp Leu Ala Ser Ile Gly Pro Ala Pro Glu Gly Gly
420 425 430

Leu Val Phe Ala Cys Leu Tyr Glu Ser Gly Ala Arg Thr Ser Tyr Asp
435 440 445

Glu Ile Ser Phe Cys Thr Phe Ser Leu Arg Glu Val Leu Glu Asn Val
450 455 460

Pro Ala Ser Pro Lys Pro Pro Asn Leu Gly Asp Lys Pro Arg Gly Cys
465 470 475 480

Cys Trp Pro Ser

<210> SEQ ID NO 11
<211> LENGTH: 496
<212> TYPE: PRT
<213> ORGANISM: Homo sapiens

<400> SEQUENCE: 11

Met Met Ser Ser Ala Ala Phe Pro Arg Trp Leu Ser Met Gly Val Pro
1 5 10 15

Arg Thr Pro Ser Arg Thr Val Leu Phe Glu Arg Glu Arg Thr Gly Leu
20 25 30

Thr Tyr Arg Val Pro Ser Leu Leu Pro Val Pro Pro Gly Pro Thr Leu
35 40 45

Leu Ala Phe Val Glu Gln Arg Leu Ser Pro Asp Asp Ser His Ala His
50 55 60

Arg Leu Val Leu Arg Arg Gly Thr Leu Ala Gly Gly Ser Val Arg Trp
65 70 75 80

Gly Ala Leu His Val Leu Gly Thr Ala Ala Leu Ala Glu His Arg Ser
85 90 95

Met Asn Pro Cys Pro Val His Asp Ala Gly Thr Gly Thr Val Phe Leu
100 105 110

Phe Phe Ile Ala Val Leu Gly His Thr Pro Glu Ala Val Gln Ile Ala
115 120 125

Thr Gly Arg Asn Ala Ala Arg Leu Cys Cys Val Ala Ser Arg Asp Ala
130 135 140

Gly Leu Ser Trp Gly Ser Ala Arg Asp Leu Thr Glu Glu Ala Ile Gly
145 150 155 160

Gly Ala Val Gln Asp Trp Ala Thr Phe Ala Val Gly Pro Gly His Gly
165 170 175

Val Gln Leu Pro Ser Gly Arg Leu Leu Val Pro Ala Tyr Thr Tyr Arg
180 185 190

Val Asp Arg Arg Glu Cys Phe Gly Lys Ile Cys Arg Thr Ser Pro His
195 200 205

Ser Phe Ala Phe Tyr Ser Asp Asp His Gly Arg Thr Trp Arg Cys Gly
210 215 220

Gly Leu Val Pro Asn Leu Arg Ser Gly Glu Cys Gln Leu Ala Ala Val
225 230 235 240

Asp Gly Gly Gln Ala Gly Ser Phe Leu Tyr Cys Asn Ala Arg Ser Pro
245 250 255

Leu Gly Ser Arg Val Gln Ala Leu Ser Thr Asp Glu Gly Thr Ser Phe
260 265 270

-continued

```
Leu Pro Ala Glu Arg Val Ala Ser Leu Pro Glu Thr Ala Trp Gly Cys
        275                 280                 285

Gln Gly Ser Ile Val Gly Phe Pro Ala Pro Ala Pro Asn Arg Pro Arg
    290                 295                 300

Asp Asp Ser Trp Ser Val Gly Pro Gly Ser Pro Leu Gln Pro Pro Leu
305                 310                 315                 320

Leu Gly Pro Gly Val His Glu Pro Pro Glu Glu Ala Ala Val Asp Pro
                325                 330                 335

Arg Gly Gly Gln Val Pro Gly Gly Pro Phe Ser Arg Leu Gln Pro Arg
            340                 345                 350

Gly Asp Gly Pro Arg Gln Pro Gly Pro Arg Pro Gly Val Ser Gly Asp
        355                 360                 365

Val Gly Ser Trp Thr Leu Ala Leu Pro Met Pro Phe Ala Ala Pro Pro
    370                 375                 380

Gln Ser Pro Thr Trp Leu Leu Tyr Ser His Pro Val Gly Arg Arg Ala
385                 390                 395                 400

Arg Leu His Met Gly Ile Arg Leu Ser Gln Ser Pro Leu Asp Pro Arg
                405                 410                 415

Ser Trp Thr Glu Pro Trp Val Ile Tyr Glu Gly Pro Ser Gly Tyr Ser
            420                 425                 430

Asp Leu Ala Ser Ile Gly Pro Ala Pro Glu Gly Gly Leu Val Phe Ala
        435                 440                 445

Cys Leu Tyr Glu Ser Gly Ala Arg Thr Ser Tyr Asp Glu Ile Ser Phe
    450                 455                 460

Cys Thr Phe Ser Leu Arg Glu Val Leu Glu Asn Val Pro Ala Ser Pro
465                 470                 475                 480

Lys Pro Pro Asn Leu Gly Asp Lys Pro Arg Gly Cys Cys Trp Pro Ser
                485                 490                 495


<210> SEQ ID NO 12
<211> LENGTH: 5
<212> TYPE: PRT
<213> ORGANISM: Homo sapiens

<400> SEQUENCE: 12

Met Ala Ser Leu Pro
1               5


<210> SEQ ID NO 13
<211> LENGTH: 4
<212> TYPE: PRT
<213> ORGANISM: Homo sapiens

<400> SEQUENCE: 13

Ala Ser Leu Pro
1


<210> SEQ ID NO 14
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Thr Val Glu Lys Ser Val Val Phe
1               5
```

<210> SEQ ID NO 15
<211> LENGTH: 12
<212> TYPE: PRT
<213> ORGANISM: Homo sapiens

<400> SEQUENCE: 15

Gly Asp Tyr Asp Ala Pro Thr His Gln Val Gln Trp
1 5 10

<210> SEQ ID NO 16
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 16

Ser Met Asp Gln Gly Ser Thr Trp
1 5

<210> SEQ ID NO 17
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 17

Ser Thr Asp Gly Gly Lys Thr Trp
1 5

<210> SEQ ID NO 18
<211> LENGTH: 8
<212> TYPE: PRT
<213> ORGANISM: Homo sapiens

<400> SEQUENCE: 18

Pro Arg Pro Pro Ala Pro Glu Ala
1 5

<210> SEQ ID NO 19
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 19

Gln Thr Pro Leu Glu Ala Ala Cys
1 5

<210> SEQ ID NO 20
<211> LENGTH: 9
<212> TYPE: PRT
<213> ORGANISM: Homo sapiens

<400> SEQUENCE: 20

Asn Pro Arg Pro Pro Ala Pro Glu Ala
1 5

<210> SEQ ID NO 21
<211> LENGTH: 7
<212> TYPE: PRT

<213> ORGANISM: Artificial Sequence
<220> FEATURE:
<223> OTHER INFORMATION: Description of Artificial Sequence: Synthetic
peptide

<400> SEQUENCE: 21

Ser Gln Asn Asp Gly Glu Ser
1 5

<210> SEQ ID NO 22
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 22

Leu Ser His Ser Leu Ser Thr
1 5

<210> SEQ ID NO 23
<211> LENGTH: 1092
<212> TYPE: DNA
<213> ORGANISM: Homo sapiens

<400> SEQUENCE: 23
gagaacgact ttggactggt gcagcctctg gtcaccatgg aacagctgct gtgggtttcc 60
ggcagacaga tcggcagcgt ggacaccttc agaatccctc tgatcaccgc cacacctaga 120
ggcaccctgc tggcctttgc cgaggccaga aagatgagca gctctgacga gggcgccaag 180
tttattgccc tgaggcggtc tatggaccag ggctctacat ggtcccctac cgccttcatc 240
gtgaacgatg gcgacgtgcc cgatggcctg aatctgggag ctgtggtgtc cgatgtggaa 300
accggcgtgg tgttcctgtt ctacagcctg tgtgcccaca aggccggttg tcaggtggcc 360
agcacaatgc tcgtgtggtc caaggacgac ggcgtgtcct ggtctacccc tagaaacctg 420
agcctggaca tcggcaccga agtgtttgct ccaggacctg gctctggcat ccagaagcag 480
agagagccca gaaagggcag actgatcgtg tgtggccacg gcacccttga gagagatggc 540
gttttctgcc tgctgagcga cgatcatggc gcctcttgga gatacggcag cggagtgtct 600
ggaatccctt acggccagcc taagcaagag aacgatttca accccgacga gtgccagcct 660
tacgagctgc ctgatggcag cgtcgtgatc aacgcccgga accagaacaa ctaccactgc 720
cactgccgga tcgtgctgag aagctacgac gcctgcgata ccctgcggcc tagagatgtg 780
accttcgatc ctgagctggt ggaccctgtt gttgccgctg gtgccgtcgt gacatctagc 840
ggcatcgtgt tcttcagcaa ccctgctcac cccgagttca gagtgaatct gaccctgcgg 900
tggtccttca gcaatggcac aagctggcgg aaagaaaccg tgcagctttg gcctggacct 960
agcggctact cttctctggc tacactggaa ggcagcatgg acggcgaaga acaggcccct 1020
cagctgtacg tgctgtacga gaagggcaga aaccactaca ccgagagcat cagcgtggcc 1080
aagatcagcg tt 1092

<210> SEQ ID NO 24
<211> LENGTH: 1140
<212> TYPE: DNA
<213> ORGANISM: Homo sapiens

<400> SEQUENCE: 24
atggccagcc tgcctgtgct gcagaaagaa agcgtgttcc agtctggcgc ccacgcctac 60
agaattcccg ctctgctgta tctgccaggc cagcagtctc tgctggcttt cgctgaacag 120
cgggccagca agaaggatga gcacgccgaa ctgatcgtgc tgcggagagg cgattacgac 180
gcccctacac atcaggtgca gtggcaggct caagaggtgg tggctcaggc tagactggac 240
ggccacagat ctatgaaccc ctgtcctctg tacgatgccc agaccggcac actgtttctg 300
ttctttatcg ctatccccgg ccaagtgacc gagcagcagc agctgcagac aagagccaac 360
gtgaccagac tgtgtcaagt gacctccacc gaccacggca gaacctggtc tagccctaga 420
gatctgaccg acgccgccat cggacctgcc tatagagagt ggtccacctt cgccgttgga 480
cctggacact gtctccagct gcacgacagg gctagatctc tggtggtgcc tgcctacgcc 540
tatagaaagc tgcaccccat ccagcggcct attcctagcg ccttctgctt tctgagccac 600
gatcacggca ggacatgggc cagaggacat ttcgtggccc aggacacact ggaatgccag 660
gtggccgaag tggaaaccgg cgagcagaga gtcgtgaccc tgaacgccag atctcacctg 720
agagccagag tgcaggccca gagcacaaac gacggcctgg atttccaaga gagccagctg 780
gtcaagaaac tggtggaacc tcctccacag ggctgtcagg gaagcgtgat cagctttcca 840
tctcctagaa gcggccctgg ctctcctgct cagtggctgc tgtatacaca ccccacacac 900
agctggcaga gagccgatct gggcgcctac ctgaatccta gacctcctgc tcctgaggct 960
tggagcgaac ctgttctgct ggccaagggc agctgtgcct acagcgatct gcagtctatg 1020
ggcacaggcc ctgatggcag ccctctgttt ggctgtctgt acgaggccaa cgactacgaa 1080
gagatcgtgt tcctgatgtt caccctgaag caggcctttc cagccgagta cctgcctcaa 1140

<210> SEQ ID NO 25
<211> LENGTH: 1284
<212> TYPE: DNA
<213> ORGANISM: Homo sapiens

<400> SEQUENCE: 25
atggaggaag tgaccacctg tagcttcaac agccctctgt tccggcaaga ggacgaccgg 60
ggcatcacct acagaatccc tgctctgctg tacatccctc ctacacacac ctttctggcc 120
ttcgccgaga agcggagcac cagacgagat gaagatgccc tgcacctggt gctgagaaga 180
ggcctgagaa tcggacagct ggtgcagtgg ggacctctga agcctctgat ggaagccaca 240
ctgcccggcc acagaaccat gaatccttgt cctgtgtggg agcagaaaag cggctgcgtg 300
ttcctgttct tcatctgcgt gcggggccac gtgaccgaga gacagcaaat cgtgtccggc 360
agaaacgccg ccagactgtg cttcatctac agccaggatg ccggctgctc ttggagcgaa 420
gttcgggatc tgaccgaaga agtgatcggc agcgagctga agcactgggc cacatttgct 480
gttggccctg gccacggaat ccagctgcaa tctggcagac tggtcatccc cgcctacacc 540
tactatatcc ccagctggtt cttctgcttc caactgcctt gcaagacccg gcctcacagc 600
ctgatgatct acagcgacga tctgggcgtg acatggcacc acggcagact gatcagaccc 660
atggtcaccg tggaatgcga ggtggccgaa gtgacaggca gagctggaca ccctgtgctg 720
tactgctctg ccagaacacc caaccggtgt agagccgagg ctctgtctac agatcacggc 780
gagggctttc agagactggc cctctctaga cagctgtgcg aacctcctca tggctgtcag 840
ggcagcgtgg tgtccttcag acctctggaa atccctcacc ggtgccagga cagcagctct 900
aaggatgccc ctaccatcca gcagtctagc cctggcagca gcctgagact ggaagaggaa 960
gccggaacac ctagcgagag ctggctgctg tactctcacc ccaccagcag aaagcagaga 1020

```
gtggacctgg gcatctacct gaatcagacc cctctggaag ccgcctgttg gagcagacct   1080

tggattctgc actgtggccc ttgcggctac tctgatctgg ccgctctgga agaagagggc   1140

ctgttcggct gcctgtttga gtgcggcaca aagcaagagt gcgagcagat cgccttccgg   1200

ctgttcaccc acagagagat cctgagccat ctgcagggcg actgcacaag cccaggcaga   1260

aatcccagcc agttcaagag caac                                          1284
```

<210> SEQ ID NO 26
<211> LENGTH: 1452
<212> TYPE: DNA
<213> ORGANISM: Homo sapiens

<400> SEQUENCE: 26

```
atgggcgtgc ccagaacacc cagcagaacc gtgctgttcg agagagagag gaccggcctg     60

acctacagag tgccttctct gctgcctgtg cctcctggac ctacactgct ggccttcgtg    120

gaacagagac tgagccccga tgattctcac gcccacagac tggtgctgag aagaggaaca    180

ctggctggcg gctctgttag atggggagca ctgcatgtgc tgggcacagc tgctcttgcc    240

gagcacagat ccatgaatcc ctgtcctgtg cacgacgccg gaaccggcac agtgtttctg    300

ttctttatcg ccgtgctggg ccacacacct gaggccgttc aaattgccac cggcagaaat    360

gccgccagac tgtgttgtgt ggcctccaga gatgccggcc tgtcttgggg atctgccaga    420

gatctgaccg aggaagccat tggcggagcc gttcaggatt gggccacatt tgctgttgga    480

cctggacacg gcgtgcagct gccaagtggt agactgctgg tgcctgccta cacatacaga    540

gtggatcgga gagagtgctt cggaaagatc tgccggacaa gccctcacag cttcgccttc    600

tactccgacg atcacggccg gacttggaga tgtggtggcc tggtgcctaa tctgagaagc    660

ggcgaatgtc aactggccgc cgttgatggt ggacaggctg gcagcttcct gtactgcaac    720

gccagatctc ctctgggctc tagagtgcag gccctgtcta ccgatgaggg caccagtttt    780

ctgcccgccg aaagagttgc ctctctgcct gaaacagcct ggggctgtca gggctctatc    840

gtgggatttc ctgctcctgc tccaaacaga ccccgggacg attcttggag tgtcggccct    900

ggatctccac tgcagcctcc attgcttgga ccaggcgttc acgagccacc tgaagaggct    960

gccgttgatc ctagaggcgg acaagttcct ggcggccctt ttagcagact gcagccaaga   1020

ggcgacggcc ctagacaacc tggaccaaga cctggcgtca gcggagatgt tggctcttgg   1080

acactggccc tgcctatgcc ttttgccgct cctcctcagt ctcctacctg gctgctgtac   1140

tctcaccctg ttggcagacg ggccagactg cacatgggca tcagactgtc tcagagccct   1200

ctggacccca gaagctggac agagccttgg gtcatctatg agggccctag cggctacagc   1260

gatctggcct ctattggccc agctcctgaa ggcggactgg tgttcgcttg tctgtatgag   1320

agcggcgcca gaaccagcta cgacgagatc agcttctgca ccttcagcct gcgcgaggtg   1380

ctggaaaatg tgcccgcctc tcctaagcct cctaacctgg gcgataagcc tagaggctgt   1440

tgctggccat ct                                                       1452
```

<210> SEQ ID NO 27
<211> LENGTH: 47
<212> TYPE: PRT
<213> ORGANISM: Homo sapiens

<400> SEQUENCE: 27

```
Met Thr Gly Glu Arg Pro Ser Thr Ala Leu Pro Asp Arg Arg Trp Gly
1               5                   10                  15
```

```
Pro Arg Ile Leu Gly Phe Trp Gly Gly Cys Arg Val Trp Val Phe Ala
            20                  25                  30

Ala Ile Phe Leu Leu Leu Ser Leu Ala Ala Ser Trp Ser Lys Ala
        35                  40                  45


<210> SEQ ID NO 28
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Met Asp Met Arg Val Pro Ala Gln Leu Leu Gly Leu Leu Leu Leu Trp
1               5                   10                  15

Leu Pro Gly Ala Arg Cys
            20


<210> SEQ ID NO 29
<211> LENGTH: 4
<212> TYPE: PRT
<213> ORGANISM: Homo sapiens

<400> SEQUENCE: 29

Tyr Gly Thr Leu
1


<210> SEQ ID NO 30
<211> LENGTH: 382
<212> TYPE: PRT
<213> ORGANISM: Salmonella typhimurium

<400> SEQUENCE: 30

Met Thr Val Glu Lys Ser Val Val Phe Lys Ala Glu Gly Glu His Phe
1               5                   10                  15

Thr Asp Gln Lys Gly Asn Thr Ile Val Gly Ser Gly Ser Gly Gly Thr
            20                  25                  30

Thr Lys Tyr Phe Arg Ile Pro Ala Met Cys Thr Thr Ser Lys Gly Thr
        35                  40                  45

Ile Val Val Phe Ala Asp Ala Arg His Asn Thr Ala Ser Asp Gln Ser
    50                  55                  60

Phe Ile Asp Thr Ala Ala Ala Arg Ser Thr Asp Gly Gly Lys Thr Trp
65                  70                  75                  80

Asn Lys Lys Ile Ala Ile Tyr Asn Asp Arg Val Asn Ser Lys Leu Ser
                85                  90                  95

Arg Val Met Asp Pro Thr Cys Ile Val Ala Asn Ile Gln Gly Arg Glu
            100                 105                 110

Thr Ile Leu Val Met Val Gly Lys Trp Asn Asn Asn Asp Lys Thr Trp
        115                 120                 125

Gly Ala Tyr Arg Asp Lys Ala Pro Asp Thr Asp Trp Asp Leu Val Leu
    130                 135                 140

Tyr Lys Ser Thr Asp Asp Gly Val Thr Phe Ser Lys Val Glu Thr Asn
145                 150                 155                 160

Ile His Asp Ile Val Thr Lys Asn Gly Thr Ile Ser Ala Met Leu Gly
                165                 170                 175

Gly Val Gly Ser Gly Leu Gln Leu Asn Asp Gly Lys Leu Val Phe Pro
            180                 185                 190

Val Gln Met Val Arg Thr Lys Asn Ile Thr Thr Val Leu Asn Thr Ser
```

```
        195                 200                 205

Phe Ile Tyr Ser Thr Asp Gly Ile Thr Trp Ser Leu Pro Ser Gly Tyr
    210                 215                 220

Cys Glu Gly Phe Gly Ser Glu Asn Asn Ile Ile Glu Phe Asn Ala Ser
225                 230                 235                 240

Leu Val Asn Asn Ile Arg Asn Ser Gly Leu Arg Arg Ser Phe Glu Thr
                245                 250                 255

Lys Asp Phe Gly Lys Thr Trp Thr Glu Phe Pro Pro Met Asp Lys Lys
            260                 265                 270

Val Asp Asn Arg Asn His Gly Val Gln Gly Ser Thr Ile Thr Ile Pro
        275                 280                 285

Ser Gly Asn Lys Leu Val Ala Ala His Ser Ser Ala Gln Asn Lys Asn
    290                 295                 300

Asn Asp Tyr Thr Arg Ser Asp Ile Ser Leu Tyr Ala His Asn Leu Tyr
305                 310                 315                 320

Ser Gly Glu Val Lys Leu Ile Asp Asp Phe Tyr Pro Lys Val Gly Asn
                325                 330                 335

Ala Ser Gly Ala Gly Tyr Ser Cys Leu Ser Tyr Arg Lys Asn Val Asp
            340                 345                 350

Lys Glu Thr Leu Tyr Val Val Tyr Glu Ala Asn Gly Ser Ile Glu Phe
        355                 360                 365

Gln Asp Leu Ser Arg His Leu Pro Val Ile Lys Ser Tyr Asn
    370                 375                 380
```

<210> SEQ ID NO 31
<211> LENGTH: 232
<212> TYPE: PRT
<213> ORGANISM: Homo sapiens

<400> SEQUENCE: 31

```
Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Glu Glu Met Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190
```

```
Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230
```

<210> SEQ ID NO 32
<211> LENGTH: 227
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 32

```
Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Glu Glu Met Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Thr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225
```

<210> SEQ ID NO 33
<211> LENGTH: 232
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 33

```
Glu Pro Lys Ser Cys Asp Lys Thr His Thr Cys Pro Pro Cys Pro Ala
1               5                   10                  15
```

-continued

```
Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Glu Glu Met Thr
    130                 135                 140

Lys Asn Gln Val Ser Leu Tyr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230
```

<210> SEQ ID NO 34
<211> LENGTH: 1383
<212> TYPE: DNA
<213> ORGANISM: Homo sapiens

<400> SEQUENCE: 34

```
atgagacctg cggacctgcc cccgcgcccc atggaagaat ccccggcgtc cagctctgcc     60

ccgacagaga cggaggagcc ggggtccagt gcagaggtca tggaagaagt gacaacatgc    120

tccttcaaca gccctctgtt ccggcaggaa gatgacagag ggattaccta ccggatccca    180

gccctgctct acatacccc cacccacacc ttcctggcct ttgcagagaa gcgttctacg    240

aggagagatg aggatgctct ccacctggtg ctgaggcgag ggttgaggat tgggcagttg    300

gtacagtggg ggcccctgaa gccactgatg gaagccacac taccggggca tcggaccatg    360

aacccctgtc ctgtatggga gcagaagagt ggttgtgtgt tcctgttctt catctgtgtg    420

cggggccatg tcacagagcg tcaacagatt gtgtcaggca ggaatgctgc ccgcctttgc    480

ttcatctaca gtcaggatgc tggatgttca tggagtgagg tgagggactt gactgaggag    540

gtcattggct cagagctgaa gcactgggcc acatttgctg tgggcccagg tcatggcatc    600

cagctgcagt cagggagact ggtcatccct gcgtatacct actacatccc ttcctggttc    660

ttttgcttcc agctaccatg taaaaccagg cctcattctc tgatgatcta cagtgatgac    720

ctaggggtca catggcacca tggtagactc attaggccca tggttacagt agaatgtgaa    780

gtggcagagg tgactgggag ggctggccac cctgtgctat attgcagtgc ccggacacca    840

aacaggtgcc gggcagaggc gctcagcact gaccatggtg aaggctttca gagactggcc    900
```

ctgagtcgac agctctgtga gcccccacat ggttgccaag ggagtgtggt aagtttccgg 960
cccctggaga tcccacatag gtgccaggac tctagcagca aagatgcacc caccattcag 1020
cagagctctc caggcagttc actgaggctg gaggaggaag ctggaacacc gtcagaatca 1080
tggctcttgt actcacaccc aaccagtagg aaacagaggg ttgacctagg tatctatctc 1140
aaccagaccc ccttggaggc tgcctgctgg tcccgcccct ggatcttgca ctgtgggccc 1200
tgtggctact ctgatctggc tgctctggag gaggagggct tgtttgggtg tttgtttgaa 1260
tgtgggacca agcaagagtg tgagcagatt gccttccgcc tgtttacaca ccgggagatc 1320
ctgagtcacc tgcaggggga ctgcaccagc cctggtagga acccaagcca attcaaaagc 1380
aat 1383

<210> SEQ ID NO 35
<211> LENGTH: 1488
<212> TYPE: DNA
<213> ORGANISM: Homo sapiens

<400> SEQUENCE: 35
atgatgagct ctgcagcctt cccaaggtgg ctgagcatgg gggtccctcg taccccttca 60
cggacagtgc tcttcgagcg ggagaggacg ggcctgacct accgcgtgcc ctcgctgctc 120
cccgtgcccc ccgggcccac cctgctggcc tttgtggagc agcggctcag ccctgacgac 180
tcccacgccc accgcctggt gctgaggagg ggcacgctgg ccgggggctc cgtgcggtgg 240
ggtgccctgc acgtgctggg gacagcagcc ctggcggagc accggtccat gaacccctgc 300
cctgtgcacg atgctggcac gggcaccgtc ttcctcttct tcatcgcggt gctgggccac 360
acgcctgagg ccgtgcagat cgccacggga aggaacgccg cgcgcctctg ctgtgtggcc 420
agccgtgacg ccggcctctc gtggggcagc gcccgggacc tcaccgagga ggccatcggt 480
ggtgccgtgc aggactgggc cacattcgct gtgggtcccg gccacggtgt gcagctgccc 540
tcaggccgcc tgctggtacc cgcctacacc taccgcgtgg accgccgaga gtgttttggc 600
aagatctgcc ggaccagccc tcactccttc gccttctaca gcgatgacca cggccgcacc 660
tggcgctgtg gaggcctcgt gcccaacctg cgctcaggcg agtgccagct ggcagcggtg 720
gacggtgggc aggccggcag cttcctctac tgcaatgccc ggagcccact gggcagccgt 780
gtgcaggcgc tcagcactga cgagggcacc tccttcctgc ccgcagagcg cgtggcttcc 840
ctgcccgaga ctgcctgggg ctgccagggc agcatcgtgg gcttcccagc ccccgccccc 900
aacaggccac gggatgacag ttggtcagtg ggccccggga gtcccctcca gcctccactc 960
ctcggtcctg gagtccacga acccccagag gaggctgctg tagacccccg tggaggccag 1020
gtgcctggtg ggcccttcag ccgtctgcag cctcgggggg atggccccag gcagcctggc 1080
cccaggcctg gggtcagtgg ggatgtgggg tcctggaccc tggcactccc catgcccttt 1140
gctgccccgc cccagagccc cacgtggctg ctgtactccc acccagtggg gcgcagggct 1200
cggctacaca tgggtatccg cctgagccag tccccgctgg acccgcgcag ctggacagag 1260
ccctgggtga tctacgaggg ccccagcggc tactccgacc tggcgtccat cgggccggcc 1320
cctgaggggg gcctggtttt tgcctgcctg tacgagagcg ggggccaggac ctcctatgat 1380 gagatttcct tttgtacatt ctccctgcgt gaggtcctgg agaacgtgcc cgccagcccc 1440
aaaccgccca accttgggga caagcctcgg gggtgctgct ggccctcc 1488

<210> SEQ ID NO 36

<211> LENGTH: 379
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 36

```
Ala Ser Leu Pro Tyr Leu Gln Lys Glu Ser Val Phe Gln Ser Gly Ala
1               5                   10                  15

His Ala Tyr Arg Ile Pro Ala Leu Leu Tyr Leu Pro Gly Gln Gln Ser
            20                  25                  30

Leu Leu Ala Phe Ala Glu Gln Arg Ala Ser Lys Lys Asp Glu His Ala
        35                  40                  45

Glu Leu Ile Val Leu Arg Arg Gly Asp Tyr Asp Ala Pro Thr His Gln
    50                  55                  60

Val Gln Trp Gln Ala Gln Glu Val Val Ala Gln Ala Arg Leu Asp Gly
65                  70                  75                  80

His Arg Ser Met Asn Pro Cys Pro Leu Tyr Asp Ala Gln Thr Gly Thr
                85                  90                  95

Leu Phe Leu Phe Phe Ile Ala Ile Pro Gly Gln Val Thr Glu Gln Gln
            100                 105                 110

Gln Leu Gln Thr Arg Ala Asn Val Thr Arg Leu Cys Gln Val Thr Ser
        115                 120                 125

Thr Asp His Gly Arg Thr Trp Ser Ser Pro Arg Asp Leu Thr Asp Ala
    130                 135                 140

Ala Ile Gly Pro Ala Tyr Arg Glu Trp Ser Thr Phe Ala Val Gly Pro
145                 150                 155                 160

Gly His Cys Leu Gln Leu His Asp Arg Ala Arg Ser Leu Val Val Pro
                165                 170                 175

Ala Tyr Ala Tyr Arg Lys Leu His Pro Lys Gln Arg Pro Ile Pro Ser
            180                 185                 190

Ala Phe Cys Phe Leu Ser His Asp His Gly Arg Thr Trp Ala Arg Gly
        195                 200                 205

His Phe Val Ala Gln Asp Thr Leu Glu Cys Gln Val Ala Glu Val Glu
    210                 215                 220

Thr Gly Glu Gln Arg Val Val Thr Leu Asn Ala Arg Ser His Leu Arg
225                 230                 235                 240

Ala Arg Val Gln Ala Gln Ser Thr Asn Asp Gly Leu Asp Phe Gln Glu
                245                 250                 255

Ser Gln Leu Val Lys Lys Leu Val Glu Pro Pro Pro Gln Gly Cys Gln
            260                 265                 270

Gly Ser Val Ile Ser Phe Pro Ser Pro Arg Ser Gly Pro Gly Ser Pro
        275                 280                 285

Ala Gln Trp Leu Leu Tyr Thr His Pro Thr His Ser Trp Gln Arg Ala
    290                 295                 300

Asp Leu Gly Ala Tyr Leu Asn Pro Arg Pro Pro Ala Pro Glu Ala Trp
305                 310                 315                 320

Ser Glu Pro Val Leu Leu Ala Lys Gly Ser Cys Ala Tyr Ser Asp Leu
                325                 330                 335

Gln Ser Met Gly Thr Gly Pro Asp Gly Ser Pro Leu Phe Gly Cys Leu
            340                 345                 350

Tyr Glu Ala Asn Asp Tyr Glu Glu Ile Val Phe Leu Met Phe Thr Leu
        355                 360                 365

Lys Gln Ala Phe Pro Ala Glu Tyr Leu Pro Gln
```

370 375

<210> SEQ ID NO 37
<211> LENGTH: 379
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 37

Ala Ser Leu Pro Tyr Leu Gln Lys Glu Ser Val Phe Gln Ser Gly Ala
1 5 10 15

His Ala Tyr Arg Ile Pro Ala Leu Leu Tyr Leu Pro Gly Gln Gln Ser
20 25 30

Leu Leu Ala Phe Ala Glu Gln Arg Ala Ser Lys Lys Asp Glu His Ala
35 40 45

Glu Leu Ile Val Leu Arg Arg Gly Asp Tyr Asp Ala Pro Thr His Gln
50 55 60

Val Gln Trp Gln Ala Gln Glu Val Val Ala Gln Ala Arg Leu Asp Gly
65 70 75 80

His Arg Ser Met Asn Pro Cys Pro Leu Tyr Asp Ala Gln Thr Gly Thr
85 90 95

Leu Phe Leu Phe Phe Ile Ala Ile Pro Gly Gln Val Thr Glu Gln Gln
100 105 110

Gln Leu Gln Thr Arg Ala Asn Val Thr Arg Leu Cys Gln Val Thr Ser
115 120 125

Thr Asp His Gly Arg Thr Trp Ser Ser Pro Arg Asp Leu Thr Asp Ala
130 135 140

Ala Ile Gly Pro Ala Tyr Arg Glu Trp Ser Thr Phe Ala Val Gly Pro
145 150 155 160

Gly His Cys Leu Gln Leu His Asp Arg Ala Arg Ser Leu Val Val Pro
165 170 175

Ala Tyr Ala Tyr Arg Lys Leu His Pro Lys Gln Arg Pro Ile Pro Ser
180 185 190

Ala Phe Cys Phe Leu Ser His Asp His Gly Arg Thr Trp Ala Arg Gly
195 200 205

His Phe Val Ala Gln Asp Thr Leu Glu Cys Gln Val Ala Glu Val Glu
210 215 220

Thr Gly Glu Gln Arg Val Val Thr Leu Asn Ala Arg Ser His Leu Arg
225 230 235 240

Ala Arg Val Gln Ala Gln Ser Thr Asn Asp Gly Leu Asp Phe Gln Glu
245 250 255

Ser Gln Leu Val Lys Lys Leu Val Glu Pro Pro Pro Gln Gly Cys Gln
260 265 270

Gly Ser Val Ile Ser Phe Pro Ser Pro Arg Ser Gly Pro Gly Ser Pro
275 280 285

Ala Gln Trp Leu Leu Tyr Thr His Pro Thr His Ser Trp Gln Arg Ala
290 295 300

Asp Leu Gly Ala Tyr Leu Asn Pro Arg Pro Pro Ala Pro Glu Ala Trp
305 310 315 320

Ser Glu Pro Val Leu Leu Ala Lys Gly Ser Ala Ala Tyr Ser Asp Leu
325 330 335

Gln Ser Met Gly Thr Gly Pro Asp Gly Ser Pro Leu Phe Gly Cys Leu
340 345 350

```
Tyr Glu Ala Asn Asp Tyr Glu Glu Ile Val Phe Leu Met Phe Thr Leu
        355                 360                 365

Lys Gln Ala Phe Pro Ala Glu Tyr Leu Pro Gln
    370                 375


<210> SEQ ID NO 38
<211> LENGTH: 380
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Ala Ala Ser Leu Pro Tyr Leu Gln Lys Glu Ser Val Phe Gln Ser Gly
1               5                   10                  15

Ala His Ala Tyr Arg Ile Pro Ala Leu Leu Tyr Leu Pro Gly Gln Gln
            20                  25                  30

Ser Leu Leu Ala Phe Ala Glu Gln Arg Ala Ser Lys Lys Asp Glu His
        35                  40                  45

Ala Glu Leu Ile Val Leu Arg Arg Gly Asp Tyr Asp Ala Pro Thr His
    50                  55                  60

Gln Val Gln Trp Gln Ala Gln Glu Val Val Ala Gln Ala Arg Leu Asp
65                  70                  75                  80

Gly His Arg Ser Met Asn Pro Cys Pro Leu Tyr Asp Ala Gln Thr Gly
                85                  90                  95

Thr Leu Phe Leu Phe Phe Ile Ala Ile Pro Gly Gln Val Thr Glu Gln
            100                 105                 110

Gln Gln Leu Gln Thr Arg Ala Asn Val Thr Arg Leu Cys Gln Val Thr
        115                 120                 125

Ser Thr Asp His Gly Arg Thr Trp Ser Ser Pro Arg Asp Leu Thr Asp
    130                 135                 140

Ala Ala Ile Gly Pro Ala Tyr Arg Glu Trp Ser Thr Phe Ala Val Gly
145                 150                 155                 160

Pro Gly His Cys Leu Gln Leu His Asp Arg Ala Arg Ser Leu Val Val
                165                 170                 175

Pro Ala Tyr Ala Tyr Arg Lys Leu His Pro Lys Gln Arg Pro Ile Pro
            180                 185                 190

Ser Ala Phe Cys Phe Leu Ser His Asp His Gly Arg Thr Trp Ala Arg
        195                 200                 205

Gly His Phe Val Ala Gln Asp Thr Leu Glu Cys Gln Val Ala Glu Val
    210                 215                 220

Glu Thr Gly Glu Gln Arg Val Val Thr Leu Asn Ala Arg Ser His Leu
225                 230                 235                 240

Arg Ala Arg Val Gln Ala Gln Ser Thr Asn Asp Gly Leu Asp Phe Gln
                245                 250                 255

Glu Ser Gln Leu Val Lys Lys Leu Val Glu Pro Pro Pro Gln Gly Cys
            260                 265                 270

Gln Gly Ser Val Ile Ser Phe Pro Ser Pro Arg Ser Gly Pro Gly Ser
        275                 280                 285

Pro Ala Gln Trp Leu Leu Tyr Thr His Pro Thr His Ser Trp Gln Arg
    290                 295                 300

Ala Asp Leu Gly Ala Tyr Leu Asn Pro Arg Pro Pro Ala Pro Glu Ala
305                 310                 315                 320

Trp Ser Glu Pro Val Leu Leu Ala Lys Gly Ser Ala Ala Tyr Ser Asp
                325                 330                 335
```

```
Leu Gln Ser Met Gly Thr Gly Pro Asp Gly Ser Pro Leu Phe Gly Cys
            340                 345                 350

Leu Tyr Glu Ala Asn Asp Tyr Glu Glu Ile Val Phe Leu Met Phe Thr
        355                 360                 365

Leu Lys Gln Ala Phe Pro Ala Glu Tyr Leu Pro Gln
    370                 375                 380


<210> SEQ ID NO 39
<211> LENGTH: 380
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Asp Ala Ser Leu Pro Tyr Leu Gln Lys Glu Ser Val Phe Gln Ser Gly
1               5                   10                  15

Ala His Ala Tyr Arg Ile Pro Ala Leu Leu Tyr Leu Pro Gly Gln Gln
            20                  25                  30

Ser Leu Leu Ala Phe Ala Glu Gln Arg Ala Ser Lys Lys Asp Glu His
        35                  40                  45

Ala Glu Leu Ile Val Leu Arg Arg Gly Asp Tyr Asp Ala Pro Thr His
    50                  55                  60

Gln Val Gln Trp Gln Ala Gln Glu Val Val Ala Gln Ala Arg Leu Asp
65                  70                  75                  80

Gly His Arg Ser Met Asn Pro Cys Pro Leu Tyr Asp Ala Gln Thr Gly
                85                  90                  95

Thr Leu Phe Leu Phe Phe Ile Ala Ile Pro Gly Gln Val Thr Glu Gln
            100                 105                 110

Gln Gln Leu Gln Thr Arg Ala Asn Val Thr Arg Leu Cys Gln Val Thr
        115                 120                 125

Ser Thr Asp His Gly Arg Thr Trp Ser Ser Pro Arg Asp Leu Thr Asp
    130                 135                 140

Ala Ala Ile Gly Pro Ala Tyr Arg Glu Trp Ser Thr Phe Ala Val Gly
145                 150                 155                 160

Pro Gly His Cys Leu Gln Leu His Asp Arg Ala Arg Ser Leu Val Val
                165                 170                 175

Pro Ala Tyr Ala Tyr Arg Lys Leu His Pro Lys Gln Arg Pro Ile Pro
            180                 185                 190

Ser Ala Phe Cys Phe Leu Ser His Asp His Gly Arg Thr Trp Ala Arg
        195                 200                 205

Gly His Phe Val Ala Gln Asp Thr Leu Glu Cys Gln Val Ala Glu Val
    210                 215                 220

Glu Thr Gly Glu Gln Arg Val Val Thr Leu Asn Ala Arg Ser His Leu
225                 230                 235                 240

Arg Ala Arg Val Gln Ala Gln Ser Thr Asn Asp Gly Leu Asp Phe Gln
                245                 250                 255

Glu Ser Gln Leu Val Lys Lys Leu Val Glu Pro Pro Pro Gln Gly Cys
            260                 265                 270

Gln Gly Ser Val Ile Ser Phe Pro Ser Pro Arg Ser Gly Pro Gly Ser
        275                 280                 285

Pro Ala Gln Trp Leu Leu Tyr Thr His Pro Thr His Ser Trp Gln Arg
    290                 295                 300

Ala Asp Leu Gly Ala Tyr Leu Asn Pro Arg Pro Pro Ala Pro Glu Ala
```

305 310 315 320

Trp Ser Glu Pro Val Leu Leu Ala Lys Gly Ser Ala Ala Tyr Ser Asp
325 330 335

Leu Gln Ser Met Gly Thr Gly Pro Asp Gly Ser Pro Leu Phe Gly Cys
340 345 350

Leu Tyr Glu Ala Asn Asp Tyr Glu Glu Ile Val Phe Leu Met Phe Thr
355 360 365

Leu Lys Gln Ala Phe Pro Ala Glu Tyr Leu Pro Gln
370 375 380

<210> SEQ ID NO 40
<211> LENGTH: 450
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 40

Glu Val Gln Leu Val Glu Ser Gly Gly Gly Leu Val Gln Pro Gly Gly
1 5 10 15

Ser Leu Arg Leu Ser Cys Ala Ala Ser Gly Phe Asn Ile Lys Asp Thr
20 25 30

Tyr Ile His Trp Val Arg Gln Ala Pro Gly Lys Gly Leu Glu Trp Val
35 40 45

Ala Arg Ile Tyr Pro Thr Asn Gly Tyr Thr Arg Tyr Ala Asp Ser Val
50 55 60

Lys Gly Arg Phe Thr Ile Ser Ala Asp Thr Ser Lys Asn Thr Ala Tyr
65 70 75 80

Leu Gln Met Asn Ser Leu Arg Ala Glu Asp Thr Ala Val Tyr Tyr Cys
85 90 95

Ser Arg Trp Gly Gly Asp Gly Phe Tyr Ala Met Asp Tyr Trp Gly Gln
100 105 110

Gly Thr Leu Val Thr Val Ser Ser Ala Ser Thr Lys Gly Pro Ser Val
115 120 125

Phe Pro Leu Ala Pro Ser Ser Lys Ser Thr Ser Gly Gly Thr Ala Ala
130 135 140

Leu Gly Cys Leu Val Lys Asp Tyr Phe Pro Glu Pro Val Thr Val Ser
145 150 155 160

Trp Asn Ser Gly Ala Leu Thr Ser Gly Val His Thr Phe Pro Ala Val
165 170 175

Leu Gln Ser Ser Gly Leu Tyr Ser Leu Ser Ser Val Val Thr Val Pro
180 185 190

Ser Ser Ser Leu Gly Thr Gln Thr Tyr Ile Cys Asn Val Asn His Lys
195 200 205

Pro Ser Asn Thr Lys Val Asp Lys Lys Val Glu Pro Lys Ser Cys Asp
210 215 220

Lys Thr His Thr Cys Pro Pro Cys Pro Ala Pro Glu Leu Leu Gly Gly
225 230 235 240

Pro Ser Val Phe Leu Phe Pro Pro Lys Pro Lys Asp Thr Leu Met Ile
245 250 255

Ser Arg Thr Pro Glu Val Thr Cys Val Val Val Asp Val Ser His Glu
260 265 270

Asp Pro Glu Val Lys Phe Asn Trp Tyr Val Asp Gly Val Glu Val His
275 280 285

```
Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Tyr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450


<210> SEQ ID NO 41
<211> LENGTH: 213
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190
```

```
Cys Glu Val Thr His Gln Gly Leu Ser Ser Pro Val Thr Lys Ser Phe
        195                 200                 205

Asn Arg Gly Glu Cys
    210


<210> SEQ ID NO 42
<211> LENGTH: 242
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Asp Ile Gln Met Thr Gln Ser Pro Ser
    130                 135                 140

Ser Leu Ser Ala Ser Val Gly Asp Arg Val Thr Ile Thr Cys Arg Ala
145                 150                 155                 160

Ser Gln Asp Val Asn Thr Ala Val Ala Trp Tyr Gln Gln Lys Pro Gly
                165                 170                 175

Lys Ala Pro Lys Leu Leu Ile Tyr Ser Ala Ser Phe Leu Tyr Ser Gly
            180                 185                 190

Val Pro Ser Arg Phe Ser Gly Ser Arg Ser Gly Thr Asp Phe Thr Leu
        195                 200                 205

Thr Ile Ser Ser Leu Gln Pro Glu Asp Phe Ala Thr Tyr Tyr Cys Gln
    210                 215                 220

Gln His Tyr Thr Thr Pro Pro Thr Phe Gly Gln Gly Thr Lys Val Glu
225                 230                 235                 240

Ile Lys


<210> SEQ ID NO 43
<211> LENGTH: 873
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Ala Ser Leu Pro Tyr Leu Gln Lys Glu Ser Val Phe Gln Ser Gly Ala
1               5                   10                  15
```

-continued

```
His Ala Tyr Arg Ile Pro Ala Leu Leu Tyr Leu Pro Gly Gln Gln Ser
            20                  25                  30

Leu Leu Ala Phe Ala Glu Gln Arg Ala Ser Lys Lys Asp Glu His Ala
        35                  40                  45

Glu Leu Ile Val Leu Arg Arg Gly Asp Tyr Asp Ala Pro Thr His Gln
    50                  55                  60

Val Gln Trp Gln Ala Gln Glu Val Val Ala Gln Ala Arg Leu Asp Gly
65                  70                  75                  80

His Arg Ser Met Asn Pro Cys Pro Leu Tyr Asp Ala Gln Thr Gly Thr
                85                  90                  95

Leu Phe Leu Phe Phe Ile Ala Ile Pro Gly Gln Val Thr Glu Gln Gln
            100                 105                 110

Gln Leu Gln Thr Arg Ala Asn Val Thr Arg Leu Cys Gln Val Thr Ser
        115                 120                 125

Thr Asp His Gly Arg Thr Trp Ser Ser Pro Arg Asp Leu Thr Asp Ala
    130                 135                 140

Ala Ile Gly Pro Ala Tyr Arg Glu Trp Ser Thr Phe Ala Val Gly Pro
145                 150                 155                 160

Gly His Cys Leu Gln Leu His Asp Arg Ala Arg Ser Leu Val Val Pro
                165                 170                 175

Ala Tyr Ala Tyr Arg Lys Leu His Pro Lys Gln Arg Pro Ile Pro Ser
            180                 185                 190

Ala Phe Cys Phe Leu Ser His Asp His Gly Arg Thr Trp Ala Arg Gly
        195                 200                 205

His Phe Val Ala Gln Asp Thr Leu Glu Cys Gln Val Ala Glu Val Glu
    210                 215                 220

Thr Gly Glu Gln Arg Val Val Thr Leu Asn Ala Arg Ser His Leu Arg
225                 230                 235                 240

Ala Arg Val Gln Ala Gln Ser Thr Asn Asp Gly Leu Asp Phe Gln Glu
                245                 250                 255

Ser Gln Leu Val Lys Lys Leu Val Glu Pro Pro Pro Gln Gly Cys Gln
            260                 265                 270

Gly Ser Val Ile Ser Phe Pro Ser Pro Arg Ser Gly Pro Gly Ser Pro
        275                 280                 285

Ala Gln Trp Leu Leu Tyr Thr His Pro Thr His Ser Trp Gln Arg Ala
    290                 295                 300

Asp Leu Gly Ala Tyr Leu Asn Pro Arg Pro Pro Ala Pro Glu Ala Trp
305                 310                 315                 320

Ser Glu Pro Val Leu Leu Ala Lys Gly Ser Cys Ala Tyr Ser Asp Leu
                325                 330                 335

Gln Ser Met Gly Thr Gly Pro Asp Gly Ser Pro Leu Phe Gly Cys Leu
            340                 345                 350

Tyr Glu Ala Asn Asp Tyr Glu Glu Ile Val Phe Leu Met Phe Thr Leu
        355                 360                 365

Lys Gln Ala Phe Pro Ala Glu Tyr Leu Pro Gln Gly Gly Gly Gly Ser
    370                 375                 380

Gly Gly Gly Gly Ser Asp Lys Thr His Thr Cys Pro Pro Cys Pro Ala
385                 390                 395                 400

Pro Glu Leu Leu Gly Gly Pro Ser Val Phe Leu Phe Pro Pro Lys Pro
                405                 410                 415

Lys Asp Thr Leu Met Ile Ser Arg Thr Pro Glu Val Thr Cys Val Val
            420                 425                 430

Val Asp Val Ser His Glu Asp Pro Glu Val Lys Phe Asn Trp Tyr Val
```

-continued

```
        435                 440                 445

Asp Gly Val Glu Val His Asn Ala Lys Thr Lys Pro Arg Glu Glu Gln
    450                 455                 460

Tyr Asn Ser Thr Tyr Arg Val Val Ser Val Leu Thr Val Leu His Gln
465                 470                 475                 480

Asp Trp Leu Asn Gly Lys Glu Tyr Lys Cys Lys Val Ser Asn Lys Ala
                485                 490                 495

Leu Pro Ala Pro Ile Glu Lys Thr Ile Ser Lys Ala Lys Gly Gln Pro
            500                 505                 510

Arg Glu Pro Gln Val Tyr Thr Leu Pro Pro Ser Arg Glu Glu Met Thr
        515                 520                 525

Lys Asn Gln Val Ser Leu Thr Cys Leu Val Lys Gly Phe Tyr Pro Ser
    530                 535                 540

Asp Ile Ala Val Glu Trp Glu Ser Asn Gly Gln Pro Glu Asn Asn Tyr
545                 550                 555                 560

Lys Thr Thr Pro Pro Val Leu Asp Ser Asp Gly Ser Phe Phe Leu Tyr
                565                 570                 575

Ser Lys Leu Thr Val Asp Lys Ser Arg Trp Gln Gln Gly Asn Val Phe
            580                 585                 590

Ser Cys Ser Val Met His Glu Ala Leu His Asn His Tyr Thr Gln Lys
        595                 600                 605

Ser Leu Ser Leu Ser Pro Gly Lys Gly Gly Gly Gly Ser Gly Gly Gly
    610                 615                 620

Gly Ser Gly Gly Gly Gly Ser Glu Val Gln Leu Val Glu Ser Gly Gly
625                 630                 635                 640

Gly Leu Val Gln Pro Gly Gly Ser Leu Arg Leu Ser Cys Ala Ala Ser
                645                 650                 655

Gly Phe Asn Ile Lys Asp Thr Tyr Ile His Trp Val Arg Gln Ala Pro
            660                 665                 670

Gly Lys Gly Leu Glu Trp Val Ala Arg Ile Tyr Pro Thr Asn Gly Tyr
        675                 680                 685

Thr Arg Tyr Ala Asp Ser Val Lys Gly Arg Phe Thr Ile Ser Ala Asp
    690                 695                 700

Thr Ser Lys Asn Thr Ala Tyr Leu Gln Met Asn Ser Leu Arg Ala Glu
705                 710                 715                 720

Asp Thr Ala Val Tyr Tyr Cys Ser Arg Trp Gly Gly Asp Gly Phe Tyr
                725                 730                 735

Ala Met Asp Tyr Trp Gly Gln Gly Thr Leu Val Thr Val Ser Ser Gly
            740                 745                 750

Gly Gly Gly Ser Gly Gly Gly Gly Ser Gly Gly Gly Gly Ser Asp Ile
        755                 760                 765

Gln Met Thr Gln Ser Pro Ser Ser Leu Ser Ala Ser Val Gly Asp Arg
    770                 775                 780

Val Thr Ile Thr Cys Arg Ala Ser Gln Asp Val Asn Thr Ala Val Ala
785                 790                 795                 800

Trp Tyr Gln Gln Lys Pro Gly Lys Ala Pro Lys Leu Leu Ile Tyr Ser
                805                 810                 815

Ala Ser Phe Leu Tyr Ser Gly Val Pro Ser Arg Phe Ser Gly Ser Arg
            820                 825                 830

Ser Gly Thr Asp Phe Thr Leu Thr Ile Ser Ser Leu Gln Pro Glu Asp
        835                 840                 845

Phe Ala Thr Tyr Tyr Cys Gln Gln His Tyr Thr Thr Pro Pro Thr Phe
    850                 855                 860
```

-continued

```
Gly Gln Gly Thr Lys Val Glu Ile Lys
865                 870


<210> SEQ ID NO 44
<211> LENGTH: 873
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Ala Ser Leu Pro Tyr Leu Gln Lys Glu Ser Val Phe Gln Ser Gly Ala
1               5                   10                  15

His Ala Tyr Arg Ile Pro Ala Leu Leu Tyr Leu Pro Gly Gln Gln Ser
            20                  25                  30

Leu Leu Ala Phe Ala Glu Gln Arg Ala Ser Lys Lys Asp Glu His Ala
        35                  40                  45

Glu Leu Ile Val Leu Arg Arg Gly Asp Tyr Asp Ala Pro Thr His Gln
    50                  55                  60

Val Gln Trp Gln Ala Gln Glu Val Val Ala Gln Ala Arg Leu Asp Gly
65                  70                  75                  80

His Arg Ser Met Asn Pro Cys Pro Leu Tyr Asp Ala Gln Thr Gly Thr
                85                  90                  95

Leu Phe Leu Phe Phe Ile Ala Ile Pro Gly Gln Val Thr Glu Gln Gln
            100                 105                 110

Gln Leu Gln Thr Arg Ala Asn Val Thr Arg Leu Cys Gln Val Thr Ser
        115                 120                 125

Thr Asp His Gly Arg Thr Trp Ser Ser Pro Arg Asp Leu Thr Asp Ala
    130                 135                 140

Ala Ile Gly Pro Ala Tyr Arg Glu Trp Ser Thr Phe Ala Val Gly Pro
145                 150                 155                 160

Gly His Cys Leu Gln Leu His Asp Arg Ala Arg Ser Leu Val Val Pro
                165                 170                 175

Ala Tyr Ala Tyr Arg Lys Leu His Pro Lys Gln Arg Pro Ile Pro Ser
            180                 185                 190

Ala Phe Cys Phe Leu Ser His Asp His Gly Arg Thr Trp Ala Arg Gly
        195                 200                 205

His Phe Val Ala Gln Asp Thr Leu Glu Cys Gln Val Ala Glu Val Glu
    210                 215                 220

Thr Gly Glu Gln Arg Val Val Thr Leu Asn Ala Arg Ser His Leu Arg
225                 230                 235                 240

Ala Arg Val Gln Ala Gln Ser Thr Asn Asp Gly Leu Asp Phe Gln Glu
                245                 250                 255

Ser Gln Leu Val Lys Lys Leu Val Glu Pro Pro Pro Gln Gly Cys Gln
            260                 265                 270

Gly Ser Val Ile Ser Phe Pro Ser Pro Arg Ser Gly Pro Gly Ser Pro
        275                 280                 285

Ala Gln Trp Leu Leu Tyr Thr His Pro Thr His Ser Trp Gln Arg Ala
    290                 295                 300

Asp Leu Gly Ala Tyr Leu Asn Pro Arg Pro Pro Ala Pro Glu Ala Trp
305                 310                 315                 320

Ser Glu Pro Val Leu Leu Ala Lys Gly Ser Ala Ala Tyr Ser Asp Leu
                325                 330                 335

Gln Ser Met Gly Thr Gly Pro Asp Gly Ser Pro Leu Phe Gly Cys Leu
```

-continued

```
            340                 345                 350

Tyr Glu Ala Asn Asp Tyr Glu Glu Ile Val Phe Leu Met Phe Thr Leu
        355                 360                 365

Lys Gln Ala Phe Pro Ala Glu Tyr Leu Pro Gln Gly Gly Gly Gly Ser
    370                 375                 380

Gly Gly Gly Gly Ser Asp Lys Thr His Thr Cys Pro Pro Cys Pro Ala
385                 390                 395                 400

Pro Glu Leu Leu Gly Gly Pro Ser Val Phe Leu Phe Pro Pro Lys Pro
                405                 410                 415

Lys Asp Thr Leu Met Ile Ser Arg Thr Pro Glu Val Thr Cys Val Val
            420                 425                 430

Val Asp Val Ser His Glu Asp Pro Glu Val Lys Phe Asn Trp Tyr Val
        435                 440                 445

Asp Gly Val Glu Val His Asn Ala Lys Thr Lys Pro Arg Glu Glu Gln
    450                 455                 460

Tyr Asn Ser Thr Tyr Arg Val Val Ser Val Leu Thr Val Leu His Gln
465                 470                 475                 480

Asp Trp Leu Asn Gly Lys Glu Tyr Lys Cys Lys Val Ser Asn Lys Ala
                485                 490                 495

Leu Pro Ala Pro Ile Glu Lys Thr Ile Ser Lys Ala Lys Gly Gln Pro
            500                 505                 510

Arg Glu Pro Gln Val Tyr Thr Leu Pro Pro Ser Arg Glu Glu Met Thr
        515                 520                 525

Lys Asn Gln Val Ser Leu Thr Cys Leu Val Lys Gly Phe Tyr Pro Ser
    530                 535                 540

Asp Ile Ala Val Glu Trp Glu Ser Asn Gly Gln Pro Glu Asn Asn Tyr
545                 550                 555                 560

Lys Thr Thr Pro Pro Val Leu Asp Ser Asp Gly Ser Phe Phe Leu Tyr
                565                 570                 575

Ser Lys Leu Thr Val Asp Lys Ser Arg Trp Gln Gln Gly Asn Val Phe
            580                 585                 590

Ser Cys Ser Val Met His Glu Ala Leu His Asn His Tyr Thr Gln Lys
        595                 600                 605

Ser Leu Ser Leu Ser Pro Gly Lys Gly Gly Gly Gly Ser Gly Gly Gly
    610                 615                 620

Gly Ser Gly Gly Gly Gly Ser Glu Val Gln Leu Val Glu Ser Gly Gly
625                 630                 635                 640

Gly Leu Val Gln Pro Gly Gly Ser Leu Arg Leu Ser Cys Ala Ala Ser
                645                 650                 655

Gly Phe Asn Ile Lys Asp Thr Tyr Ile His Trp Val Arg Gln Ala Pro
            660                 665                 670

Gly Lys Gly Leu Glu Trp Val Ala Arg Ile Tyr Pro Thr Asn Gly Tyr
        675                 680                 685

Thr Arg Tyr Ala Asp Ser Val Lys Gly Arg Phe Thr Ile Ser Ala Asp
    690                 695                 700

Thr Ser Lys Asn Thr Ala Tyr Leu Gln Met Asn Ser Leu Arg Ala Glu
705                 710                 715                 720

Asp Thr Ala Val Tyr Tyr Cys Ser Arg Trp Gly Gly Asp Gly Phe Tyr
                725                 730                 735

Ala Met Asp Tyr Trp Gly Gln Gly Thr Leu Val Thr Val Ser Ser Gly
            740                 745                 750

Gly Gly Gly Ser Gly Gly Gly Gly Ser Gly Gly Gly Gly Ser Asp Ile
        755                 760                 765
```

Gln Met Thr Gln Ser Pro Ser Ser Leu Ser Ala Ser Val Gly Asp Arg
770 775 780

Val Thr Ile Thr Cys Arg Ala Ser Gln Asp Val Asn Thr Ala Val Ala
785 790 795 800

Trp Tyr Gln Gln Lys Pro Gly Lys Ala Pro Lys Leu Leu Ile Tyr Ser
805 810 815

Ala Ser Phe Leu Tyr Ser Gly Val Pro Ser Arg Phe Ser Gly Ser Arg
820 825 830

Ser Gly Thr Asp Phe Thr Leu Thr Ile Ser Ser Leu Gln Pro Glu Asp
835 840 845

Phe Ala Thr Tyr Tyr Cys Gln Gln His Tyr Thr Thr Pro Pro Thr Phe
850 855 860

Gly Gln Gly Thr Lys Val Glu Ile Lys
865 870

<210> SEQ ID NO 45
<211> LENGTH: 874
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 45

Ala Ala Ser Leu Pro Tyr Leu Gln Lys Glu Ser Val Phe Gln Ser Gly
1 5 10 15

Ala His Ala Tyr Arg Ile Pro Ala Leu Leu Tyr Leu Pro Gly Gln Gln
20 25 30

Ser Leu Leu Ala Phe Ala Glu Gln Arg Ala Ser Lys Lys Asp Glu His
35 40 45

Ala Glu Leu Ile Val Leu Arg Arg Gly Asp Tyr Asp Ala Pro Thr His
50 55 60

Gln Val Gln Trp Gln Ala Gln Glu Val Val Ala Gln Ala Arg Leu Asp
65 70 75 80

Gly His Arg Ser Met Asn Pro Cys Pro Leu Tyr Asp Ala Gln Thr Gly
85 90 95

Thr Leu Phe Leu Phe Phe Ile Ala Ile Pro Gly Gln Val Thr Glu Gln
100 105 110

Gln Gln Leu Gln Thr Arg Ala Asn Val Thr Arg Leu Cys Gln Val Thr
115 120 125

Ser Thr Asp His Gly Arg Thr Trp Ser Ser Pro Arg Asp Leu Thr Asp
130 135 140

Ala Ala Ile Gly Pro Ala Tyr Arg Glu Trp Ser Thr Phe Ala Val Gly
145 150 155 160

Pro Gly His Cys Leu Gln Leu His Asp Arg Ala Arg Ser Leu Val Val
165 170 175

Pro Ala Tyr Ala Tyr Arg Lys Leu His Pro Lys Gln Arg Pro Ile Pro
180 185 190

Ser Ala Phe Cys Phe Leu Ser His Asp His Gly Arg Thr Trp Ala Arg
195 200 205

Gly His Phe Val Ala Gln Asp Thr Leu Glu Cys Gln Val Ala Glu Val
210 215 220

Glu Thr Gly Glu Gln Arg Val Val Thr Leu Asn Ala Arg Ser His Leu
225 230 235 240

Arg Ala Arg Val Gln Ala Gln Ser Thr Asn Asp Gly Leu Asp Phe Gln

```
                245                 250                 255

Glu Ser Gln Leu Val Lys Lys Leu Val Glu Pro Pro Pro Gln Gly Cys
            260                 265                 270

Gln Gly Ser Val Ile Ser Phe Pro Ser Pro Arg Ser Gly Pro Gly Ser
        275                 280                 285

Pro Ala Gln Trp Leu Leu Tyr Thr His Pro Thr His Ser Trp Gln Arg
    290                 295                 300

Ala Asp Leu Gly Ala Tyr Leu Asn Pro Arg Pro Pro Ala Pro Glu Ala
305                 310                 315                 320

Trp Ser Glu Pro Val Leu Leu Ala Lys Gly Ser Cys Ala Tyr Ser Asp
                325                 330                 335

Leu Gln Ser Met Gly Thr Gly Pro Asp Gly Ser Pro Leu Phe Gly Cys
            340                 345                 350

Leu Tyr Glu Ala Asn Asp Tyr Glu Glu Ile Val Phe Leu Met Phe Thr
        355                 360                 365

Leu Lys Gln Ala Phe Pro Ala Glu Tyr Leu Pro Gln Gly Gly Gly Gly
    370                 375                 380

Ser Gly Gly Gly Gly Ser Asp Lys Thr His Thr Cys Pro Pro Cys Pro
385                 390                 395                 400

Ala Pro Glu Leu Leu Gly Gly Pro Ser Val Phe Leu Phe Pro Pro Lys
                405                 410                 415

Pro Lys Asp Thr Leu Met Ile Ser Arg Thr Pro Glu Val Thr Cys Val
            420                 425                 430

Val Val Asp Val Ser His Glu Asp Pro Glu Val Lys Phe Asn Trp Tyr
        435                 440                 445

Val Asp Gly Val Glu Val His Asn Ala Lys Thr Lys Pro Arg Glu Glu
    450                 455                 460

Gln Tyr Asn Ser Thr Tyr Arg Val Val Ser Val Leu Thr Val Leu His
465                 470                 475                 480

Gln Asp Trp Leu Asn Gly Lys Glu Tyr Lys Cys Lys Val Ser Asn Lys
                485                 490                 495

Ala Leu Pro Ala Pro Ile Glu Lys Thr Ile Ser Lys Ala Lys Gly Gln
            500                 505                 510

Pro Arg Glu Pro Gln Val Tyr Thr Leu Pro Pro Ser Arg Glu Glu Met
        515                 520                 525

Thr Lys Asn Gln Val Ser Leu Thr Cys Leu Val Lys Gly Phe Tyr Pro
    530                 535                 540

Ser Asp Ile Ala Val Glu Trp Glu Ser Asn Gly Gln Pro Glu Asn Asn
545                 550                 555                 560

Tyr Lys Thr Thr Pro Pro Val Leu Asp Ser Asp Gly Ser Phe Phe Leu
                565                 570                 575

Tyr Ser Lys Leu Thr Val Asp Lys Ser Arg Trp Gln Gln Gly Asn Val
            580                 585                 590

Phe Ser Cys Ser Val Met His Glu Ala Leu His Asn His Tyr Thr Gln
        595                 600                 605

Lys Ser Leu Ser Leu Ser Pro Gly Lys Gly Gly Gly Gly Ser Gly Gly
    610                 615                 620

Gly Gly Ser Gly Gly Gly Gly Ser Glu Val Gln Leu Val Glu Ser Gly
625                 630                 635                 640

Gly Gly Leu Val Gln Pro Gly Gly Ser Leu Arg Leu Ser Cys Ala Ala
                645                 650                 655

Ser Gly Phe Asn Ile Lys Asp Thr Tyr Ile His Trp Val Arg Gln Ala
            660                 665                 670
```

Pro Gly Lys Gly Leu Glu Trp Val Ala Arg Ile Tyr Pro Thr Asn Gly
675 680 685

Tyr Thr Arg Tyr Ala Asp Ser Val Lys Gly Arg Phe Thr Ile Ser Ala
690 695 700

Asp Thr Ser Lys Asn Thr Ala Tyr Leu Gln Met Asn Ser Leu Arg Ala
705 710 715 720

Glu Asp Thr Ala Val Tyr Tyr Cys Ser Arg Trp Gly Gly Asp Gly Phe
725 730 735

Tyr Ala Met Asp Tyr Trp Gly Gln Gly Thr Leu Val Thr Val Ser Ser
740 745 750

Gly Gly Gly Gly Ser Gly Gly Gly Gly Ser Gly Gly Gly Gly Ser Asp
755 760 765

Ile Gln Met Thr Gln Ser Pro Ser Ser Leu Ser Ala Ser Val Gly Asp
770 775 780

Arg Val Thr Ile Thr Cys Arg Ala Ser Gln Asp Val Asn Thr Ala Val
785 790 795 800

Ala Trp Tyr Gln Gln Lys Pro Gly Lys Ala Pro Lys Leu Leu Ile Tyr
805 810 815

Ser Ala Ser Phe Leu Tyr Ser Gly Val Pro Ser Arg Phe Ser Gly Ser
820 825 830

Arg Ser Gly Thr Asp Phe Thr Leu Thr Ile Ser Ser Leu Gln Pro Glu
835 840 845

Asp Phe Ala Thr Tyr Tyr Cys Gln Gln His Tyr Thr Thr Pro Pro Thr
850 855 860

Phe Gly Gln Gly Thr Lys Val Glu Ile Lys
865 870

<210> SEQ ID NO 46
<211> LENGTH: 874
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 46

Asp Ala Ser Leu Pro Tyr Leu Gln Lys Glu Ser Val Phe Gln Ser Gly
1 5 10 15

Ala His Ala Tyr Arg Ile Pro Ala Leu Leu Tyr Leu Pro Gly Gln Gln
20 25 30

Ser Leu Leu Ala Phe Ala Glu Gln Arg Ala Ser Lys Lys Asp Glu His
35 40 45

Ala Glu Leu Ile Val Leu Arg Arg Gly Asp Tyr Asp Ala Pro Thr His
50 55 60

Gln Val Gln Trp Gln Ala Gln Glu Val Val Ala Gln Ala Arg Leu Asp
65 70 75 80

Gly His Arg Ser Met Asn Pro Cys Pro Leu Tyr Asp Ala Gln Thr Gly
85 90 95

Thr Leu Phe Leu Phe Phe Ile Ala Ile Pro Gly Gln Val Thr Glu Gln
100 105 110

Gln Gln Leu Gln Thr Arg Ala Asn Val Thr Arg Leu Cys Gln Val Thr
115 120 125

Ser Thr Asp His Gly Arg Thr Trp Ser Ser Pro Arg Asp Leu Thr Asp
130 135 140

Ala Ala Ile Gly Pro Ala Tyr Arg Glu Trp Ser Thr Phe Ala Val Gly

-continued

```
145                 150                 155                 160

Pro Gly His Cys Leu Gln Leu His Asp Arg Ala Arg Ser Leu Val Val
                165                 170                 175

Pro Ala Tyr Ala Tyr Arg Lys Leu His Pro Lys Gln Arg Pro Ile Pro
            180                 185                 190

Ser Ala Phe Cys Phe Leu Ser His Asp His Gly Arg Thr Trp Ala Arg
        195                 200                 205

Gly His Phe Val Ala Gln Asp Thr Leu Glu Cys Gln Val Ala Glu Val
    210                 215                 220

Glu Thr Gly Glu Gln Arg Val Val Thr Leu Asn Ala Arg Ser His Leu
225                 230                 235                 240

Arg Ala Arg Val Gln Ala Gln Ser Thr Asn Asp Gly Leu Asp Phe Gln
                245                 250                 255

Glu Ser Gln Leu Val Lys Lys Leu Val Glu Pro Pro Pro Gln Gly Cys
            260                 265                 270

Gln Gly Ser Val Ile Ser Phe Pro Ser Pro Arg Ser Gly Pro Gly Ser
        275                 280                 285

Pro Ala Gln Trp Leu Leu Tyr Thr His Pro Thr His Ser Trp Gln Arg
    290                 295                 300

Ala Asp Leu Gly Ala Tyr Leu Asn Pro Arg Pro Pro Ala Pro Glu Ala
305                 310                 315                 320

Trp Ser Glu Pro Val Leu Leu Ala Lys Gly Ser Cys Ala Tyr Ser Asp
                325                 330                 335

Leu Gln Ser Met Gly Thr Gly Pro Asp Gly Ser Pro Leu Phe Gly Cys
            340                 345                 350

Leu Tyr Glu Ala Asn Asp Tyr Glu Glu Ile Val Phe Leu Met Phe Thr
        355                 360                 365

Leu Lys Gln Ala Phe Pro Ala Glu Tyr Leu Pro Gln Gly Gly Gly Gly
    370                 375                 380

Ser Gly Gly Gly Gly Ser Asp Lys Thr His Thr Cys Pro Pro Cys Pro
385                 390                 395                 400

Ala Pro Glu Leu Leu Gly Gly Pro Ser Val Phe Leu Phe Pro Pro Lys
                405                 410                 415

Pro Lys Asp Thr Leu Met Ile Ser Arg Thr Pro Glu Val Thr Cys Val
            420                 425                 430

Val Val Asp Val Ser His Glu Asp Pro Glu Val Lys Phe Asn Trp Tyr
        435                 440                 445

Val Asp Gly Val Glu Val His Asn Ala Lys Thr Lys Pro Arg Glu Glu
    450                 455                 460

Gln Tyr Asn Ser Thr Tyr Arg Val Val Ser Val Leu Thr Val Leu His
465                 470                 475                 480

Gln Asp Trp Leu Asn Gly Lys Glu Tyr Lys Cys Lys Val Ser Asn Lys
                485                 490                 495

Ala Leu Pro Ala Pro Ile Glu Lys Thr Ile Ser Lys Ala Lys Gly Gln
            500                 505                 510

Pro Arg Glu Pro Gln Val Tyr Thr Leu Pro Pro Ser Arg Glu Glu Met
        515                 520                 525

Thr Lys Asn Gln Val Ser Leu Thr Cys Leu Val Lys Gly Phe Tyr Pro
    530                 535                 540

Ser Asp Ile Ala Val Glu Trp Glu Ser Asn Gly Gln Pro Glu Asn Asn
545                 550                 555                 560

Tyr Lys Thr Thr Pro Pro Val Leu Asp Ser Asp Gly Ser Phe Phe Leu
                565                 570                 575
```

Tyr Ser Lys Leu Thr Val Asp Lys Ser Arg Trp Gln Gln Gly Asn Val
580 585 590

Phe Ser Cys Ser Val Met His Glu Ala Leu His Asn His Tyr Thr Gln
595 600 605

Lys Ser Leu Ser Leu Ser Pro Gly Lys Gly Gly Gly Gly Ser Gly Gly
610 615 620

Gly Gly Ser Gly Gly Gly Gly Ser Glu Val Gln Leu Val Glu Ser Gly
625 630 635 640

Gly Gly Leu Val Gln Pro Gly Gly Ser Leu Arg Leu Ser Cys Ala Ala
645 650 655

Ser Gly Phe Asn Ile Lys Asp Thr Tyr Ile His Trp Val Arg Gln Ala
660 665 670

Pro Gly Lys Gly Leu Glu Trp Val Ala Arg Ile Tyr Pro Thr Asn Gly
675 680 685

Tyr Thr Arg Tyr Ala Asp Ser Val Lys Gly Arg Phe Thr Ile Ser Ala
690 695 700

Asp Thr Ser Lys Asn Thr Ala Tyr Leu Gln Met Asn Ser Leu Arg Ala
705 710 715 720

Glu Asp Thr Ala Val Tyr Tyr Cys Ser Arg Trp Gly Gly Asp Gly Phe
725 730 735

Tyr Ala Met Asp Tyr Trp Gly Gln Gly Thr Leu Val Thr Val Ser Ser
740 745 750

Gly Gly Gly Gly Ser Gly Gly Gly Gly Ser Gly Gly Gly Gly Ser Asp
755 760 765

Ile Gln Met Thr Gln Ser Pro Ser Ser Leu Ser Ala Ser Val Gly Asp
770 775 780

Arg Val Thr Ile Thr Cys Arg Ala Ser Gln Asp Val Asn Thr Ala Val
785 790 795 800

Ala Trp Tyr Gln Gln Lys Pro Gly Lys Ala Pro Lys Leu Leu Ile Tyr
805 810 815

Ser Ala Ser Phe Leu Tyr Ser Gly Val Pro Ser Arg Phe Ser Gly Ser
820 825 830

Arg Ser Gly Thr Asp Phe Thr Leu Thr Ile Ser Ser Leu Gln Pro Glu
835 840 845

Asp Phe Ala Thr Tyr Tyr Cys Gln Gln His Tyr Thr Thr Pro Pro Thr
850 855 860

Phe Gly Gln Gly Thr Lys Val Glu Ile Lys
865 870

<210> SEQ ID NO 47
<211> LENGTH: 874
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 47

Ala Ala Ser Leu Pro Tyr Leu Gln Lys Glu Ser Val Phe Gln Ser Gly
1 5 10 15

Ala His Ala Tyr Arg Ile Pro Ala Leu Leu Tyr Leu Pro Gly Gln Gln
20 25 30

Ser Leu Leu Ala Phe Ala Glu Gln Arg Ala Ser Lys Lys Asp Glu His
35 40 45

Ala Glu Leu Ile Val Leu Arg Arg Gly Asp Tyr Asp Ala Pro Thr His

-continued

```
    50                  55                  60

Gln Val Gln Trp Gln Ala Gln Glu Val Val Ala Gln Ala Arg Leu Asp
65                  70                  75                  80

Gly His Arg Ser Met Asn Pro Cys Pro Leu Tyr Asp Ala Gln Thr Gly
                85                  90                  95

Thr Leu Phe Leu Phe Phe Ile Ala Ile Pro Gly Gln Val Thr Glu Gln
            100                 105                 110

Gln Gln Leu Gln Thr Arg Ala Asn Val Thr Arg Leu Cys Gln Val Thr
        115                 120                 125

Ser Thr Asp His Gly Arg Thr Trp Ser Ser Pro Arg Asp Leu Thr Asp
    130                 135                 140

Ala Ala Ile Gly Pro Ala Tyr Arg Glu Trp Ser Thr Phe Ala Val Gly
145                 150                 155                 160

Pro Gly His Cys Leu Gln Leu His Asp Arg Ala Arg Ser Leu Val Val
                165                 170                 175

Pro Ala Tyr Ala Tyr Arg Lys Leu His Pro Lys Gln Arg Pro Ile Pro
            180                 185                 190

Ser Ala Phe Cys Phe Leu Ser His Asp His Gly Arg Thr Trp Ala Arg
        195                 200                 205

Gly His Phe Val Ala Gln Asp Thr Leu Glu Cys Gln Val Ala Glu Val
    210                 215                 220

Glu Thr Gly Glu Gln Arg Val Val Thr Leu Asn Ala Arg Ser His Leu
225                 230                 235                 240

Arg Ala Arg Val Gln Ala Gln Ser Thr Asn Asp Gly Leu Asp Phe Gln
                245                 250                 255

Glu Ser Gln Leu Val Lys Lys Leu Val Glu Pro Pro Pro Gln Gly Cys
            260                 265                 270

Gln Gly Ser Val Ile Ser Phe Pro Ser Pro Arg Ser Gly Pro Gly Ser
        275                 280                 285

Pro Ala Gln Trp Leu Leu Tyr Thr His Pro Thr His Ser Trp Gln Arg
    290                 295                 300

Ala Asp Leu Gly Ala Tyr Leu Asn Pro Arg Pro Pro Ala Pro Glu Ala
305                 310                 315                 320

Trp Ser Glu Pro Val Leu Leu Ala Lys Gly Ser Ala Ala Tyr Ser Asp
                325                 330                 335

Leu Gln Ser Met Gly Thr Gly Pro Asp Gly Ser Pro Leu Phe Gly Cys
            340                 345                 350

Leu Tyr Glu Ala Asn Asp Tyr Glu Glu Ile Val Phe Leu Met Phe Thr
        355                 360                 365

Leu Lys Gln Ala Phe Pro Ala Glu Tyr Leu Pro Gln Gly Gly Gly Gly
    370                 375                 380

Ser Gly Gly Gly Gly Ser Asp Lys Thr His Thr Cys Pro Pro Cys Pro
385                 390                 395                 400

Ala Pro Glu Leu Leu Gly Gly Pro Ser Val Phe Leu Phe Pro Pro Lys
                405                 410                 415

Pro Lys Asp Thr Leu Met Ile Ser Arg Thr Pro Glu Val Thr Cys Val
            420                 425                 430

Val Val Asp Val Ser His Glu Asp Pro Glu Val Lys Phe Asn Trp Tyr
        435                 440                 445

Val Asp Gly Val Glu Val His Asn Ala Lys Thr Lys Pro Arg Glu Glu
    450                 455                 460

Gln Tyr Asn Ser Thr Tyr Arg Val Val Ser Val Leu Thr Val Leu His
465                 470                 475                 480
```

```
Gln Asp Trp Leu Asn Gly Lys Glu Tyr Lys Cys Lys Val Ser Asn Lys
                485                 490                 495

Ala Leu Pro Ala Pro Ile Glu Lys Thr Ile Ser Lys Ala Lys Gly Gln
            500                 505                 510

Pro Arg Glu Pro Gln Val Tyr Thr Leu Pro Pro Ser Arg Glu Glu Met
        515                 520                 525

Thr Lys Asn Gln Val Ser Leu Thr Cys Leu Val Lys Gly Phe Tyr Pro
    530                 535                 540

Ser Asp Ile Ala Val Glu Trp Glu Ser Asn Gly Gln Pro Glu Asn Asn
545                 550                 555                 560

Tyr Lys Thr Thr Pro Pro Val Leu Asp Ser Asp Gly Ser Phe Phe Leu
                565                 570                 575

Tyr Ser Lys Leu Thr Val Asp Lys Ser Arg Trp Gln Gln Gly Asn Val
            580                 585                 590

Phe Ser Cys Ser Val Met His Glu Ala Leu His Asn His Tyr Thr Gln
        595                 600                 605

Lys Ser Leu Ser Leu Ser Pro Gly Lys Gly Gly Gly Gly Ser Gly Gly
    610                 615                 620

Gly Gly Ser Gly Gly Gly Gly Ser Glu Val Gln Leu Val Glu Ser Gly
625                 630                 635                 640

Gly Gly Leu Val Gln Pro Gly Gly Ser Leu Arg Leu Ser Cys Ala Ala
                645                 650                 655

Ser Gly Phe Asn Ile Lys Asp Thr Tyr Ile His Trp Val Arg Gln Ala
            660                 665                 670

Pro Gly Lys Gly Leu Glu Trp Val Ala Arg Ile Tyr Pro Thr Asn Gly
        675                 680                 685

Tyr Thr Arg Tyr Ala Asp Ser Val Lys Gly Arg Phe Thr Ile Ser Ala
    690                 695                 700

Asp Thr Ser Lys Asn Thr Ala Tyr Leu Gln Met Asn Ser Leu Arg Ala
705                 710                 715                 720

Glu Asp Thr Ala Val Tyr Tyr Cys Ser Arg Trp Gly Gly Asp Gly Phe
                725                 730                 735

Tyr Ala Met Asp Tyr Trp Gly Gln Gly Thr Leu Val Thr Val Ser Ser
            740                 745                 750

Gly Gly Gly Gly Ser Gly Gly Gly Gly Ser Gly Gly Gly Gly Ser Asp
        755                 760                 765

Ile Gln Met Thr Gln Ser Pro Ser Ser Leu Ser Ala Ser Val Gly Asp
    770                 775                 780

Arg Val Thr Ile Thr Cys Arg Ala Ser Gln Asp Val Asn Thr Ala Val
785                 790                 795                 800

Ala Trp Tyr Gln Gln Lys Pro Gly Lys Ala Pro Lys Leu Leu Ile Tyr
                805                 810                 815

Ser Ala Ser Phe Leu Tyr Ser Gly Val Pro Ser Arg Phe Ser Gly Ser
            820                 825                 830

Arg Ser Gly Thr Asp Phe Thr Leu Thr Ile Ser Ser Leu Gln Pro Glu
        835                 840                 845

Asp Phe Ala Thr Tyr Tyr Cys Gln Gln His Tyr Thr Thr Pro Pro Thr
    850                 855                 860

Phe Gly Gln Gly Thr Lys Val Glu Ile Lys
865                 870

<210> SEQ ID NO 48
<211> LENGTH: 874
```

<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

```
Asp Ala Ser Leu Pro Tyr Leu Gln Lys Glu Ser Val Phe Gln Ser Gly
1               5                   10                  15

Ala His Ala Tyr Arg Ile Pro Ala Leu Leu Tyr Leu Pro Gly Gln Gln
            20                  25                  30

Ser Leu Leu Ala Phe Ala Glu Gln Arg Ala Ser Lys Lys Asp Glu His
        35                  40                  45

Ala Glu Leu Ile Val Leu Arg Arg Gly Asp Tyr Asp Ala Pro Thr His
    50                  55                  60

Gln Val Gln Trp Gln Ala Gln Glu Val Val Ala Gln Ala Arg Leu Asp
65                  70                  75                  80

Gly His Arg Ser Met Asn Pro Cys Pro Leu Tyr Asp Ala Gln Thr Gly
                85                  90                  95

Thr Leu Phe Leu Phe Phe Ile Ala Ile Pro Gly Gln Val Thr Glu Gln
            100                 105                 110

Gln Gln Leu Gln Thr Arg Ala Asn Val Thr Arg Leu Cys Gln Val Thr
        115                 120                 125

Ser Thr Asp His Gly Arg Thr Trp Ser Ser Pro Arg Asp Leu Thr Asp
    130                 135                 140

Ala Ala Ile Gly Pro Ala Tyr Arg Glu Trp Ser Thr Phe Ala Val Gly
145                 150                 155                 160

Pro Gly His Cys Leu Gln Leu His Asp Arg Ala Arg Ser Leu Val Val
                165                 170                 175

Pro Ala Tyr Ala Tyr Arg Lys Leu His Pro Lys Gln Arg Pro Ile Pro
            180                 185                 190

Ser Ala Phe Cys Phe Leu Ser His Asp His Gly Arg Thr Trp Ala Arg
        195                 200                 205

Gly His Phe Val Ala Gln Asp Thr Leu Glu Cys Gln Val Ala Glu Val
    210                 215                 220

Glu Thr Gly Glu Gln Arg Val Val Thr Leu Asn Ala Arg Ser His Leu
225                 230                 235                 240

Arg Ala Arg Val Gln Ala Gln Ser Thr Asn Asp Gly Leu Asp Phe Gln
                245                 250                 255

Glu Ser Gln Leu Val Lys Lys Leu Val Glu Pro Pro Pro Gln Gly Cys
            260                 265                 270

Gln Gly Ser Val Ile Ser Phe Pro Ser Pro Arg Ser Gly Pro Gly Ser
        275                 280                 285

Pro Ala Gln Trp Leu Leu Tyr Thr His Pro Thr His Ser Trp Gln Arg
    290                 295                 300

Ala Asp Leu Gly Ala Tyr Leu Asn Pro Arg Pro Pro Ala Pro Glu Ala
305                 310                 315                 320

Trp Ser Glu Pro Val Leu Leu Ala Lys Gly Ser Ala Ala Tyr Ser Asp
                325                 330                 335

Leu Gln Ser Met Gly Thr Gly Pro Asp Gly Ser Pro Leu Phe Gly Cys
            340                 345                 350

Leu Tyr Glu Ala Asn Asp Tyr Glu Glu Ile Val Phe Leu Met Phe Thr
        355                 360                 365

Leu Lys Gln Ala Phe Pro Ala Glu Tyr Leu Pro Gln Gly Gly Gly Gly
    370                 375                 380
```

-continued

```
Ser Gly Gly Gly Gly Ser Asp Lys Thr His Thr Cys Pro Pro Cys Pro
385                 390                 395                 400

Ala Pro Glu Leu Leu Gly Gly Pro Ser Val Phe Leu Phe Pro Pro Lys
                405                 410                 415

Pro Lys Asp Thr Leu Met Ile Ser Arg Thr Pro Glu Val Thr Cys Val
            420                 425                 430

Val Val Asp Val Ser His Glu Asp Pro Glu Val Lys Phe Asn Trp Tyr
        435                 440                 445

Val Asp Gly Val Glu Val His Asn Ala Lys Thr Lys Pro Arg Glu Glu
    450                 455                 460

Gln Tyr Asn Ser Thr Tyr Arg Val Val Ser Val Leu Thr Val Leu His
465                 470                 475                 480

Gln Asp Trp Leu Asn Gly Lys Glu Tyr Lys Cys Lys Val Ser Asn Lys
                485                 490                 495

Ala Leu Pro Ala Pro Ile Glu Lys Thr Ile Ser Lys Ala Lys Gly Gln
            500                 505                 510

Pro Arg Glu Pro Gln Val Tyr Thr Leu Pro Pro Ser Arg Glu Glu Met
        515                 520                 525

Thr Lys Asn Gln Val Ser Leu Thr Cys Leu Val Lys Gly Phe Tyr Pro
    530                 535                 540

Ser Asp Ile Ala Val Glu Trp Glu Ser Asn Gly Gln Pro Glu Asn Asn
545                 550                 555                 560

Tyr Lys Thr Thr Pro Pro Val Leu Asp Ser Asp Gly Ser Phe Phe Leu
                565                 570                 575

Tyr Ser Lys Leu Thr Val Asp Lys Ser Arg Trp Gln Gln Gly Asn Val
            580                 585                 590

Phe Ser Cys Ser Val Met His Glu Ala Leu His Asn His Tyr Thr Gln
        595                 600                 605

Lys Ser Leu Ser Leu Ser Pro Gly Lys Gly Gly Gly Gly Ser Gly Gly
    610                 615                 620

Gly Gly Ser Gly Gly Gly Gly Ser Glu Val Gln Leu Val Glu Ser Gly
625                 630                 635                 640

Gly Gly Leu Val Gln Pro Gly Gly Ser Leu Arg Leu Ser Cys Ala Ala
                645                 650                 655

Ser Gly Phe Asn Ile Lys Asp Thr Tyr Ile His Trp Val Arg Gln Ala
            660                 665                 670

Pro Gly Lys Gly Leu Glu Trp Val Ala Arg Ile Tyr Pro Thr Asn Gly
        675                 680                 685

Tyr Thr Arg Tyr Ala Asp Ser Val Lys Gly Arg Phe Thr Ile Ser Ala
    690                 695                 700

Asp Thr Ser Lys Asn Thr Ala Tyr Leu Gln Met Asn Ser Leu Arg Ala
705                 710                 715                 720

Glu Asp Thr Ala Val Tyr Tyr Cys Ser Arg Trp Gly Gly Asp Gly Phe
                725                 730                 735

Tyr Ala Met Asp Tyr Trp Gly Gln Gly Thr Leu Val Thr Val Ser Ser
            740                 745                 750

Gly Gly Gly Gly Ser Gly Gly Gly Gly Ser Gly Gly Gly Gly Ser Asp
        755                 760                 765

Ile Gln Met Thr Gln Ser Pro Ser Ser Leu Ser Ala Ser Val Gly Asp
    770                 775                 780

Arg Val Thr Ile Thr Cys Arg Ala Ser Gln Asp Val Asn Thr Ala Val
785                 790                 795                 800
```

-continued

```
Ala Trp Tyr Gln Gln Lys Pro Gly Lys Ala Pro Lys Leu Leu Ile Tyr
                805                 810                 815

Ser Ala Ser Phe Leu Tyr Ser Gly Val Pro Ser Arg Phe Ser Gly Ser
            820                 825                 830

Arg Ser Gly Thr Asp Phe Thr Leu Thr Ile Ser Ser Leu Gln Pro Glu
        835                 840                 845

Asp Phe Ala Thr Tyr Tyr Cys Gln Gln His Tyr Thr Thr Pro Pro Thr
    850                 855                 860

Phe Gly Gln Gly Thr Lys Val Glu Ile Lys
865                 870
```

<210> SEQ ID NO 49
<211> LENGTH: 213
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 49

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210
```

<210> SEQ ID NO 50
<211> LENGTH: 450
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 50

-continued

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Tyr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
```

```
            420                 425                 430

Glu Ala Leu His Asn His Tyr Thr Gln Lys Ser Leu Ser Leu Ser Pro
        435                 440                 445

Gly Lys
    450


<210> SEQ ID NO 51
<211> LENGTH: 616
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

Ala Ser Leu Pro Tyr Leu Gln Lys Glu Ser Val Phe Gln Ser Gly Ala
1               5                   10                  15

His Ala Tyr Arg Ile Pro Ala Leu Leu Tyr Leu Pro Gly Gln Gln Ser
            20                  25                  30

Leu Leu Ala Phe Ala Glu Gln Arg Ala Ser Lys Lys Asp Glu His Ala
        35                  40                  45

Glu Leu Ile Val Leu Arg Arg Gly Asp Tyr Asp Ala Pro Thr His Gln
    50                  55                  60

Val Gln Trp Gln Ala Gln Glu Val Val Ala Gln Ala Arg Leu Asp Gly
65                  70                  75                  80

His Arg Ser Met Asn Pro Cys Pro Leu Tyr Asp Ala Gln Thr Gly Thr
                85                  90                  95

Leu Phe Leu Phe Phe Ile Ala Ile Pro Gly Gln Val Thr Glu Gln Gln
            100                 105                 110

Gln Leu Gln Thr Arg Ala Asn Val Thr Arg Leu Cys Gln Val Thr Ser
        115                 120                 125

Thr Asp His Gly Arg Thr Trp Ser Ser Pro Arg Asp Leu Thr Asp Ala
    130                 135                 140

Ala Ile Gly Pro Ala Tyr Arg Glu Trp Ser Thr Phe Ala Val Gly Pro
145                 150                 155                 160

Gly His Cys Leu Gln Leu His Asp Arg Ala Arg Ser Leu Val Val Pro
                165                 170                 175

Ala Tyr Ala Tyr Arg Lys Leu His Pro Lys Gln Arg Pro Ile Pro Ser
            180                 185                 190

Ala Phe Cys Phe Leu Ser His Asp His Gly Arg Thr Trp Ala Arg Gly
        195                 200                 205

His Phe Val Ala Gln Asp Thr Leu Glu Cys Gln Val Ala Glu Val Glu
    210                 215                 220

Thr Gly Glu Gln Arg Val Val Thr Leu Asn Ala Arg Ser His Leu Arg
225                 230                 235                 240

Ala Arg Val Gln Ala Gln Ser Thr Asn Asp Gly Leu Asp Phe Gln Glu
                245                 250                 255

Ser Gln Leu Val Lys Lys Leu Val Glu Pro Pro Pro Gln Gly Cys Gln
            260                 265                 270

Gly Ser Val Ile Ser Phe Pro Ser Pro Arg Ser Gly Pro Gly Ser Pro
        275                 280                 285

Ala Gln Trp Leu Leu Tyr Thr His Pro Thr His Ser Trp Gln Arg Ala
    290                 295                 300

Asp Leu Gly Ala Tyr Leu Asn Pro Arg Pro Pro Ala Pro Glu Ala Trp
305                 310                 315                 320
```

Ser Glu Pro Val Leu Leu Ala Lys Gly Ser Cys Ala Tyr Ser Asp Leu
325 330 335

Gln Ser Met Gly Thr Gly Pro Asp Gly Ser Pro Leu Phe Gly Cys Leu
340 345 350

Tyr Glu Ala Asn Asp Tyr Glu Glu Ile Val Phe Leu Met Phe Thr Leu
355 360 365

Lys Gln Ala Phe Pro Ala Glu Tyr Leu Pro Gln Gly Gly Gly Gly Ser
370 375 380

Gly Gly Gly Gly Ser Asp Lys Thr His Thr Cys Pro Pro Cys Pro Ala
385 390 395 400

Pro Glu Leu Leu Gly Gly Pro Ser Val Phe Leu Phe Pro Pro Lys Pro
405 410 415

Lys Asp Thr Leu Met Ile Ser Arg Thr Pro Glu Val Thr Cys Val Val
420 425 430

Val Asp Val Ser His Glu Asp Pro Glu Val Lys Phe Asn Trp Tyr Val
435 440 445

Asp Gly Val Glu Val His Asn Ala Lys Thr Lys Pro Arg Glu Glu Gln
450 455 460

Tyr Asn Ser Thr Tyr Arg Val Val Ser Val Leu Thr Val Leu His Gln
465 470 475 480

Asp Trp Leu Asn Gly Lys Glu Tyr Lys Cys Lys Val Ser Asn Lys Ala
485 490 495

Leu Pro Ala Pro Ile Glu Lys Thr Ile Ser Lys Ala Lys Gly Gln Pro
500 505 510

Arg Glu Pro Gln Val Tyr Thr Leu Pro Pro Ser Arg Glu Glu Met Thr
515 520 525

Lys Asn Gln Val Ser Leu Thr Cys Leu Val Lys Gly Phe Tyr Pro Ser
530 535 540

Asp Ile Ala Val Glu Trp Glu Ser Asn Gly Gln Pro Glu Asn Asn Tyr
545 550 555 560

Lys Thr Thr Pro Pro Val Leu Asp Ser Asp Gly Ser Phe Phe Leu Thr
565 570 575

Ser Lys Leu Thr Val Asp Lys Ser Arg Trp Gln Gln Gly Asn Val Phe
580 585 590

Ser Cys Ser Val Met His Glu Ala Leu His Asn His Tyr Thr Gln Lys
595 600 605

Ser Leu Ser Leu Ser Pro Gly Lys
610 615

<210> SEQ ID NO 52
<211> LENGTH: 616
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 52

Ala Ser Leu Pro Tyr Leu Gln Lys Glu Ser Val Phe Gln Ser Gly Ala
1 5 10 15

His Ala Tyr Arg Ile Pro Ala Leu Leu Tyr Leu Pro Gly Gln Gln Ser
20 25 30

Leu Leu Ala Phe Ala Glu Gln Arg Ala Ser Lys Lys Asp Glu His Ala
35 40 45

Glu Leu Ile Val Leu Arg Arg Gly Asp Tyr Asp Ala Pro Thr His Gln
50 55 60

Val Gln Trp Gln Ala Gln Glu Val Val Ala Gln Ala Arg Leu Asp Gly
65 70 75 80

His Arg Ser Met Asn Pro Cys Pro Leu Tyr Asp Ala Gln Thr Gly Thr
85 90 95

Leu Phe Leu Phe Phe Ile Ala Ile Pro Gly Gln Val Thr Glu Gln Gln
100 105 110

Gln Leu Gln Thr Arg Ala Asn Val Thr Arg Leu Cys Gln Val Thr Ser
115 120 125

Thr Asp His Gly Arg Thr Trp Ser Ser Pro Arg Asp Leu Thr Asp Ala
130 135 140

Ala Ile Gly Pro Ala Tyr Arg Glu Trp Ser Thr Phe Ala Val Gly Pro
145 150 155 160

Gly His Cys Leu Gln Leu His Asp Arg Ala Arg Ser Leu Val Val Pro
165 170 175

Ala Tyr Ala Tyr Arg Lys Leu His Pro Lys Gln Arg Pro Ile Pro Ser
180 185 190

Ala Phe Cys Phe Leu Ser His Asp His Gly Arg Thr Trp Ala Arg Gly
195 200 205

His Phe Val Ala Gln Asp Thr Leu Glu Cys Gln Val Ala Glu Val Glu
210 215 220

Thr Gly Glu Gln Arg Val Val Thr Leu Asn Ala Arg Ser His Leu Arg
225 230 235 240

Ala Arg Val Gln Ala Gln Ser Thr Asn Asp Gly Leu Asp Phe Gln Glu
245 250 255

Ser Gln Leu Val Lys Lys Leu Val Glu Pro Pro Pro Gln Gly Cys Gln
260 265 270

Gly Ser Val Ile Ser Phe Pro Ser Pro Arg Ser Gly Pro Gly Ser Pro
275 280 285

Ala Gln Trp Leu Leu Tyr Thr His Pro Thr His Ser Trp Gln Arg Ala
290 295 300

Asp Leu Gly Ala Tyr Leu Asn Pro Arg Pro Pro Ala Pro Glu Ala Trp
305 310 315 320

Ser Glu Pro Val Leu Leu Ala Lys Gly Ser Ala Ala Tyr Ser Asp Leu
325 330 335

Gln Ser Met Gly Thr Gly Pro Asp Gly Ser Pro Leu Phe Gly Cys Leu
340 345 350

Tyr Glu Ala Asn Asp Tyr Glu Glu Ile Val Phe Leu Met Phe Thr Leu
355 360 365

Lys Gln Ala Phe Pro Ala Glu Tyr Leu Pro Gln Gly Gly Gly Gly Ser
370 375 380

Gly Gly Gly Gly Ser Asp Lys Thr His Thr Cys Pro Pro Cys Pro Ala
385 390 395 400

Pro Glu Leu Leu Gly Gly Pro Ser Val Phe Leu Phe Pro Pro Lys Pro
405 410 415

Lys Asp Thr Leu Met Ile Ser Arg Thr Pro Glu Val Thr Cys Val Val
420 425 430

Val Asp Val Ser His Glu Asp Pro Glu Val Lys Phe Asn Trp Tyr Val
435 440 445

Asp Gly Val Glu Val His Asn Ala Lys Thr Lys Pro Arg Glu Glu Gln
450 455 460

Tyr Asn Ser Thr Tyr Arg Val Val Ser Val Leu Thr Val Leu His Gln
465 470 475 480

```
Asp Trp Leu Asn Gly Lys Glu Tyr Lys Cys Lys Val Ser Asn Lys Ala
                485                 490                 495

Leu Pro Ala Pro Ile Glu Lys Thr Ile Ser Lys Ala Lys Gly Gln Pro
            500                 505                 510

Arg Glu Pro Gln Val Tyr Thr Leu Pro Pro Ser Arg Glu Glu Met Thr
        515                 520                 525

Lys Asn Gln Val Ser Leu Thr Cys Leu Val Lys Gly Phe Tyr Pro Ser
    530                 535                 540

Asp Ile Ala Val Glu Trp Glu Ser Asn Gly Gln Pro Glu Asn Asn Tyr
545                 550                 555                 560

Lys Thr Thr Pro Pro Val Leu Asp Ser Asp Gly Ser Phe Phe Leu Thr
                565                 570                 575

Ser Lys Leu Thr Val Asp Lys Ser Arg Trp Gln Gln Gly Asn Val Phe
            580                 585                 590

Ser Cys Ser Val Met His Glu Ala Leu His Asn His Tyr Thr Gln Lys
        595                 600                 605

Ser Leu Ser Leu Ser Pro Gly Lys
    610                 615


<210> SEQ ID NO 53
<211> LENGTH: 617
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

Ala Ala Ser Leu Pro Tyr Leu Gln Lys Glu Ser Val Phe Gln Ser Gly
1               5                   10                  15

Ala His Ala Tyr Arg Ile Pro Ala Leu Leu Tyr Leu Pro Gly Gln Gln
            20                  25                  30

Ser Leu Leu Ala Phe Ala Glu Gln Arg Ala Ser Lys Lys Asp Glu His
        35                  40                  45

Ala Glu Leu Ile Val Leu Arg Arg Gly Asp Tyr Asp Ala Pro Thr His
    50                  55                  60

Gln Val Gln Trp Gln Ala Gln Glu Val Val Ala Gln Ala Arg Leu Asp
65                  70                  75                  80

Gly His Arg Ser Met Asn Pro Cys Pro Leu Tyr Asp Ala Gln Thr Gly
                85                  90                  95

Thr Leu Phe Leu Phe Phe Ile Ala Ile Pro Gly Gln Val Thr Glu Gln
            100                 105                 110

Gln Gln Leu Gln Thr Arg Ala Asn Val Thr Arg Leu Cys Gln Val Thr
        115                 120                 125

Ser Thr Asp His Gly Arg Thr Trp Ser Ser Pro Arg Asp Leu Thr Asp
    130                 135                 140

Ala Ala Ile Gly Pro Ala Tyr Arg Glu Trp Ser Thr Phe Ala Val Gly
145                 150                 155                 160

Pro Gly His Cys Leu Gln Leu His Asp Arg Ala Arg Ser Leu Val Val
                165                 170                 175

Pro Ala Tyr Ala Tyr Arg Lys Leu His Pro Lys Gln Arg Pro Ile Pro
            180                 185                 190

Ser Ala Phe Cys Phe Leu Ser His Asp His Gly Arg Thr Trp Ala Arg
        195                 200                 205

Gly His Phe Val Ala Gln Asp Thr Leu Glu Cys Gln Val Ala Glu Val
    210                 215                 220
```

Glu Thr Gly Glu Gln Arg Val Val Thr Leu Asn Ala Arg Ser His Leu
225 230 235 240

Arg Ala Arg Val Gln Ala Gln Ser Thr Asn Asp Gly Leu Asp Phe Gln
245 250 255

Glu Ser Gln Leu Val Lys Lys Leu Val Glu Pro Pro Pro Gln Gly Cys
260 265 270

Gln Gly Ser Val Ile Ser Phe Pro Ser Pro Arg Ser Gly Pro Gly Ser
275 280 285

Pro Ala Gln Trp Leu Leu Tyr Thr His Pro Thr His Ser Trp Gln Arg
290 295 300

Ala Asp Leu Gly Ala Tyr Leu Asn Pro Arg Pro Pro Ala Pro Glu Ala
305 310 315 320

Trp Ser Glu Pro Val Leu Leu Ala Lys Gly Ser Ala Ala Tyr Ser Asp
325 330 335

Leu Gln Ser Met Gly Thr Gly Pro Asp Gly Ser Pro Leu Phe Gly Cys
340 345 350

Leu Tyr Glu Ala Asn Asp Tyr Glu Glu Ile Val Phe Leu Met Phe Thr
355 360 365

Leu Lys Gln Ala Phe Pro Ala Glu Tyr Leu Pro Gln Gly Gly Gly Gly
370 375 380

Ser Gly Gly Gly Gly Ser Asp Lys Thr His Thr Cys Pro Pro Cys Pro
385 390 395 400

Ala Pro Glu Leu Leu Gly Gly Pro Ser Val Phe Leu Phe Pro Pro Lys
405 410 415

Pro Lys Asp Thr Leu Met Ile Ser Arg Thr Pro Glu Val Thr Cys Val
420 425 430

Val Val Asp Val Ser His Glu Asp Pro Glu Val Lys Phe Asn Trp Tyr
435 440 445

Val Asp Gly Val Glu Val His Asn Ala Lys Thr Lys Pro Arg Glu Glu
450 455 460

Gln Tyr Asn Ser Thr Tyr Arg Val Val Ser Val Leu Thr Val Leu His
465 470 475 480

Gln Asp Trp Leu Asn Gly Lys Glu Tyr Lys Cys Lys Val Ser Asn Lys
485 490 495

Ala Leu Pro Ala Pro Ile Glu Lys Thr Ile Ser Lys Ala Lys Gly Gln
500 505 510

Pro Arg Glu Pro Gln Val Tyr Thr Leu Pro Pro Ser Arg Glu Glu Met
515 520 525

Thr Lys Asn Gln Val Ser Leu Thr Cys Leu Val Lys Gly Phe Tyr Pro
530 535 540

Ser Asp Ile Ala Val Glu Trp Glu Ser Asn Gly Gln Pro Glu Asn Asn
545 550 555 560

Tyr Lys Thr Thr Pro Pro Val Leu Asp Ser Asp Gly Ser Phe Phe Leu
565 570 575

Thr Ser Lys Leu Thr Val Asp Lys Ser Arg Trp Gln Gln Gly Asn Val
580 585 590

Phe Ser Cys Ser Val Met His Glu Ala Leu His Asn His Tyr Thr Gln
595 600 605

Lys Ser Leu Ser Leu Ser Pro Gly Lys
610 615

<210> SEQ ID NO 54
<211> LENGTH: 617

<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 54

Asp Ala Ser Leu Pro Tyr Leu Gln Lys Glu Ser Val Phe Gln Ser Gly
1 5 10 15

Ala His Ala Tyr Arg Ile Pro Ala Leu Leu Tyr Leu Pro Gly Gln Gln
20 25 30

Ser Leu Leu Ala Phe Ala Glu Gln Arg Ala Ser Lys Lys Asp Glu His
35 40 45

Ala Glu Leu Ile Val Leu Arg Arg Gly Asp Tyr Asp Ala Pro Thr His
50 55 60

Gln Val Gln Trp Gln Ala Gln Glu Val Val Ala Gln Ala Arg Leu Asp
65 70 75 80

Gly His Arg Ser Met Asn Pro Cys Pro Leu Tyr Asp Ala Gln Thr Gly
85 90 95

Thr Leu Phe Leu Phe Phe Ile Ala Ile Pro Gly Gln Val Thr Glu Gln
100 105 110

Gln Gln Leu Gln Thr Arg Ala Asn Val Thr Arg Leu Cys Gln Val Thr
115 120 125

Ser Thr Asp His Gly Arg Thr Trp Ser Ser Pro Arg Asp Leu Thr Asp
130 135 140

Ala Ala Ile Gly Pro Ala Tyr Arg Glu Trp Ser Thr Phe Ala Val Gly
145 150 155 160

Pro Gly His Cys Leu Gln Leu His Asp Arg Ala Arg Ser Leu Val Val
165 170 175

Pro Ala Tyr Ala Tyr Arg Lys Leu His Pro Lys Gln Arg Pro Ile Pro
180 185 190

Ser Ala Phe Cys Phe Leu Ser His Asp His Gly Arg Thr Trp Ala Arg
195 200 205

Gly His Phe Val Ala Gln Asp Thr Leu Glu Cys Gln Val Ala Glu Val
210 215 220

Glu Thr Gly Glu Gln Arg Val Val Thr Leu Asn Ala Arg Ser His Leu
225 230 235 240

Arg Ala Arg Val Gln Ala Gln Ser Thr Asn Asp Gly Leu Asp Phe Gln
245 250 255

Glu Ser Gln Leu Val Lys Lys Leu Val Glu Pro Pro Pro Gln Gly Cys
260 265 270

Gln Gly Ser Val Ile Ser Phe Pro Ser Pro Arg Ser Gly Pro Gly Ser
275 280 285

Pro Ala Gln Trp Leu Leu Tyr Thr His Pro Thr His Ser Trp Gln Arg
290 295 300

Ala Asp Leu Gly Ala Tyr Leu Asn Pro Arg Pro Pro Ala Pro Glu Ala
305 310 315 320

Trp Ser Glu Pro Val Leu Leu Ala Lys Gly Ser Ala Ala Tyr Ser Asp
325 330 335

Leu Gln Ser Met Gly Thr Gly Pro Asp Gly Ser Pro Leu Phe Gly Cys
340 345 350

Leu Tyr Glu Ala Asn Asp Tyr Glu Glu Ile Val Phe Leu Met Phe Thr
355 360 365

Leu Lys Gln Ala Phe Pro Ala Glu Tyr Leu Pro Gln Gly Gly Gly Gly
370 375 380

-continued

```
Ser Gly Gly Gly Gly Ser Asp Lys Thr His Thr Cys Pro Pro Cys Pro
385                 390                 395                 400

Ala Pro Glu Leu Leu Gly Gly Pro Ser Val Phe Leu Phe Pro Pro Lys
                405                 410                 415

Pro Lys Asp Thr Leu Met Ile Ser Arg Thr Pro Glu Val Thr Cys Val
            420                 425                 430

Val Val Asp Val Ser His Glu Asp Pro Glu Val Lys Phe Asn Trp Tyr
        435                 440                 445

Val Asp Gly Val Glu Val His Asn Ala Lys Thr Lys Pro Arg Glu Glu
    450                 455                 460

Gln Tyr Asn Ser Thr Tyr Arg Val Val Ser Val Leu Thr Val Leu His
465                 470                 475                 480

Gln Asp Trp Leu Asn Gly Lys Glu Tyr Lys Cys Lys Val Ser Asn Lys
                485                 490                 495

Ala Leu Pro Ala Pro Ile Glu Lys Thr Ile Ser Lys Ala Lys Gly Gln
            500                 505                 510

Pro Arg Glu Pro Gln Val Tyr Thr Leu Pro Pro Ser Arg Glu Glu Met
        515                 520                 525

Thr Lys Asn Gln Val Ser Leu Thr Cys Leu Val Lys Gly Phe Tyr Pro
    530                 535                 540

Ser Asp Ile Ala Val Glu Trp Glu Ser Asn Gly Gln Pro Glu Asn Asn
545                 550                 555                 560

Tyr Lys Thr Thr Pro Pro Val Leu Asp Ser Asp Gly Ser Phe Phe Leu
                565                 570                 575

Thr Ser Lys Leu Thr Val Asp Lys Ser Arg Trp Gln Gln Gly Asn Val
            580                 585                 590

Phe Ser Cys Ser Val Met His Glu Ala Leu His Asn His Tyr Thr Gln
        595                 600                 605

Lys Ser Leu Ser Leu Ser Pro Gly Lys
    610                 615


<210> SEQ ID NO 55
<211> LENGTH: 618
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

Thr Val Glu Lys Ser Val Val Phe Lys Ala Glu Gly Glu His Phe Thr
1               5                   10                  15

Asp Gln Lys Gly Asn Thr Ile Val Gly Ser Gly Ser Gly Gly Thr Thr
            20                  25                  30

Lys Tyr Phe Arg Ile Pro Ala Met Cys Thr Thr Ser Lys Gly Thr Ile
        35                  40                  45

Val Val Phe Ala Asp Ala Arg His Asn Thr Ala Ser Asp Gln Ser Phe
    50                  55                  60

Ile Asp Thr Ala Ala Ala Arg Ser Thr Asp Gly Gly Lys Thr Trp Asn
65                  70                  75                  80

Lys Lys Ile Ala Ile Tyr Asn Asp Arg Val Asn Ser Lys Leu Ser Arg
                85                  90                  95

Val Met Asp Pro Thr Cys Ile Val Ala Asn Ile Gln Gly Arg Glu Thr
            100                 105                 110

Ile Leu Val Met Val Gly Lys Trp Asn Asn Asn Asp Lys Thr Trp Gly
```

```
        115                 120                 125

Ala Tyr Arg Asp Lys Ala Pro Asp Thr Asp Trp Asp Leu Val Leu Tyr
    130                 135                 140

Lys Ser Thr Asp Asp Gly Val Thr Phe Ser Lys Val Glu Thr Asn Ile
145                 150                 155                 160

His Asp Ile Val Thr Lys Asn Gly Thr Ile Ser Ala Met Leu Gly Gly
                165                 170                 175

Val Gly Ser Gly Leu Gln Leu Asn Asp Gly Lys Leu Val Phe Pro Val
            180                 185                 190

Gln Met Val Arg Thr Lys Asn Ile Thr Thr Val Leu Asn Thr Ser Phe
        195                 200                 205

Ile Tyr Ser Thr Asp Gly Ile Thr Trp Ser Leu Pro Ser Gly Tyr Cys
    210                 215                 220

Glu Gly Phe Gly Ser Glu Asn Asn Ile Ile Glu Phe Asn Ala Ser Leu
225                 230                 235                 240

Val Asn Asn Ile Arg Asn Ser Gly Leu Arg Arg Ser Phe Glu Thr Lys
                245                 250                 255

Asp Phe Gly Lys Thr Trp Thr Glu Phe Pro Pro Met Asp Lys Lys Val
            260                 265                 270

Asp Asn Arg Asn His Gly Val Gln Gly Ser Thr Ile Thr Ile Pro Ser
        275                 280                 285

Gly Asn Lys Leu Val Ala Ala His Ser Ser Ala Gln Asn Lys Asn Asn
    290                 295                 300

Asp Tyr Thr Arg Ser Asp Ile Ser Leu Tyr Ala His Asn Leu Tyr Ser
305                 310                 315                 320

Gly Glu Val Lys Leu Ile Asp Asp Phe Tyr Pro Lys Val Gly Asn Ala
                325                 330                 335

Ser Gly Ala Gly Tyr Ser Cys Leu Ser Tyr Arg Lys Asn Val Asp Lys
            340                 345                 350

Glu Thr Leu Tyr Val Val Tyr Glu Ala Asn Gly Ser Ile Glu Phe Gln
        355                 360                 365

Asp Leu Ser Arg His Leu Pro Val Ile Lys Ser Tyr Asn Gly Gly Gly
    370                 375                 380

Gly Ser Gly Gly Gly Gly Ser Asp Lys Thr His Thr Cys Pro Pro Cys
385                 390                 395                 400

Pro Ala Pro Glu Leu Leu Gly Gly Pro Ser Val Phe Leu Phe Pro Pro
                405                 410                 415

Lys Pro Lys Asp Thr Leu Met Ile Ser Arg Thr Pro Glu Val Thr Cys
            420                 425                 430

Val Val Val Asp Val Ser His Glu Asp Pro Glu Val Lys Phe Asn Trp
        435                 440                 445

Tyr Val Asp Gly Val Glu Val His Asn Ala Lys Thr Lys Pro Arg Glu
    450                 455                 460

Glu Gln Tyr Asn Ser Thr Tyr Arg Val Val Ser Val Leu Thr Val Leu
465                 470                 475                 480

His Gln Asp Trp Leu Asn Gly Lys Glu Tyr Lys Cys Lys Val Ser Asn
                485                 490                 495

Lys Ala Leu Pro Ala Pro Ile Glu Lys Thr Ile Ser Lys Ala Lys Gly
            500                 505                 510

Gln Pro Arg Glu Pro Gln Val Tyr Thr Leu Pro Pro Ser Arg Glu Glu
        515                 520                 525

Met Thr Lys Asn Gln Val Ser Leu Thr Cys Leu Val Lys Gly Phe Tyr
    530                 535                 540
```

```
Pro Ser Asp Ile Ala Val Glu Trp Glu Ser Asn Gly Gln Pro Glu Asn
545                 550                 555                 560

Asn Tyr Lys Thr Thr Pro Pro Val Leu Asp Ser Asp Gly Ser Phe Phe
                565                 570                 575

Leu Thr Ser Lys Leu Thr Val Asp Lys Ser Arg Trp Gln Gln Gly Asn
            580                 585                 590

Val Phe Ser Cys Ser Val Met His Glu Ala Leu His Asn His Tyr Thr
        595                 600                 605

Gln Lys Ser Leu Ser Leu Ser Pro Gly Lys
    610                 615


<210> SEQ ID NO 56
<211> LENGTH: 1854
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 56

acagtggaaa agtccgtggt gttcaaggcc gagggcgagc acttcaccga ccagaaaggc     60

aataccatcg tcggctctgg cagcggcggc accaccaagt actttagaat ccccgccatg    120

tgcaccacca gcaagggcac cattgtggtg ttcgccgacg ccagacacaa caccgccagc    180

gatcagagct tcatcgatac cgctgccgcc agatctaccg atggcggcaa gacctggaac    240

aagaagatcg ccatctacaa cgaccgcgtg aacagcaagc tgagcagagt gatggaccct    300

acctgcatcg tggccaacat ccagggcaga gaaaccatcc tggtcatggt cggaaagtgg    360

aacaacaacg ataagacctg ggcgcctac agagacaagg cccctgatac cgattgggac    420

ctcgtgctgt acaagagcac cgatgacggc gtgaccttca gcaaggtgga aacaaacatc    480

cacgacatcg tgaccaagaa cggcaccatc tctgccatgc tcggcggcgt tggatctggc    540

ctgcaactga atgatggcaa gctggtgttc cccgtgcaga tggtccgaac aaagaatatc    600

accaccgtgc tgaataccag cttcatctac agcaccgacg gcatcacatg gtccctgcct    660

agcggctact gtgaaggctt tggcagcgag aacaacatca tcgagttcaa cgccagcctg    720

gtcaacaaca tccggaacag cggcctgcgg agaagcttcg agacaaagga cttcggaaag    780

acgtggaccg agtttcctcc aatggacaag aaggtggaca accggaacca cggcgtgcag    840

ggcagcacaa tcacaatccc tagcggcaac aaactggtgg ccgctcactc tagcgcccag    900

aacaagaaca acgactacac cagaagcgac atcagcctgt acgcccacaa cctgtacagc    960

ggcgaagtga agctgatcga cgacttctac cccaaagtgg gcaatgccag cggagccggc   1020

tacagctgtc tgagctaccg gaaaaatgtg gacaaagaaa ccctgtacgt ggtgtacgag   1080

gccaacggca gcatcgagtt tcaggacctg agcagacatc tgcccgtgat caagagctac   1140

aacggcggag gtggaagtgg cggaggcgga tccgacaaaa ctcacacatg cccaccgtgc   1200

ccagcacctg aactcctggg gggaccgtca gtcttcctct tccccccaaa acccaaggac   1260

accctcatga tctcccggac ccctgaggtc acatgcgtgg tggtggacgt gagccacgaa   1320

gaccctgagg tcaagttcaa ctggtacgtg gacggcgtgg aggtgcataa tgccaagaca   1380

aagccgcggg aggagcagta caacagcacg taccgtgtgg tcagcgtcct caccgtcctg   1440

caccaggact ggctgaatgg caaggagtac aagtgcaagg tctccaacaa agccctccca   1500

gcccccatcg agaaaaccat ctccaaagcc aaagggcagc cccgagaacc acaggtctac   1560
```

accctgcccc catcccggga ggagatgacc aagaaccagg tcagcctgac ctgcctggtc 1620
aaaggcttct atcccagcga catcgccgtg gagtgggaga gcaatgggca gccggagaac 1680
aactacaaga ccacgcctcc cgtgctggac tccgacggct ccttcttcct cactagcaag 1740
ctcaccgtgg acaagagcag gtggcagcag gggaacgtct tctcatgctc cgtgatgcat 1800
gaggctctgc acaaccacta cacgcagaag agcctctccc tgtctccggg taaa 1854

<210> SEQ ID NO 57
<211> LENGTH: 450
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 57

Glu Val Gln Leu Val Glu Ser Gly Gly Gly Leu Val Gln Pro Gly Gly
1 5 10 15

Ser Leu Arg Leu Ser Cys Ala Ala Ser Gly Phe Asn Ile Lys Asp Thr
20 25 30

Tyr Ile His Trp Val Arg Gln Ala Pro Gly Lys Gly Leu Glu Trp Val
35 40 45

Ala Arg Ile Tyr Pro Thr Asn Gly Tyr Thr Arg Tyr Ala Asp Ser Val
50 55 60

Lys Gly Arg Phe Thr Ile Ser Ala Asp Thr Ser Lys Asn Thr Ala Tyr
65 70 75 80

Leu Gln Met Asn Ser Leu Arg Ala Glu Asp Thr Ala Val Tyr Tyr Cys
85 90 95

Ser Arg Trp Gly Gly Asp Gly Phe Tyr Ala Met Asp Tyr Trp Gly Gln
100 105 110

Gly Thr Leu Val Thr Val Ser Ser Ala Ser Thr Lys Gly Pro Ser Val
115 120 125

Phe Pro Leu Ala Pro Ser Ser Lys Ser Thr Ser Gly Gly Thr Ala Ala
130 135 140

Leu Gly Cys Leu Val Lys Asp Tyr Phe Pro Glu Pro Val Thr Val Ser
145 150 155 160

Trp Asn Ser Gly Ala Leu Thr Ser Gly Val His Thr Phe Pro Ala Val
165 170 175

Leu Gln Ser Ser Gly Leu Tyr Ser Leu Ser Ser Val Val Thr Val Pro
180 185 190

Ser Ser Ser Leu Gly Thr Gln Thr Tyr Ile Cys Asn Val Asn His Lys
195 200 205

Pro Ser Asn Thr Lys Val Asp Lys Lys Val Glu Pro Lys Ser Cys Asp
210 215 220

Lys Thr His Thr Cys Pro Pro Cys Pro Ala Pro Glu Leu Leu Gly Gly
225 230 235 240

Pro Ser Val Phe Leu Phe Pro Pro Lys Pro Lys Asp Thr Leu Met Ile
245 250 255

Ser Arg Thr Pro Glu Val Thr Cys Val Val Val Asp Val Ser His Glu
260 265 270

Asp Pro Glu Val Lys Phe Asn Trp Tyr Val Asp Gly Val Glu Val His
275 280 285

Asn Ala Lys Thr Lys Pro Arg Glu Glu Gln Tyr Asn Ser Thr Tyr Arg
290 295 300

Val Val Ser Val Leu Thr Val Leu His Gln Asp Trp Leu Asn Gly Lys

-continued 305 310 315 320

Glu Tyr Lys Cys Lys Val Ser Asn Lys Ala Leu Pro Ala Pro Ile Glu
325 330 335

Lys Thr Ile Ser Lys Ala Lys Gly Gln Pro Arg Glu Pro Gln Val Tyr
340 345 350

Thr Leu Pro Pro Ser Arg Glu Glu Met Thr Lys Asn Gln Val Ser Leu
355 360 365

Tyr Cys Leu Val Lys Gly Phe Tyr Pro Ser Asp Ile Ala Val Glu Trp
370 375 380

Glu Ser Asn Gly Gln Pro Glu Asn Asn Tyr Lys Thr Thr Pro Pro Val
385 390 395 400

Leu Asp Ser Asp Gly Ser Phe Phe Leu Tyr Ser Lys Leu Thr Val Asp
405 410 415

Lys Ser Arg Trp Gln Gln Gly Asn Val Phe Ser Cys Ser Val Met His
420 425 430

Glu Ala Leu His Asn His Tyr Thr Gln Lys Ser Leu Ser Leu Ser Pro
435 440 445

Gly Lys
450

<210> SEQ ID NO 58
<211> LENGTH: 1350
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 58
gaggtgcagc tggttgaatc tggcggagga ctggttcagc ctggcggatc tctgagactg 60
tcttgtgccg ccagcggctt caacatcaag gacacctaca tccactgggt ccgacaggcc 120
cctggcaaag gacttgaatg ggtcgccaga atctacccca ccaacggcta caccagatac 180
gccgactctg tgaagggcag attcaccatc agcgccgaca ccagcaagaa caccgcctac 240
ctgcagatga acagcctgag agccgaggac accgccgtgt actactgttc tagatgggga 300
ggcgacggct tctacgccat ggattattgg ggccagggca ccctggtcac cgtttcttct 360
gctagcacca agggcccatc cgtcttcccc ctggcaccct cctccaagag cacctctggg 420
ggcacagcgg ccctgggctg cctggtcaag gactacttcc ccgaaccggt gacggtgtcc 480
tggaactcag gcgctctgac cagcggcgtg cacaccttcc cggctgtcct acagtcctca 540
ggactctact ccctcagcag cgtggtgacc gtgccctcca gcagcttggg cacccagacc 600
tacatctgca acgtgaatca caagcccagc aacaccaagg tggacaagaa agttgagccc 660
aaatcttgtg acaaaactca cacatgccca ccgtgcccag cacctgaact cctgggggga 720
ccgtcagtct tcctcttccc cccaaaaccc aaggacaccc tcatgatctc ccggacccct 780
gaggtcacat gcgtggtggt ggacgtgagc cacgaagacc ctgaggtcaa gttcaactgg 840
tacgtggacg gcgtggaggt gcataatgcc aagacaaagc cgcgggagga gcagtacaac 900
agcacgtacc gtgtggtcag cgtcctcacc gtcctgcacc aggactggct gaatggcaag 960
gagtacaagt gcaaggtctc caacaaagcc ctcccagccc ccatcgagaa aaccatctcc 1020
aaagccaaag ggcagccccg agaaccacag gtctacaccc tgcccccatc ccgggaggag 1080
atgaccaaga accaggtcag cctgtactgc ctggtcaaag gcttctatcc cagcgacatc 1140
gccgtggagt gggagagcaa tgggcagccg gagaacaact acaagaccac gcctcccgtg 1200

```
ctggactccg acggctcctt cttcctctat agcaagctca ccgtggacaa gagcaggtgg   1260

cagcagggga acgtcttctc atgctccgtg atgcatgagg ctctgcacaa ccactacacg   1320

cagaagagcc tctccctgtc tccgggtaaa                                    1350


<210> SEQ ID NO 59
<211> LENGTH: 846
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
```

-continued

```
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys Gly Gly Gly Gly Ser Gly Gly Gly Gly Ser Gly Gly Gly Gly
    450                 455                 460

Ser Thr Val Glu Lys Ser Val Val Phe Lys Ala Glu Gly Glu His Phe
465                 470                 475                 480

Thr Asp Gln Lys Gly Asn Thr Ile Val Gly Ser Gly Ser Gly Gly Thr
                485                 490                 495

Thr Lys Tyr Phe Arg Ile Pro Ala Met Cys Thr Thr Ser Lys Gly Thr
            500                 505                 510

Ile Val Val Phe Ala Asp Ala Arg His Asn Thr Ala Ser Asp Gln Ser
        515                 520                 525

Phe Ile Asp Thr Ala Ala Ala Arg Ser Thr Asp Gly Gly Lys Thr Trp
    530                 535                 540

Asn Lys Lys Ile Ala Ile Tyr Asn Asp Arg Val Asn Ser Lys Leu Ser
545                 550                 555                 560

Arg Val Met Asp Pro Thr Cys Ile Val Ala Asn Ile Gln Gly Arg Glu
                565                 570                 575

Thr Ile Leu Val Met Val Gly Lys Trp Asn Asn Asn Asp Lys Thr Trp
            580                 585                 590

Gly Ala Tyr Arg Asp Lys Ala Pro Asp Thr Asp Trp Asp Leu Val Leu
        595                 600                 605

Tyr Lys Ser Thr Asp Asp Gly Val Thr Phe Ser Lys Val Glu Thr Asn
    610                 615                 620

Ile His Asp Ile Val Thr Lys Asn Gly Thr Ile Ser Ala Met Leu Gly
625                 630                 635                 640

Gly Val Gly Ser Gly Leu Gln Leu Asn Asp Gly Lys Leu Val Phe Pro
                645                 650                 655

Val Gln Met Val Arg Thr Lys Asn Ile Thr Thr Val Leu Asn Thr Ser
            660                 665                 670

Phe Ile Tyr Ser Thr Asp Gly Ile Thr Trp Ser Leu Pro Ser Gly Tyr
        675                 680                 685

Cys Glu Gly Phe Gly Ser Glu Asn Asn Ile Ile Glu Phe Asn Ala Ser
    690                 695                 700

Leu Val Asn Asn Ile Arg Asn Ser Gly Leu Arg Arg Ser Phe Glu Thr
705                 710                 715                 720

Lys Asp Phe Gly Lys Thr Trp Thr Glu Phe Pro Pro Met Asp Lys Lys
                725                 730                 735

Val Asp Asn Arg Asn His Gly Val Gln Gly Ser Thr Ile Thr Ile Pro
            740                 745                 750
```

```
Ser Gly Asn Lys Leu Val Ala Ala His Ser Ser Ala Gln Asn Lys Asn
        755                 760                 765

Asn Asp Tyr Thr Arg Ser Asp Ile Ser Leu Tyr Ala His Asn Leu Tyr
    770                 775                 780

Ser Gly Glu Val Lys Leu Ile Asp Asp Phe Tyr Pro Lys Val Gly Asn
785                 790                 795                 800

Ala Ser Gly Ala Gly Tyr Ser Cys Leu Ser Tyr Arg Lys Asn Val Asp
                805                 810                 815

Lys Glu Thr Leu Tyr Val Val Tyr Glu Ala Asn Gly Ser Ile Glu Phe
            820                 825                 830

Gln Asp Leu Ser Arg His Leu Pro Val Ile Lys Ser Tyr Asn
        835                 840                 845


<210> SEQ ID NO 60
<211> LENGTH: 2538
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 60

gaggtgcagc tggttgaatc tggcggagga ctggttcagc ctggcggatc tctgagactg     60

tcttgtgccg ccagcggctt caacatcaag gacacctaca tccactgggt ccgacaggcc    120

cctggcaaag gacttgaatg ggtcgccaga atctacccca ccaacggcta caccagatac    180

gccgactctg tgaagggcag attcaccatc agcgccgaca ccagcaagaa caccgcctac    240

ctgcagatga acagcctgag agccgaggac accgccgtgt actactgttc tagatgggga    300

ggcgacggct tctacgccat ggattattgg ggccagggca ccctggtcac cgtttcttct    360

gctagcacca agggcccatc cgtcttcccc ctggcaccct cctccaagag cacctctggg    420

ggcacagcgg ccctgggctg cctggtcaag gactacttcc ccgaaccggt gacggtgtcc    480

tggaactcag gcgctctgac cagcggcgtg cacaccttcc cggctgtcct acagtcctca    540

ggactctact ccctcagcag cgtggtgacc gtgccctcca gcagcttggg cacccagacc    600

tacatctgca acgtgaatca caagcccagc aacaccaagg tggacaagaa agttgagccc    660

aaatcttgtg acaaaactca cacatgccca ccgtgcccag cacctgaact cctgggggga    720

ccgtcagtct tcctcttccc cccaaaaccc aaggacaccc tcatgatctc ccggacccct    780

gaggtcacat gcgtggtggt ggacgtgagc cacgaagacc ctgaggtcaa gttcaactgg    840

tacgtggacg gcgtggaggt gcataatgcc aagacaaagc cgcgggagga gcagtacaac    900

agcacgtacc gtgtggtcag cgtcctcacc gtcctgcacc aggactggct gaatggcaag    960

gagtacaagt gcaaggtctc caacaaagcc ctcccagccc ccatcgagaa aaccatctcc   1020

aaagccaaag ggcagccccg agaaccacag gtctacaccc tgcccccatc ccgggaggag   1080

atgaccaaga accaggtcag cctgacctgc ctggtcaaag gcttctatcc cagcgacatc   1140

gccgtggagt gggagagcaa tgggcagccg gagaacaact acaagaccac gcctcccgtg   1200

ctggactccg acggctcctt cttcctctat agcaagctca ccgtggacaa gagcaggtgg   1260

cagcagggga acgtcttctc atgctccgtg atgcatgagg ctctgcacaa ccactacacg   1320

cagaagagcc tctccctgtc tccgggtaaa ggtggcggag gatctggcgg aggtggaagc   1380

ggcggaggcg gatctacagt ggaaaagtcc gtggtgttca aggccgaggg cgagcacttc   1440

accgaccaga aaggcaatac catcgtcggc tctggcagcg gcggcaccac caagtacttt   1500
```

```
agaatccccg ccatgtgcac caccagcaag ggcaccattg tggtgttcgc cgacgccaga   1560

cacaacaccg ccagcgatca gagcttcatc gataccgctg ccgccagaag tacagacggc   1620

ggcaagacct ggaacaagaa gatcgccatc tacaacgacc gcgtgaacag caagctgagc   1680

agagtgatgg accctacctg catcgtggcc aacatccagg gcagagaaac catcctggtc   1740

atggtcggaa agtggaacaa caacgataag acctggggcg cctacagaga caaggcccct   1800

gataccgatt gggacctcgt gctgtataag agcaccgacg acggcgtgac cttcagcaag   1860

gtggaaacaa acatccacga catcgtgacc aagaacggca ccatctctgc catgctcggc   1920

ggcgttggat ctggcctgca actgaatgat ggcaagctgg tgttccccgt gcagatggtc   1980

cgaacaaaga acatcaccac cgtgctgaat accagcttca tctactccac cgacggcatc   2040

acatggtccc tgcctagcgg ctactgtgaa ggctttggca gcgagaacaa catcatcgag   2100

ttcaacgcca gcctggtcaa caacatccgg aacagcggcc tgcggagaag cttcgagaca   2160

aaggacttcg gaaagacgtg gaccgagttt cctccaatgg acaagaaggt ggacaaccgg   2220

aaccacggcg tgcagggcag cacaatcaca atccctagcg gcaacaaact ggtggccgct   2280

cactctagcg cccagaacaa gaacaacgat tacaccagaa gcgacatcag cctgtacgcc   2340

cacaacctgt actccggcga agtgaagctg atcgacgact tctaccccaa agtgggcaat   2400

gccagcggag ccggctacag ctgtctgagc taccggaaaa atgtggacaa agaaaccctg   2460

tacgtggtgt acgaggccaa cggcagcatc gagtttcagg acctgagcag acatctgccc   2520

gtgatcaaga gctacaat                                                 2538
```

```
<210> SEQ ID NO 61
<211> LENGTH: 618
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

Thr Val Glu Lys Ser Val Val Phe Lys Ala Glu Gly Glu His Phe Thr
1               5                   10                  15

Asp Gln Lys Gly Asn Thr Ile Val Gly Ser Gly Ser Gly Gly Thr Thr
            20                  25                  30

Lys Tyr Phe Arg Ile Pro Ala Met Cys Thr Thr Ser Lys Gly Thr Ile
        35                  40                  45

Val Val Phe Ala Asp Ala Arg His Asn Thr Ala Ser Asp Gln Ser Phe
    50                  55                  60

Ile Asp Thr Ala Ala Ala Arg Ser Thr Asp Gly Gly Lys Thr Trp Asn
65                  70                  75                  80

Lys Lys Ile Ala Ile Tyr Asn Asp Arg Val Asn Ser Lys Leu Ser Arg
                85                  90                  95

Val Met Val Pro Thr Cys Ile Val Ala Asn Ile Gln Gly Arg Glu Thr
            100                 105                 110

Ile Leu Val Met Val Gly Lys Trp Asn Asn Asn Asp Lys Thr Trp Gly
        115                 120                 125

Ala Tyr Arg Asp Lys Ala Pro Asp Thr Asp Trp Asp Leu Val Leu Tyr
    130                 135                 140

Lys Ser Thr Asp Asp Gly Val Thr Phe Ser Lys Val Glu Thr Asn Ile
145                 150                 155                 160

His Asp Ile Val Thr Lys Asn Gly Thr Ile Ser Ala Met Leu Gly Gly
```

-continued

```
                165                 170                 175

Val Gly Ser Gly Leu Gln Leu Asn Asp Gly Lys Leu Val Phe Pro Val
            180                 185                 190

Gln Met Val Arg Thr Lys Asn Ile Thr Thr Val Leu Asn Thr Ser Phe
        195                 200                 205

Ile Tyr Ser Thr Asp Gly Ile Thr Trp Ser Leu Pro Ser Gly Tyr Cys
    210                 215                 220

Glu Gly Phe Gly Ser Val Asn Asn Ile Ile Glu Phe Asn Ala Ser Leu
225                 230                 235                 240

Val Asn Asn Ile Arg Asn Ser Gly Leu Arg Arg Ser Phe Glu Thr Lys
                245                 250                 255

Asp Phe Gly Lys Thr Trp Thr Glu Phe Pro Pro Met Asp Lys Lys Val
            260                 265                 270

Asp Asn Arg Asn His Gly Val Gln Gly Ser Thr Ile Thr Ile Pro Ser
        275                 280                 285

Gly Asn Lys Leu Val Ala Ala His Ser Ser Ala Gln Asn Lys Asn Asn
    290                 295                 300

Asp Tyr Thr Arg Ser Asp Ile Ser Leu Tyr Ala His Asn Leu Tyr Ser
305                 310                 315                 320

Gly Glu Val Lys Leu Ile Asp Asp Phe Tyr Pro Lys Val Gly Asn Ala
                325                 330                 335

Ser Gly Ala Gly Tyr Ser Cys Leu Ser Tyr Arg Lys Asn Val Asp Lys
            340                 345                 350

Glu Thr Leu Tyr Val Val Tyr Glu Ala Asn Gly Ser Ile Glu Phe Gln
        355                 360                 365

Asp Leu Ser Arg His Leu Pro Val Ile Lys Ser Tyr Asn Gly Gly Gly
    370                 375                 380

Gly Ser Gly Gly Gly Gly Ser Asp Lys Thr His Thr Cys Pro Pro Cys
385                 390                 395                 400

Pro Ala Pro Glu Leu Leu Gly Gly Pro Ser Val Phe Leu Phe Pro Pro
                405                 410                 415

Lys Pro Lys Asp Thr Leu Met Ile Ser Arg Thr Pro Glu Val Thr Cys
            420                 425                 430

Val Val Val Asp Val Ser His Glu Asp Pro Glu Val Lys Phe Asn Trp
        435                 440                 445

Tyr Val Asp Gly Val Glu Val His Asn Ala Lys Thr Lys Pro Arg Glu
    450                 455                 460

Glu Gln Tyr Asn Ser Thr Tyr Arg Val Val Ser Val Leu Thr Val Leu
465                 470                 475                 480

His Gln Asp Trp Leu Asn Gly Lys Glu Tyr Lys Cys Lys Val Ser Asn
                485                 490                 495

Lys Ala Leu Pro Ala Pro Ile Glu Lys Thr Ile Ser Lys Ala Lys Gly
            500                 505                 510

Gln Pro Arg Glu Pro Gln Val Tyr Thr Leu Pro Pro Ser Arg Glu Glu
        515                 520                 525

Met Thr Lys Asn Gln Val Ser Leu Thr Cys Leu Val Lys Gly Phe Tyr
    530                 535                 540

Pro Ser Asp Ile Ala Val Glu Trp Glu Ser Asn Gly Gln Pro Glu Asn
545                 550                 555                 560

Asn Tyr Lys Thr Thr Pro Pro Val Leu Asp Ser Asp Gly Ser Phe Phe
                565                 570                 575

Leu Thr Ser Lys Leu Thr Val Asp Lys Ser Arg Trp Gln Gln Gly Asn
            580                 585                 590
```

```
Val Phe Ser Cys Ser Val Met His Glu Ala Leu His Asn His Tyr Thr
        595                 600                 605

Gln Lys Ser Leu Ser Leu Ser Pro Gly Lys
    610                 615


<210> SEQ ID NO 62
<211> LENGTH: 1854
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 62

acagtggaaa agtccgtggt gttcaaggcc gagggcgagc acttcaccga ccagaaaggc     60

aataccatcg tcggctctgg cagcggcggc accaccaagt actttagaat ccccgccatg    120

tgcaccacca gcaagggcac cattgtggtg ttcgccgacg ccagacacaa caccgccagc    180

gatcagagct tcatcgatac cgctgccgcc agaagtacag acggcggcaa gacctggaac    240

aagaagatcg ccatctacaa cgaccgcgtg aacagcaagc tgagcagagt gatggtccct    300

acctgcatcg tggccaacat ccagggcaga gaaaccatcc tggtcatggt cggaaagtgg    360

aacaacaacg ataagacctg ggcgcctac agagacaagg cccctgatac cgattgggac    420

ctcgtgctgt ataagagcac cgacgacggc gtgaccttca gcaaggtgga aacaaacatc    480

cacgacatcg tgaccaagaa cggcaccatc tctgccatgc tcggcggcgt tggatctggc    540

ctgcaactga atgatggcaa gctggtgttc cccgtgcaga tggtccgaac aaagaacatc    600

accaccgtgc tgaataccag cttcatctac tccaccgacg gcatcacatg gtccctgcct    660

agcggctact gtgaaggctt tggcagcgtg aacaacatca tcgagttcaa cgccagcctg    720

gtcaacaaca tccggaacag cggcctgcgg agaagcttcg agacaaagga cttcggaaag    780

acgtggaccg agtttcctcc aatggacaag aaggtggaca accggaacca cggcgtgcag    840

ggcagcacaa tcacaatccc tagcggcaac aaactggtgg ccgctcactc tagcgcccag    900

aacaagaaca acgattacac cagaagcgac atcagcctgt acgcccacaa cctgtactcc    960

ggcgaagtga agctgatcga cgacttctac cccaaagtgg gcaatgccag cggagccggc   1020

tacagctgtc tgagctaccg gaaaaatgtg gacaaagaaa ccctgtacgt ggtgtacgag   1080

gccaacggca gcatcgagtt tcaggacctg agcagacatc tgcccgtgat caagagctac   1140

aatggcggag gtggaagtgg cggaggcgga tccgacaaaa ctcacacatg cccaccgtgc   1200

ccagcacctg aactcctggg gggaccgtca gtcttcctct tcccccaaaa acccaaggac   1260

accctcatga tctcccggac ccctgaggtc acatgcgtgg tggtggacgt gagccacgaa   1320

gaccctgagg tcaagttcaa ctggtacgtg gacggcgtgg aggtgcataa tgccaagaca   1380

aagccgcggg aggagcagta caacagcacg taccgtgtgg tcagcgtcct caccgtcctg   1440

caccaggact ggctgaatgg caaggagtac aagtgcaagg tctccaacaa agccctccca   1500

gcccccatcg agaaaaccat ctccaaagcc aaagggcagc cccgagaacc acaggtctac   1560

accctgcccc catcccggga ggagatgacc aagaaccagg tcagcctgac ctgcctggtc   1620

aaaggcttct atcccagcga catcgccgtg gagtgggaga gcaatgggca gccggagaac   1680

aactacaaga ccacgcctcc cgtgctggac tccgacggct ccttcttcct cactagcaag   1740

ctcaccgtgg acaagagcag gtggcagcag gggaacgtct tctcatgctc cgtgatgcat   1800

gaggctctgc acaaccacta cacgcagaag agcctctccc tgtctccggg taaa         1854
```

<210> SEQ ID NO 63
<211> LENGTH: 386
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 63

```
Met Glu Asp Leu Arg Pro Met Ala Ser Leu Pro Val Leu Gln Lys Glu
1               5                   10                  15

Ser Val Phe Gln Ser Gly Ala His Ala Tyr Arg Ile Pro Ala Leu Leu
            20                  25                  30

Tyr Leu Pro Gly Gln Gln Ser Leu Leu Ala Phe Ala Glu Gln Arg Ala
        35                  40                  45

Ser Lys Lys Asp Glu His Ala Glu Leu Ile Val Leu Arg Arg Gly Asp
    50                  55                  60

Tyr Asp Ala Pro Thr His Gln Val Gln Trp Gln Ala Gln Glu Val Val
65                  70                  75                  80

Ala Gln Ala Arg Leu Asp Gly His Arg Ser Met Asn Pro Cys Pro Leu
                85                  90                  95

Tyr Asp Ala Gln Thr Gly Thr Leu Phe Leu Phe Phe Ile Ala Ile Pro
            100                 105                 110

Gly Gln Val Thr Glu Gln Gln Gln Leu Gln Thr Arg Ala Asn Val Thr
        115                 120                 125

Arg Leu Cys Gln Val Thr Ser Thr Asp His Gly Arg Thr Trp Ser Ser
    130                 135                 140

Pro Arg Asp Leu Thr Asp Ala Ala Ile Gly Pro Ala Tyr Arg Glu Trp
145                 150                 155                 160

Ser Thr Phe Ala Val Gly Pro Gly His Cys Leu Gln Leu His Asp Arg
                165                 170                 175

Ala Arg Ser Leu Val Val Pro Ala Tyr Ala Tyr Arg Lys Leu His Pro
            180                 185                 190

Ile Gln Arg Pro Ile Pro Ser Ala Phe Cys Phe Leu Ser His Asp His
        195                 200                 205

Gly Arg Thr Trp Ala Arg Gly His Phe Val Ala Gln Asp Thr Leu Glu
    210                 215                 220

Cys Gln Val Ala Glu Val Glu Thr Gly Glu Gln Arg Val Val Thr Leu
225                 230                 235                 240

Asn Ala Arg Ser His Leu Arg Ala Arg Val Gln Ala Gln Ser Thr Asn
                245                 250                 255

Asp Gly Leu Asp Phe Gln Glu Ser Gln Leu Val Lys Lys Leu Val Glu
            260                 265                 270

Pro Pro Pro Gln Gly Cys Gln Gly Ser Val Ile Ser Phe Pro Ser Pro
        275                 280                 285

Arg Ser Gly Pro Gly Ser Pro Ala Gln Trp Leu Leu Tyr Thr His Pro
    290                 295                 300

Thr His Ser Trp Gln Arg Ala Asp Leu Gly Ala Tyr Leu Asn Pro Arg
305                 310                 315                 320

Pro Pro Ala Pro Glu Ala Trp Ser Glu Pro Val Leu Leu Ala Lys Gly
                325                 330                 335

Ser Cys Ala Tyr Ser Asp Leu Gln Ser Met Gly Thr Gly Pro Asp Gly
            340                 345                 350

Ser Pro Leu Phe Gly Cys Leu Tyr Glu Ala Asn Asp Tyr Glu Glu Ile
```

355 360 365

Val Phe Leu Met Phe Thr Leu Lys Gln Ala Phe Pro Ala Glu Tyr Leu
370 375 380

Pro Gln
385

<210> SEQ ID NO 64
<211> LENGTH: 1158
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 64
atggaagatc tcaggcccat ggcatctctg cctgtgctgc agaaagaaag cgtgttccag 60
tctggcgccc acgcctacag aattcccgct ctgctgtatc tgccaggcca gcagtctctg 120
ctggctttcg ctgaacagcg ggccagcaag aaggatgagc acgccgaact gatcgtgctg 180
cggagaggcg attacgacgc ccctacacat caggtgcagt ggcaggctca agaggtggtg 240
gctcaggcta gactggacgg ccacagatct atgaacccct gtcctctgta cgatgcccag 300
accggcacac tgtttctgtt ctttatcgct atccccggcc aagtgaccga gcagcagcag 360
ctgcagacaa gagccaacgt gaccagactg tgtcaagtga cctccaccga ccacggcaga 420
acctggtcta gccctagaga tctgaccgac gccgccatcg gacctgccta tagagagtgg 480
tccaccttcg ccgttggacc tggacactgt ctccagctgc acgacagggc tagatctctg 540
gtggtgcctg cctacgccta tagaaagctg caccccatcc agcggcctat tcctagcgcc 600
ttctgctttc tgagccacga tcacggcagg acatgggcca gaggacattt cgtggcccag 660
gacacactgg aatgccaggt ggccgaagtg gaaaccggcg agcagagagt cgtgaccctg 720
aacgccagat ctcacctgag agccagagtg caggcccaga gcacaaacga cggcctggat 780
ttccaagaga gccagctggt caagaaactg gtggaacctc ctccacaggg ctgtcaggga 840
agcgtgatca gctttccatc tcctagaagc ggccctggct ctcctgctca gtggctgctg 900
tatacacacc ccacacacag ctggcagaga gccgatctgg gcgcctacct gaatcctaga 960
cctcctgctc ctgaggcttg gagcgaacct gttctgctgg ccaagggcag ctgtgcctac 1020
agcgatctgc agtctatggg cacaggccct gatggcagcc ctctgtttgg ctgtctgtac 1080
gaggccaacg actacgaaga gatcgtgttc ctgatgttca ccctgaagca ggcctttcca 1140
gccgagtacc tgcctcaa 1158

<210> SEQ ID NO 65
<211> LENGTH: 873
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 65

Ala Ser Leu Pro Tyr Leu Gln Lys Glu Ser Val Phe Gln Ser Gly Ala
1 5 10 15

His Ala Tyr Arg Ile Pro Ala Leu Leu Tyr Leu Pro Gly Gln Gln Ser
20 25 30

Leu Leu Ala Phe Ala Glu Gln Arg Ala Ser Lys Lys Asp Glu His Ala
35 40 45

-continued

```
Glu Leu Ile Val Leu Arg Arg Gly Asp Tyr Asp Ala Pro Thr His Gln
    50                  55                  60

Val Gln Trp Gln Ala Gln Glu Val Val Ala Gln Ala Arg Leu Asp Gly
65                  70                  75                  80

His Arg Ser Met Asn Pro Cys Pro Leu Tyr Asp Ala Gln Thr Gly Thr
                85                  90                  95

Leu Phe Leu Phe Phe Ile Ala Ile Pro Gly Gln Val Thr Glu Gln Gln
            100                 105                 110

Gln Leu Gln Thr Arg Ala Asn Val Thr Arg Leu Cys Gln Val Thr Ser
        115                 120                 125

Thr Asp His Gly Arg Thr Trp Ser Ser Pro Arg Asp Leu Thr Asp Ala
    130                 135                 140

Ala Ile Gly Pro Ala Tyr Arg Glu Trp Ser Thr Phe Ala Val Gly Pro
145                 150                 155                 160

Gly His Cys Leu Gln Leu His Asp Arg Ala Arg Ser Leu Val Val Pro
                165                 170                 175

Ala Tyr Ala Tyr Arg Lys Leu His Pro Lys Gln Arg Pro Ile Pro Ser
            180                 185                 190

Ala Phe Cys Phe Leu Ser His Asp His Gly Arg Thr Trp Ala Arg Gly
        195                 200                 205

His Phe Val Ala Gln Asp Thr Leu Glu Cys Gln Val Ala Glu Val Glu
    210                 215                 220

Thr Gly Glu Gln Arg Val Val Thr Leu Asn Ala Arg Ser His Leu Arg
225                 230                 235                 240

Ala Arg Val Gln Ala Gln Ser Thr Asn Asp Gly Leu Asp Phe Gln Glu
                245                 250                 255

Ser Gln Leu Val Lys Lys Leu Val Glu Pro Pro Pro Gln Gly Cys Gln
            260                 265                 270

Gly Ser Val Ile Ser Phe Pro Ser Pro Arg Ser Gly Pro Gly Ser Pro
        275                 280                 285

Ala Gln Trp Leu Leu Tyr Thr His Pro Thr His Ser Trp Gln Arg Ala
    290                 295                 300

Asp Leu Gly Ala Tyr Leu Asn Pro Arg Pro Pro Ala Pro Glu Ala Trp
305                 310                 315                 320

Ser Glu Pro Val Leu Leu Ala Lys Gly Ser Cys Ala Tyr Ser Asp Leu
                325                 330                 335

Gln Ser Met Gly Thr Gly Pro Asp Gly Ser Pro Leu Phe Gly Cys Leu
            340                 345                 350

Tyr Glu Ala Asn Asp Tyr Glu Glu Ile Val Phe Leu Met Phe Thr Leu
        355                 360                 365

Lys Gln Ala Phe Pro Ala Glu Tyr Leu Pro Gln Gly Gly Gly Gly Ser
    370                 375                 380

Gly Gly Gly Gly Ser Asp Lys Thr His Thr Cys Pro Pro Cys Pro Ala
385                 390                 395                 400

Pro Glu Leu Leu Gly Gly Pro Ser Val Phe Leu Phe Pro Pro Lys Pro
                405                 410                 415

Lys Asp Thr Leu Met Ile Ser Arg Thr Pro Glu Val Thr Cys Val Val
            420                 425                 430

Val Asp Val Ser His Glu Asp Pro Glu Val Lys Phe Asn Trp Tyr Val
        435                 440                 445

Asp Gly Val Glu Val His Asn Ala Lys Thr Lys Pro Arg Glu Glu Gln
    450                 455                 460

Tyr Asn Ser Thr Tyr Arg Val Val Ser Val Leu Thr Val Leu His Gln
```

465 470 475 480

Asp Trp Leu Asn Gly Lys Glu Tyr Lys Cys Lys Val Ser Asn Lys Ala
485 490 495

Leu Pro Ala Pro Ile Glu Lys Thr Ile Ser Lys Ala Lys Gly Gln Pro
500 505 510

Arg Glu Pro Gln Val Tyr Thr Leu Pro Pro Ser Arg Glu Glu Met Thr
515 520 525

Lys Asn Gln Val Ser Leu Thr Cys Leu Val Lys Gly Phe Tyr Pro Ser
530 535 540

Asp Ile Ala Val Glu Trp Glu Ser Asn Gly Gln Pro Glu Asn Asn Tyr
545 550 555 560

Lys Thr Thr Pro Pro Val Leu Asp Ser Asp Gly Ser Phe Phe Leu Tyr
565 570 575

Ser Lys Leu Thr Val Asp Lys Ser Arg Trp Gln Gln Gly Asn Val Phe
580 585 590

Ser Cys Ser Val Met His Glu Ala Leu His Asn His Tyr Thr Gln Lys
595 600 605

Ser Leu Ser Leu Ser Pro Gly Lys Gly Gly Gly Gly Ser Gly Gly Gly
610 615 620

Gly Ser Gly Gly Gly Gly Ser Glu Val Gln Leu Val Glu Ser Gly Gly
625 630 635 640

Gly Leu Val Gln Pro Gly Gly Ser Leu Arg Leu Ser Cys Ala Ala Ser
645 650 655

Gly Phe Asn Ile Lys Asp Thr Tyr Ile His Trp Val Arg Gln Ala Pro
660 665 670

Gly Lys Gly Leu Glu Trp Val Ala Arg Ile Tyr Pro Thr Asn Gly Tyr
675 680 685

Thr Arg Tyr Ala Asp Ser Val Lys Gly Arg Phe Thr Ile Ser Ala Asp
690 695 700

Thr Ser Lys Asn Thr Ala Tyr Leu Gln Met Asn Ser Leu Arg Ala Glu
705 710 715 720

Asp Thr Ala Val Tyr Tyr Cys Ser Arg Trp Gly Gly Asp Gly Phe Tyr
725 730 735

Ala Met Asp Tyr Trp Gly Gln Gly Thr Leu Val Thr Val Ser Ser Gly
740 745 750

Gly Gly Gly Ser Gly Gly Gly Gly Ser Gly Gly Gly Gly Ser Asp Ile
755 760 765

Gln Met Thr Gln Ser Pro Ser Ser Leu Ser Ala Ser Val Gly Asp Arg
770 775 780

Val Thr Ile Thr Cys Arg Ala Ser Gln Asp Val Asn Thr Ala Val Ala
785 790 795 800

Trp Tyr Gln Gln Lys Pro Gly Lys Ala Pro Lys Leu Leu Ile Tyr Ser
805 810 815

Ala Ser Phe Leu Tyr Ser Gly Val Pro Ser Arg Phe Ser Gly Ser Arg
820 825 830

Ser Gly Thr Asp Phe Thr Leu Thr Ile Ser Ser Leu Gln Pro Glu Asp
835 840 845

Phe Ala Thr Tyr Tyr Cys Gln Gln His Tyr Thr Thr Pro Pro Thr Phe
850 855 860

Gly Gln Gly Thr Lys Val Glu Ile Lys
865 870

<210> SEQ ID NO 66

<211> LENGTH: 2619
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 66

```
gcatctctgc cttacctgca gaaagaaagc gtgttccagt ctggcgccca cgcctacaga     60
attcccgctc tgctgtatct gccaggccag cagtctctgc tggctttcgc tgaacagcgg    120
gccagcaaga aggatgagca cgccgaactg atcgtgctgc ggagaggcga ttacgacgcc    180
cctacacatc aggtgcagtg gcaggctcaa gaggtggtgg ctcaggctag actggacggc    240
cacagatcta tgaacccctg tcctctgtac gatgcccaga ccggcacact gtttctgttc    300
tttatcgcta tccccggcca agtgaccgag cagcagcagc tgcagacaag agccaacgtg    360
accagactgt gtcaagtgac ctccaccgac cacggcagaa cctggtctag ccctagagat    420
ctgaccgacg ccgccatcgg acctgcctat agagagtggt ccaccttcgc cgttggacct    480
ggacactgtc tccagctgca cgacagggct agatctctgg tggtgcctgc ctacgcctat    540
agaaagctgc accccaaaca gcggcctatt cctagcgcct tctgctttct gagccacgat    600
cacggcagga catgggccag aggacatttc gtggcccagg acacactgga atgccaggtg    660
gccgaagtgg aaaccggcga gcagagagtc gtgaccctga acgccagatc tcacctgaga    720
gccagagtgc aggcccagag cacaaacgac ggcctggatt tccaagagag ccagctggtc    780
aagaaactgg tggaacctcc tccacagggc tgtcagggaa gcgtgatcag ctttccatct    840
cctagaagcg gccctggctc tcctgctcag tggctgctgt atacacaccc cacacacagc    900
tggcagagag ccgatctggg cgcctacctg aatcctagac ctcctgctcc tgaggcttgg    960
agcgaacctg ttctgctggc caagggcagc tgtgcctaca gcgatctgca gtctatgggc   1020
acaggccctg atggcagccc tctgtttggc tgtctgtacg aggccaacga ctacgaagag   1080
atcgtgttcc tgatgttcac cctgaagcag gcctttccag ccgagtacct gcctcaaggc   1140
ggaggtggaa gtggcggagg cggatccgac aaaactcaca catgcccacc gtgcccagca   1200
cctgaactcc tggggggacc gtcagtcttc ctcttccccc caaaacccaa ggacaccctc   1260
atgatctccc ggacccctga ggtcacatgc gtggtggtgg acgtgagcca cgaagaccct   1320
gaggtcaagt tcaactggta cgtggacggc gtggaggtgc ataatgccaa gacaaagccg   1380
cgggaggagc agtacaacag cacgtaccgt gtggtcagcg tcctcaccgt cctgcaccag   1440
gactggctga atggcaagga gtacaagtgc aaggtctcca acaaagccct cccagccccc   1500
atcgagaaaa ccatctccaa agccaaaggg cagccccgag aaccacaggt ctacaccctg   1560
cccccatccc gggaggagat gaccaagaac caggtcagcc tgacctgcct ggtcaaaggc   1620
ttctatccca gcgacatcgc cgtggagtgg gagagcaatg ggcagccgga gaacaactac   1680
aagaccacgc ctcccgtgct ggactccgac ggctccttct tcctctatag caagctcacc   1740
gtggacaaga gcaggtggca gcaggggaac gtcttctcat gctccgtgat gcatgaggct   1800
ctgcacaacc actacacgca gaagagcctc tccctgtctc cgggtaaagg aggcggagga   1860
tctggcggag gtggaagtgg cggaggcgga tctgaggtgc agctggttga atctggcgga   1920
ggactggttc agcctggcgg atctctgaga ctgtcttgtg ccgccagcgg cttcaacatc   1980
aaggacacct acatccactg ggtccgacag gcccctggca aaggacttga atgggtcgcc   2040
agaatctacc ccaccaacgg ctacaccaga tacgccgact ctgtgaaggg cagattcacc   2100
```

-continued

```
atcagcgccg acaccagcaa gaacaccgcc tacctgcaga tgaacagcct gagagccgag   2160

gacaccgccg tgtactactg ttctagatgg ggaggcgacg gcttctacgc catggattat   2220

tggggccagg gcaccctggt caccgtttct tctggcggag gaggatctgg cggaggcgga   2280

agtggcggag gcggatctga catccagatg acacagagcc ctagcagcct gtctgccagc   2340

gtgggagaca gagtgaccat cacctgtaga gccagccagg acgtgaacac agccgtggct   2400

tggtatcagc agaagcctgg caaggcccct aagctgctga tctacagcgc cagctttctg   2460

tactccggcg tgcccagcag attcagcggc tctagaagcg gcaccgactt caccctgacc   2520

ataagcagtc tgcagcccga ggacttcgcc acctactact gtcagcagca ctacaccaca   2580

cctccaacct ttggccaggg caccaaggtg gaaatcaag                          2619
```

<210> SEQ ID NO 67
<211> LENGTH: 214
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 67

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 68
<211> LENGTH: 642
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 68

```
gacatccaga tgacacagag ccctagcagc ctgtctgcca gcgtgggaga cagagtgacc     60

atcacctgta gagccagcca ggacgtgaac acagccgtgg cttggtatca gcagaagcct    120

ggcaaggccc ctaagctgct gatctacagc gccagctttc tgtactccgg cgtgcccagc    180

agattcagcg gctctagaag cggcaccgac ttcaccctga ccataagcag tctgcagccc    240

gaggacttcg ccacctacta ctgtcagcag cactacacca cacctccaac ctttggccag    300

ggcaccaagg tggaaatcaa gcgtacggtg gctgcaccat ctgtcttcat cttcccgcca    360

tctgatgagc agttgaaatc tggaactgcc tctgttgtgt gcctgctgaa taacttctat    420

cccagagagg ccaaagtaca gtggaaggtg gataacgccc tccaatcggg taactcccag    480

gagagtgtca cagagcagga cagcaaggac agcacctaca gcctcagcag caccctgacg    540

ctgagcaaag cagactacga gaaacacaaa gtctacgcct gcgaagtcac ccatcagggc    600

ctgagctcgc ccgtcacaaa gagcttcaac aggggagagt gt                       642
```

<210> SEQ ID NO 69
<211> LENGTH: 227
<212> TYPE: PRT
<213> ORGANISM: Homo sapiens

<400> SEQUENCE: 69

```
Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Glu Glu Met Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225
```

-continued

<210> SEQ ID NO 70
<211> LENGTH: 380
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 70

```
Met Ala Ser Leu Pro Tyr Leu Gln Lys Glu Ser Val Phe Gln Ser Gly
1               5                   10                  15

Ala His Ala Tyr Arg Ile Pro Ala Leu Leu Tyr Leu Pro Gly Gln Gln
            20                  25                  30

Ser Leu Leu Ala Phe Ala Glu Gln Arg Ala Ser Lys Lys Asp Glu His
        35                  40                  45

Ala Glu Leu Ile Val Leu Arg Arg Gly Asp Tyr Asp Ala Pro Thr His
    50                  55                  60

Gln Val Gln Trp Gln Ala Gln Glu Val Val Ala Gln Ala Arg Leu Asp
65                  70                  75                  80

Gly His Arg Ser Met Asn Pro Cys Pro Leu Tyr Asp Ala Gln Thr Gly
                85                  90                  95

Thr Leu Phe Leu Phe Phe Ile Ala Ile Pro Gly Gln Val Thr Glu Gln
            100                 105                 110

Gln Gln Leu Gln Thr Arg Ala Asn Val Thr Arg Leu Cys Gln Val Thr
        115                 120                 125

Ser Thr Asp His Gly Arg Thr Trp Ser Ser Pro Arg Asp Leu Thr Asp
    130                 135                 140

Ala Ala Ile Gly Pro Ala Tyr Arg Glu Trp Ser Thr Phe Ala Val Gly
145                 150                 155                 160

Pro Gly His Cys Leu Gln Leu His Asp Arg Ala Arg Ser Leu Val Val
                165                 170                 175

Pro Ala Tyr Ala Tyr Arg Lys Leu His Pro Lys Gln Arg Pro Ile Pro
            180                 185                 190

Ser Ala Phe Cys Phe Leu Ser His Asp His Gly Arg Thr Trp Ala Arg
        195                 200                 205

Gly His Phe Val Ala Gln Asp Thr Leu Glu Cys Gln Val Ala Glu Val
    210                 215                 220

Glu Thr Gly Glu Gln Arg Val Val Thr Leu Asn Ala Arg Ser His Leu
225                 230                 235                 240

Arg Ala Arg Val Gln Ala Gln Ser Thr Asn Asp Gly Leu Asp Phe Gln
                245                 250                 255

Glu Ser Gln Leu Val Lys Lys Leu Val Glu Pro Pro Pro Gln Gly Cys
            260                 265                 270

Gln Gly Ser Val Ile Ser Phe Pro Ser Pro Arg Ser Gly Pro Gly Ser
        275                 280                 285

Pro Ala Gln Trp Leu Leu Tyr Thr His Pro Thr His Ser Trp Gln Arg
    290                 295                 300

Ala Asp Leu Gly Ala Tyr Leu Asn Pro Arg Pro Pro Ala Pro Glu Ala
305                 310                 315                 320

Trp Ser Glu Pro Val Leu Leu Ala Lys Gly Ser Cys Ala Tyr Ser Asp
                325                 330                 335

Leu Gln Ser Met Gly Thr Gly Pro Asp Gly Ser Pro Leu Phe Gly Cys
            340                 345                 350

Leu Tyr Glu Ala Asn Asp Tyr Glu Glu Ile Val Phe Leu Met Phe Thr
        355                 360                 365
```

```
Leu Lys Gln Ala Phe Pro Ala Glu Tyr Leu Pro Gln
    370                 375                 380


<210> SEQ ID NO 71
<211> LENGTH: 380
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 71

Met Ala Ser Leu Pro Tyr Leu Gln Lys Glu Ser Val Phe Gln Ser Gly
1               5                   10                  15

Ala His Ala Tyr Arg Ile Pro Ala Leu Leu Tyr Leu Pro Gly Gln Gln
            20                  25                  30

Ser Leu Leu Ala Phe Ala Glu Gln Arg Ala Ser Lys Lys Asp Glu His
        35                  40                  45

Ala Glu Leu Ile Val Leu Arg Arg Gly Asp Tyr Asp Ala Pro Thr His
    50                  55                  60

Gln Val Gln Trp Gln Ala Gln Glu Val Val Ala Gln Ala Arg Leu Asp
65                  70                  75                  80

Gly His Arg Ser Met Asn Pro Cys Pro Leu Tyr Asp Ala Gln Thr Gly
                85                  90                  95

Thr Leu Phe Leu Phe Phe Ile Ala Ile Pro Gly Gln Val Thr Glu Gln
            100                 105                 110

Gln Gln Leu Gln Thr Arg Ala Asn Val Thr Arg Leu Cys Gln Val Thr
        115                 120                 125

Ser Thr Asp His Gly Arg Thr Trp Ser Ser Pro Arg Asp Leu Thr Asp
    130                 135                 140

Ala Ala Ile Gly Pro Ala Tyr Arg Glu Trp Ser Thr Phe Ala Val Gly
145                 150                 155                 160

Pro Gly His Cys Leu Gln Leu His Asp Arg Ala Arg Ser Leu Val Val
                165                 170                 175

Pro Ala Tyr Ala Tyr Arg Lys Leu His Pro Lys Gln Arg Pro Ile Pro
            180                 185                 190

Ser Ala Phe Cys Phe Leu Ser His Asp His Gly Arg Thr Trp Ala Arg
        195                 200                 205

Gly His Phe Val Ala Gln Asp Thr Leu Glu Cys Gln Val Ala Glu Val
    210                 215                 220

Glu Thr Gly Glu Gln Arg Val Val Thr Leu Asn Ala Arg Ser His Leu
225                 230                 235                 240

Arg Ala Arg Val Gln Ala Gln Ser Thr Asn Asp Gly Leu Asp Phe Gln
                245                 250                 255

Glu Ser Gln Leu Val Lys Lys Leu Val Glu Pro Pro Pro Gln Gly Cys
            260                 265                 270

Gln Gly Ser Val Ile Ser Phe Pro Ser Pro Arg Ser Gly Pro Gly Ser
        275                 280                 285

Pro Ala Gln Trp Leu Leu Tyr Thr His Pro Thr His Ser Trp Gln Arg
    290                 295                 300

Ala Asp Leu Gly Ala Tyr Leu Asn Pro Arg Pro Pro Ala Pro Glu Ala
305                 310                 315                 320

Trp Ser Glu Pro Val Leu Leu Ala Lys Gly Ser Ala Ala Tyr Ser Asp
                325                 330                 335

Leu Gln Ser Met Gly Thr Gly Pro Asp Gly Ser Pro Leu Phe Gly Cys
            340                 345                 350
```

```
Leu Tyr Glu Ala Asn Asp Tyr Glu Glu Ile Val Phe Leu Met Phe Thr
        355                 360                 365

Leu Lys Gln Ala Phe Pro Ala Glu Tyr Leu Pro Gln
    370                 375                 380


<210> SEQ ID NO 72
<211> LENGTH: 380
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 72

Ala Ala Ser Leu Pro Tyr Leu Gln Lys Glu Ser Val Phe Gln Ser Gly
1               5                   10                  15

Ala His Ala Tyr Arg Ile Pro Ala Leu Leu Tyr Leu Pro Gly Gln Gln
            20                  25                  30

Ser Leu Leu Ala Phe Ala Glu Gln Arg Ala Ser Lys Lys Asp Glu His
        35                  40                  45

Ala Glu Leu Ile Val Leu Arg Arg Gly Asp Tyr Asp Ala Pro Thr His
    50                  55                  60

Gln Val Gln Trp Gln Ala Gln Glu Val Val Ala Gln Ala Arg Leu Asp
65                  70                  75                  80

Gly His Arg Ser Met Asn Pro Cys Pro Leu Tyr Asp Ala Gln Thr Gly
                85                  90                  95

Thr Leu Phe Leu Phe Phe Ile Ala Ile Pro Gly Gln Val Thr Glu Gln
            100                 105                 110

Gln Gln Leu Gln Thr Arg Ala Asn Val Thr Arg Leu Cys Gln Val Thr
        115                 120                 125

Ser Thr Asp His Gly Arg Thr Trp Ser Ser Pro Arg Asp Leu Thr Asp
    130                 135                 140

Ala Ala Ile Gly Pro Ala Tyr Arg Glu Trp Ser Thr Phe Ala Val Gly
145                 150                 155                 160

Pro Gly His Cys Leu Gln Leu His Asp Arg Ala Arg Ser Leu Val Val
                165                 170                 175

Pro Ala Tyr Ala Tyr Arg Lys Leu His Pro Lys Gln Arg Pro Ile Pro
            180                 185                 190

Ser Ala Phe Cys Phe Leu Ser His Asp His Gly Arg Thr Trp Ala Arg
        195                 200                 205

Gly His Phe Val Ala Gln Asp Thr Leu Glu Cys Gln Val Ala Glu Val
    210                 215                 220

Glu Thr Gly Glu Gln Arg Val Val Thr Leu Asn Ala Arg Ser His Leu
225                 230                 235                 240

Arg Ala Arg Val Gln Ala Gln Ser Thr Asn Asp Gly Leu Asp Phe Gln
                245                 250                 255

Glu Ser Gln Leu Val Lys Lys Leu Val Glu Pro Pro Pro Gln Gly Cys
            260                 265                 270

Gln Gly Ser Val Ile Ser Phe Pro Ser Pro Arg Ser Gly Pro Gly Ser
        275                 280                 285

Pro Ala Gln Trp Leu Leu Tyr Thr His Pro Thr His Ser Trp Gln Arg
    290                 295                 300

Ala Asp Leu Gly Ala Tyr Leu Asn Pro Arg Pro Pro Ala Pro Glu Ala
305                 310                 315                 320

Trp Ser Glu Pro Val Leu Leu Ala Lys Gly Ser Cys Ala Tyr Ser Asp
```

```
                325                 330                 335

Leu Gln Ser Met Gly Thr Gly Pro Asp Gly Ser Pro Leu Phe Gly Cys
            340                 345                 350

Leu Tyr Glu Ala Asn Asp Tyr Glu Glu Ile Val Phe Leu Met Phe Thr
        355                 360                 365

Leu Lys Gln Ala Phe Pro Ala Glu Tyr Leu Pro Gln
    370                 375                 380


<210> SEQ ID NO 73
<211> LENGTH: 380
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 73

Asp Ala Ser Leu Pro Tyr Leu Gln Lys Glu Ser Val Phe Gln Ser Gly
1               5                   10                  15

Ala His Ala Tyr Arg Ile Pro Ala Leu Leu Tyr Leu Pro Gly Gln Gln
            20                  25                  30

Ser Leu Leu Ala Phe Ala Glu Gln Arg Ala Ser Lys Lys Asp Glu His
        35                  40                  45

Ala Glu Leu Ile Val Leu Arg Arg Gly Asp Tyr Asp Ala Pro Thr His
    50                  55                  60

Gln Val Gln Trp Gln Ala Gln Glu Val Val Ala Gln Ala Arg Leu Asp
65                  70                  75                  80

Gly His Arg Ser Met Asn Pro Cys Pro Leu Tyr Asp Ala Gln Thr Gly
                85                  90                  95

Thr Leu Phe Leu Phe Phe Ile Ala Ile Pro Gly Gln Val Thr Glu Gln
            100                 105                 110

Gln Gln Leu Gln Thr Arg Ala Asn Val Thr Arg Leu Cys Gln Val Thr
        115                 120                 125

Ser Thr Asp His Gly Arg Thr Trp Ser Ser Pro Arg Asp Leu Thr Asp
    130                 135                 140

Ala Ala Ile Gly Pro Ala Tyr Arg Glu Trp Ser Thr Phe Ala Val Gly
145                 150                 155                 160

Pro Gly His Cys Leu Gln Leu His Asp Arg Ala Arg Ser Leu Val Val
                165                 170                 175

Pro Ala Tyr Ala Tyr Arg Lys Leu His Pro Lys Gln Arg Pro Ile Pro
            180                 185                 190

Ser Ala Phe Cys Phe Leu Ser His Asp His Gly Arg Thr Trp Ala Arg
        195                 200                 205

Gly His Phe Val Ala Gln Asp Thr Leu Glu Cys Gln Val Ala Glu Val
    210                 215                 220

Glu Thr Gly Glu Gln Arg Val Val Thr Leu Asn Ala Arg Ser His Leu
225                 230                 235                 240

Arg Ala Arg Val Gln Ala Gln Ser Thr Asn Asp Gly Leu Asp Phe Gln
                245                 250                 255

Glu Ser Gln Leu Val Lys Lys Leu Val Glu Pro Pro Pro Gln Gly Cys
            260                 265                 270

Gln Gly Ser Val Ile Ser Phe Pro Ser Pro Arg Ser Gly Pro Gly Ser
        275                 280                 285

Pro Ala Gln Trp Leu Leu Tyr Thr His Pro Thr His Ser Trp Gln Arg
    290                 295                 300
```

-continued

Ala Asp Leu Gly Ala Tyr Leu Asn Pro Arg Pro Pro Ala Pro Glu Ala
305 310 315 320

Trp Ser Glu Pro Val Leu Leu Ala Lys Gly Ser Cys Ala Tyr Ser Asp
325 330 335

Leu Gln Ser Met Gly Thr Gly Pro Asp Gly Ser Pro Leu Phe Gly Cys
340 345 350

Leu Tyr Glu Ala Asn Asp Tyr Glu Glu Ile Val Phe Leu Met Phe Thr
355 360 365

Leu Lys Gln Ala Phe Pro Ala Glu Tyr Leu Pro Gln
370 375 380

<210> SEQ ID NO 74
<211> LENGTH: 874
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 74

Met Ala Ser Leu Pro Tyr Leu Gln Lys Glu Ser Val Phe Gln Ser Gly
1 5 10 15

Ala His Ala Tyr Arg Ile Pro Ala Leu Leu Tyr Leu Pro Gly Gln Gln
20 25 30

Ser Leu Leu Ala Phe Ala Glu Gln Arg Ala Ser Lys Lys Asp Glu His
35 40 45

Ala Glu Leu Ile Val Leu Arg Arg Gly Asp Tyr Asp Ala Pro Thr His
50 55 60

Gln Val Gln Trp Gln Ala Gln Glu Val Val Ala Gln Ala Arg Leu Asp
65 70 75 80

Gly His Arg Ser Met Asn Pro Cys Pro Leu Tyr Asp Ala Gln Thr Gly
85 90 95

Thr Leu Phe Leu Phe Phe Ile Ala Ile Pro Gly Gln Val Thr Glu Gln
100 105 110

Gln Gln Leu Gln Thr Arg Ala Asn Val Thr Arg Leu Cys Gln Val Thr
115 120 125

Ser Thr Asp His Gly Arg Thr Trp Ser Ser Pro Arg Asp Leu Thr Asp
130 135 140

Ala Ala Ile Gly Pro Ala Tyr Arg Glu Trp Ser Thr Phe Ala Val Gly
145 150 155 160

Pro Gly His Cys Leu Gln Leu His Asp Arg Ala Arg Ser Leu Val Val
165 170 175

Pro Ala Tyr Ala Tyr Arg Lys Leu His Pro Lys Gln Arg Pro Ile Pro
180 185 190

Ser Ala Phe Cys Phe Leu Ser His Asp His Gly Arg Thr Trp Ala Arg
195 200 205

Gly His Phe Val Ala Gln Asp Thr Leu Glu Cys Gln Val Ala Glu Val
210 215 220

Glu Thr Gly Glu Gln Arg Val Val Thr Leu Asn Ala Arg Ser His Leu
225 230 235 240

Arg Ala Arg Val Gln Ala Gln Ser Thr Asn Asp Gly Leu Asp Phe Gln
245 250 255

Glu Ser Gln Leu Val Lys Lys Leu Val Glu Pro Pro Pro Gln Gly Cys
260 265 270

Gln Gly Ser Val Ile Ser Phe Pro Ser Pro Arg Ser Gly Pro Gly Ser
275 280 285

-continued

Pro Ala Gln Trp Leu Leu Tyr Thr His Pro Thr His Ser Trp Gln Arg
290 295 300

Ala Asp Leu Gly Ala Tyr Leu Asn Pro Arg Pro Pro Ala Pro Glu Ala
305 310 315 320

Trp Ser Glu Pro Val Leu Leu Ala Lys Gly Ser Cys Ala Tyr Ser Asp
325 330 335

Leu Gln Ser Met Gly Thr Gly Pro Asp Gly Ser Pro Leu Phe Gly Cys
340 345 350

Leu Tyr Glu Ala Asn Asp Tyr Glu Glu Ile Val Phe Leu Met Phe Thr
355 360 365

Leu Lys Gln Ala Phe Pro Ala Glu Tyr Leu Pro Gln Gly Gly Gly Gly
370 375 380

Ser Gly Gly Gly Gly Ser Asp Lys Thr His Thr Cys Pro Pro Cys Pro
385 390 395 400

Ala Pro Glu Leu Leu Gly Gly Pro Ser Val Phe Leu Phe Pro Pro Lys
405 410 415

Pro Lys Asp Thr Leu Met Ile Ser Arg Thr Pro Glu Val Thr Cys Val
420 425 430

Val Val Asp Val Ser His Glu Asp Pro Glu Val Lys Phe Asn Trp Tyr
435 440 445

Val Asp Gly Val Glu Val His Asn Ala Lys Thr Lys Pro Arg Glu Glu
450 455 460

Gln Tyr Asn Ser Thr Tyr Arg Val Val Ser Val Leu Thr Val Leu His
465 470 475 480

Gln Asp Trp Leu Asn Gly Lys Glu Tyr Lys Cys Lys Val Ser Asn Lys
485 490 495

Ala Leu Pro Ala Pro Ile Glu Lys Thr Ile Ser Lys Ala Lys Gly Gln
500 505 510

Pro Arg Glu Pro Gln Val Tyr Thr Leu Pro Pro Ser Arg Glu Glu Met
515 520 525

Thr Lys Asn Gln Val Ser Leu Thr Cys Leu Val Lys Gly Phe Tyr Pro
530 535 540

Ser Asp Ile Ala Val Glu Trp Glu Ser Asn Gly Gln Pro Glu Asn Asn
545 550 555 560

Tyr Lys Thr Thr Pro Pro Val Leu Asp Ser Asp Gly Ser Phe Phe Leu
565 570 575

Tyr Ser Lys Leu Thr Val Asp Lys Ser Arg Trp Gln Gln Gly Asn Val
580 585 590

Phe Ser Cys Ser Val Met His Glu Ala Leu His Asn His Tyr Thr Gln
595 600 605

Lys Ser Leu Ser Leu Ser Pro Gly Lys Gly Gly Gly Gly Ser Gly Gly
610 615 620

Gly Gly Ser Gly Gly Gly Gly Ser Glu Val Gln Leu Val Glu Ser Gly
625 630 635 640

Gly Gly Leu Val Gln Pro Gly Gly Ser Leu Arg Leu Ser Cys Ala Ala
645 650 655

Ser Gly Phe Asn Ile Lys Asp Thr Tyr Ile His Trp Val Arg Gln Ala
660 665 670

Pro Gly Lys Gly Leu Glu Trp Val Ala Arg Ile Tyr Pro Thr Asn Gly
675 680 685

Tyr Thr Arg Tyr Ala Asp Ser Val Lys Gly Arg Phe Thr Ile Ser Ala
690 695 700

```
Asp Thr Ser Lys Asn Thr Ala Tyr Leu Gln Met Asn Ser Leu Arg Ala
705                 710                 715                 720

Glu Asp Thr Ala Val Tyr Tyr Cys Ser Arg Trp Gly Gly Asp Gly Phe
                725                 730                 735

Tyr Ala Met Asp Tyr Trp Gly Gln Gly Thr Leu Val Thr Val Ser Ser
            740                 745                 750

Gly Gly Gly Gly Ser Gly Gly Gly Gly Ser Gly Gly Gly Gly Ser Asp
        755                 760                 765

Ile Gln Met Thr Gln Ser Pro Ser Ser Leu Ser Ala Ser Val Gly Asp
    770                 775                 780

Arg Val Thr Ile Thr Cys Arg Ala Ser Gln Asp Val Asn Thr Ala Val
785                 790                 795                 800

Ala Trp Tyr Gln Gln Lys Pro Gly Lys Ala Pro Lys Leu Leu Ile Tyr
                805                 810                 815

Ser Ala Ser Phe Leu Tyr Ser Gly Val Pro Ser Arg Phe Ser Gly Ser
            820                 825                 830

Arg Ser Gly Thr Asp Phe Thr Leu Thr Ile Ser Ser Leu Gln Pro Glu
        835                 840                 845

Asp Phe Ala Thr Tyr Tyr Cys Gln Gln His Tyr Thr Thr Pro Pro Thr
    850                 855                 860

Phe Gly Gln Gly Thr Lys Val Glu Ile Lys
865                 870
```

<210> SEQ ID NO 75
<211> LENGTH: 874
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 75

```
Met Ala Ser Leu Pro Tyr Leu Gln Lys Glu Ser Val Phe Gln Ser Gly
1               5                   10                  15

Ala His Ala Tyr Arg Ile Pro Ala Leu Leu Tyr Leu Pro Gly Gln Gln
            20                  25                  30

Ser Leu Leu Ala Phe Ala Glu Gln Arg Ala Ser Lys Lys Asp Glu His
        35                  40                  45

Ala Glu Leu Ile Val Leu Arg Arg Gly Asp Tyr Asp Ala Pro Thr His
    50                  55                  60

Gln Val Gln Trp Gln Ala Gln Glu Val Val Ala Gln Ala Arg Leu Asp
65                  70                  75                  80

Gly His Arg Ser Met Asn Pro Cys Pro Leu Tyr Asp Ala Gln Thr Gly
                85                  90                  95

Thr Leu Phe Leu Phe Phe Ile Ala Ile Pro Gly Gln Val Thr Glu Gln
            100                 105                 110

Gln Gln Leu Gln Thr Arg Ala Asn Val Thr Arg Leu Cys Gln Val Thr
        115                 120                 125

Ser Thr Asp His Gly Arg Thr Trp Ser Ser Pro Arg Asp Leu Thr Asp
    130                 135                 140

Ala Ala Ile Gly Pro Ala Tyr Arg Glu Trp Ser Thr Phe Ala Val Gly
145                 150                 155                 160

Pro Gly His Cys Leu Gln Leu His Asp Arg Ala Arg Ser Leu Val Val
                165                 170                 175

Pro Ala Tyr Ala Tyr Arg Lys Leu His Pro Lys Gln Arg Pro Ile Pro
            180                 185                 190
```

```
Ser Ala Phe Cys Phe Leu Ser His Asp His Gly Arg Thr Trp Ala Arg
        195                 200                 205

Gly His Phe Val Ala Gln Asp Thr Leu Glu Cys Gln Val Ala Glu Val
    210                 215                 220

Glu Thr Gly Glu Gln Arg Val Val Thr Leu Asn Ala Arg Ser His Leu
225                 230                 235                 240

Arg Ala Arg Val Gln Ala Gln Ser Thr Asn Asp Gly Leu Asp Phe Gln
                245                 250                 255

Glu Ser Gln Leu Val Lys Lys Leu Val Glu Pro Pro Pro Gln Gly Cys
            260                 265                 270

Gln Gly Ser Val Ile Ser Phe Pro Ser Pro Arg Ser Gly Pro Gly Ser
        275                 280                 285

Pro Ala Gln Trp Leu Leu Tyr Thr His Pro Thr His Ser Trp Gln Arg
    290                 295                 300

Ala Asp Leu Gly Ala Tyr Leu Asn Pro Arg Pro Pro Ala Pro Glu Ala
305                 310                 315                 320

Trp Ser Glu Pro Val Leu Leu Ala Lys Gly Ser Ala Ala Tyr Ser Asp
                325                 330                 335

Leu Gln Ser Met Gly Thr Gly Pro Asp Gly Ser Pro Leu Phe Gly Cys
            340                 345                 350

Leu Tyr Glu Ala Asn Asp Tyr Glu Glu Ile Val Phe Leu Met Phe Thr
        355                 360                 365

Leu Lys Gln Ala Phe Pro Ala Glu Tyr Leu Pro Gln Gly Gly Gly Gly
    370                 375                 380

Ser Gly Gly Gly Gly Ser Asp Lys Thr His Thr Cys Pro Pro Cys Pro
385                 390                 395                 400

Ala Pro Glu Leu Leu Gly Gly Pro Ser Val Phe Leu Phe Pro Pro Lys
                405                 410                 415

Pro Lys Asp Thr Leu Met Ile Ser Arg Thr Pro Glu Val Thr Cys Val
            420                 425                 430

Val Val Asp Val Ser His Glu Asp Pro Glu Val Lys Phe Asn Trp Tyr
        435                 440                 445

Val Asp Gly Val Glu Val His Asn Ala Lys Thr Lys Pro Arg Glu Glu
    450                 455                 460

Gln Tyr Asn Ser Thr Tyr Arg Val Val Ser Val Leu Thr Val Leu His
465                 470                 475                 480

Gln Asp Trp Leu Asn Gly Lys Glu Tyr Lys Cys Lys Val Ser Asn Lys
                485                 490                 495

Ala Leu Pro Ala Pro Ile Glu Lys Thr Ile Ser Lys Ala Lys Gly Gln
            500                 505                 510

Pro Arg Glu Pro Gln Val Tyr Thr Leu Pro Pro Ser Arg Glu Glu Met
        515                 520                 525

Thr Lys Asn Gln Val Ser Leu Thr Cys Leu Val Lys Gly Phe Tyr Pro
    530                 535                 540

Ser Asp Ile Ala Val Glu Trp Glu Ser Asn Gly Gln Pro Glu Asn Asn
545                 550                 555                 560

Tyr Lys Thr Thr Pro Pro Val Leu Asp Ser Asp Gly Ser Phe Phe Leu
                565                 570                 575

Tyr Ser Lys Leu Thr Val Asp Lys Ser Arg Trp Gln Gln Gly Asn Val
            580                 585                 590

Phe Ser Cys Ser Val Met His Glu Ala Leu His Asn His Tyr Thr Gln
        595                 600                 605
```

-continued

```
Lys Ser Leu Ser Leu Ser Pro Gly Lys Gly Gly Gly Gly Ser Gly Gly
    610                 615                 620

Gly Gly Ser Gly Gly Gly Gly Ser Glu Val Gln Leu Val Glu Ser Gly
625                 630                 635                 640

Gly Gly Leu Val Gln Pro Gly Gly Ser Leu Arg Leu Ser Cys Ala Ala
                645                 650                 655

Ser Gly Phe Asn Ile Lys Asp Thr Tyr Ile His Trp Val Arg Gln Ala
            660                 665                 670

Pro Gly Lys Gly Leu Glu Trp Val Ala Arg Ile Tyr Pro Thr Asn Gly
        675                 680                 685

Tyr Thr Arg Tyr Ala Asp Ser Val Lys Gly Arg Phe Thr Ile Ser Ala
    690                 695                 700

Asp Thr Ser Lys Asn Thr Ala Tyr Leu Gln Met Asn Ser Leu Arg Ala
705                 710                 715                 720

Glu Asp Thr Ala Val Tyr Tyr Cys Ser Arg Trp Gly Gly Asp Gly Phe
                725                 730                 735

Tyr Ala Met Asp Tyr Trp Gly Gln Gly Thr Leu Val Thr Val Ser Ser
            740                 745                 750

Gly Gly Gly Gly Ser Gly Gly Gly Gly Ser Gly Gly Gly Gly Ser Asp
        755                 760                 765

Ile Gln Met Thr Gln Ser Pro Ser Ser Leu Ser Ala Ser Val Gly Asp
    770                 775                 780

Arg Val Thr Ile Thr Cys Arg Ala Ser Gln Asp Val Asn Thr Ala Val
785                 790                 795                 800

Ala Trp Tyr Gln Gln Lys Pro Gly Lys Ala Pro Lys Leu Leu Ile Tyr
                805                 810                 815

Ser Ala Ser Phe Leu Tyr Ser Gly Val Pro Ser Arg Phe Ser Gly Ser
            820                 825                 830

Arg Ser Gly Thr Asp Phe Thr Leu Thr Ile Ser Ser Leu Gln Pro Glu
        835                 840                 845

Asp Phe Ala Thr Tyr Tyr Cys Gln Gln His Tyr Thr Thr Pro Pro Thr
    850                 855                 860

Phe Gly Gln Gly Thr Lys Val Glu Ile Lys
865                 870
```

<210> SEQ ID NO 76
<211> LENGTH: 617
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 76

```
Ala Ala Ser Leu Pro Tyr Leu Gln Lys Glu Ser Val Phe Gln Ser Gly
1               5                   10                  15

Ala His Ala Tyr Arg Ile Pro Ala Leu Leu Tyr Leu Pro Gly Gln Gln
            20                  25                  30

Ser Leu Leu Ala Phe Ala Glu Gln Arg Ala Ser Lys Lys Asp Glu His
        35                  40                  45

Ala Glu Leu Ile Val Leu Arg Arg Gly Asp Tyr Asp Ala Pro Thr His
    50                  55                  60

Gln Val Gln Trp Gln Ala Gln Glu Val Val Ala Gln Ala Arg Leu Asp
65                  70                  75                  80

Gly His Arg Ser Met Asn Pro Cys Pro Leu Tyr Asp Ala Gln Thr Gly
                85                  90                  95
```

-continued

```
Thr Leu Phe Leu Phe Phe Ile Ala Ile Pro Gly Gln Val Thr Glu Gln
            100                 105                 110

Gln Gln Leu Gln Thr Arg Ala Asn Val Thr Arg Leu Cys Gln Val Thr
        115                 120                 125

Ser Thr Asp His Gly Arg Thr Trp Ser Ser Pro Arg Asp Leu Thr Asp
    130                 135                 140

Ala Ala Ile Gly Pro Ala Tyr Arg Glu Trp Ser Thr Phe Ala Val Gly
145                 150                 155                 160

Pro Gly His Cys Leu Gln Leu His Asp Arg Ala Arg Ser Leu Val Val
                165                 170                 175

Pro Ala Tyr Ala Tyr Arg Lys Leu His Pro Lys Gln Arg Pro Ile Pro
            180                 185                 190

Ser Ala Phe Cys Phe Leu Ser His Asp His Gly Arg Thr Trp Ala Arg
        195                 200                 205

Gly His Phe Val Ala Gln Asp Thr Leu Glu Cys Gln Val Ala Glu Val
    210                 215                 220

Glu Thr Gly Glu Gln Arg Val Val Thr Leu Asn Ala Arg Ser His Leu
225                 230                 235                 240

Arg Ala Arg Val Gln Ala Gln Ser Thr Asn Asp Gly Leu Asp Phe Gln
                245                 250                 255

Glu Ser Gln Leu Val Lys Lys Leu Val Glu Pro Pro Pro Gln Gly Cys
            260                 265                 270

Gln Gly Ser Val Ile Ser Phe Pro Ser Pro Arg Ser Gly Pro Gly Ser
        275                 280                 285

Pro Ala Gln Trp Leu Leu Tyr Thr His Pro Thr His Ser Trp Gln Arg
    290                 295                 300

Ala Asp Leu Gly Ala Tyr Leu Asn Pro Arg Pro Pro Ala Pro Glu Ala
305                 310                 315                 320

Trp Ser Glu Pro Val Leu Leu Ala Lys Gly Ser Cys Ala Tyr Ser Asp
                325                 330                 335

Leu Gln Ser Met Gly Thr Gly Pro Asp Gly Ser Pro Leu Phe Gly Cys
            340                 345                 350

Leu Tyr Glu Ala Asn Asp Tyr Glu Glu Ile Val Phe Leu Met Phe Thr
        355                 360                 365

Leu Lys Gln Ala Phe Pro Ala Glu Tyr Leu Pro Gln Gly Gly Gly Gly
    370                 375                 380

Ser Gly Gly Gly Gly Ser Asp Lys Thr His Thr Cys Pro Pro Cys Pro
385                 390                 395                 400

Ala Pro Glu Leu Leu Gly Gly Pro Ser Val Phe Leu Phe Pro Pro Lys
                405                 410                 415

Pro Lys Asp Thr Leu Met Ile Ser Arg Thr Pro Glu Val Thr Cys Val
            420                 425                 430

Val Val Asp Val Ser His Glu Asp Pro Glu Val Lys Phe Asn Trp Tyr
        435                 440                 445

Val Asp Gly Val Glu Val His Asn Ala Lys Thr Lys Pro Arg Glu Glu
    450                 455                 460

Gln Tyr Asn Ser Thr Tyr Arg Val Val Ser Val Leu Thr Val Leu His
465                 470                 475                 480

Gln Asp Trp Leu Asn Gly Lys Glu Tyr Lys Cys Lys Val Ser Asn Lys
                485                 490                 495

Ala Leu Pro Ala Pro Ile Glu Lys Thr Ile Ser Lys Ala Lys Gly Gln
            500                 505                 510
```

```
Pro Arg Glu Pro Gln Val Tyr Thr Leu Pro Pro Ser Arg Glu Glu Met
        515                 520                 525

Thr Lys Asn Gln Val Ser Leu Thr Cys Leu Val Lys Gly Phe Tyr Pro
    530                 535                 540

Ser Asp Ile Ala Val Glu Trp Glu Ser Asn Gly Gln Pro Glu Asn Asn
545                 550                 555                 560

Tyr Lys Thr Thr Pro Pro Val Leu Asp Ser Asp Gly Ser Phe Phe Leu
                565                 570                 575

Thr Ser Lys Leu Thr Val Asp Lys Ser Arg Trp Gln Gln Gly Asn Val
            580                 585                 590

Phe Ser Cys Ser Val Met His Glu Ala Leu His Asn His Tyr Thr Gln
        595                 600                 605

Lys Ser Leu Ser Leu Ser Pro Gly Lys
    610                 615


<210> SEQ ID NO 77
<211> LENGTH: 617
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 77

Asp Ala Ser Leu Pro Tyr Leu Gln Lys Glu Ser Val Phe Gln Ser Gly
1               5                   10                  15

Ala His Ala Tyr Arg Ile Pro Ala Leu Leu Tyr Leu Pro Gly Gln Gln
            20                  25                  30

Ser Leu Leu Ala Phe Ala Glu Gln Arg Ala Ser Lys Lys Asp Glu His
        35                  40                  45

Ala Glu Leu Ile Val Leu Arg Arg Gly Asp Tyr Asp Ala Pro Thr His
    50                  55                  60

Gln Val Gln Trp Gln Ala Gln Glu Val Val Ala Gln Ala Arg Leu Asp
65                  70                  75                  80

Gly His Arg Ser Met Asn Pro Cys Pro Leu Tyr Asp Ala Gln Thr Gly
                85                  90                  95

Thr Leu Phe Leu Phe Phe Ile Ala Ile Pro Gly Gln Val Thr Glu Gln
            100                 105                 110

Gln Gln Leu Gln Thr Arg Ala Asn Val Thr Arg Leu Cys Gln Val Thr
        115                 120                 125

Ser Thr Asp His Gly Arg Thr Trp Ser Ser Pro Arg Asp Leu Thr Asp
    130                 135                 140

Ala Ala Ile Gly Pro Ala Tyr Arg Glu Trp Ser Thr Phe Ala Val Gly
145                 150                 155                 160

Pro Gly His Cys Leu Gln Leu His Asp Arg Ala Arg Ser Leu Val Val
                165                 170                 175

Pro Ala Tyr Ala Tyr Arg Lys Leu His Pro Lys Gln Arg Pro Ile Pro
            180                 185                 190

Ser Ala Phe Cys Phe Leu Ser His Asp His Gly Arg Thr Trp Ala Arg
        195                 200                 205

Gly His Phe Val Ala Gln Asp Thr Leu Glu Cys Gln Val Ala Glu Val
    210                 215                 220

Glu Thr Gly Glu Gln Arg Val Val Thr Leu Asn Ala Arg Ser His Leu
225                 230                 235                 240

Arg Ala Arg Val Gln Ala Gln Ser Thr Asn Asp Gly Leu Asp Phe Gln
                245                 250                 255
```

```
Glu Ser Gln Leu Val Lys Lys Leu Val Glu Pro Pro Pro Gln Gly Cys
            260                 265                 270

Gln Gly Ser Val Ile Ser Phe Pro Ser Pro Arg Ser Gly Pro Gly Ser
        275                 280                 285

Pro Ala Gln Trp Leu Leu Tyr Thr His Pro Thr His Ser Trp Gln Arg
    290                 295                 300

Ala Asp Leu Gly Ala Tyr Leu Asn Pro Arg Pro Pro Ala Pro Glu Ala
305                 310                 315                 320

Trp Ser Glu Pro Val Leu Leu Ala Lys Gly Ser Cys Ala Tyr Ser Asp
                325                 330                 335

Leu Gln Ser Met Gly Thr Gly Pro Asp Gly Ser Pro Leu Phe Gly Cys
            340                 345                 350

Leu Tyr Glu Ala Asn Asp Tyr Glu Glu Ile Val Phe Leu Met Phe Thr
        355                 360                 365

Leu Lys Gln Ala Phe Pro Ala Glu Tyr Leu Pro Gln Gly Gly Gly Gly
    370                 375                 380

Ser Gly Gly Gly Gly Ser Asp Lys Thr His Thr Cys Pro Pro Cys Pro
385                 390                 395                 400

Ala Pro Glu Leu Leu Gly Gly Pro Ser Val Phe Leu Phe Pro Pro Lys
                405                 410                 415

Pro Lys Asp Thr Leu Met Ile Ser Arg Thr Pro Glu Val Thr Cys Val
            420                 425                 430

Val Val Asp Val Ser His Glu Asp Pro Glu Val Lys Phe Asn Trp Tyr
        435                 440                 445

Val Asp Gly Val Glu Val His Asn Ala Lys Thr Lys Pro Arg Glu Glu
    450                 455                 460

Gln Tyr Asn Ser Thr Tyr Arg Val Val Ser Val Leu Thr Val Leu His
465                 470                 475                 480

Gln Asp Trp Leu Asn Gly Lys Glu Tyr Lys Cys Lys Val Ser Asn Lys
                485                 490                 495

Ala Leu Pro Ala Pro Ile Glu Lys Thr Ile Ser Lys Ala Lys Gly Gln
            500                 505                 510

Pro Arg Glu Pro Gln Val Tyr Thr Leu Pro Pro Ser Arg Glu Glu Met
        515                 520                 525

Thr Lys Asn Gln Val Ser Leu Thr Cys Leu Val Lys Gly Phe Tyr Pro
    530                 535                 540

Ser Asp Ile Ala Val Glu Trp Glu Ser Asn Gly Gln Pro Glu Asn Asn
545                 550                 555                 560

Tyr Lys Thr Thr Pro Pro Val Leu Asp Ser Asp Gly Ser Phe Phe Leu
                565                 570                 575

Thr Ser Lys Leu Thr Val Asp Lys Ser Arg Trp Gln Gln Gly Asn Val
            580                 585                 590

Phe Ser Cys Ser Val Met His Glu Ala Leu His Asn His Tyr Thr Gln
        595                 600                 605

Lys Ser Leu Ser Leu Ser Pro Gly Lys
    610                 615
```

<210> SEQ ID NO 78
<211> LENGTH: 617
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 78

```
Met Ala Ser Leu Pro Tyr Leu Gln Lys Glu Ser Val Phe Gln Ser Gly
1               5                   10                  15

Ala His Ala Tyr Arg Ile Pro Ala Leu Leu Tyr Leu Pro Gly Gln Gln
            20                  25                  30

Ser Leu Leu Ala Phe Ala Glu Gln Arg Ala Ser Lys Lys Asp Glu His
        35                  40                  45

Ala Glu Leu Ile Val Leu Arg Arg Gly Asp Tyr Asp Ala Pro Thr His
    50                  55                  60

Gln Val Gln Trp Gln Ala Gln Glu Val Val Ala Gln Ala Arg Leu Asp
65                  70                  75                  80

Gly His Arg Ser Met Asn Pro Cys Pro Leu Tyr Asp Ala Gln Thr Gly
                85                  90                  95

Thr Leu Phe Leu Phe Phe Ile Ala Ile Pro Gly Gln Val Thr Glu Gln
            100                 105                 110

Gln Gln Leu Gln Thr Arg Ala Asn Val Thr Arg Leu Cys Gln Val Thr
        115                 120                 125

Ser Thr Asp His Gly Arg Thr Trp Ser Ser Pro Arg Asp Leu Thr Asp
    130                 135                 140

Ala Ala Ile Gly Pro Ala Tyr Arg Glu Trp Ser Thr Phe Ala Val Gly
145                 150                 155                 160

Pro Gly His Cys Leu Gln Leu His Asp Arg Ala Arg Ser Leu Val Val
                165                 170                 175

Pro Ala Tyr Ala Tyr Arg Lys Leu His Pro Lys Gln Arg Pro Ile Pro
            180                 185                 190

Ser Ala Phe Cys Phe Leu Ser His Asp His Gly Arg Thr Trp Ala Arg
        195                 200                 205

Gly His Phe Val Ala Gln Asp Thr Leu Glu Cys Gln Val Ala Glu Val
    210                 215                 220

Glu Thr Gly Glu Gln Arg Val Val Thr Leu Asn Ala Arg Ser His Leu
225                 230                 235                 240

Arg Ala Arg Val Gln Ala Gln Ser Thr Asn Asp Gly Leu Asp Phe Gln
                245                 250                 255

Glu Ser Gln Leu Val Lys Lys Leu Val Glu Pro Pro Pro Gln Gly Cys
            260                 265                 270

Gln Gly Ser Val Ile Ser Phe Pro Ser Pro Arg Ser Gly Pro Gly Ser
        275                 280                 285

Pro Ala Gln Trp Leu Leu Tyr Thr His Pro Thr His Ser Trp Gln Arg
    290                 295                 300

Ala Asp Leu Gly Ala Tyr Leu Asn Pro Arg Pro Pro Ala Pro Glu Ala
305                 310                 315                 320

Trp Ser Glu Pro Val Leu Leu Ala Lys Gly Ser Cys Ala Tyr Ser Asp
                325                 330                 335

Leu Gln Ser Met Gly Thr Gly Pro Asp Gly Ser Pro Leu Phe Gly Cys
            340                 345                 350

Leu Tyr Glu Ala Asn Asp Tyr Glu Glu Ile Val Phe Leu Met Phe Thr
        355                 360                 365

Leu Lys Gln Ala Phe Pro Ala Glu Tyr Leu Pro Gln Gly Gly Gly Gly
    370                 375                 380

Ser Gly Gly Gly Gly Ser Asp Lys Thr His Thr Cys Pro Pro Cys Pro
385                 390                 395                 400

Ala Pro Glu Leu Leu Gly Gly Pro Ser Val Phe Leu Phe Pro Pro Lys
                405                 410                 415
```

Pro Lys Asp Thr Leu Met Ile Ser Arg Thr Pro Glu Val Thr Cys Val
420 425 430

Val Val Asp Val Ser His Glu Asp Pro Glu Val Lys Phe Asn Trp Tyr
435 440 445

Val Asp Gly Val Glu Val His Asn Ala Lys Thr Lys Pro Arg Glu Glu
450 455 460

Gln Tyr Asn Ser Thr Tyr Arg Val Val Ser Val Leu Thr Val Leu His
465 470 475 480

Gln Asp Trp Leu Asn Gly Lys Glu Tyr Lys Cys Lys Val Ser Asn Lys
485 490 495

Ala Leu Pro Ala Pro Ile Glu Lys Thr Ile Ser Lys Ala Lys Gly Gln
500 505 510

Pro Arg Glu Pro Gln Val Tyr Thr Leu Pro Pro Ser Arg Glu Glu Met
515 520 525

Thr Lys Asn Gln Val Ser Leu Thr Cys Leu Val Lys Gly Phe Tyr Pro
530 535 540

Ser Asp Ile Ala Val Glu Trp Glu Ser Asn Gly Gln Pro Glu Asn Asn
545 550 555 560

Tyr Lys Thr Thr Pro Pro Val Leu Asp Ser Asp Gly Ser Phe Phe Leu
565 570 575

Thr Ser Lys Leu Thr Val Asp Lys Ser Arg Trp Gln Gln Gly Asn Val
580 585 590

Phe Ser Cys Ser Val Met His Glu Ala Leu His Asn His Tyr Thr Gln
595 600 605

Lys Ser Leu Ser Leu Ser Pro Gly Lys
610 615

<210> SEQ ID NO 79
<211> LENGTH: 617
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 79

Met Ala Ser Leu Pro Tyr Leu Gln Lys Glu Ser Val Phe Gln Ser Gly
1 5 10 15

Ala His Ala Tyr Arg Ile Pro Ala Leu Leu Tyr Leu Pro Gly Gln Gln
20 25 30

Ser Leu Leu Ala Phe Ala Glu Gln Arg Ala Ser Lys Lys Asp Glu His
35 40 45

Ala Glu Leu Ile Val Leu Arg Arg Gly Asp Tyr Asp Ala Pro Thr His
50 55 60

Gln Val Gln Trp Gln Ala Gln Glu Val Val Ala Gln Ala Arg Leu Asp
65 70 75 80

Gly His Arg Ser Met Asn Pro Cys Pro Leu Tyr Asp Ala Gln Thr Gly
85 90 95

Thr Leu Phe Leu Phe Phe Ile Ala Ile Pro Gly Gln Val Thr Glu Gln
100 105 110

Gln Gln Leu Gln Thr Arg Ala Asn Val Thr Arg Leu Cys Gln Val Thr
115 120 125

Ser Thr Asp His Gly Arg Thr Trp Ser Ser Pro Arg Asp Leu Thr Asp
130 135 140

Ala Ala Ile Gly Pro Ala Tyr Arg Glu Trp Ser Thr Phe Ala Val Gly

-continued

```
145                 150                 155                 160

Pro Gly His Cys Leu Gln Leu His Asp Arg Ala Arg Ser Leu Val Val
                165                 170                 175

Pro Ala Tyr Ala Tyr Arg Lys Leu His Pro Lys Gln Arg Pro Ile Pro
            180                 185                 190

Ser Ala Phe Cys Phe Leu Ser His Asp His Gly Arg Thr Trp Ala Arg
        195                 200                 205

Gly His Phe Val Ala Gln Asp Thr Leu Glu Cys Gln Val Ala Glu Val
    210                 215                 220

Glu Thr Gly Glu Gln Arg Val Val Thr Leu Asn Ala Arg Ser His Leu
225                 230                 235                 240

Arg Ala Arg Val Gln Ala Gln Ser Thr Asn Asp Gly Leu Asp Phe Gln
                245                 250                 255

Glu Ser Gln Leu Val Lys Lys Leu Val Glu Pro Pro Pro Gln Gly Cys
            260                 265                 270

Gln Gly Ser Val Ile Ser Phe Pro Ser Pro Arg Ser Gly Pro Gly Ser
        275                 280                 285

Pro Ala Gln Trp Leu Leu Tyr Thr His Pro Thr His Ser Trp Gln Arg
    290                 295                 300

Ala Asp Leu Gly Ala Tyr Leu Asn Pro Arg Pro Pro Ala Pro Glu Ala
305                 310                 315                 320

Trp Ser Glu Pro Val Leu Leu Ala Lys Gly Ser Ala Ala Tyr Ser Asp
                325                 330                 335

Leu Gln Ser Met Gly Thr Gly Pro Asp Gly Ser Pro Leu Phe Gly Cys
            340                 345                 350

Leu Tyr Glu Ala Asn Asp Tyr Glu Glu Ile Val Phe Leu Met Phe Thr
        355                 360                 365

Leu Lys Gln Ala Phe Pro Ala Glu Tyr Leu Pro Gln Gly Gly Gly Gly
    370                 375                 380

Ser Gly Gly Gly Gly Ser Asp Lys Thr His Thr Cys Pro Pro Cys Pro
385                 390                 395                 400

Ala Pro Glu Leu Leu Gly Gly Pro Ser Val Phe Leu Phe Pro Pro Lys
                405                 410                 415

Pro Lys Asp Thr Leu Met Ile Ser Arg Thr Pro Glu Val Thr Cys Val
            420                 425                 430

Val Val Asp Val Ser His Glu Asp Pro Glu Val Lys Phe Asn Trp Tyr
        435                 440                 445

Val Asp Gly Val Glu Val His Asn Ala Lys Thr Lys Pro Arg Glu Glu
    450                 455                 460

Gln Tyr Asn Ser Thr Tyr Arg Val Val Ser Val Leu Thr Val Leu His
465                 470                 475                 480

Gln Asp Trp Leu Asn Gly Lys Glu Tyr Lys Cys Lys Val Ser Asn Lys
                485                 490                 495

Ala Leu Pro Ala Pro Ile Glu Lys Thr Ile Ser Lys Ala Lys Gly Gln
            500                 505                 510

Pro Arg Glu Pro Gln Val Tyr Thr Leu Pro Pro Ser Arg Glu Glu Met
        515                 520                 525

Thr Lys Asn Gln Val Ser Leu Thr Cys Leu Val Lys Gly Phe Tyr Pro
    530                 535                 540

Ser Asp Ile Ala Val Glu Trp Glu Ser Asn Gly Gln Pro Glu Asn Asn
545                 550                 555                 560

Tyr Lys Thr Thr Pro Pro Val Leu Asp Ser Asp Gly Ser Phe Phe Leu
                565                 570                 575
```

Thr Ser Lys Leu Thr Val Asp Lys Ser Arg Trp Gln Gln Gly Asn Val
580 585 590

Phe Ser Cys Ser Val Met His Glu Ala Leu His Asn His Tyr Thr Gln
595 600 605

Lys Ser Leu Ser Leu Ser Pro Gly Lys
610 615

<210> SEQ ID NO 80
<211> LENGTH: 1143
<212> TYPE: DNA
<213> ORGANISM: Salmonella typhimurium

<400> SEQUENCE: 80
acagtggaaa agtccgtggt gttcaaggcc gagggcgagc acttcaccga ccagaaaggc 60
aataccatcg tcggctctgg cagcggcggc accaccaagt actttagaat ccccgccatg 120
tgcaccacca gcaagggcac cattgtggtg ttcgccgacg ccagacacaa caccgccagc 180
gatcagagct tcatcgatac cgctgccgcc agatctaccg atggcggcaa gacctggaac 240
aagaagatcg ccatctacaa cgaccgcgtg aacagcaagc tgagcagagt gatggaccct 300
acctgcatcg tggccaacat ccagggcaga gaaaccatcc tggtcatggt cggaaagtgg 360
aacaacaacg ataagacctg gggcgcctac agagacaagg cccctgatac cgattgggac 420
ctcgtgctgt acaagagcac cgatgacggc gtgaccttca gcaaggtgga aacaaacatc 480
cacgacatcg tgaccaagaa cggcaccatc tctgccatgc tcggcggcgt tggatctggc 540
ctgcaactga atgatggcaa gctggtgttc cccgtgcaga tggtccgaac aaagaatatc 600
accaccgtgc tgaataccag cttcatctac agcaccgacg gcatcacatg gtccctgcct 660
agcggctact gtgaaggctt tggcagcgag aacaacatca tcgagttcaa cgccagcctg 720
gtcaacaaca tccggaacag cggcctgcgg agaagcttcg agacaaagga cttcggaaag 780
acgtggaccg agtttcctcc aatggacaag aaggtggaca accggaacca cggcgtgcag 840
ggcagcacaa tcacaatccc tagcggcaac aaactggtgg ccgctcactc tagcgcccag 900
aacaagaaca acgactacac cagaagcgac atcagcctgt acgcccacaa cctgtacagc 960
ggcgaagtga agctgatcga cgacttctac cccaaagtgg gcaatgccag cggagccggc 1020
tacagctgtc tgagctaccg gaaaaatgtg gacaaagaaa ccctgtacgt ggtgtacgag 1080
gccaacggca gcatcgagtt tcaggacctg agcagacatc tgcccgtgat caagagctac 1140
aac 1143

<210> SEQ ID NO 81
<211> LENGTH: 781
<212> TYPE: PRT
<213> ORGANISM: Vibrio cholera

<400> SEQUENCE: 81

Met Arg Phe Lys Asn Val Lys Lys Thr Ala Leu Met Leu Ala Met Phe
1 5 10 15

Gly Met Ala Thr Ser Ser Asn Ala Ala Leu Phe Asp Tyr Asn Ala Thr
20 25 30

Gly Asp Thr Glu Phe Asp Ser Pro Ala Lys Gln Gly Trp Met Gln Asp
35 40 45

Asn Thr Asn Asn Gly Ser Gly Val Leu Thr Asn Ala Asp Gly Met Pro
50 55 60

Ala Trp Leu Val Gln Gly Ile Gly Gly Arg Ala Gln Trp Thr Tyr Ser

-continued

```
65                  70                  75                  80

Leu Ser Thr Asn Gln His Ala Gln Ala Ser Ser Phe Gly Trp Arg Met
                85                  90                  95

Thr Thr Glu Met Lys Val Leu Ser Gly Gly Met Ile Thr Asn Tyr Tyr
            100                 105                 110

Ala Asn Gly Thr Gln Arg Val Leu Pro Ile Ile Ser Leu Asp Ser Ser
        115                 120                 125

Gly Asn Leu Val Val Glu Phe Glu Gly Gln Thr Gly Arg Thr Val Leu
    130                 135                 140

Ala Thr Gly Thr Ala Ala Thr Glu Tyr His Lys Phe Glu Leu Val Phe
145                 150                 155                 160

Leu Pro Gly Ser Asn Pro Ser Ala Ser Phe Tyr Phe Asp Gly Lys Leu
                165                 170                 175

Ile Arg Asp Asn Ile Gln Pro Thr Ala Ser Lys Gln Asn Met Ile Val
            180                 185                 190

Trp Gly Asn Gly Ser Ser Asn Thr Asp Gly Val Ala Ala Tyr Arg Asp
        195                 200                 205

Ile Lys Phe Glu Ile Gln Gly Asp Val Ile Phe Arg Gly Pro Asp Arg
    210                 215                 220

Ile Pro Ser Ile Val Ala Ser Ser Val Thr Pro Gly Val Val Thr Ala
225                 230                 235                 240

Phe Ala Glu Lys Arg Val Gly Gly Gly Asp Pro Gly Ala Leu Ser Asn
                245                 250                 255

Thr Asn Asp Ile Ile Thr Arg Thr Ser Arg Asp Gly Gly Ile Thr Trp
            260                 265                 270

Asp Thr Glu Leu Asn Leu Thr Glu Gln Ile Asn Val Ser Asp Glu Phe
        275                 280                 285

Asp Phe Ser Asp Pro Arg Pro Ile Tyr Asp Pro Ser Ser Asn Thr Val
    290                 295                 300

Leu Val Ser Tyr Ala Arg Trp Pro Thr Asp Ala Ala Gln Asn Gly Asp
305                 310                 315                 320

Arg Ile Lys Pro Trp Met Pro Asn Gly Ile Phe Tyr Ser Val Tyr Asp
                325                 330                 335

Val Ala Ser Gly Asn Trp Gln Ala Pro Ile Asp Val Thr Asp Gln Val
            340                 345                 350

Lys Glu Arg Ser Phe Gln Ile Ala Gly Trp Gly Gly Ser Glu Leu Tyr
        355                 360                 365

Arg Arg Asn Thr Ser Leu Asn Ser Gln Gln Asp Trp Gln Ser Asn Ala
    370                 375                 380

Lys Ile Arg Ile Val Asp Gly Ala Ala Asn Gln Ile Gln Val Ala Asp
385                 390                 395                 400

Gly Ser Arg Lys Tyr Val Val Thr Leu Ser Ile Asp Glu Ser Gly Gly
                405                 410                 415

Leu Val Ala Asn Leu Asn Gly Val Ser Ala Pro Ile Ile Leu Gln Ser
            420                 425                 430

Glu His Ala Lys Val His Ser Phe His Asp Tyr Glu Leu Gln Tyr Ser
        435                 440                 445

Ala Leu Asn His Thr Thr Thr Leu Phe Val Asp Gly Gln Gln Ile Thr
    450                 455                 460

Thr Trp Ala Gly Glu Val Ser Gln Glu Asn Asn Ile Gln Phe Gly Asn
465                 470                 475                 480

Ala Asp Ala Gln Ile Asp Gly Arg Leu His Val Gln Lys Ile Val Leu
                485                 490                 495
```

-continued

Thr Gln Gln Gly His Asn Leu Val Glu Phe Asp Ala Phe Tyr Leu Ala
500 505 510

Gln Gln Thr Pro Glu Val Glu Lys Asp Leu Glu Lys Leu Gly Trp Thr
515 520 525

Lys Ile Lys Thr Gly Asn Thr Met Ser Leu Tyr Gly Asn Ala Ser Val
530 535 540

Asn Pro Gly Pro Gly His Gly Ile Thr Leu Thr Arg Gln Gln Asn Ile
545 550 555 560

Ser Gly Ser Gln Asn Gly Arg Leu Ile Tyr Pro Ala Ile Val Leu Asp
565 570 575

Arg Phe Phe Leu Asn Val Met Ser Ile Tyr Ser Asp Asp Gly Gly Ser
580 585 590

Asn Trp Gln Thr Gly Ser Thr Leu Pro Ile Pro Phe Arg Trp Lys Ser
595 600 605

Ser Ser Ile Leu Glu Thr Leu Glu Pro Ser Glu Ala Asp Met Val Glu
610 615 620

Leu Gln Asn Gly Asp Leu Leu Leu Thr Ala Arg Leu Asp Phe Asn Gln
625 630 635 640

Ile Val Asn Gly Val Asn Tyr Ser Pro Arg Gln Gln Phe Leu Ser Lys
645 650 655

Asp Gly Gly Ile Thr Trp Ser Leu Leu Glu Ala Asn Asn Ala Asn Val
660 665 670

Phe Ser Asn Ile Ser Thr Gly Thr Val Asp Ala Ser Ile Thr Arg Phe
675 680 685

Glu Gln Ser Asp Gly Ser His Phe Leu Leu Phe Thr Asn Pro Gln Gly
690 695 700

Asn Pro Ala Gly Thr Asn Gly Arg Gln Asn Leu Gly Leu Trp Phe Ser
705 710 715 720

Phe Asp Glu Gly Val Thr Trp Lys Gly Pro Ile Gln Leu Val Asn Gly
725 730 735

Ala Ser Ala Tyr Ser Asp Ile Tyr Gln Leu Asp Ser Glu Asn Ala Ile
740 745 750

Val Ile Val Glu Thr Asp Asn Ser Asn Met Arg Ile Leu Arg Met Pro
755 760 765

Ile Thr Leu Leu Lys Gln Lys Leu Thr Leu Ser Gln Asn
770 775 780

<210> SEQ ID NO 82
<211> LENGTH: 2424
<212> TYPE: DNA
<213> ORGANISM: Vibrio cholera

<400> SEQUENCE: 82
ttgtcaatca agatgacttc acaacgaaga agagcatcga ttcacaagga aacagattct 60
aatataaagg gagtagatat gcgtttcaaa aacgtaaaga aaaccgcttt aatgcttgca 120
atgttcggta tggcgacaag ctcaaacgcc gcactttttg actataacgc aacgggtgac 180
actgagtttg acagtccagc caaacaggga tggatgcaag acaacacgaa taatggcagc 240
ggcgttttaa ccaatgcaga tggaatgccc gcttggttgg tgcaaggtat tggagggaga 300
gctcaatgga catattctct ctctactaat caacatgccc aagcatcaag tttcggttgg 360
cgaatgacga cagaaatgaa agtgctcagt ggtggaatga tcacaaacta ctacgccaac 420
ggcactcagc gtgtcttacc catcatttca ttagatagca gtggtaactt agttgttgag 480

```
tttgaagggc aaactggacg caccgttttg gcaaccggca cagcagcaac ggaatatcat    540

aaatttgaat tggtattcct tcctggaagt aacccatccg ctagctttta cttcgatggc    600

aaactcattc gtgacaacat ccagccgact gcatcaaaac aaaatatgat cgtatggggg    660

aatggctcat caaatacgga tggtgtcgcc gcttatcgtg atattaagtt tgaaattcaa    720

ggcgacgtca tcttcagagg cccagaccgt ataccgtcca ttgtagcaag tagcgtaaca    780

ccaggggtgg taaccgcatt tgcagagaaa cgtgtggggg gaggagatcc cggtgctctg    840

agtaatacca atgacataat cactcgtacc tcacgagatg gcggtataac ttgggatacc    900

gagctcaacc tcactgagca aatcaatgtc agtgatgagt ttgatttctc cgatcctcgg    960

cctatctatg atccttcctc caatacggtt cttgtctctt atgctcgatg gccgaccgat   1020

gccgctcaaa acggagatcg aataaaacca tggatgccaa acggtatttt ttacagcgtc   1080

tatgatgttg catcagggaa ctggcaagcg cctatcgatg ttaccgatca ggtgaaagaa   1140

cgcagtttcc aaatcgctgg ttggggtggt tcagagctgt atcgccgaaa taccagccta   1200

aatagccagc aagactggca atcaaacgct aagatccgaa ttgttgatgg tgcagcgaac   1260

cagatacaag ttgccgatgg tagccgaaaa tatgttgtca cactgagtat tgatgaatca   1320

ggtggtctag tcgctaatct aaacggtgtt agtgctccga ttatcctgca atctgaacac   1380

gcaaaggtac actctttcca tgactacgaa cttcaatatt cggcgttaaa ccacaccaca   1440

acgttattcg tggatggtca gcaaatcaca acttgggctg gcgaagtatc gcaggagaac   1500

aacattcagt ttggtaatgc ggatgcccaa attgacggca gactgcatgt gcaaaaaatt   1560

gttctcacac agcaaggcca taacctcgtg gagtttgatg ctttctattt agcacagcaa   1620

acccctgaag tagagaaaga ccttgaaaag cttggttgga caaaaattaa aacgggcaac   1680

accatgagtt tgtatggaaa tgccagtgtc aacccaggac cgggtcatgg catcacccct   1740

actcgacaac aaaatatcag tggcagccaa aacggccgct tgatctaccc agcgattgtg   1800

cttgatcgtt tcttcttgaa cgtcatgtct atttacagtg atgatggcgg ttcaaactgg   1860

caaaccggtt caacactccc tatccccttt cgctggaaga gttcgagtat cctagaaact   1920

ctcgaaccta gtgaagctga tatggttgaa ctccaaaacg gtgatctact ccttactgca   1980

cgccttgatt ttaaccaaat cgttaatggt gtgaactata gcccacgcca gcaatttttg   2040

agtaaagatg gtggaatcac gtggagccta cttgaggcta acaacgctaa cgtctttagc   2100

aatatcagta ctggtaccgt tgatgcttct attactcggt tcgagcaaag tgacggtagc   2160

catttcttac tctttactaa cccacaagga aaccctgcgg ggacaaatgg caggcaaaat   2220

ctaggcttat ggtttagctt cgatgaaggg gtgacatgga aaggaccaat tcaacttgtt   2280

aatggtgcat cggcatattc tgatatttat caattggatt cggaaaatgc gattgtcatt   2340

gttgaaacgg ataattcaaa tatgcgaatt cttcgtatgc ctatcacatt gctaaaacag   2400

aagctgacct tatcgcaaaa ctaa                                          2424
```

<210> SEQ ID NO 83
<211> LENGTH: 409
<212> TYPE: PRT
<213> ORGANISM: Mus sp.

<400> SEQUENCE: 83

```
Met Val Gly Ala Asp Pro Thr Arg Pro Arg Gly Pro Leu Ser Tyr Trp
1               5                   10                  15

Ala Gly Arg Arg Gly Gln Gly Leu Ala Ala Ile Phe Leu Leu Leu Val
            20                  25                  30
```

```
Ser Ala Ala Glu Ser Glu Ala Arg Ala Glu Asp Asp Phe Ser Leu Val
        35                  40                  45

Gln Pro Leu Val Thr Met Glu Gln Leu Leu Trp Val Ser Gly Lys Gln
    50                  55                  60

Ile Gly Ser Val Asp Thr Phe Arg Ile Pro Leu Ile Thr Ala Thr Pro
65                  70                  75                  80

Arg Gly Thr Leu Leu Ala Phe Ala Glu Ala Arg Lys Lys Ser Ala Ser
                85                  90                  95

Asp Glu Gly Ala Lys Phe Ile Ala Met Arg Arg Ser Thr Asp Gln Gly
            100                 105                 110

Ser Thr Trp Ser Ser Thr Ala Phe Ile Val Asp Asp Gly Glu Ala Ser
        115                 120                 125

Asp Gly Leu Asn Leu Gly Ala Val Val Asn Asp Val Asp Thr Gly Ile
    130                 135                 140

Val Phe Leu Ile Tyr Thr Leu Cys Ala His Lys Val Asn Cys Gln Val
145                 150                 155                 160

Ala Ser Thr Met Leu Val Trp Ser Lys Asp Asp Gly Ile Ser Trp Ser
                165                 170                 175

Pro Pro Arg Asn Leu Ser Val Asp Ile Gly Thr Glu Met Phe Ala Pro
            180                 185                 190

Gly Pro Gly Ser Gly Ile Gln Lys Gln Arg Glu Pro Gly Lys Gly Arg
        195                 200                 205

Leu Ile Val Cys Gly His Gly Thr Leu Glu Arg Asp Gly Val Phe Cys
    210                 215                 220

Leu Leu Ser Asp Asp His Gly Ala Ser Trp His Tyr Gly Thr Gly Val
225                 230                 235                 240

Ser Gly Ile Pro Phe Gly Gln Pro Lys His Asp His Asp Phe Asn Pro
                245                 250                 255

Asp Glu Cys Gln Pro Tyr Glu Leu Pro Asp Gly Ser Val Ile Ile Asn
            260                 265                 270

Ala Arg Asn Gln Asn Asn Tyr His Cys Arg Cys Arg Ile Val Leu Arg
        275                 280                 285

Ser Tyr Asp Ala Cys Asp Thr Leu Arg Pro Arg Asp Val Thr Phe Asp
    290                 295                 300

Pro Glu Leu Val Asp Pro Val Val Ala Ala Gly Ala Leu Ala Thr Ser
305                 310                 315                 320

Ser Gly Ile Val Phe Phe Ser Asn Pro Ala His Pro Glu Phe Arg Val
                325                 330                 335

Asn Leu Thr Leu Arg Trp Ser Phe Ser Asn Gly Thr Ser Trp Leu Lys
            340                 345                 350

Glu Arg Val Gln Val Trp Pro Gly Pro Ser Gly Tyr Ser Ser Leu Thr
        355                 360                 365

Ala Leu Glu Asn Ser Thr Asp Gly Lys Lys Gln Pro Pro Gln Leu Phe
    370                 375                 380

Val Leu Tyr Glu Lys Gly Leu Asn Arg Tyr Thr Glu Ser Ile Ser Met
385                 390                 395                 400

Val Lys Ile Ser Val Tyr Gly Thr Leu
                405
```

<210> SEQ ID NO 84
<211> LENGTH: 393
<212> TYPE: PRT
<213> ORGANISM: Mus sp.

<400> SEQUENCE: 84

Met Thr Val Gln Pro Ser Pro Trp Phe Ser Asp Leu Arg Pro Met Ala
1               5                   10                  15

Thr Cys Pro Val Leu Gln Lys Glu Thr Leu Phe Arg Thr Gly Val His
            20                  25                  30

Ala Tyr Arg Ile Pro Ala Leu Leu Tyr Leu Lys Lys Gln Lys Thr Leu
        35                  40                  45

Leu Ala Phe Ala Glu Lys Arg Ala Ser Lys Thr Asp Glu His Ala Glu
    50                  55                  60

Leu Ile Val Leu Arg Arg Gly Ser Tyr Asn Glu Ala Thr Asn Arg Val
65                  70                  75                  80

Lys Trp Gln Pro Glu Glu Val Val Thr Gln Ala Gln Leu Glu Gly His
                85                  90                  95

Arg Ser Met Asn Pro Cys Pro Leu Tyr Asp Lys Gln Thr Lys Thr Leu
            100                 105                 110

Phe Leu Phe Phe Ile Ala Val Pro Gly Arg Val Ser Glu His His Gln
        115                 120                 125

Leu His Thr Lys Val Asn Val Thr Arg Leu Cys Cys Val Ser Ser Thr
    130                 135                 140

Asp His Gly Arg Thr Trp Ser Pro Ile Gln Asp Leu Thr Glu Thr Thr
145                 150                 155                 160

Ile Gly Ser Thr His Gln Glu Trp Ala Thr Phe Ala Val Gly Pro Gly
                165                 170                 175

His Cys Leu Gln Leu Arg Asn Pro Ala Gly Ser Leu Leu Val Pro Ala
            180                 185                 190

Tyr Ala Tyr Arg Lys Leu His Pro Ala Gln Lys Pro Thr Pro Phe Ala
        195                 200                 205

Phe Cys Phe Ile Ser Leu Asp His Gly His Thr Trp Lys Leu Gly Asn
    210                 215                 220

Phe Val Ala Glu Asn Ser Leu Glu Cys Gln Val Ala Glu Val Gly Thr
225                 230                 235                 240

Gly Ala Gln Arg Met Val Tyr Leu Asn Ala Arg Ser Phe Leu Gly Ala
                245                 250                 255

Arg Val Gln Ala Gln Ser Pro Asn Asp Gly Leu Asp Phe Gln Asp Asn
            260                 265                 270

Arg Val Val Ser Lys Leu Val Glu Pro Pro His Gly Cys His Gly Ser
        275                 280                 285

Val Val Ala Phe His Asn Pro Ile Ser Lys Pro His Ala Leu Asp Thr
    290                 295                 300

Trp Leu Leu Tyr Thr His Pro Thr Asp Ser Arg Asn Arg Thr Asn Leu
305                 310                 315                 320

Gly Val Tyr Leu Asn Gln Met Pro Leu Asp Pro Thr Ala Trp Ser Glu
                325                 330                 335

Pro Thr Leu Leu Ala Met Gly Ile Cys Ala Tyr Ser Asp Leu Gln Asn
            340                 345                 350

Met Gly Gln Gly Pro Asp Gly Ser Pro Gln Phe Gly Cys Leu Tyr Glu
        355                 360                 365

Ser Gly Asn Tyr Glu Glu Ile Ile Phe Leu Ile Phe Thr Leu Lys Gln
    370                 375                 380

Ala Phe Pro Thr Val Phe Asp Ala Gln
385                 390

<210> SEQ ID NO 85

<211> LENGTH: 418
<212> TYPE: PRT
<213> ORGANISM: Mus sp.

<400> SEQUENCE: 85

```
Met Glu Glu Val Pro Pro Tyr Ser Leu Ser Ser Thr Leu Phe Gln Gln
1               5                   10                  15

Glu Glu Gln Ser Gly Val Thr Tyr Arg Ile Pro Ala Leu Leu Tyr Leu
            20                  25                  30

Pro Pro Thr His Thr Phe Leu Ala Phe Ala Glu Lys Arg Thr Ser Val
        35                  40                  45

Arg Asp Glu Asp Ala Ala Cys Leu Val Leu Arg Arg Gly Leu Met Lys
    50                  55                  60

Gly Arg Ser Val Gln Trp Gly Pro Gln Arg Leu Leu Met Glu Ala Thr
65                  70                  75                  80

Leu Pro Gly His Arg Thr Met Asn Pro Cys Pro Val Trp Glu Lys Asn
                85                  90                  95

Thr Gly Arg Val Tyr Leu Phe Phe Ile Cys Val Arg Gly His Val Thr
            100                 105                 110

Glu Arg Cys Gln Ile Val Trp Gly Lys Asn Ala Ala Arg Leu Cys Phe
        115                 120                 125

Leu Cys Ser Glu Asp Ala Gly Cys Ser Trp Gly Glu Val Lys Asp Leu
    130                 135                 140

Thr Glu Glu Val Ile Gly Ser Glu Val Lys Arg Trp Ala Thr Phe Ala
145                 150                 155                 160

Val Gly Pro Gly His Gly Ile Gln Leu His Ser Gly Arg Leu Ile Ile
                165                 170                 175

Pro Ala Tyr Ala Tyr Tyr Val Ser Arg Trp Phe Leu Cys Phe Ala Cys
            180                 185                 190

Ser Val Lys Pro His Ser Leu Met Ile Tyr Ser Asp Asp Phe Gly Val
        195                 200                 205

Thr Trp His His Gly Lys Phe Ile Glu Pro Gln Val Thr Gly Glu Cys
    210                 215                 220

Gln Val Ala Glu Val Ala Gly Thr Ala Gly Asn Pro Val Leu Tyr Cys
225                 230                 235                 240

Ser Ala Arg Thr Pro Ser Arg Phe Arg Ala Glu Ala Phe Ser Thr Asp
                245                 250                 255

Ser Gly Gly Cys Phe Gln Lys Pro Thr Leu Asn Pro Gln Leu His Glu
            260                 265                 270

Pro Arg Thr Gly Cys Gln Gly Ser Val Val Ser Phe Arg Pro Leu Lys
        275                 280                 285

Met Pro Asn Thr Tyr Gln Asp Ser Ile Gly Lys Gly Ala Pro Ala Thr
    290                 295                 300

Gln Lys Cys Pro Leu Leu Asp Ser Pro Leu Glu Val Glu Lys Gly Ala
305                 310                 315                 320

Glu Thr Pro Ser Ala Thr Trp Leu Leu Tyr Ser His Pro Thr Ser Lys
                325                 330                 335

Arg Lys Arg Ile Asn Leu Gly Ile Tyr Tyr Asn Arg Asn Pro Leu Glu
            340                 345                 350

Val Asn Cys Trp Ser Arg Pro Trp Ile Leu Asn Arg Gly Pro Ser Gly
        355                 360                 365

Tyr Ser Asp Leu Ala Val Val Glu Glu Gln Asp Leu Val Ala Cys Leu
    370                 375                 380

Phe Glu Cys Gly Glu Lys Asn Glu Tyr Glu Arg Ile Asp Phe Cys Leu
```

```
385                 390                 395                 400

Phe Ser Asp His Glu Val Leu Ser Cys Glu Asp Cys Thr Ser Pro Ser
                405                 410                 415

Ser Asp


<210> SEQ ID NO 86
<211> LENGTH: 501
<212> TYPE: PRT
<213> ORGANISM: Mus sp.

<400> SEQUENCE: 86

Met Glu Thr Ala Gly Ala Pro Phe Cys Phe His Val Asp Ser Leu Val
1               5                   10                  15

Pro Cys Ser Tyr Trp Lys Val Met Gly Pro Thr Arg Val Pro Arg Arg
            20                  25                  30

Thr Val Leu Phe Gln Arg Glu Arg Thr Gly Leu Thr Tyr Arg Val Pro
        35                  40                  45

Ala Leu Leu Cys Val Pro Pro Arg Pro Thr Leu Leu Ala Phe Ala Glu
    50                  55                  60

Gln Arg Leu Ser Pro Asp Asp Ser His Ala His Arg Leu Val Leu Arg
65                  70                  75                  80

Arg Gly Thr Leu Thr Arg Gly Ser Val Arg Trp Gly Thr Leu Ser Val
                85                  90                  95

Leu Glu Thr Ala Val Leu Glu Glu His Arg Ser Met Asn Pro Cys Pro
            100                 105                 110

Val Leu Asp Glu His Ser Gly Thr Ile Phe Leu Phe Phe Ile Ala Val
        115                 120                 125

Leu Gly His Thr Pro Glu Ala Val Gln Ile Ala Thr Gly Lys Asn Ala
    130                 135                 140

Ala Arg Leu Cys Cys Val Thr Ser Cys Asp Ala Gly Leu Thr Trp Gly
145                 150                 155                 160

Ser Val Arg Asp Leu Thr Glu Glu Ala Ile Gly Ala Ala Leu Gln Asp
                165                 170                 175

Trp Ala Thr Phe Ala Val Gly Pro Gly His Gly Val Gln Leu Arg Ser
            180                 185                 190

Gly Arg Leu Leu Val Pro Ala Tyr Thr Tyr His Val Asp Arg Arg Glu
        195                 200                 205

Cys Phe Gly Lys Ile Cys Trp Thr Ser Pro His Ser Leu Ala Phe Tyr
    210                 215                 220

Ser Asp Asp His Gly Ile Ser Trp His Cys Gly Gly Leu Val Pro Asn
225                 230                 235                 240

Leu Arg Ser Gly Glu Cys Gln Leu Ala Ala Val Asp Gly Asp Phe Leu
                245                 250                 255

Tyr Cys Asn Ala Arg Ser Pro Leu Gly Asn Arg Val Gln Ala Leu Ser
            260                 265                 270

Ala Asp Glu Gly Thr Ser Phe Leu Pro Gly Glu Leu Val Pro Thr Leu
        275                 280                 285

Ala Glu Thr Ala Arg Gly Cys Gln Gly Ser Ile Val Gly Phe Leu Ala
    290                 295                 300

Pro Pro Ser Ile Glu Pro Gln Asp Asp Arg Trp Thr Gly Ser Pro Arg
305                 310                 315                 320

Asn Thr Pro His Ser Pro Cys Phe Asn Leu Arg Val Gln Glu Ser Ser
                325                 330                 335

Gly Glu Gly Ala Arg Gly Leu Leu Glu Arg Trp Met Pro Arg Leu Pro
```

```
            340                 345                 350

Leu Cys Tyr Pro Gln Ser Arg Ser Pro Glu Asn His Gly Leu Glu Pro
        355                 360                 365

Gly Ser Asp Gly Asp Lys Thr Ser Trp Thr Pro Glu Cys Pro Met Ser
    370                 375                 380

Ser Asp Ser Met Leu Gln Ser Pro Thr Trp Leu Leu Tyr Ser His Pro
385                 390                 395                 400

Ala Gly Arg Arg Ala Arg Leu His Met Gly Ile Tyr Leu Ser Arg Ser
                405                 410                 415

Pro Leu Asp Pro His Ser Trp Thr Glu Pro Trp Val Ile Tyr Glu Gly
            420                 425                 430

Pro Ser Gly Tyr Ser Asp Leu Ala Phe Leu Gly Pro Met Pro Gly Ala
        435                 440                 445

Ser Leu Val Phe Ala Cys Leu Phe Glu Ser Gly Thr Arg Thr Ser Tyr
    450                 455                 460

Glu Asp Ile Ser Phe Cys Leu Phe Ser Leu Ala Asp Val Leu Glu Asn
465                 470                 475                 480

Val Pro Thr Gly Leu Glu Met Leu Ser Leu Arg Asp Lys Ala Gln Gly
                485                 490                 495

His Cys Trp Pro Ser
            500


<210> SEQ ID NO 87
<211> LENGTH: 3850
<212> TYPE: DNA
<213> ORGANISM: Mus sp.

<400> SEQUENCE: 87

gggtcacatg ctgatggact aattggagtc gcggcagcgc gggctgcggc ccccaagggg      60

aggggtcgga gtgacgtgcg cgcttttaaa gggccgaggt cagctgacgg cttgccaccg     120

gtgaccagtt cctggacagg gatcgccggg agctatggtg ggggcagacc cgaccagacc     180

ccggggaccg ctgagctatt gggcgggccg tcggggtcag ggctcgcag cgatcttcct     240

gctcctggtg tccgcggcgg aatccgaggc cagggcagag gatgacttca gcctggtgca     300

gccgctggtg accatggagc agctgctgtg ggtgagcggg aagcagatcg gctctgtaga     360

cactttccgc atcccgctca tcacagccac ccctcggggc acgctcctgg ccttcgctga     420

ggccaggaaa aaatctgcat ccgatgaggg ggccaagttc atcgccatga ggaggtccac     480

ggaccagggt agcacgtggt cctctacagc cttcatcgta gacgatgggg aggcctccga     540

tggcctgaac ctgggcgctg tggtgaacga tgtagacaca gggatagtgt tccttatcta     600

taccctctgt gctcacaagg tcaactgcca ggtggcctct accatgttgg tttggagtaa     660

ggacgacggc atttcctgga gcccaccccg gaatctctct gtggatattg gcacagagat     720

gtttgcccct ggacctggct caggcattca gaaacagcgg gagcctggga agggccggct     780

cattgtgtgt ggacacggga cgctggagcg agatggggtc ttctgtctcc tcagtgatga     840

ccacggtgcc tcctggcact acggcactgg agtgagcggc attccctttg gccagcccaa     900

acacgatcac gatttcaacc ccgacgagtg ccagccctac gagcttccag atggctcggt     960

catcatcaac gcccggaacc agaataacta ccattgccgc tgcaggatcg tcctccgcag    1020

ctatgacgcc tgtgacaccc tcaggccccg ggatgtgacc ttcgaccctg agctcgtgga    1080

ccctgtggta gctgcaggag cactagccac cagctccggc attgtcttct tctccaatcc    1140

agcccaccct gagttccgag tgaacctgac cctgcgctgg agtttcagca atggtacatc    1200
```

```
ctggcagaag gagagggtcc aggtgtggcc gggacccagc ggctactcgt ccctgacagc   1260
cctggaaaac agcacggatg gaaagaagca gcccccgcag ctgttcgttc tgtacgagaa   1320
aggcctgaac cggtacaccg agagcatctc catggtcaaa atcagcgtct acggcacgct   1380
ctgagccccg tgcccaaagg acaccaagtc ctggtcgctg acttcacagc tctctggacc   1440
atctgcagag ggtgcctgaa acacagctct tcctctgaac tctgaccttt tgcaacttct   1500
catcaacagg gaagtctctt cgttatgact taacacccag cttcctctcg gggcaggaag   1560
tccctccgtc accaagagca ctttttttcca gtatgctggg gatggcccct gtccattctc   1620
ttccaggaca acggagctgt gcctttctgg gacaggatgg gggaggggct ccccctggag   1680
agatgaacag atacgaactc agggaactga gaaggcccgg tgtcctaggg tacaaaggca   1740
ggtactagat gtgattgctg aaagtcccca gggcagagtg tcctttcaga gcaaggataa   1800
gcacacctac gtgtgcacct ttgattattt atgaatcgaa atatttgtaa cttaaaattt   1860
ttgatgcaga aaaagcgttt gtggagtctg tggttctgtc tgctcacgcc ttcccaattg   1920
cctcctggag agacaggaag gcagctggaa gaggagccga tgtacttact gggaagcaga   1980
aacccctaga ttccatcctg gctgctgctg tttgcaagtg tcaaagatgg gggggcgtgt   2040
ttatatttta tatttctaag atggggtggc ataggaaata gggaacagat gtgtaaaacc   2100
agatgggaag gacagtctgt gagaaaggag caagcagttg ctgcaggtgt gggagagcaa   2160
agcccttctc cacgtggaaa gagcccagat ggacgctaag catgttgggc acctgtaacc   2220
ccgcactcgc tggactgacg gtgtagctca gtggtggagc tagtacttgg aacgcctaag   2280
actctgggtt cagtccttgg gggggggggt atgtgtttat tgagaggaag gtgtacgtac   2340
tgtaggtcag aggacagctt actggagttg tctctctcct tcacgctgtg agtcctgtgg   2400
aatgacctca ggtgtcagag ttgggggcag gtgcctttgc cagctgagcc atcttgctgt   2460
ctctgcttta atttaaaaaa aaaaaaaaaa aagaatatta aggtctgagg gattcgggct   2520
gcgttcattt caattagagg gtcatatttc ttttgacatt tcttctctaa gaaatgttaa   2580
gatcatttgt tctgtgtgat agaggtatag ctccattgta tgtcagcagt gagggatcct   2640
gtgcatttta tccagagttt gtacggtgtt ctaggggctg ctagtgcagc ccagtgctaa   2700
acacttcagc atgcacaagg cctcaatcag tgcatgcatg tgcacacaca cacagacaca   2760
cacgtacaca ctgacacagg tacacaaata cacactggcc cacatgtaca catcgactca   2820
caggtacaca gacccacttt gacacacata tacacagaca caaacgcact ggcacacaca   2880
tatacacagg cacacatgga tagatggaca cacgtgtaca catacacaca cacacagaaa   2940
tacaaatgtt caggttttct aaaaaaaaaa aaattagaga cgtgttgact tcatttttag   3000
caaaaatcct gtcatgtatc ttaaagtgga ttgaacccac tatgtagccc aggctggcct   3060
ccaaatgggc atccttctgc ctcagtctcc cgagggctag gataacagga gtatgccatc   3120
acacctggct aatagaaatt ttcaaaattg tttgtttgaa ggtgactctt actatattgc   3180
ctaactgatc tccagttcgt gaaatcctcc tgcctcagaa ccaggactgt caatataacc   3240
caccaagaca ggccaacatt cacaattgat tgttagtttg tggtctgaat caaggtctta   3300
tactgtagcc caggctagcc cggaatacac gatatctcca gtgcttcaga tcctcagttc   3360
taactaagca tggccacatc catgtttaac tgcaaatttg atgttaccat ggtttggttt   3420
ggtttggttt ggtttggttt ggtttggttt ggtttttgg ccattttttt tttctcatgc   3480
tgaggccttg tgctctcaag ttggggagac agcatggagg gtagctgcaa ctgtaacccc   3540
```

agttccaggg gacctgacac cctctggcct ccacaagtat taggcacatc tgtggtgcac 3600
agacatacaa tcaggcaaaa tattcataca cataaaataa aataatttaa aacaaaagca 3660
aaaatcagga cctaagaaaa aaatctattc ctgattcttt tatgttttgt ttgtatttta 3720
tcaagacagg gttgtttctc tgtatagccc tggctgtctt ggaattcact ctgtagacca 3780
ggctggcctc aaactcagaa atcctcctgc ctttgccttc caagtgctgg aattaaaggc 3840
atgcgccacc 3850

<210> SEQ ID NO 88
<211> LENGTH: 1722
<212> TYPE: DNA
<213> ORGANISM: Mus sp.

<400> SEQUENCE: 88
gacatgaccc aaacggcccc tggctgcaag gtaatatcgg aagttgacta agaatggacg 60
ccccaccact gactgacccg ccccctgagt ctgagattgg acttgtctct ggatacagtc 120
atactttgag gtactacaag ttagaaactg ttaggttact cagttcagtc catgacagtc 180
caaccttctc catggttttc cgatctcagg cccatggcga cctgccctgt cctgcagaag 240
gagacactgt tccgcacagg cgtccatgct tacagaatcc ctgctctgct ctacctgaag 300
aagcagaaga ccctgctggc ctttgcggaa aagcgagcca gcaagacgga tgagcacgca 360
gagttgattg tcctgagaag aggaagctac aacgaagcca ccaaccgtgt caagtggcag 420
cctgaggaag tggtgaccca agcccagctg gaaggccacc gctccatgaa tccatgtccc 480
ttgtatgaca agcaaacaaa gaccctcttc cttttcttca tcgctgtccc tgggcgtgta 540
tcagaacatc atcagctcca cactaaggtt aatgtcacac ggctgtgctg tgtcagcagc 600
actgaccatg ggaggacctg gagccccatc caggacctca cagagaccac cattggcagc 660
actcatcagg aatgggccac atttgctgtg ggtcctgggc attgtctgca gctgcggaac 720
ccagctggga gcctgctggt acctgcttat gcctaccgga aactgcaccc tgctcagaag 780
cctaccccct ttgccttctg cttcatcagc cttgaccatg ggcacacatg gaaactaggc 840
aactttgtgg ctgaaaactc actggagtgc caggtggctg aggttggcac tggagctcag 900
aggatggtat atctcaatgc taggagcttc ctgggagcca gggtccaggc acaaagtcct 960
aatgatggtc tggatttcca ggacaaccgg gtagtgagta agcttgtaga gcccccccac 1020
gggtgtcatg gaagtgtggt tgccttccac aaccccatct ctaagccaca tgccttagac 1080
acatggcttc tttatacaca ccctacagac tccaggaata gaaccaacct gggtgtgtac 1140
ctaaaccaga tgccactaga tcccacagcc tggtcagagc ccaccctgct ggccatgggc 1200
atctgtgcct actcagactt acagaacatg ggcaaggcc ctgatggctc cccacagttt 1260
gggtgtctgt atgaatcagg taactatgaa gagatcattt tcctcatatt caccctgaag 1320
caagctttcc ccactgtatt tgatgcccag tgatctcagt gcacgtggcc caaagggctt 1380
ccttgtgctt caaaacaccc atctctcttt gcttccagca tcctctggac tcttgagtcc 1440
agctcttggg taacttcctc aggaggatgc agagaatttg gtctcttgac tctctgcagg 1500
ccttattgtt tcagcctctg gttctctttt cagcccagaa atcaaaggag cctggctttc 1560
ctcagcctgt tggcagggca ggtggggaca gtatatatag aggctgccat tctgcatgtc 1620
ggttgtcact atgctagttt aacctgcctg tttccccatg cctagtgttt gaatgagtat 1680
taataaaata tccaacccag cccatttctt cctggaaaaa aa 1722

<210> SEQ ID NO 89
<211> LENGTH: 3340
<212> TYPE: DNA
<213> ORGANISM: Mus sp.

<400> SEQUENCE: 89
actgcgcggt gaaggggcgt ggcctggccg gggaggttga cacccagacg ctgctctcag 60
tcctctggcg cctgctcccc agcgcattcc ttctgctcct gggatatttg tctcattact 120
gccagttctt gcgcagcggt cactgggttc gtttcagcgt ctgtggtttc tgtcgctgtt 180
atccagtctc catcgcccca gctcagcttc aggccttctt ccgagactcc acgggagagc 240
ccagagagcc tccggagccg aagccatgga ggaagtccca ccctactccc tcagcagcac 300
cctgttccag caggaagaac agagtggggt gacctaccgg atcccagccc tgctgtacct 360
tcctcccacc cacaccttcc tggcctttgc agagaagcgg acctcagtca gagatgagga 420
tgctgcctgc ctggtgctca gacgagggct gatgaagggg cgctctgtac agtggggccc 480
ccaacggcta ctgatggagg ccacattacc tgggcatcgc accatgaacc cctgccctgt 540
gtgggagaaa aatactggcc gtgtgtacct gtttttcatc tgtgtgcggg gccatgttac 600
tgagaggtgc cagattgtgt ggggcaaaaa tgccgcccgt ctctgcttcc tttgcagtga 660
agatgccggc tgctcttggg gtgaagtgaa agacttgacc gaggaggtca ttggctcaga 720
ggtgaagcgc tgggccacat ttgctgtggg cccaggtcat ggcatccagc tacactcggg 780
aaggctgatc atccccgcct atgcctacta tgtctcacgt tggtttctct gctttgcgtg 840
ttcagtcaag ccccattccc tgatgatcta cagtgatgac tttggagtca catggcacca 900
tggcaagttc attgagcccc aggtgacagg ggagtgccaa gtggccgaag tggctgggac 960
ggctggtaac cctgtgctca ctgcagtgcc cgaacaccaa gccgatttcg agcagaggct 1020
tttagtactg atagtggtgg ctgctttcag aagccaaccc tgaacccaca actccatgag 1080
cctcgaaccg gctgccaagg tagtgtagtg agcttccggc ctttgaagat gccaaatacc 1140
tatcaagact caattggcaa aggtgctccc gctactcaga agtgccctct gctggacagt 1200
cctctggagg tggagaaagg agctgaaaca ccatcagcaa catggctctt gtactcacat 1260
ccaactagca agaggaagag gattaaccta ggcatctact acaaccggaa ccccttggag 1320
gtgaactgct ggtcccgccc gtggatcttg aaccgtgggc ccagtggcta ctctgatctg 1380
gctgttgtgg aagaacagga cttggtggcg tgtttgtttg agtgtgggga gaagaatgag 1440
tatgagcgga ttgacttctg tctgttttca gaccatgagg tcctgagctg tgaagactgt 1500
accagcccta gtagcgacta aagccaaatc aagacggatg agtgaggccc agcttcccac 1560
agaaaggaat ggcagctaca gccagggtaa cagaggtctc tgatgtctag agaaaactct 1620
aaaaactaat aatctgctcc ttgaattttt tcacttttcc cttcaatgag catggtgaaa 1680
attgtgccat atcttacata acgaggctct tgaactggga gtttgaatct cttctcttcc 1740
cattaaaagg agaggccatg tgctcgcttc gcgttcgaca aagcctggat tctgatcttg 1800
agtggaagcc acaggcttgt cttttccaat ggttcactgc tcacctgagt attaggtgat 1860
gtgtaggtgc cttggccaga agaaagatct gtgttgttgt attttttaa atttatttat 1920 ttactatatg taagtacact gcagctgtct tcagacacac cagaagaggg cgtcagatct 1980
cattagagat ggttgtgagc caccatgtgg ttgctgggat ttgaactcag gaccttcaga 2040
agagcagtca gtgctcttaa ctactgagcc atctctcaag ccccgcattg ctgtattttt 2100
aataagaaaa atgcccttat ccttccaata atgcctggag ctgtacaaat tctctgtctt 2160

-continued agaagacttg agaaagcaga actgtaaggt cagatgcttt ctccagcctt gatgctgtgt 2220
tccaccttcc cttcctcatc cagaaaacag ttactaggga gaaaatgaga aacccatgcc 2280
agctgccctt gatgatggtt gataacggtg cttattgctt ttgatgtcat tacctctgtt 2340
agagatgaat cagagtcaga ggtccttagc tgcatccacc catttccagg gggacattct 2400
aacactgctg aacagtcagc taaaatgaga gctgtgtgtc ctagcctgat tccaggttag 2460
tcatgatgct tcctggagct gggcttttat ctaatcccag gagccatcta ggggaggctc 2520
agagctagca ggtgatcttc ctgagatggt ttcaccgtga caggtgaacc atgagccctt 2580
ccaagcaagg ccaaaggaca acattatagg aaagatttct agtattaata tgccttttct 2640
ctgtgtgtgt actgtcttgt agtgatgcta tatagacaaa tagatgattt cttatttttt 2700
gtttgtttgt ttgttttttt gtttttctgt agccctagct gtcctggaac tcactttgta 2760
aaccaggctg gcctcgatct cagaaatccg cctgcctctg cctcccgagt gctgggatta 2820
aaggtgtgca ccaccacacc ttaatgatga tcctataagt attcctaaaa ttatactagt 2880
aattattaac tcctttataa taggactgct attaaagccc tcgctgatat gaaaactaca 2940
gtgagaactc tgccagtctt cacatgtcat aattacttct gagatagaaa gcaggcattt 3000
acaacttaga acacatttct tagagctgta aaacaattaa ctagaggtca taaaagggaa 3060
tgaaagattt attgtaggtg ctaggacaga acataaaata ttgactgggc ttatctatat 3120
gaaacttcat tgttaacttt tacacaagaa ttatggtttt taactttcag tgaacctgcg 3180
gagctagtga cagaagagaa atgtctagtt agataactac tcttaatgga aattcacata 3240
aacatctgtt gccatcttct ttttgaattt atgtttaaac ttgtgaatgt ttgaattaga 3300
cactacgcga gcacatagaa aataaagaac taagcgtgaa 3340

<210> SEQ ID NO 90
<211> LENGTH: 4608
<212> TYPE: DNA
<213> ORGANISM: Mus sp.

<400> SEQUENCE: 90
ggacagtgtg catcacggag cttgtggccc agactgtgcc tggcagaccc agaggaccta 60
aggcttggct ctagtggtgg tcagcacagc cctcggtggt ctgcggagcc tgatattgct 120
ttacgtaagg gctgttctgc tgtgcatctc ctgtgtctga agctattcgc catggagact 180
gctggagctc ccttctgctt ccatgtggac tccctggtac cttgctccta ctggaaggtt 240
atggggccca cgcgtgttcc caggagaacg gtgctcttcc agagggaaag gacgggcctg 300
acctaccgtg tgcctgcgtt actctgtgtg cctcccaggc ctactctgct ggccttcgcg 360
gaacagcgac ttagccctga tgactcccat gcccaccgcc tggtgctacg gaggggcacg 420
ctgaccaggg gctcagtgcg gtggggcact ctgagtgtac tggagactgc agtactggag 480
gagcacaggt ctatgaaccc ttgcccggtg ctggatgagc actctggtac catcttcctc 540
ttcttcattg ccgtgctggg ccacacaccg gaggccgtgc aaatcgccac tggcaagaac 600
gctgctcgcc tctgctgtgt gaccagctgt gacgctggcc tcacctgggg cagtgttcga 660
gatctcactg aggaagccat tggtgctgca ttgcaggact gggccacctt tgctgtgggt 720
ccgggccatg gagttcagct gcgctcgggt cgcctgcttg ttcctgctta cacctatcat 780
gtggaccgac gggaatgttt tggcaagatc tgctggacca gtccccactc cttggcattc 840
tacagtgatg atcatgggat ctcctggcat tgtggaggcc ttgtgcccaa cctacgctct 900
ggagagtgcc aactggctgc ggtagatgga gactttctct actgtaatgc tcgaagccct 960

```
ctgggtaacc gtgtgcaggc actgagtgct gatgaaggca cgtccttcct accaggggag   1020
ctggtgccta cattggcaga gacggctcgt ggttgccagg gtagcattgt gggcttccta   1080
gctccaccct caatcgagcc tcaggatgac cggtggacag ggagtcctag gaacacccca   1140
cattccccat gcttcaatct cagagtacag gagtcttcgg gggaaggtgc cagaggtctt   1200
cttgaacgtt ggatgcccag gttgcctctc tgctacccac agtcccggag cccagagaat   1260
catggcctag agcctgggtc agatggagat aagacatcct ggactccgga atgtcctatg   1320
tcctctgatt ccatgcttca gagccccaca tggctactat attcccaccc agcagggcgt   1380
agagctcggc tccacatggg aatctacctg agccgatccc ccttggatcc ccacagctgg   1440
acagagccct gggtgatcta tgagggcccc agtggctact ctgaccttgc ctttcttggg   1500
cctatgcctg gggcatccct ggtttttgcc tgtctgtttg agagcgggac caggacttcc   1560
tatgaagaca tttctttttg cttgttctca ctggcggatg tcctggagaa tgtgcccact   1620
ggcttagaga tgctaagtct cagggataag gctcaggggc attgctggcc ctcttgatgg   1680
cctcaccctc tcgtagccgc ctggagagga agggtagact atatagagga ggttaggggt   1740
aggtcagcat gatgctagga tggagagagc tctgtcccct cgtggatggt ggtggtgact   1800
cacccggggg gccagctgct ttctgagtgc aaatgagaaa aataaagagc tgcgctgtga   1860
cttttctttc cacatcaaag cttgggtgtc agtgctttag cttgatgctc tgatcaccat   1920
gcaaatcttc caccggcgcc ttgctcagct ttcatatccc aagggtgcct gggaggaagg   1980
caacagggac agtggacatc actgcaccac tttccacgac cctgtgtgcc aacctcagcc   2040
actttgaaac atgctgatga ctgaggtctg ttcactttct taatttcaag caggagaagc   2100
aggttgggga gccagcctcc ccagctagag ggacagaac ttgacttgag caggggggta   2160
cctcctagga cctgctccat gtgcctactt ctttaccctt ctctagagag ggctcttgtc   2220
ctgtcagagc tgttttctcc cttctcttgt tttttctttt tcaagactgt ttctctgtgt   2280
tagccctggc tgtcctggat ctcactctgt agatcaggct gaccttgagt tcaaagctcc   2340
atctgcctct acttctcaca ttactgtgat taaaggcata tactaccact gcctggtgcc   2400
cttttgtatt tcttattaaa gtcctaatgt ctgattataa aaacagtctg tgtgggctgg   2460
agtgatggct tactcagtaa agcacttgcc atggaatctg ggcaatctga gtttcatttt   2520
tagcatcctg taaaaatccc aatttgatgg tgtacttgta atgtcagcat ggagaggcag   2580
agataggtaa gttccccaag actctttgaa ccgacagctt ggcctcactg gcacattcca   2640
ggtctcagtg agagaccctg cctcaaaata caaagaaaga gctgctgaag agtgggtcag   2700
agttgacctc tgatctccgg aagtatatga tacacacccg tgcatgcact cttccttaca   2760
aaataaaaag caaaacaaaa ccccaacagg tatatggcca ttttagaaaa attagaagat   2820
ttagaaagct atacataaaa aaaaatgacc taaagaaaaa tctttactgt tctgggcact   2880
atccctatca aaccactgtg ttctttggcc aagccttggg gtggacactg ttttgaggtg   2940
ggtcctgtta tctccactag gtagtggagt tttgtgtcag actaactggg tcttaaagct   3000
gtctttaagg ccatcaggag ctactgactt gcctgcctca gcagagcata tcctgaaggt   3060
cggggttaag tctccttccc gagcgagttg ccttccagtg ggcccctgga ctcctaggtc   3120
ctcagcgctc atcagctgcc aaggactctg agggaatgtc ctctgactgt ggccccgaaa   3180
ggtaggggag ggggatgtgc ttaggcttag gacagggtcc tgtttcagtc tgccttcact   3240
gttagtagca ctgtgccaca tggcacagac tgggcgagct ttaaaggaag gaggttgata   3300
```

-continued

```
ttggttccca cttctgggga tcatggttga gcagccttgt ctgatgatgg ttgtcttgat   3360

ggtagatcgt gaggtagttg atgaaggtat gacatggtga gaaactctgt gtgtgtgtgt   3420

tattttctct gtgttctacc tatacatcta tctatgtata tatgtatcta tctatctacc   3480

tggaggctgg agagatagct tagtggttaa gaacatttgt tgttcttgca tagtcctgga   3540

tttaaatttt cagcacccac atggcagctc acaacaaccc ataaatccag tttcagagga   3600

tccaacctct gatataccat gtcagccaga gcagacacgg ctgaaggtgg tttgatcccc   3660

gtatggagag gtgacaattg ggaagagaga aagatcaact taaccatgca aggaacagga   3720

agttaaatac tgaacaggga aggtaaaggc aggaagtaga tgtagagggc aaatcaatga   3780

aacccaaaca tacccaaatt acgctaaaca cacactgaca tgccaattaa aaggacaaat   3840

tggctccact ggcaaaacca aaacagacac tgaagatcca aacagtcaca tgccaactac   3900

cgcggaggga gacagacaca gagaagaccg tgacagacac ttggacactc ttgagagtgg   3960

atgtgcagga agagagctct gccagtggag aagaaagcac tcagaagaaa gtgacagcag   4020

ctgtaaattt gtattctgct aatgttatgt tccaaagttg aaagcaaaat tgtaccaatt   4080

cataagaaca aacaggctga ctctcagttg tgactgaacg tctctcagta actgacgggg   4140

cgagcaggcc aaaggagagt cggctcagaa gggtgcatag ccacgccaaa tcaaataagc   4200

aagtacaacc ggcaggctct atttctagca caaaggggtc tgtgcctcat tctgtgcttg   4260

ggtcagagct tgggtctctc atttggatgt aagtggtgta gtggagaagc aggaaataat   4320

ccggagcgca tattttgatt ttaacataag tgctgatttg ggagggagtt ttgtcaaatt   4380

gtgtttttac aatgtttttt ttttttaaa tgatgctttt ttgtaaagtg tacaaatgtg   4440

atataagatt ggttctgcta cattcagttt ctataaaagt ggttctaaaa tattgtactg   4500

tcaatcatct catgattatt ctactgtaca cattactgac tttgtatgta ataattaata   4560

ttagaagaaa atataattta tttgaatata aaaaaaaaaa aaaaaaaa                4608
```

```
<210> SEQ ID NO 91
<211> LENGTH: 380
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Ala, Arg, Asn, Asp, Gln, Glu, Gly, His, Leu,
      Lys, Met, Phe, Thr, Val, or not present
<220> FEATURE:
<221> NAME/KEY: MOD_RES
<222> LOCATION: (6)..(6)
<223> OTHER INFORMATION: Phe, Trp, Tyr or Val
<220> FEATURE:
<221> NAME/KEY: MOD_RES
<222> LOCATION: (187)..(187)
<223> OTHER INFORMATION: Arg, Ile or Lys
<220> FEATURE:
<221> NAME/KEY: MOD_RES
<222> LOCATION: (332)..(332)
<223> OTHER INFORMATION: Ala, Cys, Ser or Val

<400> SEQUENCE: 91

Xaa Ala Ser Leu Pro Xaa Leu Gln Lys Glu Ser Val Phe Gln Ser Gly
1               5                   10                  15

Ala His Ala Tyr Arg Ile Pro Ala Leu Leu Tyr Leu Pro Gly Gln Gln
            20                  25                  30

Ser Leu Leu Ala Phe Ala Glu Gln Arg Ala Ser Lys Lys Asp Glu His
```

```
        35                  40                  45

Ala Glu Leu Ile Val Leu Arg Arg Gly Asp Tyr Asp Ala Pro Thr His
    50                  55                  60

Gln Val Gln Trp Gln Ala Gln Glu Val Val Ala Gln Ala Arg Leu Asp
65                  70                  75                  80

Gly His Arg Ser Met Asn Pro Cys Pro Leu Tyr Asp Ala Gln Thr Gly
                85                  90                  95

Thr Leu Phe Leu Phe Phe Ile Ala Ile Pro Gly Gln Val Thr Glu Gln
            100                 105                 110

Gln Gln Leu Gln Thr Arg Ala Asn Val Thr Arg Leu Cys Gln Val Thr
        115                 120                 125

Ser Thr Asp His Gly Arg Thr Trp Ser Ser Pro Arg Asp Leu Thr Asp
    130                 135                 140

Ala Ala Ile Gly Pro Ala Tyr Arg Glu Trp Ser Thr Phe Ala Val Gly
145                 150                 155                 160

Pro Gly His Cys Leu Gln Leu His Asp Arg Ala Arg Ser Leu Val Val
                165                 170                 175

Pro Ala Tyr Ala Tyr Arg Lys Leu His Pro Xaa Gln Arg Pro Ile Pro
            180                 185                 190

Ser Ala Phe Cys Phe Leu Ser His Asp His Gly Arg Thr Trp Ala Arg
        195                 200                 205

Gly His Phe Val Ala Gln Asp Thr Leu Glu Cys Gln Val Ala Glu Val
    210                 215                 220

Glu Thr Gly Glu Gln Arg Val Val Thr Leu Asn Ala Arg Ser His Leu
225                 230                 235                 240

Arg Ala Arg Val Gln Ala Gln Ser Thr Asn Asp Gly Leu Asp Phe Gln
                245                 250                 255

Glu Ser Gln Leu Val Lys Lys Leu Val Glu Pro Pro Pro Gln Gly Cys
            260                 265                 270

Gln Gly Ser Val Ile Ser Phe Pro Ser Pro Arg Ser Gly Pro Gly Ser
        275                 280                 285

Pro Ala Gln Trp Leu Leu Tyr Thr His Pro Thr His Ser Trp Gln Arg
    290                 295                 300

Ala Asp Leu Gly Ala Tyr Leu Asn Pro Arg Pro Pro Ala Pro Glu Ala
305                 310                 315                 320

Trp Ser Glu Pro Val Leu Leu Ala Lys Gly Ser Xaa Ala Tyr Ser Asp
                325                 330                 335

Leu Gln Ser Met Gly Thr Gly Pro Asp Gly Ser Pro Leu Phe Gly Cys
            340                 345                 350

Leu Tyr Glu Ala Asn Asp Tyr Glu Glu Ile Val Phe Leu Met Phe Thr
        355                 360                 365

Leu Lys Gln Ala Phe Pro Ala Glu Tyr Leu Pro Gln
    370                 375                 380


<210> SEQ ID NO 92
<211> LENGTH: 617
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Ala, Arg, Asn, Asp, Gln, Glu, Gly, His, Leu,
      Lys, Met, Phe, Thr, Val, or not present
<220> FEATURE:
```

```
<221> NAME/KEY: MOD_RES
<222> LOCATION: (6)..(6)
<223> OTHER INFORMATION: Phe, Trp, Tyr or Val
<220> FEATURE:
<221> NAME/KEY: MOD_RES
<222> LOCATION: (187)..(187)
<223> OTHER INFORMATION: Arg, Ile or Lys
<220> FEATURE:
<221> NAME/KEY: MOD_RES
<222> LOCATION: (332)..(332)
<223> OTHER INFORMATION: Ala, Cys, Ser or Val

<400> SEQUENCE: 92

Xaa Ala Ser Leu Pro Xaa Leu Gln Lys Glu Ser Val Phe Gln Ser Gly
1               5                   10                  15

Ala His Ala Tyr Arg Ile Pro Ala Leu Leu Tyr Leu Pro Gly Gln Gln
            20                  25                  30

Ser Leu Leu Ala Phe Ala Glu Gln Arg Ala Ser Lys Lys Asp Glu His
        35                  40                  45

Ala Glu Leu Ile Val Leu Arg Arg Gly Asp Tyr Asp Ala Pro Thr His
    50                  55                  60

Gln Val Gln Trp Gln Ala Gln Glu Val Val Ala Gln Ala Arg Leu Asp
65                  70                  75                  80

Gly His Arg Ser Met Asn Pro Cys Pro Leu Tyr Asp Ala Gln Thr Gly
                85                  90                  95

Thr Leu Phe Leu Phe Phe Ile Ala Ile Pro Gly Gln Val Thr Glu Gln
            100                 105                 110

Gln Gln Leu Gln Thr Arg Ala Asn Val Thr Arg Leu Cys Gln Val Thr
        115                 120                 125

Ser Thr Asp His Gly Arg Thr Trp Ser Ser Pro Arg Asp Leu Thr Asp
    130                 135                 140

Ala Ala Ile Gly Pro Ala Tyr Arg Glu Trp Ser Thr Phe Ala Val Gly
145                 150                 155                 160

Pro Gly His Cys Leu Gln Leu His Asp Arg Ala Arg Ser Leu Val Val
                165                 170                 175

Pro Ala Tyr Ala Tyr Arg Lys Leu His Pro Xaa Gln Arg Pro Ile Pro
            180                 185                 190

Ser Ala Phe Cys Phe Leu Ser His Asp His Gly Arg Thr Trp Ala Arg
        195                 200                 205

Gly His Phe Val Ala Gln Asp Thr Leu Glu Cys Gln Val Ala Glu Val
    210                 215                 220

Glu Thr Gly Glu Gln Arg Val Val Thr Leu Asn Ala Arg Ser His Leu
225                 230                 235                 240

Arg Ala Arg Val Gln Ala Gln Ser Thr Asn Asp Gly Leu Asp Phe Gln
                245                 250                 255

Glu Ser Gln Leu Val Lys Lys Leu Val Glu Pro Pro Pro Gln Gly Cys
            260                 265                 270

Gln Gly Ser Val Ile Ser Phe Pro Ser Pro Arg Ser Gly Pro Gly Ser
        275                 280                 285

Pro Ala Gln Trp Leu Leu Tyr Thr His Pro Thr His Ser Trp Gln Arg
    290                 295                 300

Ala Asp Leu Gly Ala Tyr Leu Asn Pro Arg Pro Pro Ala Pro Glu Ala
305                 310                 315                 320

Trp Ser Glu Pro Val Leu Leu Ala Lys Gly Ser Xaa Ala Tyr Ser Asp
                325                 330                 335

Leu Gln Ser Met Gly Thr Gly Pro Asp Gly Ser Pro Leu Phe Gly Cys
            340                 345                 350
```

Leu Tyr Glu Ala Asn Asp Tyr Glu Glu Ile Val Phe Leu Met Phe Thr
355 360 365

Leu Lys Gln Ala Phe Pro Ala Glu Tyr Leu Pro Gln Gly Gly Gly Gly
370 375 380

Ser Gly Gly Gly Gly Ser Asp Lys Thr His Thr Cys Pro Pro Cys Pro
385 390 395 400

Ala Pro Glu Leu Leu Gly Gly Pro Ser Val Phe Leu Phe Pro Pro Lys
405 410 415

Pro Lys Asp Thr Leu Met Ile Ser Arg Thr Pro Glu Val Thr Cys Val
420 425 430

Val Val Asp Val Ser His Glu Asp Pro Glu Val Lys Phe Asn Trp Tyr
435 440 445

Val Asp Gly Val Glu Val His Asn Ala Lys Thr Lys Pro Arg Glu Glu
450 455 460

Gln Tyr Asn Ser Thr Tyr Arg Val Val Ser Val Leu Thr Val Leu His
465 470 475 480

Gln Asp Trp Leu Asn Gly Lys Glu Tyr Lys Cys Lys Val Ser Asn Lys
485 490 495

Ala Leu Pro Ala Pro Ile Glu Lys Thr Ile Ser Lys Ala Lys Gly Gln
500 505 510

Pro Arg Glu Pro Gln Val Tyr Thr Leu Pro Pro Ser Arg Glu Glu Met
515 520 525

Thr Lys Asn Gln Val Ser Leu Thr Cys Leu Val Lys Gly Phe Tyr Pro
530 535 540

Ser Asp Ile Ala Val Glu Trp Glu Ser Asn Gly Gln Pro Glu Asn Asn
545 550 555 560

Tyr Lys Thr Thr Pro Pro Val Leu Asp Ser Asp Gly Ser Phe Phe Leu
565 570 575

Thr Ser Lys Leu Thr Val Asp Lys Ser Arg Trp Gln Gln Gly Asn Val
580 585 590

Phe Ser Cys Ser Val Met His Glu Ala Leu His Asn His Tyr Thr Gln
595 600 605

Lys Ser Leu Ser Leu Ser Pro Gly Lys
610 615

<210> SEQ ID NO 93
<211> LENGTH: 874
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (1)..(1)
<223> OTHER INFORMATION: Ala, Arg, Asn, Asp, Gln, Glu, Gly, His, Leu, Lys, Met, Phe, Thr, Val, or not present
<220> FEATURE:
<221> NAME/KEY: MOD_RES
<222> LOCATION: (6)..(6)
<223> OTHER INFORMATION: Phe, Trp, Tyr or Val
<220> FEATURE:
<221> NAME/KEY: MOD_RES
<222> LOCATION: (187)..(187)
<223> OTHER INFORMATION: Arg, Ile or Lys
<220> FEATURE:
<221> NAME/KEY: MOD_RES
<222> LOCATION: (332)..(332)
<223> OTHER INFORMATION: Ala, Cys, Ser or Val

<400> SEQUENCE: 93

-continued

```
Xaa Ala Ser Leu Pro Xaa Leu Gln Lys Glu Ser Val Phe Gln Ser Gly
1               5                   10                  15

Ala His Ala Tyr Arg Ile Pro Ala Leu Leu Tyr Leu Pro Gly Gln Gln
            20                  25                  30

Ser Leu Leu Ala Phe Ala Glu Gln Arg Ala Ser Lys Lys Asp Glu His
        35                  40                  45

Ala Glu Leu Ile Val Leu Arg Arg Gly Asp Tyr Asp Ala Pro Thr His
    50                  55                  60

Gln Val Gln Trp Gln Ala Gln Glu Val Val Ala Gln Ala Arg Leu Asp
65                  70                  75                  80

Gly His Arg Ser Met Asn Pro Cys Pro Leu Tyr Asp Ala Gln Thr Gly
                85                  90                  95

Thr Leu Phe Leu Phe Phe Ile Ala Ile Pro Gly Gln Val Thr Glu Gln
            100                 105                 110

Gln Gln Leu Gln Thr Arg Ala Asn Val Thr Arg Leu Cys Gln Val Thr
        115                 120                 125

Ser Thr Asp His Gly Arg Thr Trp Ser Ser Pro Arg Asp Leu Thr Asp
    130                 135                 140

Ala Ala Ile Gly Pro Ala Tyr Arg Glu Trp Ser Thr Phe Ala Val Gly
145                 150                 155                 160

Pro Gly His Cys Leu Gln Leu His Asp Arg Ala Arg Ser Leu Val Val
                165                 170                 175

Pro Ala Tyr Ala Tyr Arg Lys Leu His Pro Xaa Gln Arg Pro Ile Pro
            180                 185                 190

Ser Ala Phe Cys Phe Leu Ser His Asp His Gly Arg Thr Trp Ala Arg
        195                 200                 205

Gly His Phe Val Ala Gln Asp Thr Leu Glu Cys Gln Val Ala Glu Val
    210                 215                 220

Glu Thr Gly Glu Gln Arg Val Val Thr Leu Asn Ala Arg Ser His Leu
225                 230                 235                 240

Arg Ala Arg Val Gln Ala Gln Ser Thr Asn Asp Gly Leu Asp Phe Gln
                245                 250                 255

Glu Ser Gln Leu Val Lys Lys Leu Val Glu Pro Pro Pro Gln Gly Cys
            260                 265                 270

Gln Gly Ser Val Ile Ser Phe Pro Ser Pro Arg Ser Gly Pro Gly Ser
        275                 280                 285

Pro Ala Gln Trp Leu Leu Tyr Thr His Pro Thr His Ser Trp Gln Arg
    290                 295                 300

Ala Asp Leu Gly Ala Tyr Leu Asn Pro Arg Pro Pro Ala Pro Glu Ala
305                 310                 315                 320

Trp Ser Glu Pro Val Leu Leu Ala Lys Gly Ser Xaa Ala Tyr Ser Asp
                325                 330                 335

Leu Gln Ser Met Gly Thr Gly Pro Asp Gly Ser Pro Leu Phe Gly Cys
            340                 345                 350

Leu Tyr Glu Ala Asn Asp Tyr Glu Glu Ile Val Phe Leu Met Phe Thr
        355                 360                 365

Leu Lys Gln Ala Phe Pro Ala Glu Tyr Leu Pro Gln Gly Gly Gly Gly
    370                 375                 380

Ser Gly Gly Gly Gly Ser Asp Lys Thr His Thr Cys Pro Pro Cys Pro
385                 390                 395                 400

Ala Pro Glu Leu Leu Gly Gly Pro Ser Val Phe Leu Phe Pro Pro Lys
                405                 410                 415
```

-continued

```
Pro Lys Asp Thr Leu Met Ile Ser Arg Thr Pro Glu Val Thr Cys Val
            420                 425                 430

Val Val Asp Val Ser His Glu Asp Pro Glu Val Lys Phe Asn Trp Tyr
        435                 440                 445

Val Asp Gly Val Glu Val His Asn Ala Lys Thr Lys Pro Arg Glu Glu
    450                 455                 460

Gln Tyr Asn Ser Thr Tyr Arg Val Val Ser Val Leu Thr Val Leu His
465                 470                 475                 480

Gln Asp Trp Leu Asn Gly Lys Glu Tyr Lys Cys Lys Val Ser Asn Lys
                485                 490                 495

Ala Leu Pro Ala Pro Ile Glu Lys Thr Ile Ser Lys Ala Lys Gly Gln
            500                 505                 510

Pro Arg Glu Pro Gln Val Tyr Thr Leu Pro Pro Ser Arg Glu Glu Met
        515                 520                 525

Thr Lys Asn Gln Val Ser Leu Thr Cys Leu Val Lys Gly Phe Tyr Pro
    530                 535                 540

Ser Asp Ile Ala Val Glu Trp Glu Ser Asn Gly Gln Pro Glu Asn Asn
545                 550                 555                 560

Tyr Lys Thr Thr Pro Pro Val Leu Asp Ser Asp Gly Ser Phe Phe Leu
                565                 570                 575

Tyr Ser Lys Leu Thr Val Asp Lys Ser Arg Trp Gln Gln Gly Asn Val
            580                 585                 590

Phe Ser Cys Ser Val Met His Glu Ala Leu His Asn His Tyr Thr Gln
        595                 600                 605

Lys Ser Leu Ser Leu Ser Pro Gly Lys Gly Gly Gly Gly Ser Gly Gly
    610                 615                 620

Gly Gly Ser Gly Gly Gly Gly Ser Glu Val Gln Leu Val Glu Ser Gly
625                 630                 635                 640

Gly Gly Leu Val Gln Pro Gly Gly Ser Leu Arg Leu Ser Cys Ala Ala
                645                 650                 655

Ser Gly Phe Asn Ile Lys Asp Thr Tyr Ile His Trp Val Arg Gln Ala
            660                 665                 670

Pro Gly Lys Gly Leu Glu Trp Val Ala Arg Ile Tyr Pro Thr Asn Gly
        675                 680                 685

Tyr Thr Arg Tyr Ala Asp Ser Val Lys Gly Arg Phe Thr Ile Ser Ala
    690                 695                 700

Asp Thr Ser Lys Asn Thr Ala Tyr Leu Gln Met Asn Ser Leu Arg Ala
705                 710                 715                 720

Glu Asp Thr Ala Val Tyr Tyr Cys Ser Arg Trp Gly Gly Asp Gly Phe
                725                 730                 735

Tyr Ala Met Asp Tyr Trp Gly Gln Gly Thr Leu Val Thr Val Ser Ser
            740                 745                 750

Gly Gly Gly Gly Ser Gly Gly Gly Gly Ser Gly Gly Gly Gly Ser Asp
        755                 760                 765

Ile Gln Met Thr Gln Ser Pro Ser Ser Leu Ser Ala Ser Val Gly Asp
    770                 775                 780

Arg Val Thr Ile Thr Cys Arg Ala Ser Gln Asp Val Asn Thr Ala Val
785                 790                 795                 800

Ala Trp Tyr Gln Gln Lys Pro Gly Lys Ala Pro Lys Leu Leu Ile Tyr
                805                 810                 815

Ser Ala Ser Phe Leu Tyr Ser Gly Val Pro Ser Arg Phe Ser Gly Ser
            820                 825                 830

Arg Ser Gly Thr Asp Phe Thr Leu Thr Ile Ser Ser Leu Gln Pro Glu
```

```
        835                 840                 845

Asp Phe Ala Thr Tyr Tyr Cys Gln Gln His Tyr Thr Thr Pro Pro Thr
    850                 855                 860

Phe Gly Gln Gly Thr Lys Val Glu Ile Lys
865                 870


<210> SEQ ID NO 94
<211> LENGTH: 216
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 94

Glu Leu Val Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Leu Val Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215


<210> SEQ ID NO 95
<211> LENGTH: 648
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 95

gagctcgtgt tgactcagcc tgcctccgtg tctgggtctc ctggacagtc gatcaccatc      60

tcctgcactg gaaccagcag tgacgttggt ggttataact atgtctcctg gtaccaacag     120

cacccaggca aagcccccaa actcatgatt tatgatgtca gtaagcggcc ctcaggggtt     180

tctaatcgct tctctggctc caagtctggc aacacggcct ccctgaccat ctctgggctc     240
```

```
caggctgagg acgaggctga ttattactgc agctcatata caagcagcag cactttggta    300

ttcggcggag ggaccaagct gaccgtccta ggtcagccca aggcggcgcc ctcggtcact    360

ctgttcccgc cctcctctga ggagcttcaa gccaacaagg ccacactggt gtgtctcata    420

agtgacttct acccgggagc cgtgacagtg gcctggaagg cagatagcag ccccgtcaag    480

gcgggagtgg agaccaccac accctccaaa caaagcaaca acaagtacgc ggccagcagc    540

tacctgagcc tgacgcctga gcagtggaag tcccacagaa gctacagctg ccaggtcacg    600

catgaaggga gcaccgtgga gaagacagtg gcccctacag aatgttca                 648
```

<210> SEQ ID NO 96
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 96

```
Glu Val Gln Leu Leu Glu Ser Gly Gly Gly Leu Val Gln Pro Gly Gly
1               5                   10                  15

Ser Leu Arg Leu Ser Cys Thr Thr Ser Gly Phe Thr Phe Asn Thr Tyr
            20                  25                  30

Ala Met Ser Trp Val Arg Gln Ala Pro Gly Lys Gly Leu Glu Trp Leu
        35                  40                  45

Ser Gly Ile Asn Asn Asn Gly Arg Thr Ala Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Ile Asn Ser Leu Arg Ala Asp Asp Thr Ala Val Tyr Phe Cys
                85                  90                  95

Ala Lys Asp Val Arg Phe Ile Ala Val Pro Gly Asp Ser Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285
```

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Tyr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 97
<211> LENGTH: 1350
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 97
gaggtgcagc tgctcgagtc agggggaggc ttggtacagc cggggggggtc cctgagactc 60 tcctgtacaa cctctggatt cacctttaac acgtatgcca tgagttgggt ccgccaggct 120
ccagggaagg ggctggaatg gctctcaggt attaataaca atggtcggac tgcattctac 180
gcagactccg tgaagggccg cttcaccatc tccagagaca actccaaaaa cacactttat 240
ctgcaaatta atagtctgag agcggacgac acggccgttt atttctgtgc gaaagatgtc 300
agatttatcg cagtgcctgg tgactcctgg ggccagggaa ccctggtcac cgtctcctca 360
gctagcacca agggcccatc cgtcttcccc ctggcaccct cctccaagag cacctctggg 420
ggcacagcgg ccctgggctg cctggtcaag gactacttcc ccgaaccggt gacggtgtcc 480
tggaactcag gcgctctgac cagcggcgtg cacaccttcc cggctgtcct acagtcctca 540
ggactctact ccctcagcag cgtggtgacc gtgccctcca gcagcttggg cacccagacc 600
tacatctgca acgtgaatca caagcccagc aacaccaagg tggacaagaa agttgagccc 660
aaatcttgtg acaaaactca cacatgccca ccgtgcccag cacctgaact cctgggggga 720
ccgtcagtct tcctcttccc cccaaaaccc aaggacaccc tcatgatctc ccggacccct 780
gaggtcacat gcgtggtggt ggacgtgagc cacgaagacc ctgaggtcaa gttcaactgg 840
tacgtggacg gcgtggaggt gcataatgcc aagacaaagc cgcgggagga gcagtacaac 900
agcacgtacc gtgtggtcag cgtcctcacc gtcctgcacc aggactggct gaatggcaag 960
gagtacaagt gcaaggtctc caacaaagcc ctcccagccc ccatcgagaa aaccatctcc 1020

```
aaagccaaag ggcagccccg agaaccacag gtctacaccc tgcccccatc ccgggaggag   1080

atgaccaaga accaggtcag cctgtactgc ctggtcaaag gcttctatcc cagcgacatc   1140

gccgtggagt gggagagcaa tgggcagccg gagaacaact acaagaccac gcctcccgtg   1200

ctggactccg acggctcctt cttcctctat agcaagctca ccgtggacaa gagcaggtgg   1260

cagcagggga acgtcttctc atgctccgtg atgcatgagg ctctgcacaa ccactacacg   1320

cagaagagcc tctccctgtc tccgggtaaa                                    1350
```

<210> SEQ ID NO 98
<211> LENGTH: 1854
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 98

```
gacgcctctt taccctattt acagaaggag agcgtctttc agtccggcgc tcacgcctat     60

aggatccccg ctttactgta tttacccggt cagcagtctt tactggcttt cgccgagcag    120

cgggcttcca agaaggacga gcacgctgag ctgatcgtgt tacgtagggg agactacgac    180

gcccccaccc atcaagttca atggcaagct caagaagtgg tggctcaagc tcggctcgat    240

ggccatcgga gcatgaaccc ttgtcccctc tacgacgccc aaaccggcac tttatttctg    300

ttcttcatcg ccatccccgg tcaagttacc gagcagcaac agctgcagac ccgggctaac    360

gtgacaaggc tgtgccaagt tacctccacc gaccacggaa ggacttggtc ctcccctcgt    420

gatctgaccg atgccgctat cggcccccgct taccgggagt ggtccacctt tgccgtggga    480

cccggccatt gtctgcagct gcatgatagg gctcggtctt tagtggtgcc cgcttacgcc    540

taccggaagc tgcaccccaa gcagcggcct atcccctccg ctttttgttt tttaagccat    600

gaccatggtc gtacttgggc tcgtggccat tttgtggccc aagatacttt agagtgccaa    660

gttgccgagg tggagactgg tgagcagcgg gtggtgactt taaatgcccg gtcccattta    720

agggctaggg tgcaagccca gtccaccaac gacggactgg atttccaaga atcccagctg    780

gtgaagaagc tcgtcgaacc tcccccccaa ggttgccaag gaagcgtgat ctccttcccc    840

tcccctagga gcggacccgg ttcccccgct cagtggctgc tctacaccca tcccacccat    900

tcttggcaga gggctgattt aggcgcctat ttaaaccctc gtcctcccgc tcccgaagct    960

tggagcgagc ccgtgctgct cgctaagggc agcgccgcct acagcgattt acagtccatg   1020

ggaaccggac ccgatggcag ccctctgttc ggctgtttat atgaggctaa cgactacgag   1080

gagatcgtgt ttctcatgtt cactttaaag caagcttttc ccgctgagta tctgccccaa   1140

ggtggaggcg gcagcggcgg cggcggctcc gacaaaactc acacatgccc accgtgccca   1200

gcacctgaac tcctgggggg accgtcagtc ttcctcttcc ccccaaaacc caaggacacc   1260

ctcatgatct cccggacccc tgaggtcaca tgcgtggtgg tggacgtgag ccacgaagac   1320

cctgaggtca agttcaactg gtacgtggac ggcgtggagg tgcataatgc caagacaaag   1380

ccgcgggagg agcagtacaa cagcacgtac cgtgtggtca gcgtcctcac cgtcctgcac   1440

caggactggc tgaatggcaa ggagtacaag tgcaaggtct ccaacaaagc cctcccagcc   1500

cccatcgaga aaaccatctc caaagccaaa gggcagcccc gagaaccaca ggtgtacacc   1560

ctgcccccat cccgggagga gatgaccaag aaccaggtca gcctgacctg cctggtcaaa   1620

ggcttctatc ccagcgacat cgccgtggag tgggagagca atgggcagcc ggagaacaac   1680
```

tacaagacca cgcctcccgt gctggactcc gacggctcct tcttcctcac cagcaagctc 1740
accgtggaca agagcaggtg gcagcagggg aacgtcttct catgctccgt gatgcatgag 1800
gctctgcaca accactacac gcagaagagc ctctccctgt ctccgggtaa atga 1854

<210> SEQ ID NO 99
<211> LENGTH: 2625
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 99
atggcctctt taccctattt acagaaggag agcgtctttc agtccggcgc tcacgcctat 60
aggatccccg ctttactgta tttacccggt cagcagtctt tactggcttt cgccgagcag 120
cgggcttcca agaaggacga gcacgctgag ctgatcgtgt tacgtagggg agactacgac 180
gcccccaccc atcaagttca atggcaagct caagaagtgg tggctcaagc tcggctcgat 240
ggccatcgga gcatgaaccc ttgtcccctc tacgacgccc aaaccggcac tttatttctg 300
ttcttcatcg ccatccccgg tcaagttacc gagcagcaac agctgcagac ccgggctaac 360
gtgacaaggc tgtgccaagt tacctccacc gaccacggaa ggacttggtc ctcccctcgt 420
gatctgaccg atgccgctat cggccccgct taccgggagt ggtccacctt tgccgtggga 480
cccggccatt gtctgcagct gcatgatagg gctcggtctt tagtggtgcc cgcttacgcc 540
taccggaagc tgcaccccaa gcagcggcct atcccctccg ctttttgttt tttaagccat 600
gaccatggtc gtacttgggc tcgtggccat tttgtggccc aagatacttt agagtgccaa 660
gttgccgagg tggagactgg tgagcagcgg gtggtgactt taaatgcccg gtcccattta 720
agggctaggg tgcaagccca gtccaccaac gacggactgg atttccaaga atcccagctg 780
gtgaagaagc tcgtcgaacc tcccccccaa ggttgccaag gaagcgtgat ctccttcccc 840
tcccctagga gcggacccgg ttcccccgct cagtggctgc tctacaccca tcccacccat 900
tcttggcaga gggctgattt aggcgcctat ttaaaccctc gtcctcccgc tcccgaagct 960
tggagcgagc ccgtgctgct cgctaagggc agctgcgcct acagcgattt acagtccatg 1020
ggaaccggac ccgatggcag ccctctgttc ggctgtttat atgaggctaa cgactacgag 1080
gagatcgtgt ttctcatgtt cactttaaag caagcttttc ccgctgagta tctgccccaa 1140
ggtggaggcg gcagcggcgg cggcggctcc gacaaaactc acacatgccc accgtgccca 1200
gcacctgaac tcctgggggg accgtcagtc ttcctcttcc ccccaaaacc caaggacacc 1260
ctcatgatct cccggacccc tgaggtcaca tgcgtggtgg tggacgtgag ccacgaagac 1320
cctgaggtca agttcaactg gtacgtggac ggcgtggagg tgcataatgc caagacaaag 1380
ccgcgggagg agcagtacaa cagcacgtac cgtgtggtca gcgtcctcac cgtcctgcac 1440
caggactggc tgaatggcaa ggagtacaag tgcaaggtct ccaacaaagc cctcccagcc 1500
cccatcgaga aaaccatctc caaagccaaa gggcagcccc gagaaccaca ggtgtacacc 1560
ctgcccccat cccgggagga gatgaccaag aaccaggtca gcctgacctg cctggtcaaa 1620
ggcttctatc ccagcgacat cgccgtggag tgggagagca atgggcagcc ggagaacaac 1680
tacaagacca cgcctcccgt gctggactcc gacggctcct tcttcctcta cagcaagctc 1740
accgtggaca agagcaggtg gcagcagggg aacgtcttct catgctccgt gatgcatgag 1800
gctctgcaca accactacac gcagaagagc ctctccctgt ctccgggtaa aggaggtggc 1860

-continued

```
ggcagcggcg gcggaggcag cggaggagga ggcagcgagg tgcagctggt ggagtccgga   1920

ggaggactgg tgcagcccgg aggatcttta aggctgagct gtgccgccag cggcttcaac   1980

atcaaggaca cctacatcca ctgggtgagg caagctcccg gcaaaggact cgagtgggtg   2040

gctcgtatct accccaccaa cggctatact cgttacgccg actccgtcaa gggtcgtttc   2100

accatttccg ccgacacctc caagaacacc gcctatttac agatgaattc tttacgggcc   2160

gaagacacag ctgtctacta ctgctcccgg tggggcggag acggattcta cgccatggac   2220

tactggggac aaggtacact ggtgacagtg tccagcggcg gaggaggatc tggcggcggc   2280

ggaagcggcg gtggcggtag cgatatccag atgacccaga gcccttcctc tttaagcgct   2340

tccgtgggcg atcgtgtcac catcacttgt agggcctccc aagatgtgaa caccgctgtg   2400

gcttggtacc agcagaagcc cggcaaggct cccaagctgc tgatctactc cgccagcttt   2460

ctgtattccg gagtgccttc tcgtttcagc ggctctcgta gcggcaccga cttcacttta   2520

accatcagct ctttacagcc cgaggacttc gccacctact actgccagca gcattacacc   2580

acacccccca ccttcggaca aggtaccaaa gtggagatca agtga                    2625
```

<210> SEQ ID NO 100
<211> LENGTH: 380
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (1)..(1)
<223> OTHER INFORMATION: Ala, Arg, Asn, Asp, Gln, Glu, Gly, His, Leu, Lys, Met, Phe, Thr, Val, or not present
<220> FEATURE:
<221> NAME/KEY: MOD_RES
<222> LOCATION: (2)..(2)
<223> OTHER INFORMATION: Ala or Lys
<220> FEATURE:
<221> NAME/KEY: MOD_RES
<222> LOCATION: (4)..(4)
<223> OTHER INFORMATION: Asn or Leu
<220> FEATURE:
<221> NAME/KEY: MOD_RES
<222> LOCATION: (6)..(6)
<223> OTHER INFORMATION: Phe, Trp, Tyr or Val
<220> FEATURE:
<221> NAME/KEY: MOD_RES
<222> LOCATION: (125)..(125)
<223> OTHER INFORMATION: Ala, Cys, Ile, Ser or Val
<220> FEATURE:
<221> NAME/KEY: MOD_RES
<222> LOCATION: (187)..(187)
<223> OTHER INFORMATION: Arg, Ile or Lys
<220> FEATURE:
<221> NAME/KEY: MOD_RES
<222> LOCATION: (196)..(196)
<223> OTHER INFORMATION: Ala, Cys, Leu or Val
<220> FEATURE:
<221> NAME/KEY: MOD_RES
<222> LOCATION: (257)..(257)
<223> OTHER INFORMATION: Glu or Lys
<220> FEATURE:
<221> NAME/KEY: MOD_RES
<222> LOCATION: (272)..(272)
<223> OTHER INFORMATION: Cys or Val
<220> FEATURE:
<221> NAME/KEY: MOD_RES
<222> LOCATION: (325)..(325)
<223> OTHER INFORMATION: Lys or Val
<220> FEATURE:
<221> NAME/KEY: MOD_RES
<222> LOCATION: (332)..(332)
<223> OTHER INFORMATION: Ala, Cys, Ser or Val
<220> FEATURE:
<221> NAME/KEY: MOD_RES
<222> LOCATION: (352)..(352)
<223> OTHER INFORMATION: Cys, Leu or Val

<400> SEQUENCE: 100

Xaa Xaa Ser Xaa Pro Xaa Leu Gln Lys Glu Ser Val Phe Gln Ser Gly
1 5 10 15

Ala His Ala Tyr Arg Ile Pro Ala Leu Leu Tyr Leu Pro Gly Gln Gln
20 25 30

Ser Leu Leu Ala Phe Ala Glu Gln Arg Ala Ser Lys Lys Asp Glu His
35 40 45

Ala Glu Leu Ile Val Leu Arg Arg Gly Asp Tyr Asp Ala Pro Thr His
50 55 60

Gln Val Gln Trp Gln Ala Gln Glu Val Val Ala Gln Ala Arg Leu Asp
65 70 75 80

Gly His Arg Ser Met Asn Pro Cys Pro Leu Tyr Asp Ala Gln Thr Gly
85 90 95

Thr Leu Phe Leu Phe Phe Ile Ala Ile Pro Gly Gln Val Thr Glu Gln
100 105 110

Gln Gln Leu Gln Thr Arg Ala Asn Val Thr Arg Leu Xaa Gln Val Thr
115 120 125

Ser Thr Asp His Gly Arg Thr Trp Ser Ser Pro Arg Asp Leu Thr Asp
130 135 140

Ala Ala Ile Gly Pro Ala Tyr Arg Glu Trp Ser Thr Phe Ala Val Gly
145 150 155 160

Pro Gly His Cys Leu Gln Leu His Asp Arg Ala Arg Ser Leu Val Val
165 170 175

Pro Ala Tyr Ala Tyr Arg Lys Leu His Pro Xaa Gln Arg Pro Ile Pro
180 185 190

Ser Ala Phe Xaa Phe Leu Ser His Asp His Gly Arg Thr Trp Ala Arg
195 200 205

Gly His Phe Val Ala Gln Asp Thr Leu Glu Cys Gln Val Ala Glu Val
210 215 220

Glu Thr Gly Glu Gln Arg Val Val Thr Leu Asn Ala Arg Ser His Leu
225 230 235 240

Arg Ala Arg Val Gln Ala Gln Ser Thr Asn Asp Gly Leu Asp Phe Gln
245 250 255

Xaa Ser Gln Leu Val Lys Lys Leu Val Glu Pro Pro Pro Gln Gly Xaa
260 265 270

Gln Gly Ser Val Ile Ser Phe Pro Ser Pro Arg Ser Gly Pro Gly Ser
275 280 285

Pro Ala Gln Trp Leu Leu Tyr Thr His Pro Thr His Ser Trp Gln Arg
290 295 300

Ala Asp Leu Gly Ala Tyr Leu Asn Pro Arg Pro Pro Ala Pro Glu Ala
305 310 315 320

Trp Ser Glu Pro Xaa Leu Leu Ala Lys Gly Ser Xaa Ala Tyr Ser Asp
325 330 335

Leu Gln Ser Met Gly Thr Gly Pro Asp Gly Ser Pro Leu Phe Gly Xaa
340 345 350

Leu Tyr Glu Ala Asn Asp Tyr Glu Glu Ile Val Phe Leu Met Phe Thr
355 360 365

Leu Lys Gln Ala Phe Pro Ala Glu Tyr Leu Pro Gln
370 375 380

```
<210> SEQ ID NO 101
<211> LENGTH: 617
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Ala, Arg, Asn, Asp, Gln, Glu, Gly, His, Leu,
      Lys, Met, Phe, Thr, Val, or not present
<220> FEATURE:
<221> NAME/KEY: MOD_RES
<222> LOCATION: (2)..(2)
<223> OTHER INFORMATION: Ala or Lys
<220> FEATURE:
<221> NAME/KEY: MOD_RES
<222> LOCATION: (4)..(4)
<223> OTHER INFORMATION: Asn or Leu
<220> FEATURE:
<221> NAME/KEY: MOD_RES
<222> LOCATION: (6)..(6)
<223> OTHER INFORMATION: Phe, Trp, Tyr or Val
<220> FEATURE:
<221> NAME/KEY: MOD_RES
<222> LOCATION: (125)..(125)
<223> OTHER INFORMATION: Ala, Cys, Ile, Ser or Val
<220> FEATURE:
<221> NAME/KEY: MOD_RES
<222> LOCATION: (187)..(187)
<223> OTHER INFORMATION: Arg, Ile or Lys
<220> FEATURE:
<221> NAME/KEY: MOD_RES
<222> LOCATION: (196)..(196)
<223> OTHER INFORMATION: Ala, Cys, Leu or Val
<220> FEATURE:
<221> NAME/KEY: MOD_RES
<222> LOCATION: (257)..(257)
<223> OTHER INFORMATION: Glu or Lys
<220> FEATURE:
<221> NAME/KEY: MOD_RES
<222> LOCATION: (272)..(272)
<223> OTHER INFORMATION: Cys or Val
<220> FEATURE:
<221> NAME/KEY: MOD_RES
<222> LOCATION: (325)..(325)
<223> OTHER INFORMATION: Lys or Val
<220> FEATURE:
<221> NAME/KEY: MOD_RES
<222> LOCATION: (332)..(332)
<223> OTHER INFORMATION: Ala, Cys, Ser or Val
<220> FEATURE:
<221> NAME/KEY: MOD_RES
<222> LOCATION: (352)..(352)
<223> OTHER INFORMATION: Cys, Leu or Val

<400> SEQUENCE: 101

Xaa Xaa Ser Xaa Pro Xaa Leu Gln Lys Glu Ser Val Phe Gln Ser Gly
1               5                   10                  15

Ala His Ala Tyr Arg Ile Pro Ala Leu Leu Tyr Leu Pro Gly Gln Gln
            20                  25                  30

Ser Leu Leu Ala Phe Ala Glu Gln Arg Ala Ser Lys Lys Asp Glu His
        35                  40                  45

Ala Glu Leu Ile Val Leu Arg Arg Gly Asp Tyr Asp Ala Pro Thr His
    50                  55                  60

Gln Val Gln Trp Gln Ala Gln Glu Val Val Ala Gln Ala Arg Leu Asp
65                  70                  75                  80

Gly His Arg Ser Met Asn Pro Cys Pro Leu Tyr Asp Ala Gln Thr Gly
                85                  90                  95

Thr Leu Phe Leu Phe Phe Ile Ala Ile Pro Gly Gln Val Thr Glu Gln
```

-continued

```
            100                 105                 110

Gln Gln Leu Gln Thr Arg Ala Asn Val Thr Arg Leu Xaa Gln Val Thr
        115                 120                 125

Ser Thr Asp His Gly Arg Thr Trp Ser Ser Pro Arg Asp Leu Thr Asp
    130                 135                 140

Ala Ala Ile Gly Pro Ala Tyr Arg Glu Trp Ser Thr Phe Ala Val Gly
145                 150                 155                 160

Pro Gly His Cys Leu Gln Leu His Asp Arg Ala Arg Ser Leu Val Val
                165                 170                 175

Pro Ala Tyr Ala Tyr Arg Lys Leu His Pro Xaa Gln Arg Pro Ile Pro
            180                 185                 190

Ser Ala Phe Xaa Phe Leu Ser His Asp His Gly Arg Thr Trp Ala Arg
        195                 200                 205

Gly His Phe Val Ala Gln Asp Thr Leu Glu Cys Gln Val Ala Glu Val
    210                 215                 220

Glu Thr Gly Glu Gln Arg Val Val Thr Leu Asn Ala Arg Ser His Leu
225                 230                 235                 240

Arg Ala Arg Val Gln Ala Gln Ser Thr Asn Asp Gly Leu Asp Phe Gln
                245                 250                 255

Xaa Ser Gln Leu Val Lys Lys Leu Val Glu Pro Pro Pro Gln Gly Xaa
            260                 265                 270

Gln Gly Ser Val Ile Ser Phe Pro Ser Pro Arg Ser Gly Pro Gly Ser
        275                 280                 285

Pro Ala Gln Trp Leu Leu Tyr Thr His Pro Thr His Ser Trp Gln Arg
    290                 295                 300

Ala Asp Leu Gly Ala Tyr Leu Asn Pro Arg Pro Pro Ala Pro Glu Ala
305                 310                 315                 320

Trp Ser Glu Pro Xaa Leu Leu Ala Lys Gly Ser Xaa Ala Tyr Ser Asp
                325                 330                 335

Leu Gln Ser Met Gly Thr Gly Pro Asp Gly Ser Pro Leu Phe Gly Xaa
            340                 345                 350

Leu Tyr Glu Ala Asn Asp Tyr Glu Glu Ile Val Phe Leu Met Phe Thr
        355                 360                 365

Leu Lys Gln Ala Phe Pro Ala Glu Tyr Leu Pro Gln Gly Gly Gly Gly
    370                 375                 380

Ser Gly Gly Gly Gly Ser Asp Lys Thr His Thr Cys Pro Pro Cys Pro
385                 390                 395                 400

Ala Pro Glu Leu Leu Gly Gly Pro Ser Val Phe Leu Phe Pro Pro Lys
                405                 410                 415

Pro Lys Asp Thr Leu Met Ile Ser Arg Thr Pro Glu Val Thr Cys Val
            420                 425                 430

Val Val Asp Val Ser His Glu Asp Pro Glu Val Lys Phe Asn Trp Tyr
        435                 440                 445

Val Asp Gly Val Glu Val His Asn Ala Lys Thr Lys Pro Arg Glu Glu
    450                 455                 460

Gln Tyr Asn Ser Thr Tyr Arg Val Val Ser Val Leu Thr Val Leu His
465                 470                 475                 480

Gln Asp Trp Leu Asn Gly Lys Glu Tyr Lys Cys Lys Val Ser Asn Lys
                485                 490                 495

Ala Leu Pro Ala Pro Ile Glu Lys Thr Ile Ser Lys Ala Lys Gly Gln
            500                 505                 510

Pro Arg Glu Pro Gln Val Tyr Thr Leu Pro Pro Ser Arg Glu Glu Met
        515                 520                 525
```

```
Thr Lys Asn Gln Val Ser Leu Thr Cys Leu Val Lys Gly Phe Tyr Pro
    530                 535                 540

Ser Asp Ile Ala Val Glu Trp Glu Ser Asn Gly Gln Pro Glu Asn Asn
545                 550                 555                 560

Tyr Lys Thr Thr Pro Pro Val Leu Asp Ser Asp Gly Ser Phe Phe Leu
                565                 570                 575

Thr Ser Lys Leu Thr Val Asp Lys Ser Arg Trp Gln Gln Gly Asn Val
            580                 585                 590

Phe Ser Cys Ser Val Met His Glu Ala Leu His Asn His Tyr Thr Gln
        595                 600                 605

Lys Ser Leu Ser Leu Ser Pro Gly Lys
    610                 615


<210> SEQ ID NO 102
<211> LENGTH: 874
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Ala, Arg, Asn, Asp, Gln, Glu, Gly, His, Leu,
      Lys, Met, Phe, Thr, Val, or not present
<220> FEATURE:
<221> NAME/KEY: MOD_RES
<222> LOCATION: (2)..(2)
<223> OTHER INFORMATION: Ala or Lys
<220> FEATURE:
<221> NAME/KEY: MOD_RES
<222> LOCATION: (4)..(4)
<223> OTHER INFORMATION: Asn or Leu
<220> FEATURE:
<221> NAME/KEY: MOD_RES
<222> LOCATION: (6)..(6)
<223> OTHER INFORMATION: Phe, Trp, Tyr or Val
<220> FEATURE:
<221> NAME/KEY: MOD_RES
<222> LOCATION: (125)..(125)
<223> OTHER INFORMATION: Ala, Cys, Ile, Ser or Val
<220> FEATURE:
<221> NAME/KEY: MOD_RES
<222> LOCATION: (187)..(187)
<223> OTHER INFORMATION: Arg, Ile or Lys
<220> FEATURE:
<221> NAME/KEY: MOD_RES
<222> LOCATION: (196)..(196)
<223> OTHER INFORMATION: Ala, Cys, Leu or Val
<220> FEATURE:
<221> NAME/KEY: MOD_RES
<222> LOCATION: (257)..(257)
<223> OTHER INFORMATION: Glu or Lys
<220> FEATURE:
<221> NAME/KEY: MOD_RES
<222> LOCATION: (272)..(272)
<223> OTHER INFORMATION: Cys or Val
<220> FEATURE:
<221> NAME/KEY: MOD_RES
<222> LOCATION: (325)..(325)
<223> OTHER INFORMATION: Lys or Val
<220> FEATURE:
<221> NAME/KEY: MOD_RES
<222> LOCATION: (332)..(332)
<223> OTHER INFORMATION: Ala, Cys, Ser or Val
<220> FEATURE:
<221> NAME/KEY: MOD_RES
<222> LOCATION: (352)..(352)
<223> OTHER INFORMATION: Cys, Leu or Val

<400> SEQUENCE: 102
```

-continued

```
Xaa Xaa Ser Xaa Pro Xaa Leu Gln Lys Glu Ser Val Phe Gln Ser Gly
1               5                   10                  15

Ala His Ala Tyr Arg Ile Pro Ala Leu Leu Tyr Leu Pro Gly Gln Gln
            20                  25                  30

Ser Leu Leu Ala Phe Ala Glu Gln Arg Ala Ser Lys Lys Asp Glu His
        35                  40                  45

Ala Glu Leu Ile Val Leu Arg Arg Gly Asp Tyr Asp Ala Pro Thr His
    50                  55                  60

Gln Val Gln Trp Gln Ala Gln Glu Val Val Ala Gln Ala Arg Leu Asp
65                  70                  75                  80

Gly His Arg Ser Met Asn Pro Cys Pro Leu Tyr Asp Ala Gln Thr Gly
                85                  90                  95

Thr Leu Phe Leu Phe Phe Ile Ala Ile Pro Gly Gln Val Thr Glu Gln
            100                 105                 110

Gln Gln Leu Gln Thr Arg Ala Asn Val Thr Arg Leu Xaa Gln Val Thr
        115                 120                 125

Ser Thr Asp His Gly Arg Thr Trp Ser Ser Pro Arg Asp Leu Thr Asp
    130                 135                 140

Ala Ala Ile Gly Pro Ala Tyr Arg Glu Trp Ser Thr Phe Ala Val Gly
145                 150                 155                 160

Pro Gly His Cys Leu Gln Leu His Asp Arg Ala Arg Ser Leu Val Val
                165                 170                 175

Pro Ala Tyr Ala Tyr Arg Lys Leu His Pro Xaa Gln Arg Pro Ile Pro
            180                 185                 190

Ser Ala Phe Xaa Phe Leu Ser His Asp His Gly Arg Thr Trp Ala Arg
        195                 200                 205

Gly His Phe Val Ala Gln Asp Thr Leu Glu Cys Gln Val Ala Glu Val
    210                 215                 220

Glu Thr Gly Glu Gln Arg Val Val Thr Leu Asn Ala Arg Ser His Leu
225                 230                 235                 240

Arg Ala Arg Val Gln Ala Gln Ser Thr Asn Asp Gly Leu Asp Phe Gln
                245                 250                 255

Xaa Ser Gln Leu Val Lys Lys Leu Val Glu Pro Pro Pro Gln Gly Xaa
            260                 265                 270

Gln Gly Ser Val Ile Ser Phe Pro Ser Pro Arg Ser Gly Pro Gly Ser
        275                 280                 285

Pro Ala Gln Trp Leu Leu Tyr Thr His Pro Thr His Ser Trp Gln Arg
    290                 295                 300

Ala Asp Leu Gly Ala Tyr Leu Asn Pro Arg Pro Pro Ala Pro Glu Ala
305                 310                 315                 320

Trp Ser Glu Pro Xaa Leu Leu Ala Lys Gly Ser Xaa Ala Tyr Ser Asp
                325                 330                 335

Leu Gln Ser Met Gly Thr Gly Pro Asp Gly Ser Pro Leu Phe Gly Xaa
            340                 345                 350

Leu Tyr Glu Ala Asn Asp Tyr Glu Glu Ile Val Phe Leu Met Phe Thr
        355                 360                 365

Leu Lys Gln Ala Phe Pro Ala Glu Tyr Leu Pro Gln Gly Gly Gly Gly
    370                 375                 380

Ser Gly Gly Gly Gly Ser Asp Lys Thr His Thr Cys Pro Pro Cys Pro
385                 390                 395                 400

Ala Pro Glu Leu Leu Gly Gly Pro Ser Val Phe Leu Phe Pro Pro Lys
                405                 410                 415

Pro Lys Asp Thr Leu Met Ile Ser Arg Thr Pro Glu Val Thr Cys Val
```

420 425 430

Val Val Asp Val Ser His Glu Asp Pro Glu Val Lys Phe Asn Trp Tyr
435 440 445

Val Asp Gly Val Glu Val His Asn Ala Lys Thr Lys Pro Arg Glu Glu
450 455 460

Gln Tyr Asn Ser Thr Tyr Arg Val Val Ser Val Leu Thr Val Leu His
465 470 475 480

Gln Asp Trp Leu Asn Gly Lys Glu Tyr Lys Cys Lys Val Ser Asn Lys
485 490 495

Ala Leu Pro Ala Pro Ile Glu Lys Thr Ile Ser Lys Ala Lys Gly Gln
500 505 510

Pro Arg Glu Pro Gln Val Tyr Thr Leu Pro Pro Ser Arg Glu Glu Met
515 520 525

Thr Lys Asn Gln Val Ser Leu Thr Cys Leu Val Lys Gly Phe Tyr Pro
530 535 540

Ser Asp Ile Ala Val Glu Trp Glu Ser Asn Gly Gln Pro Glu Asn Asn
545 550 555 560

Tyr Lys Thr Thr Pro Pro Val Leu Asp Ser Asp Gly Ser Phe Phe Leu
565 570 575

Tyr Ser Lys Leu Thr Val Asp Lys Ser Arg Trp Gln Gln Gly Asn Val
580 585 590

Phe Ser Cys Ser Val Met His Glu Ala Leu His Asn His Tyr Thr Gln
595 600 605

Lys Ser Leu Ser Leu Ser Pro Gly Lys Gly Gly Gly Gly Ser Gly Gly
610 615 620

Gly Gly Ser Gly Gly Gly Gly Ser Glu Val Gln Leu Val Glu Ser Gly
625 630 635 640

Gly Gly Leu Val Gln Pro Gly Gly Ser Leu Arg Leu Ser Cys Ala Ala
645 650 655

Ser Gly Phe Asn Ile Lys Asp Thr Tyr Ile His Trp Val Arg Gln Ala
660 665 670

Pro Gly Lys Gly Leu Glu Trp Val Ala Arg Ile Tyr Pro Thr Asn Gly
675 680 685

Tyr Thr Arg Tyr Ala Asp Ser Val Lys Gly Arg Phe Thr Ile Ser Ala
690 695 700

Asp Thr Ser Lys Asn Thr Ala Tyr Leu Gln Met Asn Ser Leu Arg Ala
705 710 715 720

Glu Asp Thr Ala Val Tyr Tyr Cys Ser Arg Trp Gly Gly Asp Gly Phe
725 730 735

Tyr Ala Met Asp Tyr Trp Gly Gln Gly Thr Leu Val Thr Val Ser Ser
740 745 750

Gly Gly Gly Gly Ser Gly Gly Gly Gly Ser Gly Gly Gly Gly Ser Asp
755 760 765

Ile Gln Met Thr Gln Ser Pro Ser Ser Leu Ser Ala Ser Val Gly Asp
770 775 780

Arg Val Thr Ile Thr Cys Arg Ala Ser Gln Asp Val Asn Thr Ala Val
785 790 795 800

Ala Trp Tyr Gln Gln Lys Pro Gly Lys Ala Pro Lys Leu Leu Ile Tyr
805 810 815

Ser Ala Ser Phe Leu Tyr Ser Gly Val Pro Ser Arg Phe Ser Gly Ser
820 825 830

Arg Ser Gly Thr Asp Phe Thr Leu Thr Ile Ser Ser Leu Gln Pro Glu
835 840 845

Asp Phe Ala Thr Tyr Tyr Cys Gln Gln His Tyr Thr Thr Pro Pro Thr
850 855 860

Phe Gly Gln Gly Thr Lys Val Glu Ile Lys
865 870

<210> SEQ ID NO 103
<211> LENGTH: 875
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 103

Thr Val Glu Lys Ser Val Val Phe Lys Ala Glu Gly Glu His Phe Thr
1 5 10 15

Asp Gln Lys Gly Asn Thr Ile Val Gly Ser Gly Ser Gly Gly Thr Thr
20 25 30

Lys Tyr Phe Arg Ile Pro Ala Met Cys Thr Thr Ser Lys Gly Thr Ile
35 40 45

Val Val Phe Ala Asp Ala Arg His Asn Thr Ala Ser Asp Gln Ser Phe
50 55 60

Ile Asp Thr Ala Ala Ala Arg Ser Thr Asp Gly Gly Lys Thr Trp Asn
65 70 75 80

Lys Lys Ile Ala Ile Tyr Asn Asp Arg Val Asn Ser Lys Leu Ser Arg
85 90 95

Val Met Asp Pro Thr Cys Ile Val Ala Asn Ile Gln Gly Arg Glu Thr
100 105 110

Ile Leu Val Met Val Gly Lys Trp Asn Asn Asn Asp Lys Thr Trp Gly
115 120 125

Ala Tyr Arg Asp Lys Ala Pro Asp Thr Asp Trp Asp Leu Val Leu Tyr
130 135 140

Lys Ser Thr Asp Asp Gly Val Thr Phe Ser Lys Val Glu Thr Asn Ile
145 150 155 160

His Asp Ile Val Thr Lys Asn Gly Thr Ile Ser Ala Met Leu Gly Gly
165 170 175

Val Gly Ser Gly Leu Gln Leu Asn Asp Gly Lys Leu Val Phe Pro Val
180 185 190

Gln Met Val Arg Thr Lys Asn Ile Thr Thr Val Leu Asn Thr Ser Phe
195 200 205

Ile Tyr Ser Thr Asp Gly Ile Thr Trp Ser Leu Pro Ser Gly Tyr Cys
210 215 220

Glu Gly Phe Gly Ser Glu Asn Asn Ile Ile Glu Phe Asn Ala Ser Leu
225 230 235 240

Val Asn Asn Ile Arg Asn Ser Gly Leu Arg Arg Ser Phe Glu Thr Lys
245 250 255

Asp Phe Gly Lys Thr Trp Thr Glu Phe Pro Pro Met Asp Lys Lys Val
260 265 270

Asp Asn Arg Asn His Gly Val Gln Gly Ser Thr Ile Thr Ile Pro Ser
275 280 285

Gly Asn Lys Leu Val Ala Ala His Ser Ser Ala Gln Asn Lys Asn Asn
290 295 300

Asp Tyr Thr Arg Ser Asp Ile Ser Leu Tyr Ala His Asn Leu Tyr Ser
305 310 315 320

Gly Glu Val Lys Leu Ile Asp Asp Phe Tyr Pro Lys Val Gly Asn Ala

-continued

```
                325                 330                 335

Ser Gly Ala Gly Tyr Ser Cys Leu Ser Tyr Arg Lys Asn Val Asp Lys
            340                 345                 350

Glu Thr Leu Tyr Val Val Tyr Glu Ala Asn Gly Ser Ile Glu Phe Gln
        355                 360                 365

Asp Leu Ser Arg His Leu Pro Val Ile Lys Ser Tyr Asn Gly Gly Gly
    370                 375                 380

Gly Ser Gly Gly Gly Gly Ser Asp Lys Thr His Thr Cys Pro Pro Cys
385                 390                 395                 400

Pro Ala Pro Glu Leu Leu Gly Gly Pro Ser Val Phe Leu Phe Pro Pro
                405                 410                 415

Lys Pro Lys Asp Thr Leu Met Ile Ser Arg Thr Pro Glu Val Thr Cys
            420                 425                 430

Val Val Val Asp Val Ser His Glu Asp Pro Glu Val Lys Phe Asn Trp
        435                 440                 445

Tyr Val Asp Gly Val Glu Val His Asn Ala Lys Thr Lys Pro Arg Glu
    450                 455                 460

Glu Gln Tyr Asn Ser Thr Tyr Arg Val Val Ser Val Leu Thr Val Leu
465                 470                 475                 480

His Gln Asp Trp Leu Asn Gly Lys Glu Tyr Lys Cys Lys Val Ser Asn
                485                 490                 495

Lys Ala Leu Pro Ala Pro Ile Glu Lys Thr Ile Ser Lys Ala Lys Gly
            500                 505                 510

Gln Pro Arg Glu Pro Gln Val Tyr Thr Leu Pro Pro Ser Arg Glu Glu
        515                 520                 525

Met Thr Lys Asn Gln Val Ser Leu Thr Cys Leu Val Lys Gly Phe Tyr
    530                 535                 540

Pro Ser Asp Ile Ala Val Glu Trp Glu Ser Asn Gly Gln Pro Glu Asn
545                 550                 555                 560

Asn Tyr Lys Thr Thr Pro Pro Val Leu Asp Ser Asp Gly Ser Phe Phe
                565                 570                 575

Leu Tyr Ser Lys Leu Thr Val Asp Lys Ser Arg Trp Gln Gln Gly Asn
            580                 585                 590

Val Phe Ser Cys Ser Val Met His Glu Ala Leu His Asn His Tyr Thr
        595                 600                 605

Gln Lys Ser Leu Ser Leu Ser Pro Gly Lys Gly Gly Gly Gly Ser Gly
    610                 615                 620

Gly Gly Gly Ser Gly Gly Gly Gly Ser Glu Val Gln Leu Val Glu Ser
625                 630                 635                 640

Gly Gly Gly Leu Val Gln Pro Gly Gly Ser Leu Arg Leu Ser Cys Ala
                645                 650                 655

Ala Ser Gly Phe Asn Ile Lys Asp Thr Tyr Ile His Trp Val Arg Gln
            660                 665                 670

Ala Pro Gly Lys Gly Leu Glu Trp Val Ala Arg Ile Tyr Pro Thr Asn
        675                 680                 685

Gly Tyr Thr Arg Tyr Ala Asp Ser Val Lys Gly Arg Phe Thr Ile Ser
    690                 695                 700

Ala Asp Thr Ser Lys Asn Thr Ala Tyr Leu Gln Met Asn Ser Leu Arg
705                 710                 715                 720

Ala Glu Asp Thr Ala Val Tyr Tyr Cys Ser Arg Trp Gly Gly Asp Gly
                725                 730                 735

Phe Tyr Ala Met Asp Tyr Trp Gly Gln Gly Thr Leu Val Thr Val Ser
            740                 745                 750
```

```
Ser Gly Gly Gly Gly Ser Gly Gly Gly Gly Ser Gly Gly Gly Gly Ser
        755                 760                 765

Asp Ile Gln Met Thr Gln Ser Pro Ser Ser Leu Ser Ala Ser Val Gly
    770                 775                 780

Asp Arg Val Thr Ile Thr Cys Arg Ala Ser Gln Asp Val Asn Thr Ala
785                 790                 795                 800

Val Ala Trp Tyr Gln Gln Lys Pro Gly Lys Ala Pro Lys Leu Leu Ile
                805                 810                 815

Tyr Ser Ala Ser Phe Leu Tyr Ser Gly Val Pro Ser Arg Phe Ser Gly
            820                 825                 830

Ser Arg Ser Gly Thr Asp Phe Thr Leu Thr Ile Ser Ser Leu Gln Pro
        835                 840                 845

Glu Asp Phe Ala Thr Tyr Tyr Cys Gln Gln His Tyr Thr Thr Pro Pro
    850                 855                 860

Thr Phe Gly Gln Gly Thr Lys Val Glu Ile Lys
865                 870                 875


<210> SEQ ID NO 104
<211> LENGTH: 2625
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 104

acagtggaaa agtccgtggt gttcaaggcc gagggcgagc acttcaccga ccagaaaggc     60

aataccatcg tcggctctgg cagcggcggc accaccaagt actttagaat ccccgccatg    120

tgcaccacca gcaagggcac cattgtggtg ttcgccgacg ccagacacaa caccgccagc    180

gatcagagct tcatcgatac cgctgccgcc agatctaccg atggcggcaa gacctggaac    240

aagaagatcg ccatctacaa cgaccgcgtg aacagcaagc tgagcagagt gatggaccct    300

acctgcatcg tggccaacat ccagggcaga gaaaccatcc tggtcatggt cggaaagtgg    360

aacaacaacg ataagacctg ggcgcctac agagacaagg cccctgatac cgattgggac    420

ctcgtgctgt acaagagcac cgatgacggc gtgaccttca gcaaggtgga aacaaacatc    480

cacgacatcg tgaccaagaa cggcaccatc tctgccatgc tcggcggcgt tggatctggc    540

ctgcaactga atgatggcaa gctggtgttc cccgtgcaga tggtccgaac aaagaatatc    600

accaccgtgc tgaataccag cttcatctac agcaccgacg gcatcacatg gtccctgcct    660

agcggctact gtgaaggctt tggcagcgag aacaacatca tcgagttcaa cgccagcctg    720

gtcaacaaca tccggaacag cggcctgcgg agaagcttcg agacaaagga cttcggaaag    780

acgtggaccg agtttcctcc aatggacaag aaggtggaca accggaacca cggcgtgcag    840

ggcagcacaa tcacaatccc tagcggcaac aaactggtgg ccgctcactc tagcgcccag    900

aacaagaaca acgactacac cagaagcgac atcagcctgt acgcccacaa cctgtacagc    960

ggcgaagtga agctgatcga cgacttctac cccaaagtgg gcaatgccag cggagccggc   1020

tacagctgtc tgagctaccg gaaaaatgtg gacaaagaaa ccctgtacgt ggtgtacgag   1080

gccaacggca gcatcgagtt tcaggacctg agcagacatc tgcccgtgat caagagctac   1140

aacggcggag gtggaagtgg cggaggcgga tccgacaaaa ctcacacatg cccaccgtgc   1200

ccagcacctg aactcctggg gggaccgtca gtcttcctct tccccccaaa acccaaggac   1260

accctcatga tctcccggac ccctgaggtc acatgcgtgg tggtggacgt gagccacgaa   1320
```

```
gaccctgagg tcaagttcaa ctggtacgtg gacggcgtgg aggtgcataa tgccaagaca   1380
aagccgcggg aggagcagta caacagcacg taccgtgtgg tcagcgtcct caccgtcctg   1440
caccaggact ggctgaatgg caaggagtac aagtgcaagg tctccaacaa agccctccca   1500
gcccccatcg agaaaaccat ctccaaagcc aaagggcagc cccgagaacc acaggtctac   1560
accctgcccc catcccggga ggagatgacc aagaaccagg tcagcctgac ctgcctggtc   1620
aaaggcttct atcccagcga catcgccgtg gagtgggaga gcaatgggca gccggagaac   1680
aactacaaga ccacgcctcc cgtgctggac tccgacggct ccttcttcct ctatagcaag   1740
ctcaccgtgg acaagagcag gtggcagcag gggaacgtct tctcatgctc cgtgatgcat   1800
gaggctctgc acaaccacta cacgcagaag agcctctccc tgtctccggg taaaggaggc   1860
ggaggatctg gcggaggtgg aagtggcgga ggcggatctg aggtgcagct ggttgaatct   1920
ggcggaggac tggttcagcc tggcggatct ctgagactgt cttgtgccgc cagcggcttc   1980
aacatcaagg acacctacat ccactgggtc cgacaggccc ctggcaaagg acttgaatgg   2040
gtcgccagaa tctaccccac caacggctac accagatacg ccgactctgt gaagggcaga   2100
ttcaccatca gcgccgacac cagcaagaac accgcctacc tgcagatgaa cagcctgaga   2160
gccgaggaca ccgccgtgta ctactgttct agatggggag gcgacggctt ctacgccatg   2220
gattattggg gccagggcac cctggtcacc gtttcttctg gcggaggagg atctggcgga   2280
ggcggaagtg gcggaggcgg atctgacatc cagatgacac agagccctag cagcctgtct   2340
gccagcgtgg gagacagagt gaccatcacc tgtagagcca gccaggacgt gaacacagcc   2400
gtggcttggt atcagcagaa gcctggcaag gcccctaagc tgctgatcta cagcgccagc   2460
tttctgtact ccggcgtgcc cagcagattc agcggctcta gaagcggcac cgacttcacc   2520
ctgaccataa gcagtctgca gcccgaggac ttcgccacct actactgtca gcagcactac   2580
accacacctc caacctttgg ccagggcacc aaggtggaaa tcaag                   2625
```

<210> SEQ ID NO 105
<211> LENGTH: 10
<212> TYPE: PRT
<213> ORGANISM: Artificial Sequence
<220> FEATURE:
<223> OTHER INFORMATION: Description of Artificial Sequence: Synthetic 10xHis tag

<400> SEQUENCE: 105

```
His His His His His His His His His His
1               5                   10
```

<210> SEQ ID NO 106
<211> LENGTH: 15
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MISC_FEATURE
<222> LOCATION: (1)..(15)
<223> OTHER INFORMATION: This sequence may encompass 1-5 “Gly Gly Pro” repeating units

<400> SEQUENCE: 106

```
Gly Gly Pro Gly Gly Pro Gly Gly Pro Gly Gly Pro Gly Gly Pro
1               5                   10                  15
```

-continued

```
<210> SEQ ID NO 107
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(25)
<223> OTHER INFORMATION: This sequence may encompass 1-5 "Gly Gly Gly
      Gly Ser" repeating units

<400> SEQUENCE: 107

Gly Gly Gly Gly Ser Gly Gly Gly Gly Ser Gly Gly Gly Gly Ser Gly
1               5                   10                  15

Gly Gly Gly Ser Gly Gly Gly Gly Ser
            20                  25


<210> SEQ ID NO 108
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Gly Gly Gly Gly Ser Gly Gly Gly Gly Ser
1               5                   10


<210> SEQ ID NO 109
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 109

His His His His His His
1               5
```